US 12,053,520 B2

(12) United States Patent
Chen et al.

(10) Patent No.: US 12,053,520 B2
(45) Date of Patent: Aug. 6, 2024

(54) GLYCAN-MASKED ENGINEERED OUTER DOMAINS OF HIV-1 gp120 AND THEIR USE

(71) Applicant: The United States of America, as represented by the Secretary, Department of Health and Human Services, Bethesda, MD (US)

(72) Inventors: Xuejun Chen, Clarksburg, MD (US); Jeffrey Boyington, Clarksburg, MD (US); Hongying Duan Holdsworth, McLean, VA (US); Cheng Cheng, Bethesda, MD (US); John R. Mascola, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 64 days.

(21) Appl. No.: 17/587,817

(22) Filed: Jan. 28, 2022

(65) Prior Publication Data

US 2022/0152194 A1  May 19, 2022

Related U.S. Application Data

(63) Continuation of application No. 16/496,912, filed as application No. PCT/US2018/024330 on Mar. 26, 2018, now Pat. No. 11,235,056.

(60) Provisional application No. 62/476,397, filed on Mar. 24, 2017.

(51) Int. Cl.
| | | |
|---|---|---|
| A61K 39/21 | (2006.01) | |
| C07K 14/005 | (2006.01) | |
| C07K 14/16 | (2006.01) | |
| C12N 7/00 | (2006.01) | |
| A61K 39/00 | (2006.01) | |

(52) U.S. Cl.
CPC ............ *A61K 39/21* (2013.01); *C07K 14/005* (2013.01); *C07K 14/162* (2013.01); *C12N 7/00* (2013.01); *C12Y 205/01078* (2013.01); *A61K 2039/5258* (2013.01); *A61K 2039/55555* (2013.01); *C07K 2319/00* (2013.01); *C12N 2740/16023* (2013.01); *C12N 2740/16043* (2013.01); *C12N 2740/16111* (2013.01); *C12N 2740/16122* (2013.01); *C12N 2740/16134* (2013.01); *C12N 2740/16171* (2013.01)

(58) Field of Classification Search
CPC .................. A61K 39/21; C07K 14/162; C12N 2740/16122
See application file for complete search history.

(56) References Cited

U.S. PATENT DOCUMENTS

| 8,227,577 | B2 | 7/2012 | Klein et al. | |
|---|---|---|---|---|
| 10,221,217 | B2 * | 3/2019 | Huang | A61K 38/00 |

FOREIGN PATENT DOCUMENTS

| WO | WO 2009/100376 A2 | 8/2009 |
|---|---|---|
| WO | WO 2011/038290 A2 | 3/2011 |
| WO | WO 2012/154312 A1 | 11/2012 |
| WO | WO 2012/158948 A1 | 11/2012 |
| WO | WO 2013/016468 A2 | 1/2013 |
| WO | WO 2013/056122 A1 * | 4/2013 |
| WO | WO 2013/142324 A1 | 9/2013 |
| WO | WO 2016/154422 A1 | 9/2016 |
| WO | WO 2016/205704 A2 | 12/2016 |

OTHER PUBLICATIONS

Abbott et al., "Precursor Frequency and Affinity Determine B Cell Competitive Fitness in Germinal Centers, Tested with Germline-Targeting HIV Vaccine Immunogens," *Immunity* 48: 133-146, 2018.
Barouch et al., "A Human T-Cell Leukemia Virus Type 1 Regulatory Element Enhances the Immunogenicity of Human Immunodeficiency Virus Type 1 DNA Vaccines in Mice and Nonhuman Primates," *J Virol.*, 79: 8828-8834, 2005.
Briney et al., "Tailored immunogens direct affinity maturation toward HIV neutralizing antibodies." *Cell* 166.6: 1459-1470, 2016.
Diskin et al., "Increasing the Potency and Breadth of an HIV Antibody by using Structure-Based Rational Design," *Science* 334: 1289-1293, 2011.
Dosenovic et al., "Immunization for HIV-1 Broadly Neutralizing Antibodies in Human Ig Knockin Mice," *Cell* 161:1505-1515, 2015.
Duan et al., "Glycan Masking Focuses Immune Responses to the HIV-1 CD4-Binding Site and Enhances Elicitation of VRC01-Class Precursor Antibodies," *Immunity* 49: 301-311, 2018.
Georgiev et al., "Delineating Antibody Recognition in Polyclonal Sera from Patterns of HIV-1 Isolate Neutralization," *Science* 340: 751-756, 2013.
He and Zhu, "Computational tools for epitope vaccine design and evaluation," *Curr Opin Virol*, 11: 103-112, 2015.
Hoot et al., "Recombinant HIV Envelope Proteins Fail to Engage Germline Versions of Anti-CD4bs bNAbs," *PLoS Pathog*, 9:e1003106, 2013 (14 pages).

(Continued)

*Primary Examiner* — Jeffrey S Parkin
(74) *Attorney, Agent, or Firm* — Klarquist Sparkman, LLP

(57) ABSTRACT

Embodiments of immunogens based on the outer domain of HIV-1 gp120 and methods of their use and production are disclosed. Nucleic acid molecules encoding the immunogens are also provided. In several embodiments, the immunogens can be used to prime an immune response to gp120 in a subject, for example, to treat or prevent an HIV-1 infection in the subject.

28 Claims, 24 Drawing Sheets

Specification includes a Sequence Listing.

(56) References Cited

OTHER PUBLICATIONS

International Search Report and Written Opinion for PCT/US2018/024330, ISA European Patent Office, mailed on Jun. 21, 2018 (18 pages).
Jardine et al., "Rational HIV immunogen design to target specific germline B cell receptors." *Science* 340.6133: 711-716, 2013.
Jardine et al., "Priming a broadly neutralizing antibody response to HIV-1 using a germline-targeting immunogen." *Science* 349.6244: 156-161, 2015.
Jardine et al., "HIV-1 broadly neutralizing antibody precursor B cells revealed by germline-targeting immunogen." *Science* 351. 6280: 1458-1463, 2016.
Jardine et al., "Minimally Mutated HIV-1 Broadly Neutralizing Antibodies to Guide Reductionist Vaccine Design," *PLoS Pathog* 12: e1005815, Aug. 2016 (33 pages).
Kwong et al., "Structure of an HIV gp120 envelope glycoprotein in complex with the CD4 receptor and a neutralizing human antibody." *Nature* 393.6686: 648-659, 1998.
Kwong and Mascola, "Human Antibodies that Neutralize HIV-1: Identification, Structures, and B Cell Ontogenies," *Immunity* 37: 412-425, 2012.
Li et al., "Mechanism of Neutralization by the Broadly Neutralizing HIV-1 Monoclonal Antibody VRC01,"*J Virol.* 85: 8954-8967, 2011.
López-Sagaseta et al., "Self-assembling protein nanoparticles in the design of vaccines," *Comput Struct Biotechnol J.* 14: 58-68, Nov. 2015.
McGuire et al., "Engineering HIV envelope protein to activate germline B cell receptors of broadly neutralizing anti-CD4 binding site antibodies," *J Exp Med.* 210: 655-663, 2013.
McGuire et al., "Specifically modified Env immunogens activate B-cell precursors of broadly neutralizing HIV-1 antibodies in transgenic mice," *Nat Commun.* 7: 10618, 2016 (10 pages).
Pantophlet et al., "Hyperglycosylated Mutants of Human Immunodeficiency Virus (HIV) Type 1 Monomeric gp120 as Novel Antigens for HIV Vaccine Design," *J Virol.* 77: 5889-5901, 2003.
Pantophlet et al., "Improved design of an antigen with enhanced specificity for the broadly HIV-neutralizing antibody b12," *Protein Eng Des Sel.* 17: 749-758, 2004.
Rudicell et al., "Enhanced Potency of a Broadly Neutralizing HIV-1 Antibody In Vitro Improves Protection against Lentiviral Infection In Vivo," *J. Virol.* 88: 12669-12682, 2012.
Scharf et al., "Structural basis for HIV-1 gp120 recognition by a germ-line version of a broadly neutralizing antibody," *Proc Natl Acad Sci USA* 110: 6049-6054, 2013.
Scheid et al., "Sequence and Structural Convergence of Broad and Potent HIV Antibodies that Mimic CD4 Binding," *Science* 333: 1633-1637, 2011.
Sok et al., "Priming HIV-1 broadly neutralizing antibody precursors in human Ig loci transgenic mice." *Science* 353.6307: 1557-1560, 2016.
Tian et al., "Induction of HIV neutralizing antibody lineages in mice with diverse precursor repertoires." *Cell* 166.6: 1471-1484, 2016.
West et al., "Structural basis for germ-line gene usage of a potent class of antibodies targeting the CD4-binding site of HIV-1 gp120," *Proc Natl Acad Sci.* 109: E2083-E2090, 2012 (8 pages).
Wu et al., "Rational Design of Envelope Identifies Broadly Neutralizing Human Monoclonal Antibodies to HIV-1," *Science* 329: 856-861, 2010.
Wu et al., "Focused Evolution of HIV-1 Neutralizing Antibodies Revealed by Structures and Deep Sequencing," *Science* 333: 1593-1602, 2011.
Yang et al., "Characterization of the outer domain of the gp120 glycoprotein from human immunodeficiency virus type 1." *Journal of Virology* 78.23: 12975-12986, 2004.
Zhou et al., "Structural Basis for Broad and Potent Neutralization of HIV-1 by Antibody VRC01," *Science* 329: 811-817, 2010.
Zhou et al., "Focused Evolution of HIV-1 Neutralizing Antibodies Revealed by Structures and Deep Sequencing," *Immunity* 39: 245-258, 2013.
Zhu et al., "De novo identification of VRC01 class HIV-1-neutralizing antibodies by next-generation sequencing of B-cell transcripts," *Proc Natl Acad Sci U.S.A.* 110.43: E4088-E4097, Oct. 2013.

\* cited by examiner

FIG. 1A eOD-GT8 → Identified surface residues → > 5 Å from the CD4bs → > 5 Å from native glycans → Sequons compatible with structure → NetNGlyc sequence score > 0.5 → 13 potential glycan sites identified → 6 glycan sites on protruding loops prioritized → Combine all 13 glycan sites into groups of 2-6 → Native Hxb2 glycans 276 and 463 added to some groups → Native glycan 289 moved to 287 in some groups → 35 glycan site combinations and 13 individual sites characterized

FIG. 1B

| | | | | | | Added Glycans | | | | | | | |
|---|---|---|---|---|---|---|---|---|---|---|---|---|---|
| Hxbc2 residue numbering | | 253 | 267 | 268 | 271 | 299 | 347 | 377 | 380 | 386 | 413 | 419 | 444 | 482 |
| Wt amino acids | | TVV | EEE | EEEV | VIR | AGH | SKL | NCG | GEF | DST | TIT | RPA | HCS | QIA |
| NO. of Glycans | Mut # | | | | | | Sequons | | | | | | | |
| Single | 1 | | | GNGT | | | | | | | | | | |
| | 2 | | NGT | | | | | | | | | | | |
| | 3 | | | | | | | | | | | | NCT | |
| | 4 | | | | | | | | | | | | | NIT |
| | 5 | NVT | | | | | | | | | | | | |
| | 6 | | | | | | | NCT | | | | | | |
| | 7 | | | | | | | | NVT | | | | | |
| | 8 | | | | | | | | | | | NIT | | |
| | 9 | | | | | | NKT | | | | | | | |
| | 10 | | | | | NGT | | | | | | | | |
| | 11 | | | | | | | | | | | NGTG | | |
| | 12 | | | | | | | | | | NST | | | |
| | 23 | | | | NGT | | | | | | | | | |
| Multiple | 15 | | GNGT | | | | | | | | | NGTG | | NIT |
| | 16 | | GNGT | | NGT | | | | NVT | | | | NCT | NIT |
| | 21 | | NGT | | NGT | | | | NVT | | | NGTG | NCT | NIT |
| | 33 | | GNGT | | | | | | NVT | | | NGTG | | NIT |

| Immunogen | eOD-GT8 | | | Mut15 | | | Mut16 | | | Mut21 | | | Mut33 | | |
|---|---|---|---|---|---|---|---|---|---|---|---|---|---|---|---|
| Specificity | Total | non-CD4bs | CD4bs | Total | non-CD4bs | CD4bs | Total | non-CD4bs | CD4bs | Total | non-CD4bs | CD4bs | Total | non-CD4bs | CD4bs |
| ED$_{50}$ (Dilution factor) | 6059 | 3534 | 2525 | 3186 | 230 | 2956 | 9069 | 1141 | 7928 | 1917 | 120 | 1797 | 6254 | 1463 | 4611 |
| eOD-GT8 response (%) | 100 | 58 | 42 | 100 | 7 | 93 | 100 | 13 | 87 | 100 | 6 | 94 | 100 | 26 | 74 |

FIG. 4E
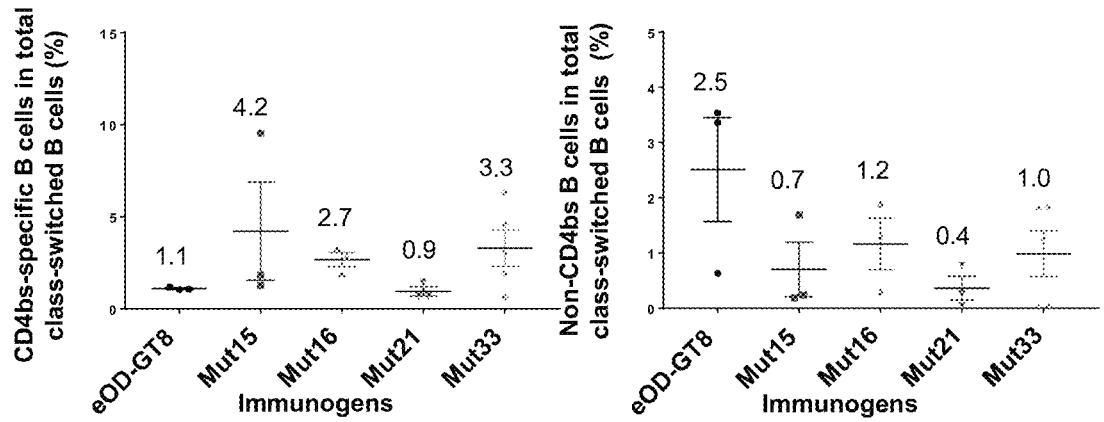
FIG. 4F
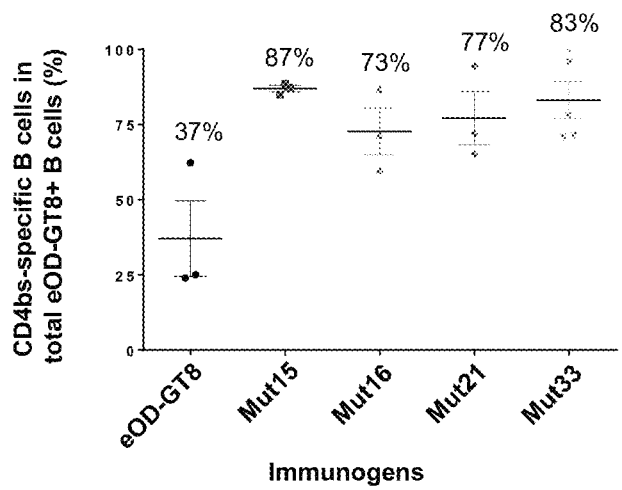
FIG. 4G
| Immunogen | No. of mice | Sorted B cells (millions) | No. CD4bs-specific B cells | No. Amplified K chains | No. of VRC01-class antibodies | VRC01-class antibodies in amplified K chains (%) |
|---|---|---|---|---|---|---|
| eOD-GT6 | 3 | 1.32 | 263 | 92 | 0 | ND |
| eOD-GT8 | 3 | 2.00 | 336 | 133 | 3 | 2.3 |
| Mut15 | 3 | 1.30 | 399 | 184 | 11 | 6.0 |
| Mut16 | 3 | 0.8 | 425 | 141 | 19 | 13.5 |
| Mut21 | 3 | 2.90 | 220 | 107 | 2 | 1.9 |
| Mut33 | 5 | 0.4 | 482 | 95 | 3 | 3.2 |

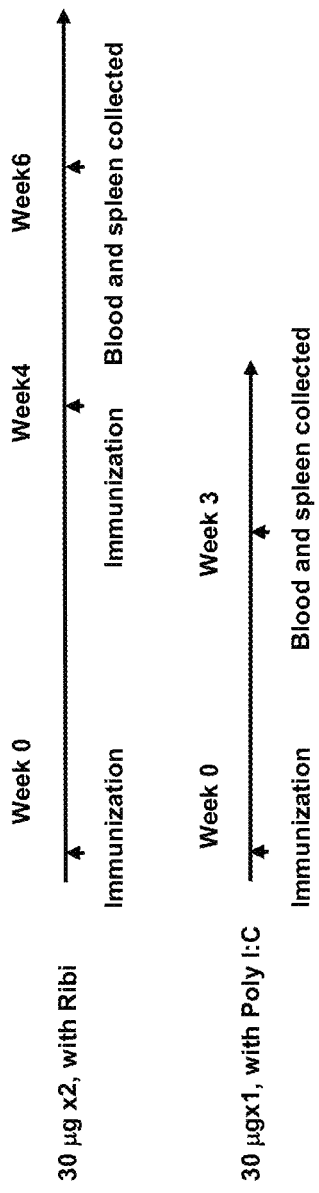
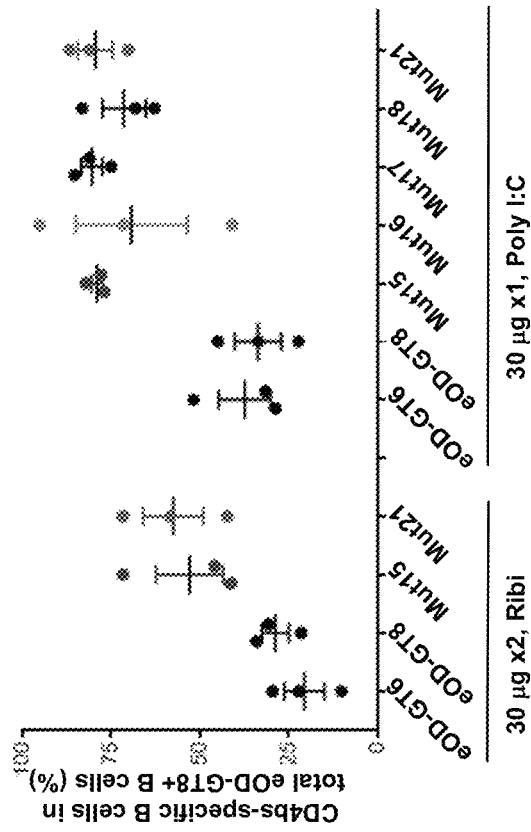
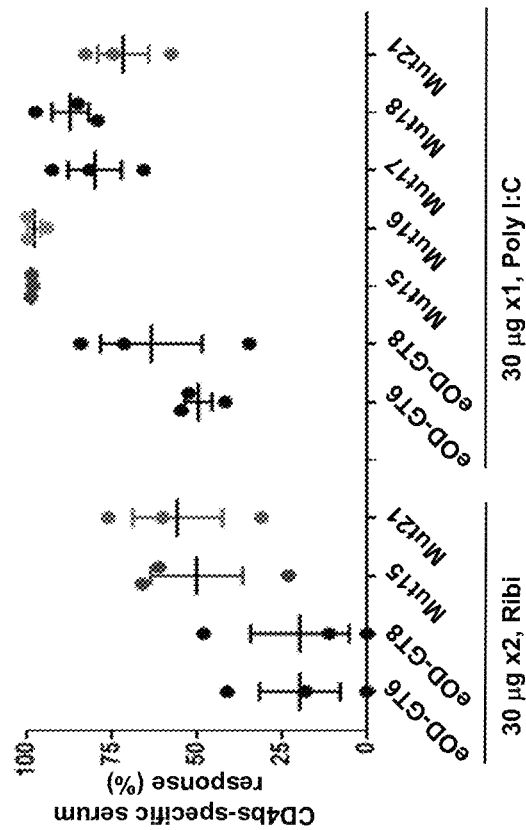
FIG. 5A
FIG. 5B
FIG. 5C

FIG. 5D

| Immunization Method | Immunogen | No. of mice | No. CD4bs-specific B cells | No. Amplified κ chains | No. of VRC01-class antibodies | VRC01-class antibodies in amplified κ chains (%) |
|---|---|---|---|---|---|---|
| 30 μg x2, Ribi | eOD-GT6 | 1 | 50 | 23 | 0 | ND |
| | eOD-GT8 | 3 | 156 | 73 | 2 | 2.7 |
| | Mut15 | 3 | 274 | 170 | 13 | 7.6 |
| | Mut21 | 3 | 107 | 40 | 0 | ND |
| 30 μg x1, Poly I:C | eOD-GT6 | 2 | 182 | 47 | 0 | ND |
| | eOD-GT8 | 3 | 228 | 96 | 2 | 2.1 |
| | Mut15 | 3 | 204 | 88 | 2 | 2.3 |
| | Mut16 | 3 | 284 | 148 | 9 | 6.1 |
| | Mut17 | 3 | 384 | 168 | 5 | 3 |
| | Mut18 | 3 | 100 | 31 | 2 | 6.5 |
| | Mut21 | 3 | 115 | 70 | 3 | 4.3 |

| Residue No. | 89 90 91 96 97 |
| VRC01 | Q Q Y E F |
| VRC01-class | X X Φ$_{E/Q}$ X |

Antibodies elicited by:

eOD-GT8 (n=24)

Mut15 (n=26)

Mut16 (n=28)

Mut17 (n=5)

Mut21 (n=5)

CDRL3 sequence

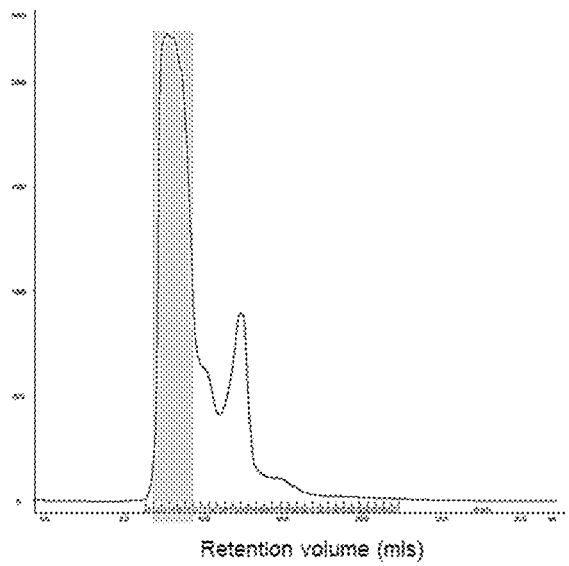
FIG. 8A
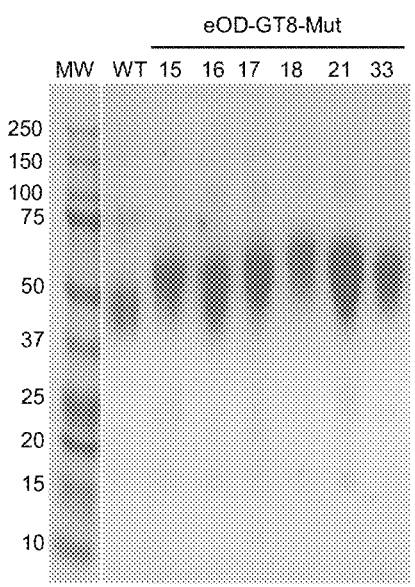
FIG. 8B
FIG. 8C
| eOD-GT8 and glycan mutant purification yields (mg/L) | | | |
|---|---|---|---|
| | Lots | | |
| Protein | 1 | 2 | Average |
| eOD-GT8 monomer | 86.0 | | 86.0 |
| Mut33 monomer | 36.0 | | 36.0 |
| eOD-GT8 60mer | 93.0 | 80.0 | 86.5 |
| Mut15 60mer | 20.0 | 61.0 | 40.5 |
| Mut16 60mer | | 53.0 | 53.0 |
| Mut17 60mer | | 46.0 | 46.0 |
| Mut18 60mer | 2.5 | | 2.5 |
| Mut21 60mer | 10.0 | | 10.0 |
| Mut33 60mer | 24.0 | | 24.0 |

A: WT IGCR1-specific gene reaction
B: ΔIGCR1-specific gene reaction

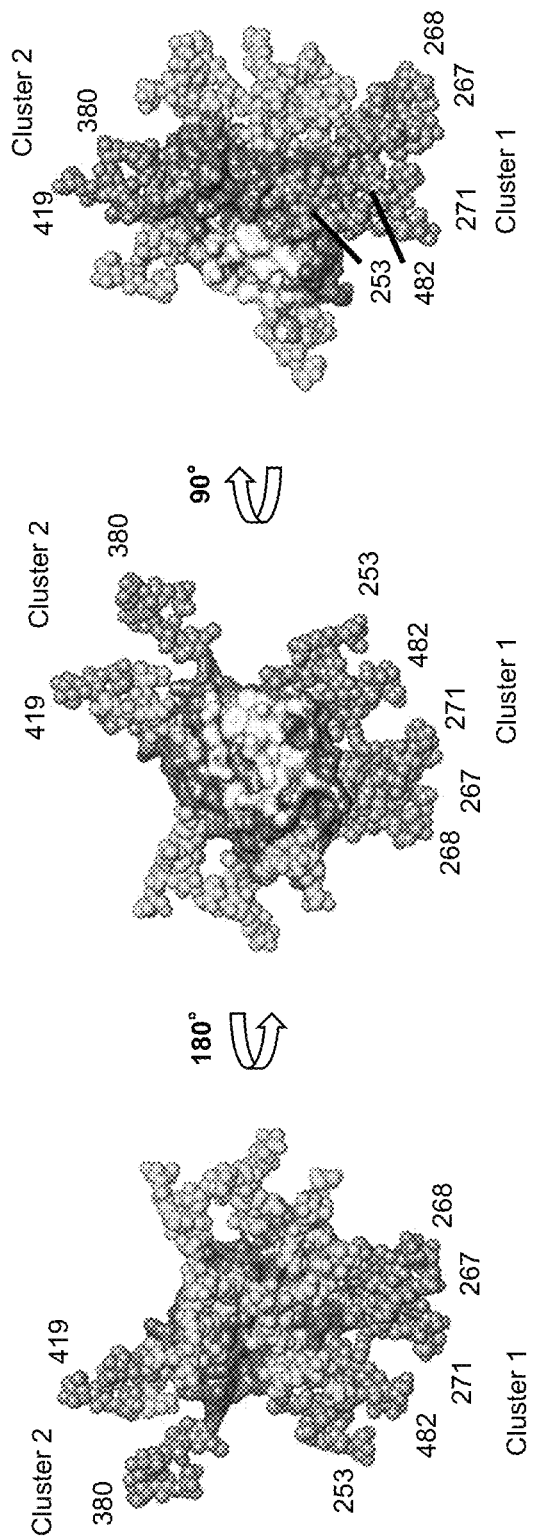

FIG. 11A

| eOD-GT8 Pos. | 2 | 6 | 14 | 10 | 33 | 52 | 56 | 65 | 70 | 71 | 74 | 79 | 90 | 92 | 98 | 102 | 106 | 113 | 121 | 129 | 146 | 150 | 153 | 159 | 165 | 170 |
|---|---|---|---|---|---|---|---|---|---|---|---|---|---|---|---|---|---|---|---|---|---|---|---|---|---|---|
| HXB2 Pos. | 413 | 419 | 444 | 446 | 463 | 462 | 253 | 262 | 267 | 266 | 271 | 276 | 287 | 289 | 295 | 299 | 332 | 339 | 347 | 356 | 373 | 377 | 380 | 386 | 392 | 397 |
| eOD-GT8 seq. | TIT | RPA | HCS | NIT | DNT | QIA | TVV | NSS | EEE | EEEV | VIP | PWR | QLN | NTS | NCS | AGH | NKS | NKT | SKL | NKT | NES | NCG | GEF | DST | NST | NST |

| Mut No. | Added glycan | 2 | 6 | 14 | 10 | 33 | 52 | 56 | 65 | 70 | 71 | 74 | 79 | 90 | 92 | 98 | 102 | 106 | 113 | 121 | 129 | 146 | 150 | 153 | 159 | 165 | 170 |
|---|---|---|---|---|---|---|---|---|---|---|---|---|---|---|---|---|---|---|---|---|---|---|---|---|---|---|---|
| 1 | 1 | | | | NIT | | | | NCS | | | | | | NTS | NCS | NKS | NKT | | | NKT | NES | | | | NST | NST |
| 2 | 1 | | | | NIT | | | | NCS | | | | | | NTS | NCS | NKS | NKT | | | NKT | NES | | | | NST | NST |
| 3 | 1 | | | NCT | NIT | | | | NCS | | | | | | NTS | NCS | NKS | NKT | | | NKT | NES | | | | NST | NST |
| 4 | 1 | | | | NIT | NIT | | | NCS | | | | | | NTS | NCS | NKS | NKT | | | NKT | NES | | | | NST | NST |
| 5 | 1 | | | | NIT | | | NVT | NCS | | | | | | NTS | NCS | NKS | NKT | | | NKT | NES | | | | NST | NST |
| 6 | 1 | | | | NIT | | | | NCS | NGT | | | | | NTS | NCS | NKS | NKT | | | NKT | NES | | | | NST | NST |
| 7 | 1 | | | | NIT | | | | NCS | | | | | | NTS | NCS | NKS | NKT | | | NKT | NES | | | | NST | NST |
| 8 | 1 | NIT | | | NIT | | | | NCS | | GNGT | | | | NTS | NCS | NKS | NKT | | | NKT | NES | | | | NST | NST |
| 9 | 1 | | | | NIT | | | | NCS | | | | | | NTS | NCS | NKS | NKT | | | NKT | NES | | | | NST | NST |
| 10 | 1 | | NGTG | | NIT | | | | NCS | | | | | | NTS | NCS | NKS | NKT | | | NKT | NES | | | | NST | NST |
| 11 | 1 | | | | NIT | | | | NCS | | | | | | NTS | NCS | NKS | NKT | | | NKT | NES | | | | NST | NST |
| 12 | 3 | | | NCT | NIT | NIT | | | NCS | | | | | | NTS | NCS | NKS | NKT | | | NKT | NES | | | | NST | NST |
| 13 | 3 | | | NCT | NIT | NIT | | NVT | NCS | | GNGT | | | | NTS | NCS | NKS | NKT | | | NKT | NES | | | | NST | NST |
| 14 | 3 | | NGTG | | NIT | NIT | | | NCS | | GNGT | | | | NTS | NCS | NKS | NKT | | | NKT | NES | | | | NST | NST |
| 15 | 3 | | NGTG | | NIT | NIT | | | NCS | | GNGT | | | | NTS | NCS | NKS | NKT | | | NKT | NES | | | | NST | NST |
| 16 | 5 | | | NCT | NIT | NIT | | NVT | NCS | | GNGT | | | | NTS | NCS | NKS | NKT | | | NKT | NES | | | | NST | NST |
| 17 | 5 | | | NCT | NIT | | | | NCS | | GNGT | | | | NTS | NCS | NKS | NKT | | | NKT | NES | NCT | NVT | NST | NST | NST |
| 18 | 6 | | | NCT | NIT | | | NVT | NCS | | GNGT | | | | NTS | NCS | NKS | NKT | | NKI | NKT | NES | NCT | | | NST | NST |
| 19 | 5 | NIT | | NCT | NIT | | | | NCS | NGT | | | | | NTS | NCS | NKS | NKT | | | NKT | NES | NCT | | | NST | NST |
| 20 | 3 | NIT | | NCT | NIT | | | | NCS | | GNGT | | | | NTS | NCS | NKS | NKT | NKT | | NKT | NES | NCT | NVT | | NST | NST |

FIG. 11B

| eOD-GT8 Pos. | 2 | 6 | 14 | 18 | 33 | 52 | 56 | 65 | 70 | 71 | 74 | 79 | 90 | 92 | 96 | 102 | 106 | 113 | 121 | 129 | 146 | 150 | 153 | 159 | 165 | 170 |
|---|---|---|---|---|---|---|---|---|---|---|---|---|---|---|---|---|---|---|---|---|---|---|---|---|---|---|
| HXB2 Pos. | 413 | 419 | 444 | 446 | 463 | 482 | 253 | 362 | 267 | 269 | 271 | 276 | 287 | 289 | 295 | 299 | 332 | 339 | 347 | 356 | 373 | 377 | 380 | 386 | 392 | 397 |
| eOD-GT8 seq. | TIT | RPA | RCS | NIT | DNT | QIA | TVV | NSS | PEE | EEKV | VIR | DWR | QLN | NTS | NCT | AGH | RLS | NNT | SKL | NKT | NHS | NCG | GEF | DST | NST | NST |
| Mut No. | Added glycan | | | | | | | | | | | | | | | | | | | | | | | | | |
| 21 | 6 | NGTG | NCT | NIT | | | | | NGT | | | | | NTS | NCT | NGT | NLS | NNT | | NKT | NHS | | | | NST | NST |
| 22 | 6 | NIT | | NCT | NIT | | NIT | NVT | NSS | GGE | | | | NTS | NCT | | NLS | NNT | | NKT | NHS | | NVT | | NST | NST |
| 23 | 1 | | | | NIT | | | | NSS | GGE | | | | NTS | NCT | | NLS | NNT | | NKT | NHS | | | | NST | NST |
| 24 | 2 | | | | NIT | | | | NSS | | GNGT | | | NTS | NCT | NGT | NLS | NNT | | NKT | NHS | | | | NST | NST |
| 25 | 2 | NGTG | | | NIT | | | | NSS | | GNGT | | | NTS | NCT | | NLS | NNT | | NKT | NHS | | | | NST | NST |
| 26 | 3 | | | | NIT | | NIT | | NSS | | GNGT | | | NTS | NCT | | NLS | NNT | | NKT | NHS | | | | NST | NST |
| 27 | 4 | | | | NIT | | | | NSS | | GNGT | | NLT | NTS | NCT | NGT | NLS | NNT | | NKT | NHS | | NVT | | NST | NST |
| 28 | 4 | | | | NIT | | | | NSS | | GNGT | | | NTS | NCT | NGT | NLS | NNT | | NKT | NHS | | NVT | | NST | NST |
| 29 | 4 | | | | NIT | | NVT | | NSS | | GNGT | | NLT | NTS | NCT | NGT | NLS | NNT | | NKT | NHS | | NVT | | NST | NST |
| 30 | 4 | NIT | | | NIT | | | | NSS | | GNGT | | | NTS | NCT | NGT | NLS | NNT | | NKT | NHS | | NVT | | NST | NST |
| 31 | 4 | | | | NIT | | | | NSS | | GNGT | | | NTS | NCT | NGT | NLS | NNT | NKT | NKT | NHS | | NVT | | NST | NST |
| 32 | 4 | | | | NIT | | NIT | | NSS | | GNGT | | | NTS | NCT | NGT | NLS | NNT | | NKT | NHS | | NVT | NST | NST | NST |
| 33 | 4 | | | | NIT | | NIT | | NSS | | GNGT | | | NTS | NCT | NGT | NLS | NNT | | NKT | NHS | | NVT | | NST | NST |
| 34 | 5 | NIT | NGTG | | NIT | | NIT | | NSS | | GNGT | | | NTS | NCT | NGT | NLS | NNT | | NKT | NHS | | NVT | | NST | NST |
| 35 | 5 | NIT | NGTG | | NIT | | NIT | | NSS | | GNGT | | | NTS | NCT | NGT | NLS | NNT | | NKT | NHS | | | NST | NST | NST |
| 36 | 5 | | NGTG | | NIT | | NIT | | NSS | | GNGT | | | NTS | NCT | NGT | NLS | NNT | | NKT | NHS | | NVT | | NST | NST |
| 37 | 5 | | NGTG | | NIT | | NIT | | NSS | | GNGT | | | NTS | NCT | NGT | NLS | NNT | | NKT | NHS | | NVT | NST | NST | NST |
| 38 | 5 | | NGTG | | NIT | | NIT | | NSS | | GNGT | | NLT | NTS | NCT | NGT | NLS | NNT | | NKT | NHS | | | | NST | NST |
| 39 | 4 | | NGTG | | NIT | | NIT | | NSS | | GNGT | | | NTS | NCT | NGT | NLS | NNT | | NKT | NHS | | NVT | | NST | NST |
| 40 | 4 | | NGTG | | NIT | | NIT | | NSS | | GNGT | | | NTS | NCT | NGT | NLS | NNT | | NKT | NHS | | | | NST | NST |

FIG. 11C

| eOD-GT8 Pos. | 2 | 8 | 14 | 19 | 33 | 52 | 56 | 65 | 70 | 71 | 74 | 79 | 90 | 92 | 98 | 102 | 106 | 113 | 121 | 129 | 146 | 150 | 153 | 159 | 165 | 170 |
|---|---|---|---|---|---|---|---|---|---|---|---|---|---|---|---|---|---|---|---|---|---|---|---|---|---|---|
| HXB2 Pos. | 413 | 419 | 444 | 440 | 463 | 402 | 253 | 262 | 267 | 268 | 271 | 276 | 287 | 289 | 295 | 299 | 332 | 339 | 347 | 356 | 373 | 377 | 380 | 386 | 392 | 397 |
| eOD-GT8 seq. | TTT | RPA | RCS | NID | DWT | QIA | TVV | NSS | KEE | EEEV | VIP | DWR | QLN | NGT | NGT | AEH | NIS | NNT | SKL | NNT | NHS | NCG | GEF | DST | NNT | NST |
| Mut No. | Added glycan | | | | | | | | | | | | | | | | | | | | | | | | | |
| 41 | 5 | | NGTG | | NIT | | NIT | | NSS | | GNGT | | | NIS | NGT | | NIS | NNT | | NNT | NHS | | NVT | | NST | NST |
| 42 | 4 | | NGTG | | NIT | | NIT | | NCG | | GNGT | | NFT | NIS | NGT | | NIS | NNT | | NNT | NHS | | | | NST | NST |
| 43 | 5 | | NGTG | | NIT | NGT | NIT | | NSS | | GNGT | | NFT | NIS | NGT | | NIS | NNT | | NNT | NHS | | | | NST | NST |
| 44 | 6 | | | NGT | NIT | | NIT | | NSS | | GNGT | | NFT | NIS | NGT | NGT | NIS | NNT | | NNT | NHS | | NVT | | NST | NST |
| 45 | 5 | | NGTG | | NIT | | NIT | | NSS | | GNGT | | NFT | NIS | NGT | | NIS | NNT | | NNT | NHS | | | | NST | NST |
| 46 | 5 | NIT | | | NIT | | NIT | | NSS | | GNGT | | NFT | NIS | NGT | NGT | NIS | NNT | | NNT | NHS | | NVT | | NST | NST |
| 47 | 5 | | | | NIT | | NIT | | NCG | | GNGT | | NFT | NIS | NGT | NGT | NIS | NNT | | NNT | NHS | | NVT | | NST | NST |
| 48 | 6 | | NGTG | | NIT | | NIT | | NSS | | GNGT | | NFT | NIS | NGT | | NIS | NNT | | NNT | NHS | | NVT | NST | NST | NST |
| 49 | 3 | | | | NIT | | NIT | NVT | NSS | GGE | | NGT | | NIS | NGT | | NIS | NNT | | NNT | NHS | | NVT | | NST | NST |
| 50 | 3 | | NGTG | | NIT | | NIT | NVT | NSS | NGT | | | | NIS | NGT | | NIS | NNT | | NNT | NHS | | NVT | | NST | NST |
| 51 | 5 | | NGTG | | NIT | | NIT | NVT | NSS | | GNGT | | | NIS | NGT | NGT | NIS | NNT | | NNT | NHS | | NVT | | NST | NST |
| 52 | 4 | | | NGT | NIT | | NIT | | NSS | | | | | NIS | NGT | | NIS | NNT | | NNT | NHS | | NVT | | NST | NST |

FIG. 12

Quantification of VRC01-class antibodies amplified from class-switched B cells of mice immunized once with 60 μg eOD-GT8 or eOD-GT8 mutant immunogens adjuvanted with Poly I:C, related to figures 4 and 6.

| Immunogen | Mouse ID | Total B220+ B cells for sorting | Total IgG+ B cells for sorting | Total sorted eOD-GT8+ΔOD-GT8-cells | Amplified K chains | No. of VRC01-class antibodies | VRC01-class antibodies in amplified K chains (%) |
|---|---|---|---|---|---|---|---|
| eOD-GT6 | 6151 | 7.50E+03 | 3.52E+02 | 11 | 0 | ND | ND |
| | 6152 | 5.35E+05 | 3.57E+03 | 71 | 25 | 0 | <1/25 |
| | 6153 | 7.88E+05 | 6.83E+03 | 192 | 67 | 0 | <1/67 |
| eOD-GT8 | 6154 | 3.12E+04 | 6.88E+02 | 27 | 12 | 1 | 8.3 |
| | 6157 | 4.89E+05 | 2.56E+03 | 38 | 19 | 1 | 5.3 |
| | 6163 | 1.49E+06 | 3.64E+04 | 271 | 102 | 1 | 1.0 |
| Mut15 | 6164 | 1.26E+05 | 4.68E+03 | 140 | 60 | 0 | <1/60 |
| | 6165 | 2.29E+04 | 6.50E+02 | 71 | 40 | 10 | 25.0 |
| | 6166 | 1.16E+06 | 1.99E+04 | 188 | 84 | 1 | 1.2 |
| Mut16 | 7580 | 2.11E+05 | 6.24E+03 | 104 | 31 | 2 | 6.5 |
| | 7581 | 5.15E+05 | 2.04E+04 | 226 | 96 | 15 | 15.6 |
| | 7582 | 5.73E+04 | 5.31E+03 | 95 | 14 | 2 | 14.3 |
| Mut21 | 6158 | 8.34E+05 | 4.90E+03 | 45 | 33 | 1 | 3.0 |
| | 6159 | 3.97E+05 | 3.87E+03 | 66 | 29 | 1 | 3.5 |
| | 6160 | 1.65E+06 | 2.10E+04 | 109 | 45 | 0 | <1/45 |
| Mut33 | 2901 | 1.83E+05 | 2.44E+03 | 133 | 32 | 0 | <1/32 |
| | 2902 | 3.78E+04 | 1.56E+03 | 82 | 4 | 0 | <1/4 |
| | 2903 | 6.37E+04 | 1.19E+03 | 90 | 13 | 0 | <1/13 |
| | 2904 | 6.45E+04 | 7.08E+03 | 96 | 13 | 2 | 15.4 |
| | 2905 | 3.08E+04 | 2.42E+03 | 81 | 33 | 1 | 3.0 |

ND, not determined.

FIG. 13

Quantification of VRC01-class antibodies amplified from class-switched B cells of mice immunized once with 30 μg eOD-GT8 or eOD-GT8 mutant immunogens adjuvanted with Poly I:C, related to figures 5 and 6.

| Immunogen | Mouse ID | Total B220+ B cells for sorting | Total IgG+ B cells for sorting | Total sorted eOD-GT8+ΔOD-GT8-cells | Amplified K chains | No. of VRC01-class antibodies | VRC01-class antibodies in amplified K chains (%) |
|---|---|---|---|---|---|---|---|
| eOD-GT6 | 7355 | 1.06E+06 | 7.85E+03 | 36 | NT | NT | NT |
|  | 7364 | 7.26E+05 | 9.14E+03 | 86 | 28 | 0 | <1/28 |
|  | 7365 | 2.30E+05 | 5.34E+03 | 96 | 19 | 0 | <1/19 |
| eOD-GT8 | 7801 | 3.67E+05 | 5.09E+03 | 96 | 39 | 1 | 2.6 |
|  | 7802 | 1.62E+05 | 3.09E+03 | 96 | 35 | 0 | <1/35 |
|  | 7803 | 2.80E+05 | 4.36E+03 | 36 | 22 | 1 | 4.5 |
| Mut15 | 7366 | 1.11E+06 | 5.24E+03 | 66 | 31 | 1 | 3.2 |
|  | 7373 | 6.38E+05 | 4.82E+03 | 59 | 26 | 0 | <1/26 |
|  | 7807 | 1.07E+06 | 1.12E+04 | 79 | 31 | 1 | 3.2 |
| Mut16 | 8656 | 4.02E+05 | 7.41E+03 | 92 | 54 | 4 | 7.4 |
|  | 8657 | 5.27E+05 | 1.01E+04 | 96 | 42 | 2 | 4.8 |
|  | 8658 | 1.16E+06 | 2.03E+04 | 96 | 52 | 3 | 5.8 |
| Mut17 | 8659 | 8.35E+05 | 1.53E+04 | 192 | 63 | 1 | 1.6 |
|  | 8660 | 4.11E+05 | 8.31E+03 | 96 | 56 | 1 | 1.8 |
|  | 8661 | 3.21E+05 | 6.87E+03 | 96 | 49 | 3 | 6.1 |
| Mut18 | 8662 | 1.01E+06 | 5.40E+03 | 34 | 20 | 2 | 10.0 |
|  | 8663 | 1.33E+06 | 1.42E+04 | 40 | 11 | 0 | <1/11 |
|  | 8664 | 8.35E+05 | 6.10E+03 | 26 | NT | NT | NT |
| Mut21 | 7811 | 7.92E+05 | 8.17E+03 | 53 | 23 | 2 | 8.7 |
|  | 7812 | 9.70E+05 | 1.02E+04 | 52 | 42 | 1 | 2.4 |
|  | 7813 | 1.26E+05 | 9.78E+02 | 10 | 5 | 0 | <1/5 |

NT, not tested.

FIG. 14

Quantification of VRC01-class antibodies amplified from class-switched B cells of mice immunized twice with 30 µg eOD-GT8 or eOD-GT8 mutant immunogens adjuvanted with Ribi, related to figures 5 and 6.

| Immunogen | Mouse ID | Total B220+ B cells for sorting | Total IgG+ B cells for sorting | Total sorted eOD-GT8+ΔOD-GT8-cells | Amplified K chains | No. of VRC01-class antibodies | VRC01-class antibodies in amplified K chains (%) |
|---|---|---|---|---|---|---|---|
| eOD-GT6 | 7359 | 8.77E+05 | 1.76E+04 | 50 | 23 | 0 | <1/23 |
|  | 7360 | 1.06E+06 | 1.13E+04 | 17 | NT | NT | NT |
|  | 7361 | 1.09E+06 | 7.99E+03 | 34 | NT | NT | NT |
| eOD-GT8 | 7804 | 4.60E+05 | 4.44E+03 | 48 | 33 | 1 | 3.0 |
|  | 7805 | 1.73E+05 | 5.00E+03 | 49 | 16 | 0 | <1/16 |
|  | 7806 | 1.02E+06 | 1.34E+04 | 59 | 24 | 1 | 4.2 |
| Mut15 | 7808 | 7.59E+05 | 1.33E+04 | 134 | 100 | 3 | 3.0 |
|  | 7809 | 6.45E+05 | 1.88E+04 | 56 | 36 | 4 | 11.1 |
|  | 7810 | 5.66E+05 | 6.38E+03 | 84 | 34 | 6 | 17.6 |
| Mut21 | 7814 | 1.31E+05 | 2.30E+03 | 14 | 10 | 0 | <1/10 |
|  | 7815 | 1.05E+06 | 1.54E+04 | 46 | 30 | 0 | <1/30 |
|  | 7816 | 6.21E+05 | 1.71E+04 | 47 | NT | NT | NT |

NT, not tested.

```
                        SEQUENCE LISTING

<160> NUMBER OF SEQ ID NOS: 113

<210> SEQ ID NO 1
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 1

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
                20                  25                  30

Asp Asn Thr Val Ile Phe Arg Pro Ser Gly Gly Asp Trp Arg Asp Ile
            35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Tyr Gly
            115                 120                 125

Asn Lys Thr Ile Ile Phe Lys Pro Ser Gly Gly Asp Pro Glu Phe
    130                 135                 140

Val Asn His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 2
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 2

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
                20                  25                  30

Asp Asn Thr Val Ile Phe Arg Pro Ser Gly Gly Asp Trp Arg Asp Ile
            35                  40                  45

Ala Arg Cys Gln Ile Ala Gly Thr Val Val Ser Thr Gln Leu Phe Leu
    50                  55                  60

Asn Gly Ser Leu Ala Asn Gly Thr Val Val Ile Arg Ser Glu Asp Trp
```

```
                65                  70                  75                  80
Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 3
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 3

Asp Thr Ile Thr Leu Pro Cys Arg Pro Ala Pro Pro Asn Cys Thr
1               5                   10                  15

Ser Asn Ile Thr Gly Leu Ile Leu Thr Arg Gln Gly Gly Tyr Ser Asn
                20                  25                  30

Asp Asn Thr Val Ile Phe Arg Pro Ser Gly Gly Asp Trp Arg Asp Ile
            35                  40                  45

Ala Arg Cys Gln Ile Ala Gly Thr Val Val Ser Thr Gln Leu Phe Leu
        50                  55                  60

Asn Gly Ser Leu Ala Glu Glu Val Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 4
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 4

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
                20                  25                  30
```

Asp Asn Thr Val Ile Phe Arg Pro Ser Gly Gly Asp Trp Arg Asp Ile
            35                  40                  45

Ala Arg Cys Asn Ile Thr Gly Thr Val Val Ser Thr Gln Leu Phe Leu
 50                  55                  60

Asn Gly Ser Leu Ala Glu Glu Val Val Ile Arg Ser Glu Asp Trp
 65                  70                  75                  80

Arg Asp Asn Ala Lys Ser Ile Cys Val Gln Leu Asn Thr Ser Val Glu
                 85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
            115                 120                 125

Asn Lys Thr Ile Ile Phe Lys Pro Ser Ser Gly Gly Asp Pro Glu Phe
            130                 135                 140

Val Asn His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 5
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 5

Asp Thr Ile Thr Leu Pro Cys Arg Pro Ala Pro Pro His Cys Ser
 1               5                  10                  15

Ser Asn Ile Thr Gly Leu Ile Leu Thr Arg Gln Gly Gly Tyr Ser Asn
                 20                  25                  30

Asp Asn Thr Val Ile Phe Arg Pro Ser Gly Gly Asp Trp Arg Asp Ile
            35                  40                  45

Ala Arg Cys Gln Ile Ala Gly Asn Val Thr Ser Thr Gln Leu Phe Leu
 50                  55                  60

Asn Gly Ser Leu Ala Glu Glu Val Val Ile Arg Ser Glu Asp Trp
 65                  70                  75                  80

Arg Asp Asn Ala Lys Ser Ile Cys Val Gln Leu Asn Thr Ser Val Glu
                 85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
            115                 120                 125

Asn Lys Thr Ile Ile Phe Lys Pro Ser Ser Gly Gly Asp Pro Glu Phe
            130                 135                 140

Val Asn His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 6
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 6

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
            20                  25                  30

Asp Asn Thr Val Ile Phe Arg Pro Ser Gly Gly Asp Trp Arg Asp Ile
        35                  40                  45

Ala Arg Cys Gln Ile Ala Gly Thr Val Val Ser Thr Gln Leu Phe Leu
50                  55                  60

Asn Gly Ser Leu Ala Glu Glu Val Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
            115                 120                 125

Asn Lys Thr Ile Ile Phe Lys Pro Ser Ser Gly Gly Asp Pro Glu Phe
130                 135                 140

Val Asn His Ser Phe Asn Cys Thr Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 7
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 7

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
            20                  25                  30

Asp Asn Thr Val Ile Phe Arg Pro Ser Gly Gly Asp Trp Arg Asp Ile
        35                  40                  45

Ala Arg Cys Gln Ile Ala Gly Thr Val Val Ser Thr Gln Leu Phe Leu
50                  55                  60

Asn Gly Ser Leu Ala Glu Glu Val Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
            115                 120                 125

Asn Lys Thr Ile Ile Phe Lys Pro Ser Ser Gly Gly Asp Pro Glu Phe
130                 135                 140

Val Asn His Ser Phe Asn Cys Gly Asn Val Thr Phe Tyr Cys Asp Ser
145                 150                 155                 160

Thr Gln Leu Phe Asn Ser Thr Trp Phe Asn Ser Thr
                165                 170

<210> SEQ ID NO 8

```
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 8

Asp Asn Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
                20                  25                  30

Asp Asn Thr Val Ile Phe Arg Pro Ser Gly Gly Asp Trp Arg Asp Ile
            35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 9
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 9

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
                20                  25                  30

Asp Asn Thr Val Ile Phe Arg Pro Ser Gly Gly Asp Trp Arg Asp Ile
            35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Asn Lys Thr Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Gly Glu Phe Phe Tyr Cys Asp Ser
```

```
145                 150                 155                 160

Thr Gln Leu Phe Asn Ser Thr Trp Phe Asn Ser Thr
                165                 170

<210> SEQ ID NO 10
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 10

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
                20                  25                  30

Asp Asn Thr Val Ile Phe Arg Pro Ser Gly Gly Asp Trp Arg Asp Ile
            35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Asn Gly Thr Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 11
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 11

Asp Thr Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
                20                  25                  30

Asn Asp Asn Thr Val Ile Phe Arg Pro Ser Gly Gly Asp Trp Arg Asp
            35                  40                  45

Ile Ala Arg Cys Gln Ile Ala Gly Thr Val Val Ser Thr Gln Leu Phe
    50                  55                  60

Leu Asn Gly Ser Leu Ala Glu Glu Val Val Ile Arg Ser Glu Asp
65                  70                  75                  80

Trp Arg Asp Asn Ala Lys Ser Ile Cys Val Gln Leu Asn Thr Ser Val
                85                  90                  95

Glu Ile Asn Cys Thr Gly Ala Gly His Cys Asn Ile Ser Arg Ala Lys
            100                 105                 110
```

Trp Asn Asn Thr Leu Lys Gln Ile Ala Ser Lys Leu Arg Glu Gln Tyr
            115                 120                 125

Gly Asn Lys Thr Ile Ile Phe Lys Pro Ser Ser Gly Gly Asp Pro Glu
        130                 135                 140

Phe Val Asn His Ser Phe Asn Cys Gly Gly Glu Phe Phe Tyr Cys Asp
145                 150                 155                 160

Ser Thr Gln Leu Phe Asn Ser Thr Trp Phe Asn Ser Thr
                165                 170

<210> SEQ ID NO 12
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 12

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
            20                  25                  30

Asp Asn Thr Val Ile Phe Arg Pro Ser Gly Gly Asp Trp Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Glu Val Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 13
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 13

Asp Thr Ile Thr Leu Pro Cys Arg Pro Ala Pro Pro Asn Cys Thr
1               5                   10                  15

Ser Asn Ile Thr Gly Leu Ile Leu Thr Arg Gln Gly Gly Tyr Ser Asn
            20                  25                  30

Asp Asn Thr Val Ile Phe Arg Pro Ser Gly Gly Asp Trp Arg Asp Ile
        35                  40                  45

Ala Arg Cys Gln Ile Ala Gly Asn Val Thr Ser Thr Gln Leu Phe Leu
    50                  55                  60

Asn Gly Ser Leu Ala Gly Asn Gly Thr Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
            165                 170

<210> SEQ ID NO 14
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 14

Asp Thr Ile Thr Leu Pro Cys Arg Pro Ala Pro Pro Asn Cys Thr
1               5                   10                  15

Ser Asn Ile Thr Gly Leu Ile Leu Thr Arg Gln Gly Gly Tyr Ser Asn
            20                  25                  30

Asp Asn Thr Val Ile Phe Arg Pro Ser Gly Gly Asp Trp Arg Asp Ile
        35                  40                  45

Ala Arg Cys Asn Ile Thr Gly Thr Val Val Ser Thr Gln Leu Phe Leu
    50                  55                  60

Asn Gly Ser Leu Ala Gly Asn Gly Thr Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
            165                 170

<210> SEQ ID NO 15
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 15

Asp Thr Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
            20                  25                  30

Asn Asp Asn Thr Val Ile Phe Arg Pro Ser Gly Gly Asp Trp Arg Asp

```
                    35                  40                  45
Ile Ala Arg Cys Asn Ile Thr Gly Thr Val Val Ser Thr Gln Leu Phe
            50                  55                  60
Leu Asn Gly Ser Leu Ala Gly Asn Gly Thr Val Ile Arg Ser Glu Asp
 65                  70                  75                  80
Trp Arg Asp Asn Ala Lys Ser Ile Cys Val Gln Leu Asn Thr Ser Val
                85                  90                  95
Glu Ile Asn Cys Thr Gly Ala Gly His Cys Asn Ile Ser Arg Ala Lys
            100                 105                 110
Trp Asn Asn Thr Leu Lys Gln Ile Ala Ser Lys Leu Arg Glu Gln Tyr
            115                 120                 125
Gly Asn Lys Thr Ile Ile Phe Lys Pro Ser Ser Gly Gly Asp Pro Glu
            130                 135                 140
Phe Val Asn His Ser Phe Asn Cys Gly Gly Glu Phe Phe Tyr Cys Asp
145                 150                 155                 160
Ser Thr Gln Leu Phe Asn Ser Thr Trp Phe Asn Ser Thr
                165                 170
```

<210> SEQ ID NO 16
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 16

```
Asp Thr Ile Thr Leu Pro Cys Arg Pro Ala Pro Pro Asn Cys Thr
 1               5                  10                  15
Ser Asn Ile Thr Gly Leu Ile Leu Thr Arg Gln Gly Gly Tyr Ser Asn
                20                  25                  30
Asp Asn Thr Val Ile Phe Arg Pro Ser Gly Gly Asp Trp Arg Asp Ile
            35                  40                  45
Ala Arg Cys Asn Ile Thr Gly Thr Val Val Ser Thr Gln Leu Phe Leu
        50                  55                  60
Asn Gly Ser Leu Ala Gly Asn Gly Thr Val Ile Arg Ser Glu Asp Trp
 65                  70                  75                  80
Arg Asp Asn Ala Lys Ser Ile Cys Val Gln Leu Asn Thr Ser Val Glu
                85                  90                  95
Ile Asn Cys Thr Gly Asn Gly Thr Cys Asn Ile Ser Arg Ala Lys Trp
            100                 105                 110
Asn Asn Thr Leu Lys Gln Ile Ala Ser Lys Leu Arg Glu Gln Tyr Gly
            115                 120                 125
Asn Lys Thr Ile Ile Phe Lys Pro Ser Ser Gly Gly Asp Pro Glu Phe
            130                 135                 140
Val Asn His Ser Phe Asn Cys Gly Asn Val Thr Phe Tyr Cys Asp Ser
145                 150                 155                 160
Thr Gln Leu Phe Asn Ser Thr Trp Phe Asn Ser Thr
                165                 170
```

<210> SEQ ID NO 17
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 17

```
Asp Thr Ile Thr Leu Pro Cys Arg Pro Ala Pro Pro Asn Cys Thr
1               5                   10                  15

Ser Asn Ile Thr Gly Leu Ile Leu Thr Arg Gln Gly Gly Tyr Ser Asn
            20                  25                  30

Asp Asn Thr Val Ile Phe Arg Pro Ser Gly Gly Asp Trp Arg Asp Ile
                35                  40                  45

Ala Arg Cys Asn Ile Thr Gly Thr Val Val Ser Thr Gln Leu Phe Leu
50                  55                  60

Asn Gly Ser Leu Ala Gly Asn Gly Thr Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Asn Gly Thr Cys Asn Ile Ser Arg Ala Lys Trp
                100                 105                 110

Asn Asn Thr Leu Lys Gln Ile Ala Ser Lys Leu Arg Glu Gln Tyr Gly
            115                 120                 125

Asn Lys Thr Ile Ile Phe Lys Pro Ser Ser Gly Gly Asp Pro Glu Phe
            130                 135                 140

Val Asn His Ser Phe Asn Cys Thr Gly Glu Phe Phe Tyr Cys Asp Ser
145                 150                 155                 160

Thr Gln Leu Phe Asn Ser Thr Trp Phe Asn Ser Thr
                165                 170
```

<210> SEQ ID NO 18
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 18

```
Asp Asn Ile Thr Leu Pro Cys Arg Pro Ala Pro Pro Asn Cys Thr
1               5                   10                  15

Ser Asn Ile Thr Gly Leu Ile Leu Thr Arg Gln Gly Gly Tyr Ser Asn
            20                  25                  30

Asp Asn Thr Val Ile Phe Arg Pro Ser Gly Gly Asp Trp Arg Asp Ile
                35                  40                  45

Ala Arg Cys Asn Ile Thr Gly Asn Val Thr Ser Thr Gln Leu Phe Leu
50                  55                  60

Asn Gly Ser Leu Ala Gly Asn Gly Thr Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Tyr Gly
            115                 120                 125

Asn Lys Thr Ile Ile Phe Lys Pro Ser Ser Gly Gly Asp Pro Glu Phe
            130                 135                 140

Val Asn His Ser Phe Asn Cys Thr Gly Glu Phe Phe Tyr Cys Asp Ser
145                 150                 155                 160

Thr Gln Leu Phe Asn Ser Thr Trp Phe Asn Ser Thr
                165                 170
```

<210> SEQ ID NO 19
<211> LENGTH: 172

```
<212> TYPE: PRT
<213> ORGANISM: Artificial Sequence
<220> FEATURE:
<223> OTHER INFORMATION: recombinant gp120 protein

<400> SEQUENCE: 19

Asp Asn Ile Thr Leu Pro Cys Arg Pro Ala Pro Pro Asn Cys Thr
1               5                   10                  15

Ser Asn Ile Thr Gly Leu Ile Leu Thr Arg Gln Gly Gly Tyr Ser Asn
                20                  25                  30

Asp Asn Thr Val Ile Phe Arg Pro Ser Gly Gly Asp Trp Arg Asp Ile
            35                  40                  45

Ala Arg Cys Gln Ile Ala Gly Thr Val Val Ser Thr Gln Leu Phe Leu
    50                  55                  60

Asn Gly Ser Leu Ala Asn Gly Thr Val Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Asn Gly Thr Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Gly Gly Asp Pro Glu Phe
    130                 135                 140

Val Asn His Ser Phe Asn Cys Thr Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 20
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 20

Asp Asn Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
                20                  25                  30

Asp Asn Thr Val Ile Phe Arg Pro Ser Gly Gly Asp Trp Arg Asp Ile
            35                  40                  45

Ala Arg Cys Gln Ile Ala Gly Thr Val Val Ser Thr Gln Leu Phe Leu
    50                  55                  60

Asn Gly Ser Leu Ala Gly Asn Gly Thr Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Asn Lys Thr Arg Glu Gln Tyr Gly
        115                 120                 125

Asn Lys Thr Ile Ile Phe Lys Pro Ser Gly Gly Asp Pro Glu Phe
    130                 135                 140

Val Asn His Ser Phe Asn Cys Gly Gly Glu Phe Phe Tyr Cys Asp Ser
145                 150                 155                 160
```

```
Thr Gln Leu Phe Asn Ser Thr Trp Phe Asn Ser Thr
            165                 170
```

<210> SEQ ID NO 21
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 21

```
Asp Thr Ile Thr Leu Pro Cys Asn Gly Thr Gly Pro Pro Asn Cys
1               5                  10                 15

Thr Ser Asn Ile Thr Gly Leu Ile Leu Thr Arg Gln Gly Gly Tyr Ser
            20                 25                 30

Asn Asp Asn Thr Val Ile Phe Arg Pro Ser Gly Gly Asp Trp Arg Asp
            35                 40                 45

Ile Ala Arg Cys Asn Ile Thr Gly Thr Val Val Ser Thr Gln Leu Phe
    50                  55                 60

Leu Asn Gly Ser Leu Ala Asn Gly Thr Val Val Ile Arg Ser Glu Asp
65              70                  75                  80

Trp Arg Asp Asn Ala Lys Ser Ile Cys Val Gln Leu Asn Thr Ser Val
                85                  90                  95

Glu Ile Asn Cys Thr Gly Asn Gly Thr Cys Asn Ile Ser Arg Ala Lys
            100                 105                 110

Trp Asn Asn Thr Leu Lys Gln Ile Ala Ser Lys Leu Arg Glu Gln Tyr
            115                 120                 125

Gly Asn Lys Thr Ile Ile Phe Lys Pro Ser Ser Gly Gly Asp Pro Glu
    130                 135                 140

Phe Val Asn His Ser Phe Asn Cys Gly Asn Val Thr Phe Tyr Cys Asp
145                 150                 155                 160

Ser Thr Gln Leu Phe Asn Ser Thr Trp Phe Asn Ser Thr
            165                 170
```

<210> SEQ ID NO 22
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 22

```
Asp Asn Ile Thr Leu Pro Cys Arg Pro Ala Pro Pro Asn Cys Thr
1               5                  10                 15

Ser Asn Ile Thr Gly Leu Ile Leu Thr Arg Gln Gly Gly Tyr Ser Asn
            20                 25                 30

Asp Asn Thr Val Ile Phe Arg Pro Ser Gly Gly Asp Trp Arg Asp Ile
            35                 40                 45

Ala Arg Cys Asn Ile Thr Gly Asn Val Thr Ser Thr Gln Leu Phe Leu
    50                  55                 60

Asn Gly Ser Leu Ala Gly Gly Glu Val Asn Gly Thr Ser Glu Asp Trp
65              70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
```

```
                115                 120                 125
Asn Lys Thr Ile Ile Phe Lys Pro Ser Ser Gly Gly Asp Pro Glu Phe
        130                 135                 140

Val Asn His Ser Phe Asn Cys Gly Asn Val Thr Phe Tyr Cys Asp Ser
145                 150                 155                 160

Thr Gln Leu Phe Asn Ser Thr Trp Phe Asn Ser Thr
                165                 170

<210> SEQ ID NO 23
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 23

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
            20                  25                  30

Asp Asn Thr Val Ile Phe Arg Pro Ser Gly Gly Asp Trp Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Gly Glu Val Asn Gly Thr Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 24
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 24

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
            20                  25                  30

Asp Asn Thr Val Ile Phe Arg Pro Ser Gly Gly Asp Trp Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Gly Asn Gly Thr Val Ile Arg Ser Glu Asp Trp
65                  70                  75                  80
```

```
Arg Asp Asn Ala Lys Ser Ile Cys Val Asn Leu Thr Thr Ser Val Glu
                 85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 25
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 25

Asp Thr Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
                20                  25                  30

Asn Asp Asn Thr Val Ile Phe Arg Pro Ser Gly Gly Asp Trp Arg Asp
            35                  40                  45

Ile Ala Arg Cys Gln Ile Ala Gly Thr Val Val Ser Thr Gln Leu Phe
    50                  55                  60

Leu Asn Gly Ser Leu Ala Gly Asn Gly Thr Val Ile Arg Ser Glu Asp
65                  70                  75                  80

Trp Arg Asp Asn Ala Lys Ser Ile Cys Val Gln Leu Asn Thr Ser Val
                85                  90                  95

Glu Ile Asn Cys Thr Gly Ala Gly His Cys Asn Ile Ser Arg Ala Lys
            100                 105                 110

Trp Asn Asn Thr Leu Lys Gln Ile Ala Ser Lys Leu Arg Glu Gln Tyr
        115                 120                 125

Gly Asn Lys Thr Ile Ile Phe Lys Pro Ser Ser Gly Gly Asp Pro Glu
    130                 135                 140

Phe Val Asn His Ser Phe Asn Cys Gly Gly Glu Phe Phe Tyr Cys Asp
145                 150                 155                 160

Ser Thr Gln Leu Phe Asn Ser Thr Trp Phe Asn Ser Thr
                165                 170

<210> SEQ ID NO 26
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 26

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
                20                  25                  30

Asp Asn Thr Val Ile Phe Arg Pro Ser Gly Gly Asp Trp Arg Asp Ile
            35                  40                  45
```

Ala Arg Cys Gln Ile Ala Gly Thr Val Val Ser Thr Gln Leu Phe Leu
    50                  55                  60

Asn Gly Ser Leu Ala Gly Asn Gly Thr Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Asn Gly Thr Cys Asn Ile Ser Arg Ala Lys Trp
                100                 105                 110

Asn Asn Thr Leu Lys Gln Ile Ala Ser Lys Leu Arg Glu Gln Tyr Gly
            115                 120                 125

Asn Lys Thr Ile Ile Phe Lys Pro Ser Ser Gly Gly Asp Pro Glu Phe
            130                 135                 140

Val Asn His Ser Phe Asn Cys Gly Asn Val Thr Phe Tyr Cys Asp Ser
145                 150                 155                 160

Thr Gln Leu Phe Asn Ser Thr Trp Phe Asn Ser Thr
                165                 170

<210> SEQ ID NO 27
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 27

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
                20                  25                  30

Asp Asn Thr Val Ile Phe Arg Pro Ser Gly Gly Asp Trp Arg Asp Ile
            35                  40                  45

Ala Arg Cys Gln Ile Ala Gly Thr Val Val Ser Thr Gln Leu Phe Leu
    50                  55                  60

Asn Gly Ser Leu Ala Gly Asn Gly Thr Val Ile Arg Ser Glu Asp Trp
65                  70                  75                  80

Arg Asp Asn Ala Lys Ser Ile Cys Val Asn Leu Thr Thr Ser Val Glu
                85                  90                  95

Ile Asn Cys Thr Gly Asn Gly Thr Cys Asn Ile Ser Arg Ala Lys Trp
                100                 105                 110

Asn Asn Thr Leu Lys Gln Ile Ala Ser Lys Leu Arg Glu Gln Tyr Gly
            115                 120                 125

Asn Lys Thr Ile Ile Phe Lys Pro Ser Ser Gly Gly Asp Pro Glu Phe
            130                 135                 140

Val Asn His Ser Phe Asn Cys Gly Asn Val Thr Phe Tyr Cys Asp Ser
145                 150                 155                 160

Thr Gln Leu Phe Asn Ser Thr Trp Phe Asn Ser Thr
                165                 170

<210> SEQ ID NO 28
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 28

Asp Thr Ile Thr Leu Pro Cys Arg Pro Ala Pro Pro His Cys Ser

```
  1               5                  10                 15
Ser Asn Ile Thr Gly Leu Ile Leu Thr Arg Gln Gly Gly Tyr Ser Asn
             20                 25                 30
Asp Asn Thr Val Ile Phe Arg Pro Ser Gly Gly Asp Trp Arg Asp Ile
             35                 40                 45
Ala Arg Cys Asn Ile Thr Gly Thr Val Val Ser Thr Gln Leu Phe Leu
      50                 55                 60
Asn Gly Ser Leu Ala Gly Asn Gly Thr Val Ile Arg Ser Glu Asp Trp
 65                 70                 75                 80
Arg Asp Asn Ala Lys Ser Ile Cys Val Gln Leu Asn Thr Ser Val Glu
                 85                 90                 95
Ile Asn Cys Thr Gly Asn Gly Thr Cys Asn Ile Ser Arg Ala Lys Trp
                100                105                110
Asn Asn Thr Leu Lys Gln Ile Ala Ser Lys Leu Arg Glu Gln Tyr Gly
                115                120                125
Asn Lys Thr Ile Ile Phe Lys Pro Ser Ser Gly Gly Asp Pro Glu Phe
                130                135                140
Val Asn His Ser Phe Asn Cys Gly Asn Val Thr Phe Tyr Cys Asp Ser
145                150                155                160
Thr Gln Leu Phe Asn Ser Thr Trp Phe Asn Ser Thr
                165                170

<210> SEQ ID NO 29
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 29

Asp Thr Ile Thr Leu Pro Cys Arg Pro Ala Pro Pro His Cys Ser
 1               5                  10                 15
Ser Asn Ile Thr Gly Leu Ile Leu Thr Arg Gln Gly Gly Tyr Ser Asn
             20                 25                 30
Asp Asn Thr Val Ile Phe Arg Pro Ser Gly Gly Asp Trp Arg Asp Ile
             35                 40                 45
Ala Arg Cys Gln Ile Ala Gly Asn Val Thr Ser Thr Gln Leu Phe Leu
      50                 55                 60
Asn Gly Ser Leu Ala Gly Asn Gly Thr Val Ile Arg Ser Glu Asp Trp
 65                 70                 75                 80
Arg Asp Asn Ala Lys Ser Ile Cys Val Gln Leu Asn Thr Ser Val Glu
                 85                 90                 95
Ile Asn Cys Thr Gly Asn Gly Thr Cys Asn Ile Ser Arg Ala Lys Trp
                100                105                110
Asn Asn Thr Leu Lys Gln Ile Ala Ser Lys Leu Arg Glu Gln Tyr Gly
                115                120                125
Asn Lys Thr Ile Ile Phe Lys Pro Ser Ser Gly Gly Asp Pro Glu Phe
                130                135                140
Val Asn His Ser Phe Asn Cys Gly Asn Val Thr Phe Tyr Cys Asp Ser
145                150                155                160
Thr Gln Leu Phe Asn Ser Thr Trp Phe Asn Ser Thr
                165                170

<210> SEQ ID NO 30
<211> LENGTH: 172
<212> TYPE: PRT
```

<213> ORGANISM: Artificial Sequence
<220> FEATURE:
<223> OTHER INFORMATION: recombinant gp120 protein

<400> SEQUENCE: 30

```
Asp Asn Ile Thr Leu Pro Cys Arg Pro Ala Pro Pro His Cys Ser
1               5                   10                  15

Ser Asn Ile Thr Gly Leu Ile Leu Thr Arg Gln Gly Tyr Ser Asn
            20                  25                  30

Asp Asn Thr Val Ile Phe Arg Pro Ser Gly Gly Asp Trp Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Gly Asn Gly Thr Val Ile Arg Ser Glu Asp Trp
65              70                  75                  80

Arg Asp Asn Ala Lys Ser Ile Cys Val Gln Leu Asn Thr Ser Val Glu
                85                  90                  95

Ile Asn Cys Thr Gly Asn Gly Thr Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Asn Val Thr Phe Tyr Cys Asp Ser
145                 150                 155                 160

Thr Gln Leu Phe Asn Ser Thr Trp Phe Asn Ser Thr
                165                 170
```

<210> SEQ ID NO 31
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 31

```
Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Tyr Ser Asn
            20                  25                  30

Asp Asn Thr Val Ile Phe Arg Pro Ser Gly Gly Asp Trp Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Gly Asn Gly Thr Val Ile Arg Ser Glu Asp Trp
65              70                  75                  80

Arg Asp Asn Ala Lys Ser Ile Cys Val Gln Leu Asn Thr Ser Val Glu
                85                  90                  95

Ile Asn Cys Thr Gly Asn Gly Thr Cys Asn Ile Ser Arg Ala Lys Trp
            100                 105                 110

Asn Asn Thr Leu Lys Gln Ile Ala Asn Lys Thr Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Asn Val Thr Phe Tyr Cys Asp Ser
145                 150                 155                 160
```

```
Thr Gln Leu Phe Asn Ser Thr Trp Phe Asn Ser Thr
            165                 170
```

<210> SEQ ID NO 32
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 32

```
Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
            20                  25                  30

Asp Asn Thr Val Ile Phe Arg Pro Ser Gly Gly Asp Trp Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Gly Asn Gly Thr Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Asn Gly Thr Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Asn Val Thr Phe Tyr Cys Asn Ser
145                 150                 155                 160

Thr Gln Leu Phe Asn Ser Thr Trp Phe Asn Ser Thr
            165                 170
```

<210> SEQ ID NO 33
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 33

```
Asp Thr Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
            20                  25                  30

Asn Asp Asn Thr Val Ile Phe Arg Pro Ser Gly Gly Asp Trp Arg Asp
        35                  40                  45

Ile Ala Arg Cys Asn Ile Thr Gly Thr Val Val Ser Thr Gln Leu Phe
    50                  55                  60

Leu Asn Gly Ser Leu Ala Gly Asn Gly Thr Val Ile Arg Ser Glu Asp
65                  70                  75                  80

Trp Arg Asp Asn Ala Lys Ser Ile Cys Val Gln Leu Asn Thr Ser Val
                85                  90                  95

Glu Ile Asn Cys Thr Gly Ala Gly His Cys Asn Ile Ser Arg Ala Lys
            100                 105                 110

Trp Asn Asn Thr Leu Lys Gln Ile Ala Ser Lys Leu Arg Glu Gln Tyr
        115                 120                 125
```

Gly Asn Lys Thr Ile Ile Phe Lys Pro Ser Ser Gly Gly Asp Pro Glu
            130                 135                 140

Phe Val Asn His Ser Phe Asn Cys Gly Asn Val Thr Phe Tyr Cys Asp
145                 150                 155                 160

Ser Thr Gln Leu Phe Asn Ser Thr Trp Phe Asn Ser Thr
            165                 170

<210> SEQ ID NO 34
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 34

Asp Asn Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
            20                  25                  30

Asn Asp Asn Thr Val Ile Phe Arg Pro Ser Gly Gly Asp Trp Arg Asp
            35                  40                  45

Ile Ala Arg Cys Asn Ile Thr Gly Thr Val Val Ser Thr Gln Leu Phe
50                  55                  60

Leu Asn Gly Ser Leu Ala Gly Asn Gly Thr Val Ile Arg Ser Glu Asp
65                  70                  75                  80

Trp Arg Asp Asn Ala Lys Ser Ile Cys Val Gln Leu Asn Thr Ser Val
                85                  90                  95

Glu Ile Asn Cys Thr Gly Ala Gly His Cys Asn Ile Ser Arg Ala Lys
            100                 105                 110

Trp Asn Asn Thr Leu Lys Gln Ile Ala Ser Lys Leu Arg Glu Gln Tyr
            115                 120                 125

Gly Asn Lys Thr Ile Ile Phe Lys Pro Ser Ser Gly Gly Asp Pro Glu
            130                 135                 140

Phe Val Asn His Ser Phe Asn Cys Gly Asn Val Thr Phe Tyr Cys Asp
145                 150                 155                 160

Ser Thr Gln Leu Phe Asn Ser Thr Trp Phe Asn Ser Thr
            165                 170

<210> SEQ ID NO 35
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 35

Asp Asn Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
            20                  25                  30

Asn Asp Asn Thr Val Ile Phe Arg Pro Ser Gly Gly Asp Trp Arg Asp
            35                  40                  45

Ile Ala Arg Cys Asn Ile Thr Gly Thr Val Val Ser Thr Gln Leu Phe
50                  55                  60

Leu Asn Gly Ser Leu Ala Gly Asn Gly Thr Val Ile Arg Ser Glu Asp
65                  70                  75                  80

Trp Arg Asp Asn Ala Lys Ser Ile Cys Val Gln Leu Asn Thr Ser Val

```
                    85                  90                  95

Glu Ile Asn Cys Thr Gly Ala Gly His Cys Asn Ile Ser Arg Ala Lys
                    100                 105                 110

Trp Asn Asn Thr Leu Lys Gln Ile Ala Ser Lys Leu Arg Glu Gln Tyr
                    115                 120                 125

Gly Asn Lys Thr Ile Ile Phe Lys Pro Ser Ser Gly Gly Asp Pro Glu
                    130                 135                 140

Phe Val Asn His Ser Phe Asn Cys Gly Gly Glu Phe Phe Tyr Cys Asn
145                 150                 155                 160

Ser Thr Gln Leu Phe Asn Ser Thr Trp Phe Asn Ser Thr
                    165                 170

<210> SEQ ID NO 36
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 36

Asp Thr Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
                    20                  25                  30

Asn Asp Asn Thr Val Ile Phe Arg Pro Ser Gly Gly Asp Trp Arg Asp
                    35                  40                  45

Ile Ala Arg Cys Asn Ile Thr Gly Thr Val Val Ser Thr Gln Leu Phe
50                  55                  60

Leu Asn Gly Ser Leu Ala Gly Asn Gly Thr Val Ile Arg Ser Glu Asp
65                  70                  75                  80

Trp Arg Asp Asn Ala Lys Ser Ile Cys Val Gln Leu Asn Thr Ser Val
                    85                  90                  95

Glu Ile Asn Cys Thr Gly Asn Gly Thr Cys Asn Ile Ser Arg Ala Lys
                    100                 105                 110

Trp Asn Asn Thr Leu Lys Gln Ile Ala Ser Lys Leu Arg Glu Gln Tyr
                    115                 120                 125

Gly Asn Lys Thr Ile Ile Phe Lys Pro Ser Ser Gly Gly Asp Pro Glu
                    130                 135                 140

Phe Val Asn His Ser Phe Asn Cys Gly Asn Val Thr Phe Tyr Cys Asp
145                 150                 155                 160

Ser Thr Gln Leu Phe Asn Ser Trp Phe Asn Ser Thr
                    165                 170

<210> SEQ ID NO 37
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 37

Asp Thr Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
                    20                  25                  30

Asn Asp Asn Thr Val Ile Phe Arg Pro Ser Gly Gly Asp Trp Arg Asp
                    35                  40                  45
```

```
Ile Ala Arg Cys Asn Ile Thr Gly Thr Val Val Ser Thr Gln Leu Phe
    50                  55                  60

Leu Asn Gly Ser Leu Ala Gly Asn Gly Thr Val Ile Arg Ser Glu Asp
65                  70                  75                  80

Trp Arg Asp Asn Ala Lys Ser Ile Cys Val Gln Leu Asn Thr Ser Val
                85                  90                  95

Glu Ile Asn Cys Thr Gly Ala Gly His Cys Asn Ile Ser Arg Ala Lys
            100                 105                 110

Trp Asn Asn Thr Leu Lys Gln Ile Ala Ser Lys Leu Arg Glu Gln Tyr
                115                 120                 125

Gly Asn Lys Thr Ile Ile Phe Lys Pro Ser Ser Gly Gly Asp Pro Glu
            130                 135                 140

Phe Val Asn His Ser Phe Asn Cys Gly Asn Val Thr Phe Tyr Cys Asn
145                 150                 155                 160

Ser Thr Gln Leu Phe Asn Ser Thr Trp Phe Asn Ser Thr
                165                 170
```

<210> SEQ ID NO 38
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 38

```
Asp Thr Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
                20                  25                  30

Asn Asp Asn Thr Val Ile Phe Arg Pro Ser Gly Gly Asp Trp Arg Asp
            35                  40                  45

Ile Ala Arg Cys Asn Ile Thr Gly Thr Val Val Ser Thr Gln Leu Phe
    50                  55                  60

Leu Asn Gly Ser Leu Ala Gly Asn Gly Thr Val Ile Arg Ser Glu Asp
65                  70                  75                  80

Trp Arg Asp Asn Ala Lys Ser Ile Cys Val Gln Leu Asn Thr Ser Val
                85                  90                  95

Glu Ile Asn Cys Thr Gly Asn Gly Thr Cys Asn Ile Ser Arg Ala Lys
            100                 105                 110

Trp Asn Asn Thr Leu Lys Gln Ile Ala Ser Lys Leu Arg Glu Gln Tyr
                115                 120                 125

Gly Asn Lys Thr Ile Ile Phe Lys Pro Ser Ser Gly Gly Asp Pro Glu
            130                 135                 140

Phe Val Asn His Ser Phe Asn Cys Gly Gly Glu Phe Phe Tyr Cys Asn
145                 150                 155                 160

Ser Thr Gln Leu Phe Asn Ser Thr Trp Phe Asn Ser Thr
                165                 170
```

<210> SEQ ID NO 39
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 39

```
Asp Thr Ile Thr Leu Pro Cys Asn Gly Thr Gly Pro Pro His Cys
1               5                   10                  15
```

Ser Ser Asn Ile Thr Gly Leu Ile Leu Thr Arg Gln Gly Gly Tyr Ser
            20                  25                  30

Asn Asp Asn Thr Val Ile Phe Arg Pro Ser Gly Gly Asp Trp Arg Asp
        35                  40                  45

Ile Ala Arg Cys Asn Ile Thr Gly Thr Val Val Ser Thr Gln Leu Phe
 50                  55                  60

Leu Asn Gly Ser Leu Ala Gly Asn Gly Thr Val Ile Arg Ser Glu Asp
 65                  70                  75                  80

Trp Arg Asp Asn Ala Lys Ser Ile Cys Val Asn Leu Thr Thr Ser Val
                 85                  90                  95

Glu Ile Asn Cys Thr Gly Ala Gly His Cys Asn Ile Ser Arg Ala Lys
            100                 105                 110

Trp Asn Asn Thr Leu Lys Gln Ile Ala Ser Lys Leu Arg Glu Gln Tyr
            115                 120                 125

Gly Asn Lys Thr Ile Ile Phe Lys Pro Ser Ser Gly Gly Asp Pro Glu
130                 135                 140

Phe Val Asn His Ser Phe Asn Cys Gly Gly Glu Phe Phe Tyr Cys Asp
145                 150                 155                 160

Ser Thr Gln Leu Phe Asn Ser Trp Phe Asn Ser Thr
            165                 170

<210> SEQ ID NO 40
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 40

Asp Thr Ile Thr Leu Pro Cys Asn Gly Thr Gly Pro Pro His Cys
 1               5                  10                  15

Ser Ser Asn Ile Thr Gly Leu Ile Leu Thr Arg Gln Gly Gly Tyr Ser
            20                  25                  30

Asn Asp Asn Thr Val Ile Phe Arg Pro Ser Gly Gly Asp Trp Arg Asn
        35                  40                  45

Leu Ala Arg Cys Asn Ile Thr Gly Thr Val Val Ser Thr Gln Leu Phe
 50                  55                  60

Leu Asn Gly Ser Leu Ala Gly Asn Gly Thr Val Ile Arg Ser Glu Asp
 65                  70                  75                  80

Trp Arg Asp Asn Ala Lys Ser Ile Cys Val Gln Leu Asn Thr Ser Val
                 85                  90                  95

Glu Ile Asn Cys Thr Gly Ala Gly His Cys Asn Ile Ser Arg Ala Lys
            100                 105                 110

Trp Asn Asn Thr Leu Lys Gln Ile Ala Ser Lys Leu Arg Glu Gln Tyr
            115                 120                 125

Gly Asn Lys Thr Ile Ile Phe Lys Pro Ser Ser Gly Gly Asp Pro Glu
130                 135                 140

Phe Val Asn His Ser Phe Asn Cys Gly Asn Val Thr Phe Tyr Cys Asp
145                 150                 155                 160

Ser Thr Gln Leu Phe Asn Ser Trp Phe Asn Ser Thr
            165                 170

<210> SEQ ID NO 41
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 41

```
Asp Thr Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
                20                  25                  30

Asn Asp Asn Thr Val Ile Phe Arg Pro Ser Gly Gly Asp Trp Arg Asn
            35                  40                  45

Leu Ala Arg Cys Asn Ile Thr Gly Thr Val Val Ser Thr Gln Leu Phe
        50                  55                  60

Leu Asn Gly Ser Leu Ala Gly Asn Gly Thr Val Ile Arg Ser Glu Asp
65                  70                  75                  80

Trp Arg Asp Asn Ala Lys Ser Ile Cys Val Gln Leu Asn Thr Ser Val
                85                  90                  95

Glu Ile Asn Cys Thr Gly Ala Gly His Cys Asn Ile Ser Arg Ala Lys
                100                 105                 110

Trp Asn Asn Thr Leu Lys Gln Ile Ala Ser Lys Leu Arg Glu Gln Tyr
            115                 120                 125

Gly Asn Lys Thr Ile Ile Phe Lys Pro Ser Ser Gly Gly Asp Pro Glu
        130                 135                 140

Phe Val Asn His Ser Phe Asn Cys Gly Asn Val Thr Phe Tyr Cys Asn
145                 150                 155                 160

Ser Thr Gln Leu Phe Asn Ser Thr Trp Phe Asn Ser Thr
                165                 170
```

<210> SEQ ID NO 42
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 42

```
Asp Thr Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
                20                  25                  30

Asn Asp Asn Thr Val Ile Phe Arg Pro Ser Gly Gly Asp Trp Arg Asp
            35                  40                  45

Ile Ala Arg Cys Asn Ile Thr Gly Thr Val Val Ser Thr Gln Leu Phe
        50                  55                  60

Leu Asn Gly Ser Leu Ala Gly Asn Gly Thr Val Ile Arg Ser Glu Asn
65                  70                  75                  80

Phe Thr Asp Asn Ala Lys Ser Ile Cys Val Gln Leu Asn Thr Ser Val
                85                  90                  95

Glu Ile Asn Cys Thr Gly Ala Gly His Cys Asn Ile Ser Arg Ala Lys
                100                 105                 110

Trp Asn Asn Thr Leu Lys Gln Ile Ala Ser Lys Leu Arg Glu Gln Tyr
            115                 120                 125

Gly Asn Lys Thr Ile Ile Phe Lys Pro Ser Ser Gly Gly Asp Pro Glu
        130                 135                 140

Phe Val Asn His Ser Phe Asn Cys Gly Gly Glu Phe Phe Tyr Cys Asp
145                 150                 155                 160

Ser Thr Gln Leu Phe Asn Ser Thr Trp Phe Asn Ser Thr
```

<210> SEQ ID NO 43
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 43

```
Asp Thr Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
            20                  25                  30

Asn Asn Gly Thr Val Ile Phe Arg Pro Ser Gly Gly Asp Trp Arg Asp
        35                  40                  45

Ile Ala Arg Cys Asn Ile Thr Gly Thr Val Val Ser Thr Gln Leu Phe
50                  55                  60

Leu Asn Gly Ser Leu Ala Gly Asn Gly Thr Val Ile Arg Ser Glu Asn
65                  70                  75                  80

Phe Thr Asp Asn Ala Lys Ser Ile Cys Val Gln Leu Asn Thr Ser Val
                85                  90                  95

Glu Ile Asn Cys Thr Gly Ala Gly His Cys Asn Ile Ser Arg Ala Lys
            100                 105                 110

Trp Asn Asn Thr Leu Lys Gln Ile Ala Ser Lys Leu Arg Glu Gln Tyr
        115                 120                 125

Gly Asn Lys Thr Ile Ile Phe Lys Pro Ser Ser Gly Gly Asp Pro Glu
    130                 135                 140

Phe Val Asn His Ser Phe Asn Cys Gly Gly Glu Phe Phe Tyr Cys Asp
145                 150                 155                 160

Ser Thr Gln Leu Phe Asn Ser Thr Trp Phe Asn Ser Thr
                165                 170
```

<210> SEQ ID NO 44
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 44

```
Asp Thr Ile Thr Leu Pro Cys Arg Pro Ala Pro Pro Asn Cys Thr
1               5                   10                  15

Ser Asn Ile Thr Gly Leu Ile Leu Thr Arg Gln Gly Gly Tyr Ser Asn
            20                  25                  30

Asp Asn Thr Val Ile Phe Arg Pro Ser Gly Gly Asp Trp Arg Asp Ile
        35                  40                  45

Ala Arg Cys Asn Ile Thr Gly Thr Val Val Ser Thr Gln Leu Phe Leu
50                  55                  60

Asn Gly Ser Leu Ala Gly Asn Gly Thr Val Ile Arg Ser Glu Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Asn Gly Thr Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125
```

Asn Lys Thr Ile Ile Phe Lys Pro Ser Ser Gly Gly Asp Pro Glu Phe
            130                 135                 140

Val Asn His Ser Phe Asn Cys Gly Asn Val Thr Phe Tyr Cys Asp Ser
145                 150                 155                 160

Thr Gln Leu Phe Asn Ser Thr Trp Phe Asn Ser Thr
            165                 170

<210> SEQ ID NO 45
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 45

Asp Thr Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
                20                  25                  30

Asn Asp Asn Thr Val Ile Phe Arg Pro Ser Gly Gly Asp Trp Arg Asn
            35                  40                  45

Leu Ala Arg Cys Asn Ile Thr Gly Thr Val Val Ser Thr Gln Leu Phe
50                  55                  60

Leu Asn Gly Ser Leu Ala Gly Asn Gly Thr Val Ile Arg Ser Glu Asn
65                  70                  75                  80

Phe Thr Asp Asn Ala Lys Ser Ile Cys Val Gln Leu Asn Thr Ser Val
                85                  90                  95

Glu Ile Asn Cys Thr Gly Ala Gly His Cys Asn Ile Ser Arg Ala Lys
            100                 105                 110

Trp Asn Asn Thr Leu Lys Gln Ile Ala Ser Lys Leu Arg Glu Gln Tyr
            115                 120                 125

Gly Asn Lys Thr Ile Ile Phe Lys Pro Ser Ser Gly Gly Asp Pro Glu
            130                 135                 140

Phe Val Asn His Ser Phe Asn Cys Gly Asn Val Thr Phe Tyr Cys Asp
145                 150                 155                 160

Ser Thr Gln Leu Phe Asn Ser Thr Trp Phe Asn Ser Thr
                165                 170

<210> SEQ ID NO 46
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 46

Asp Asn Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
                20                  25                  30

Asp Asn Thr Val Ile Phe Arg Pro Ser Gly Gly Asp Trp Arg Asp Ile
            35                  40                  45

Ala Arg Cys Gln Ile Ala Gly Thr Val Val Ser Thr Gln Leu Phe Leu
50                  55                  60

Asn Gly Ser Leu Ala Gly Asn Gly Thr Val Ile Arg Ser Glu Asn Phe
65                  70                  75                  80

Thr Asp Asn Ala Lys Ser Ile Cys Val Gln Leu Asn Thr Ser Val Glu
                85                  90                  95

```
Ile Asn Cys Thr Gly Asn Gly Thr Cys Asn Ile Ser Arg Ala Lys Trp
                100                 105                 110

Asn Asn Thr Leu Lys Gln Ile Ala Ser Lys Leu Arg Glu Gln Tyr Gly
            115                 120                 125

Asn Lys Thr Ile Ile Phe Lys Pro Ser Ser Gly Gly Asp Pro Glu Phe
130                 135                 140

Val Asn His Ser Phe Asn Cys Gly Asn Val Thr Phe Tyr Cys Asp Ser
145                 150                 155                 160

Thr Gln Leu Phe Asn Ser Thr Trp Phe Asn Ser Thr
                165                 170
```

<210> SEQ ID NO 47
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 47

```
Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
                20                  25                  30

Asp Asn Thr Val Ile Phe Arg Pro Ser Gly Gly Asp Trp Arg Asp Ile
            35                  40                  45

Ala Arg Cys Asn Ile Thr Gly Thr Val Val Ser Thr Gln Leu Phe Leu
        50                  55                  60

Asn Gly Ser Leu Ala Gly Asn Gly Thr Val Ile Arg Ser Glu Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Asn Gly Thr Cys Asn Ile Ser Arg Ala Lys Trp
                100                 105                 110

Asn Asn Thr Leu Lys Gln Ile Ala Ser Lys Leu Arg Glu Gln Tyr Gly
            115                 120                 125

Asn Lys Thr Ile Ile Phe Lys Pro Ser Ser Gly Gly Asp Pro Glu Phe
130                 135                 140

Val Asn His Ser Phe Asn Cys Gly Asn Val Thr Phe Tyr Cys Asp Ser
145                 150                 155                 160

Thr Gln Leu Phe Asn Ser Thr Trp Phe Asn Ser Thr
                165                 170
```

<210> SEQ ID NO 48
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 48

```
Asp Thr Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
                20                  25                  30

Asn Asp Asn Thr Val Ile Phe Arg Pro Ser Gly Gly Asp Trp Arg Asp
            35                  40                  45

Ile Ala Arg Cys Asn Ile Thr Gly Thr Val Val Ser Thr Gln Leu Phe
```

```
                50                  55                  60
Leu Asn Gly Ser Leu Ala Gly Asn Gly Thr Val Ile Arg Ser Glu Asn
 65                  70                  75                  80

Phe Thr Asp Asn Ala Lys Ser Ile Cys Val Gln Leu Asn Thr Ser Val
                 85                  90                  95

Glu Ile Asn Cys Thr Gly Ala Gly His Cys Asn Ile Ser Arg Ala Lys
                100                 105                 110

Trp Asn Asn Thr Leu Lys Gln Ile Ala Ser Lys Leu Arg Glu Gln Tyr
                115                 120                 125

Gly Asn Lys Thr Ile Ile Phe Lys Pro Ser Ser Gly Gly Asp Pro Glu
                130                 135                 140

Phe Val Asn His Ser Phe Asn Cys Gly Asn Val Thr Phe Tyr Cys Asn
145                 150                 155                 160

Ser Thr Gln Leu Phe Asn Ser Trp Phe Asn Ser Thr
                165                 170

<210> SEQ ID NO 49
<211> LENGTH: 173
<212> TYPE: PRT
<213> ORGANISM: Artificial Sequence
<220> FEATURE:
<223> OTHER INFORMATION: Signal peptide

<400> SEQUENCE: 49

Met Gly Trp Ser Cys Ile Ile Leu Phe Leu Val Ala Thr Ala Thr Gly
 1               5                  10                  15

Val His Ser Met Gln Ile Tyr Glu Gly Lys Leu Thr Ala Glu Gly Leu
                 20                  25                  30

Arg Phe Gly Ile Val Ala Ser Arg Phe Asn His Ala Leu Val Asp Arg
                 35                  40                  45

Leu Val Glu Gly Ala Ile Asp Ala Ile Val Arg His Gly Gly Arg Glu
             50                  55                  60

Glu Asp Ile Thr Leu Val Arg Val Pro Gly Ser Trp Glu Ile Pro Val
 65                  70                  75                  80

Ala Ala Gly Glu Leu Ala Arg Lys Glu Asp Ile Asp Ala Val Ile Ala
                 85                  90                  95

Ile Gly Val Leu Ile Arg Gly Ala Thr Pro His Phe Asp Tyr Ile Ala
                100                 105                 110

Ser Glu Val Ser Lys Gly Leu Ala Asp Leu Ser Leu Glu Leu Arg Lys
                115                 120                 125

Pro Ile Thr Phe Gly Val Ile Thr Ala Asp Thr Leu Glu Gln Ala Ile
                130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg
                165                 170

<210> SEQ ID NO 50
<211> LENGTH: 15
<212> TYPE: PRT
<213> ORGANISM: Artificial Sequence
<220> FEATURE:
<223> OTHER INFORMATION: Peptide linker

<400> SEQUENCE: 50

Gly Gly Ser Gly Ser Gly Gly Ser Gly Ser Gly Gly Gly
 1               5                  10                  15
```

<210> SEQ ID NO 51
<211> LENGTH: 361
<212> TYPE: PRT
<213> ORGANISM: Artificial Sequence
<220> FEATURE:
<223> OTHER INFORMATION: recombinant gp120 lumazine synthase fusion protein

<400> SEQUENCE: 51

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
            20                  25                  30

Arg Phe Gly Ile Val Ala Ser Arg Phe Asn His Ala Leu Val Asp Arg
        35                  40                  45

Leu Val Glu Gly Ala Ile Asp Ala Ile Val Arg His Gly Gly Arg Glu
    50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
    130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Gly Ser
                165                 170                 175

Gly Gly Ser Gly Gly Ser Gly Gly Ser Gly Gly Asp Thr Ile Thr
            180                 185                 190

Leu Pro Cys Asn Gly Thr Gly Pro Pro His Cys Ser Ser Asn Ile
        195                 200                 205

Thr Gly Leu Ile Leu Thr Arg Gln Gly Gly Tyr Ser Asn Asp Asn Thr
    210                 215                 220

Val Ile Phe Arg Pro Ser Gly Gly Asp Trp Arg Asp Ile Ala Arg Cys
225                 230                 235                 240

Asn Ile Thr Gly Thr Val Val Ser Thr Gln Leu Phe Leu Asn Gly Ser
                245                 250                 255

Leu Ala Gly Asn Gly Thr Val Ile Arg Ser Glu Asp Trp Arg Asp Asn
            260                 265                 270

Ala Lys Ser Ile Cys Val Gln Leu Asn Thr Ser Val Glu Ile Asn Cys
        275                 280                 285

Thr Gly Ala Gly His Cys Asn Ile Ser Arg Ala Lys Trp Asn Asn Thr
    290                 295                 300

Leu Lys Gln Ile Ala Ser Lys Leu Arg Glu Gln Tyr Gly Asn Lys Thr
305                 310                 315                 320

Ile Ile Phe Lys Pro Ser Ser Gly Gly Asp Pro Glu Phe Val Asn His
                325                 330                 335

Ser Phe Asn Cys Gly Gly Glu Phe Phe Tyr Cys Asp Ser Thr Gln Leu
            340                 345                 350

Phe Asn Ser Thr Trp Phe Asn Ser Thr
        355                 360

<210> SEQ ID NO 52
<211> LENGTH: 360
<212> TYPE: PRT
<213> ORGANISM: Artificial Sequence
<220> FEATURE:
<223> OTHER INFORMATION: recombinant gp120 lumazine synthase fusion protein

<400> SEQUENCE: 52

```
Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
            20                  25                  30

Arg Phe Gly Ile Val Ala Ser Arg Phe Asn His Ala Leu Val Asp Arg
        35                  40                  45

Leu Val Glu Gly Ala Ile Asp Ala Ile Val Arg His Gly Gly Arg Glu
    50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
    130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Ser
                165                 170                 175

Gly Gly Ser Gly Gly Ser Gly Ser Gly Gly Asp Thr Ile Thr
            180                 185                 190

Leu Pro Cys Arg Pro Ala Pro Pro Asn Cys Thr Ser Asn Ile Thr
        195                 200                 205

Gly Leu Ile Leu Thr Arg Gln Gly Gly Tyr Ser Asn Asp Asn Thr Val
    210                 215                 220

Ile Phe Arg Pro Ser Gly Gly Asp Trp Arg Asp Ile Ala Arg Cys Asn
225                 230                 235                 240

Ile Thr Gly Thr Val Val Ser Thr Gln Leu Phe Leu Asn Gly Ser Leu
                245                 250                 255

Ala Gly Asn Gly Thr Val Ile Arg Ser Glu Asp Trp Arg Asp Asn Ala
            260                 265                 270

Lys Ser Ile Cys Val Gln Leu Asn Thr Ser Val Glu Ile Asn Cys Thr
        275                 280                 285

Gly Asn Gly Thr Cys Asn Ile Ser Arg Ala Lys Trp Asn Asn Thr Leu
    290                 295                 300

Lys Gln Ile Ala Ser Lys Leu Arg Glu Gln Tyr Gly Asn Lys Thr Ile
305                 310                 315                 320

Ile Phe Lys Pro Ser Ser Gly Gly Asp Pro Glu Phe Val Asn His Ser
                325                 330                 335

Phe Asn Cys Gly Asn Val Thr Phe Tyr Cys Asp Ser Thr Gln Leu Phe
            340                 345                 350

Asn Ser Thr Trp Phe Asn Ser Thr
```

<210> SEQ ID NO 53
<211> LENGTH: 360
<212> TYPE: PRT
<213> ORGANISM: Artificial Sequence
<220> FEATURE:
<223> OTHER INFORMATION: recombinant gp120 lumazine synthase fusion protein

<400> SEQUENCE: 53

```
Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
            20                  25                  30

Arg Phe Gly Ile Val Ala Ser Arg Phe Asn His Ala Leu Val Asp Arg
        35                  40                  45

Leu Val Glu Gly Ala Ile Asp Ala Ile Val Arg His

Asn Ser Thr Trp Phe Asn Ser Thr
            355                 360

<210> SEQ ID NO 54
<211> LENGTH: 360
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 54

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
            20                  25                  30

Arg Phe Gly Ile Val Ala Ser Arg Phe Asn His Ala Leu Val Asp Arg
        35                  40                  45

Leu Val Glu Gly Ala Ile Asp Ala Ile Val Arg His Gly Gly Arg Glu
    50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
    130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Gly Ser
                165                 170                 175

Gly Gly Ser Gly Gly Ser Gly Gly Ser Gly Gly Gly Asp Asn Ile Thr
            180                 185                 190

Leu Pro Cys Arg Pro Ala Pro Pro Asn Cys Thr Ser Asn Ile Thr
        195                 200                 205

Gly Leu Ile Leu Thr Arg Gln Gly Gly Tyr Ser Asn Asp Asn Thr Val
    210                 215                 220

Ile Phe Arg Pro Ser Gly Gly Asp Trp Arg Asp Ile Ala Arg Cys Asn
225                 230                 235                 240

Ile Thr Gly Asn Val Thr Ser Thr Gln Leu Phe Leu Asn Gly Ser Leu
                245                 250                 255

Ala Gly Asn Gly Thr Val Ile Arg Ser Glu Asp Trp Arg Asp Asn Ala
            260                 265                 270

Lys Ser Ile Cys Val Gln Leu Asn Thr Ser Val Glu Ile Asn Cys Thr
        275                 280                 285

Gly Ala Gly His Cys Asn Ile Ser Arg Ala Lys Trp Asn Asn Thr Leu
    290                 295                 300

Lys Gln Ile Ala Ser Lys Leu Arg Glu Gln Tyr Gly Asn Lys Thr Ile
305                 310                 315                 320

Ile Phe Lys Pro Ser Ser Gly Gly Asp Pro Glu Phe Val Asn His Ser
                325                 330                 335

Phe Asn Cys Thr Gly Glu Phe Phe Tyr Cys Asp Ser Thr Gln Leu Phe
            340                 345                 350

Asn Ser Thr Trp Phe Asn Ser Thr
     355                 360

<210> SEQ ID NO 55
<211> LENGTH: 360
<212> TYPE: PRT
<213> ORGANISM: Artificial Sequence
<220> FEATURE:
<223> OTHER INFORMATION: recombinant gp120 lumazine synthase fusion protein

<400> SEQUENCE: 55

Met Gly Trp Ser Cys Ile Ile Leu Phe Leu Val Ala Thr Ala Thr Gly
1               5                   10               15

Val His Ser Met Gln Ile Tyr Glu Gly Lys Leu Thr Ala Glu Gly Leu
            20                 25               30

Arg Phe Gly Ile Val Ala Ser Arg Phe Asn His Ala Leu Val Asp Arg
        35                 40               45

Leu Val Glu Gly Ala Ile Asp Ala Ile Val Arg His Gly Gly Arg Glu
    50                 55               60

Glu Asp Ile Thr Leu Val Arg Val Pro Gly Ser Trp Glu Ile Pro Val
65                  70               75               80

Ala Ala Gly Glu Leu Ala Arg Lys Glu Asp Ile Asp Ala Val Ile Ala
            85                 90               95

Ile Gly Val Leu Ile Arg Gly Ala Thr Pro His Phe Asp Tyr Ile Ala
              100                105             110

Ser Glu Val Ser Lys Gly Leu Ala Asp Leu Ser Leu Glu Leu Arg Lys
       115                120             125

Pro Ile Thr Phe Gly Val Ile Thr Ala Asp Thr Leu Glu Gln Ala Ile
   130                 135               140

Glu Arg Ala Gly Thr Lys His Gly Asn Lys Gly Trp Glu Ala Ala Leu
145                 150              155              160

Ser Ala Ile Glu Met Ala Asn Leu Phe Lys Ser Leu Arg Gly Gly Ser
              165                170             175

Gly Gly Ser Gly Gly Ser Gly Gly Ser Gly Gly Gly Asp Asn Ile Thr
       180                185             190

Leu Pro Cys Arg Pro Ala Pro Pro Asn Cys Thr Ser Asn Ile Thr
   195                 200               205

Gly Leu Ile Leu Thr Arg Gln Gly Gly Tyr Ser Asn Asp Asn Thr Val
       210                215             220

Ile Phe Arg Pro Ser Gly Gly Asp Trp Arg Asp Ile Ala Arg Cys Gln
225                 230              235              240

Ile Ala Gly Thr Val Val Ser Thr Gln Leu Phe Leu Asn Gly Ser Leu
              245                250             255

Ala Asn Gly Thr Val Val Ile Arg Ser Glu Asp Trp Arg Asp Asn Ala
       260                265             270

Lys Ser Ile Cys Val Gln Leu Asn Thr Ser Val Glu Ile Asn Cys Thr
   275                 280               285

Gly Asn Gly Thr Cys Asn Ile Ser Arg Ala Lys Trp Asn Asn Thr Leu
       290                295             300

Lys Gln Ile Ala Ser Lys Leu Arg Glu Gln Tyr Gly Asn Lys Thr Ile
305                 310              315              320

Ile Phe Lys Pro Ser Ser Gly Gly Asp Pro Glu Phe Val Asn His Ser
              325                330             335

Phe Asn Cys Thr Gly Glu Phe Phe Tyr Cys Asp Ser Thr Gln Leu Phe

```
                340              345              350
Asn Ser Thr Trp Phe Asn Ser Thr
            355              360

<210> SEQ ID NO 56
<211> LENGTH: 361
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 56

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
            20                  25                  30

Arg Phe Gly Ile Val Ala Ser Arg Phe Asn His Ala Leu Val Asp Arg
        35                  40                  45

Leu Val Glu Gly Ala Ile Asp Ala Ile Val Arg His Gly Gly Arg Glu
    50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
    130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Gly Ser
                165                 170                 175

Gly Gly Ser Gly Gly Ser Gly Gly Ser Gly Gly Asp Thr Ile Thr
            180                 185                 190

Leu Pro Cys Asn Gly Thr Gly Pro Pro Asn Cys Thr Ser Asn Ile
        195                 200                 205

Thr Gly Leu Ile Leu Thr Arg Gln Gly Gly Tyr Ser Asn Asp Asn Thr
    210                 215                 220

Val Ile Phe Arg Pro Ser Gly Gly Asp Trp Arg Asp Ile Ala Arg Cys
225                 230                 235                 240

Asn Ile Thr Gly Thr Val Val Ser Thr Gln Leu Phe Leu Asn Gly Ser
                245                 250                 255

Leu Ala Asn Gly Thr Val Val Ile Arg Ser Glu Asp Trp Arg Asp Asn
            260                 265                 270

Ala Lys Ser Ile Cys Val Gln Leu Asn Thr Ser Val Glu Ile Asn Cys
        275                 280                 285

Thr Gly Asn Gly Thr Cys Asn Ile Ser Arg Ala Lys Trp Asn Asn Thr
    290                 295                 300

Leu Lys Gln Ile Ala Ser Lys Leu Arg Glu Gln Tyr Gly Asn Lys Thr
305                 310                 315                 320

Ile Ile Phe Lys Pro Ser Ser Gly Gly Asp Pro Glu Phe Val Asn His
                325                 330                 335
```

```
Ser Phe Asn Cys Gly Asn Val Thr Phe Tyr Cys Asp Ser Thr Gln Leu
                340                 345                 350

Phe Asn Ser Thr Trp Phe Asn Ser Thr
            355                 360

<210> SEQ ID NO 57
<211> LENGTH: 360
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 57

Met Gly Trp Ser Cys Ile Ile Leu Phe Leu Val Ala Thr Ala Thr Gly
1               5                  10                  15

Val His Ser Met Gln Ile Tyr Glu Gly Lys Leu Thr Ala Glu Gly Leu
                20                  25                  30

Arg Phe Gly Ile Val Ala Ser Arg Phe Asn His Ala Leu Val Asp Arg
            35                  40                  45

Leu Val Glu Gly Ala Ile Asp Ala Ile Val Arg His Gly Gly Arg Glu
        50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Gly Ser
                165                 170                 175

Gly Gly Ser Gly Gly Ser Gly Gly Ser Gly Gly Gly Asp Thr Ile Thr
            180                 185                 190

Leu Pro Cys Arg Pro Ala Pro Pro His Cys Ser Ser Asn Ile Thr
        195                 200                 205

Gly Leu Ile Leu Thr Arg Gln Gly Gly Tyr Ser Asn Asp Asn Thr Val
210                 215                 220

Ile Phe Arg Pro Ser Gly Gly Asp Trp Arg Asp Ile Ala Arg Cys Gln
225                 230                 235                 240

Ile Ala Gly Thr Val Val Ser Thr Gln Leu Phe Leu Asn Gly Ser Leu
                245                 250                 255

Ala Gly Asn Gly Thr Val Ile Arg Ser Glu Asp Trp Arg Asp Asn Ala
            260                 265                 270

Lys Ser Ile Cys Val Asn Leu Thr Thr Ser Val Glu Ile Asn Cys Thr
        275                 280                 285

Gly Asn Gly Thr Cys Asn Ile Ser Arg Ala Lys Trp Asn Asn Thr Leu
290                 295                 300

Lys Gln Ile Ala Ser Lys Leu Arg Glu Gln Tyr Gly Asn Lys Thr Ile
305                 310                 315                 320

Ile Phe Lys Pro Ser Ser Gly Gly Asp Pro Glu Phe Val Asn His Ser
                325                 330                 335
```

```
Phe Asn Cys Gly Asn Val Thr Phe Tyr Cys Asp Ser Thr Gln Leu Phe
                340                 345                 350

Asn Ser Thr Trp Phe Asn Ser Thr
            355                 360

<210> SEQ ID NO 58
<211> LENGTH: 360
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 58

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
                20                  25                  30

Arg Phe Gly Ile Val Ala Ser Arg Phe Asn His Ala Leu Val Asp Arg
            35                  40                  45

Leu Val Glu Gly Ala Ile Asp Ala Ile Val Arg His Gly Gly Arg Glu
        50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Gly Ser
                165                 170                 175

Gly Gly Ser Gly Gly Ser Gly Gly Ser Gly Gly Gly Asp Thr Ile Thr
            180                 185                 190

Leu Pro Cys Arg Pro Ala Pro Pro His Cys Ser Ser Asn Ile Thr
        195                 200                 205

Gly Leu Ile Leu Thr Arg Gln Gly Gly Tyr Ser Asn Asp Asn Thr Val
    210                 215                 220

Ile Phe Arg Pro Ser Gly Gly Asp Trp Arg Asp Ile Ala Arg Cys Asn
225                 230                 235                 240

Ile Thr Gly Thr Val Val Ser Thr Gln Leu Phe Leu Asn Gly Ser Leu
                245                 250                 255

Ala Gly Asn Gly Thr Val Ile Arg Ser Glu Asp Trp Arg Asp Asn Ala
            260                 265                 270

Lys Ser Ile Cys Val Gln Leu Asn Thr Ser Val Glu Ile Asn Cys Thr
        275                 280                 285

Gly Asn Gly Thr Cys Asn Ile Ser Arg Ala Lys Trp Asn Asn Thr Leu
    290                 295                 300

Lys Gln Ile Ala Ser Lys Leu Arg Glu Gln Tyr Gly Asn Lys Thr Ile
305                 310                 315                 320

Ile Phe Lys Pro Ser Ser Gly Gly Asp Pro Glu Phe Val Asn His Ser
```

-continued

```
                325                 330                 335
Phe Asn Cys Gly Asn Val Thr Phe Tyr Cys Asp Ser Thr Gln Leu Phe
                340                 345                 350
Asn Ser Thr Trp Phe Asn Ser Thr
                355                 360

<210> SEQ ID NO 59
<211> LENGTH: 360
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 59

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
                20                  25                  30

Arg Phe Gly Ile Val Ala Ser Arg Phe Asn His Ala Leu Val Asp Arg
            35                  40                  45

Leu Val Glu Gly Ala Ile Asp Ala Ile Val Arg His Gly Gly Arg Glu
        50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
    130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Gly Ser
                165                 170                 175

Gly Gly Ser Gly Gly Ser Gly Gly Ser Gly Gly Gly Asp Thr Ile Thr
            180                 185                 190

Leu Pro Cys Arg Pro Ala Pro Pro His Cys Ser Ser Asn Ile Thr
        195                 200                 205

Gly Leu Ile Leu Thr Arg Gln Gly Gly Tyr Ser Asn Asp Asn Thr Val
    210                 215                 220

Ile Phe Arg Pro Ser Gly Gly Asp Trp Arg Asp Ile Ala Arg Cys Gln
225                 230                 235                 240

Ile Ala Gly Asn Val Thr Ser Thr Gln Leu Phe Leu Asn Gly Ser Leu
                245                 250                 255

Ala Gly Asn Gly Thr Val Ile Arg Ser Glu Asp Trp Arg Asp Asn Ala
            260                 265                 270

Lys Ser Ile Cys Val Gln Leu Asn Thr Ser Val Glu Ile Asn Cys Thr
        275                 280                 285

Gly Asn Gly Thr Cys Asn Ile Ser Arg Ala Lys Trp Asn Asn Thr Leu
    290                 295                 300

Lys Gln Ile Ala Ser Lys Leu Arg Glu Gln Tyr Gly Asn Lys Thr Ile
305                 310                 315                 320
```

```
Ile Phe Lys Pro Ser Ser Gly Gly Asp Pro Glu Phe Val Asn His Ser
                325                 330                 335

Phe Asn Cys Gly Asn Val Thr Phe Tyr Cys Asp Ser Thr Gln Leu Phe
            340                 345                 350

Asn Ser Thr Trp Phe Asn Ser Thr
            355                 360

<210> SEQ ID NO 60
<211> LENGTH: 361
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 60

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
            20                  25                  30

Arg Phe Gly Ile Val Ala Ser Arg Phe Asn His Ala Leu Val Asp Arg
        35                  40                  45

Leu Val Glu Gly Ala Ile Asp Ala Ile Val Arg His Gly Gly Arg Glu
    50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
    130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Gly Ser
                165                 170                 175

Gly Gly Ser Gly Gly Ser Gly Gly Ser Gly Gly Asp Thr Ile Thr
            180                 185                 190

Leu Pro Cys Asn Gly Thr Gly Pro Pro His Cys Ser Ser Asn Ile
        195                 200                 205

Thr Gly Leu Ile Leu Thr Arg Gln Gly Gly Tyr Ser Asn Asp Asn Thr
    210                 215                 220

Val Ile Phe Arg Pro Ser Gly Gly Asp Trp Arg Asp Ile Ala Arg Cys
225                 230                 235                 240

Asn Ile Thr Gly Thr Val Val Ser Thr Gln Leu Phe Leu Asn Gly Ser
                245                 250                 255

Leu Ala Gly Asn Gly Thr Val Ile Arg Ser Glu Asp Trp Arg Asp Asn
            260                 265                 270

Ala Lys Ser Ile Cys Val Gln Leu Asn Thr Ser Val Glu Ile Asn Cys
        275                 280                 285

Thr Gly Ala Gly His Cys Asn Ile Ser Arg Ala Lys Trp Asn Asn Thr
    290                 295                 300

Leu Lys Gln Ile Ala Ser Lys Leu Arg Glu Gln Tyr Gly Asn Lys Thr
305                 310                 315                 320
```

-continued

```
Ile Ile Phe Lys Pro Ser Ser Gly Gly Asp Pro Glu Phe Val Asn His
                325                 330                 335

Ser Phe Asn Cys Gly Asn Val Thr Phe Tyr Cys Asp Ser Thr Gln Leu
            340                 345                 350

Phe Asn Ser Thr Trp Phe Asn Ser Thr
        355                 360

<210> SEQ ID NO 61
<211> LENGTH: 361
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 61

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
            20                  25                  30

Arg Phe Gly Ile Val Ala Ser Arg Phe Asn His Ala Leu Val Asp Arg
        35                  40                  45

Leu Val Glu Gly Ala Ile Asp Ala Ile Val Arg His Gly Gly Arg Glu
50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
    130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Gly Ser
                165                 170                 175

Gly Gly Ser Gly Gly Ser Gly Gly Ser Gly Gly Asp Asn Ile Thr
            180                 185                 190

Leu Pro Cys Asn Gly Thr Gly Pro Pro His Cys Ser Ser Asn Ile
        195                 200                 205

Thr Gly Leu Ile Leu Thr Arg Gln Gly Gly Tyr Ser Asn Asp Asn Thr
    210                 215                 220

Val Ile Phe Arg Pro Ser Gly Gly Asp Trp Arg Asp Ile Ala Arg Cys
225                 230                 235                 240

Asn Ile Thr Gly Thr Val Val Ser Thr Gln Leu Phe Leu Asn Gly Ser
                245                 250                 255

Leu Ala Gly Asn Gly Thr Val Ile Arg Ser Glu Asp Trp Arg Asp Asn
            260                 265                 270

Ala Lys Ser Ile Cys Val Gln Leu Asn Thr Ser Val Glu Ile Asn Cys
        275                 280                 285

Thr Gly Ala Gly His Cys Asn Ile Ser Arg Ala Lys Trp Asn Asn Thr
    290                 295                 300

Leu Lys Gln Ile Ala Ser Lys Leu Arg Glu Gln Tyr Gly Asn Lys Thr
```

```
                        305                 310                 315                 320
Ile Ile Phe Lys Pro Ser Ser Gly Gly Asp Pro Glu Phe Val Asn His
                    325                 330                 335

Ser Phe Asn Cys Gly Asn Val Thr Phe Tyr Cys Asp Ser Thr Gln Leu
                340                 345                 350

Phe Asn Ser Thr Trp Phe Asn Ser Thr
            355                 360

<210> SEQ ID NO 62
<211> LENGTH: 361
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 62

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
            20                  25                  30

Arg Phe Gly Ile Val Ala Ser Arg Phe Asn His Ala Leu Val Asp Arg
        35                  40                  45

Leu Val Glu Gly Ala Ile Asp Ala Ile Val Arg His Gly Gly Arg Glu
    50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
    130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Gly Ser
                165                 170                 175

Gly Gly Ser Gly Gly Ser Gly Gly Ser Gly Gly Asp Asn Ile Thr
            180                 185                 190

Leu Pro Cys Asn Gly Thr Gly Pro Pro His Cys Ser Ser Asn Ile
        195                 200                 205

Thr Gly Leu Ile Leu Thr Arg Gln Gly Gly Tyr Ser Asn Asp Asn Thr
    210                 215                 220

Val Ile Phe Arg Pro Ser Gly Gly Asp Trp Arg Asp Ile Ala Arg Cys
225                 230                 235                 240

Asn Ile Thr Gly Thr Val Val Ser Thr Gln Leu Phe Leu Asn Gly Ser
                245                 250                 255

Leu Ala Gly Asn Gly Thr Val Ile Arg Ser Glu Asp Trp Arg Asp Asn
            260                 265                 270

Ala Lys Ser Ile Cys Val Gln Leu Asn Thr Ser Val Glu Ile Asn Cys
        275                 280                 285

Thr Gly Ala Gly His Cys Asn Ile Ser Arg Ala Lys Trp Asn Asn Thr
    290                 295                 300
```

```
Leu Lys Gln Ile Ala Ser Lys Leu Arg Glu Gln Tyr Gly Asn Lys Thr
305                 310                 315                 320

Ile Ile Phe Lys Pro Ser Ser Gly Gly Asp Pro Glu Phe Val Asn His
                325                 330                 335

Ser Phe Asn Cys Gly Gly Glu Phe Phe Tyr Cys Asn Ser Thr Gln Leu
                340                 345                 350

Phe Asn Ser Thr Trp Phe Asn Ser Thr
                355                 360

<210> SEQ ID NO 63
<211> LENGTH: 361
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 63

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
                20                  25                  30

Arg Phe Gly Ile Val Ala Ser Arg Phe Asn His Ala Leu Val Asp Arg
                35                  40                  45

Leu Val Glu Gly Ala Ile Asp Ala Ile Val Arg His Gly Gly Arg Glu
50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
                100                 105                 110

Ser Glu Val Ser Lys Gly Leu Ala Asp Leu Ser Leu Glu Leu Arg Lys
                115                 120                 125

Pro Ile Thr Phe Gly Val Ile Thr Ala Asp Thr Leu Glu Gln Ala Ile
130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Gly Ser
                165                 170                 175

Gly Gly Ser Gly Gly Ser Gly Gly Ser Gly Gly Asp Thr Ile Thr
                180                 185                 190

Leu Pro Cys Asn Gly Thr Gly Pro Pro His Cys Ser Ser Asn Ile
                195                 200                 205

Thr Gly Leu Ile Leu Thr Arg Gln Gly Gly Tyr Ser Asn Asp Asn Thr
                210                 215                 220

Val Ile Phe Arg Pro Ser Gly Gly Asp Trp Arg Asp Ile Ala Arg Cys
225                 230                 235                 240

Asn Ile Thr Gly Thr Val Val Ser Thr Gln Leu Phe Leu Asn Gly Ser
                245                 250                 255

Leu Ala Gly Asn Gly Thr Val Ile Arg Ser Glu Asp Trp Arg Asp Asn
                260                 265                 270

Ala Lys Ser Ile Cys Val Gln Leu Asn Thr Ser Val Glu Ile Asn Cys
                275                 280                 285

Thr Gly Asn Gly Thr Cys Asn Ile Ser Arg Ala Lys Trp Asn Asn Thr
                290                 295                 300
```

```
Leu Lys Gln Ile Ala Ser Lys Leu Arg Glu Gln Tyr Gly Asn Lys Thr
305                 310                 315                 320

Ile Ile Phe Lys Pro Ser Ser Gly Gly Asp Pro Glu Phe Val Asn His
                325                 330                 335

Ser Phe Asn Cys Gly Asn Val Thr Phe Tyr Cys Asp Ser Thr Gln Leu
            340                 345                 350

Phe Asn Ser Thr Trp Phe Asn Ser Thr
        355                 360

<210> SEQ ID NO 64
<211> LENGTH: 361
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 64

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
            20                  25                  30

Arg Phe Gly Ile Val Ala Ser Arg Phe Asn His Ala Leu Val Asp Arg
        35                  40                  45

Leu Val Glu Gly Ala Ile Asp Ala Ile Val Arg His Gly Gly Arg Glu
    50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
    130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Gly Ser
                165                 170                 175

Gly Gly Ser Gly Gly Ser Gly Ser Gly Gly Asp Thr Ile Thr
            180                 185                 190

Leu Pro Cys Asn Gly Thr Gly Pro Pro His Cys Ser Ser Asn Ile
    195                 200                 205

Thr Gly Leu Ile Leu Thr Arg Gln Gly Gly Tyr Ser Asn Asp Asn Thr
210                 215                 220

Val Ile Phe Arg Pro Ser Gly Gly Asp Trp Arg Asp Ile Ala Arg Cys
225                 230                 235                 240

Asn Ile Thr Gly Thr Val Val Ser Thr Gln Leu Phe Leu Asn Gly Ser
                245                 250                 255

Leu Ala Gly Asn Gly Thr Val Ile Arg Ser Glu Asp Trp Arg Asp Asn
            260                 265                 270

Ala Lys Ser Ile Cys Val Gln Leu Asn Thr Ser Val Glu Ile Asn Cys
        275                 280                 285

Thr Gly Ala Gly His Cys Asn Ile Ser Arg Ala Lys Trp Asn Asn Thr
```

```
                    290                 295                 300

Leu Lys Gln Ile Ala Ser Lys Leu Arg Glu Gln Tyr Gly Asn Lys Thr
305                 310                 315                 320

Ile Ile Phe Lys Pro Ser Ser Gly Gly Asp Pro Glu Phe Val Asn His
                    325                 330                 335

Ser Phe Asn Cys Gly Asn Val Thr Phe Tyr Cys Asn Ser Thr Gln Leu
                340                 345                 350

Phe Asn Ser Thr Trp Phe Asn Ser Thr
            355                 360

<210> SEQ ID NO 65
<211> LENGTH: 361
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 65

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
            20                  25                  30

Ar

```
Thr Gly Asn Gly Thr Cys Asn Ile Ser Arg Ala Lys Trp Asn Asn Thr
    290                 295                 300

Leu Lys Gln Ile Ala Ser Lys Leu Arg Glu Gln Tyr Gly Asn Lys Thr
305                 310                 315                 320

Ile Ile Phe Lys Pro Ser Ser Gly Gly Asp Pro Glu Phe Val Asn His
                325                 330                 335

Ser Phe Asn Cys Gly Gly Glu Phe Phe Tyr Cys Asn Ser Thr Gln Leu
                340                 345                 350

Phe Asn Ser Thr Trp Phe Asn Ser Thr
                355                 360

<210> SEQ ID NO 66
<211> LENGTH: 856
<212> TYPE: PRT
<213> ORGANISM: Human immunodeficiency virus type 1

<400> SEQUENCE: 66

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
        50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
                100                 105                 110

Asp Gln Ser Leu Lys Pro Cys Val Lys Leu Thr Pro Leu Cys Val Ser
            115                 120                 125

Leu Lys Cys Thr Asp Leu Lys Asn Asp Thr Asn Thr Asn Ser Ser Ser
130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
                180                 185                 190

Leu Thr Ser Cys Asn Thr Ser Val Ile Thr Gln Ala Cys Pro Lys Val
            195                 200                 205

Ser Phe Glu Pro Ile Pro Ile His Tyr Cys Ala Pro Ala Gly Phe Ala
210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
                260                 265                 270

Arg Ser Val Asn Phe Thr Asp Asn Ala Lys Thr Ile Ile Val Gln Leu
            275                 280                 285

Asn Thr Ser Val Glu Ile Asn Cys Thr Arg Pro Asn Asn Asn Thr Arg
290                 295                 300
```

```
Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
            325                 330                 335

Lys Trp Asn Asn Thr Leu Lys Gln Ile Ala Ser Lys Leu Arg Glu Gln
        340                 345                 350

Phe Gly Asn Asn Lys Thr Ile Ile Phe Lys Gln Ser Ser Gly Gly Asp
            355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
            435                 440                 445

Ile Thr Gly Leu Leu Leu Thr Arg Asp Gly Gly Asn Ser Asn Asn Glu
450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
            515                 520                 525

Thr Met Gly Ala Ala Ser Met Thr Leu Thr Val Gln Ala Arg Gln Leu
    530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
            595                 600                 605

Pro Trp Asn Ala Ser Trp Ser Asn Lys Ser Leu Glu Gln Ile Trp Asn
    610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
            675                 680                 685

Val Gly Gly Leu Val Gly Leu Arg Ile Val Phe Ala Val Leu Ser Ile
            690                 695                 700

Val Asn Arg Val Arg Gln Gly Tyr Ser Pro Leu Ser Phe Gln Thr His
705                 710                 715                 720
```

```
Leu Pro Thr Pro Arg Gly Pro Asp Arg Pro Glu Gly Ile Glu Glu Glu
            725                 730                 735

Gly Gly Glu Arg Asp Arg Asp Arg Ser Ile Arg Leu Val Asn Gly Ser
        740                 745                 750

Leu Ala Leu Ile Trp Asp Asp Leu Arg Ser Leu Cys Leu Phe Ser Tyr
    755                 760                 765

His Arg Leu Arg Asp Leu Leu Leu Ile Val Thr Arg Ile Val Glu Leu
770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855

<210> SEQ ID NO 67
<211> LENGTH: 154
<212> TYPE: PRT
<213> ORGANISM: Artificial Sequence
<220> FEATURE:
<223> OTHER INFORMATION: recombinant lumazine synthase subunit

<400> SEQUENCE: 67

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Ala Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150

<210> SEQ ID NO 68
<211> LENGTH: 154
<212> TYPE: PRT
<213> ORGANISM: Artificial Sequence
<220> FEATURE:
<223> OTHER INFORMATION: recombinant lumazine synthase subunit

<400> SEQUENCE: 68

Met Gln Ile Tyr Glu Gly Lys Leu Thr Ala Glu Gly Leu Arg Phe Gly
1               5                   10                  15
```

```
Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
 50                  55                  60

Glu Leu Ala Arg Lys Glu Asp Ile Asp Ala Val Ile Ala Ile Gly Val
 65                  70                  75                  80

Leu Ile Arg Gly Ala Thr Pro Ser Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Ala Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150

<210> SEQ ID NO 69
<211> LENGTH: 154
<212> TYPE: PRT
<213> ORGANISM: Artificial Sequence
<220> FEATURE:
<223> OTHER INFORMATION: recombinant lumazine synthase subunit

<400> SEQUENCE: 69

Met Gln Ile Tyr Glu Gly Lys Leu Thr Ala Glu Gly Leu Arg Phe Gly
1               5                   10                  15

Ile Val Ala Ser Arg Ala Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
 50                  55                  60

Glu Leu Ala Arg Lys Glu Asp Ile Asp Ala Val Ile Ala Ile Gly Val
 65                  70                  75                  80

Leu Ile Arg Gly Ala Thr Pro Ser Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Ala Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150

<210> SEQ ID NO 70
<211> LENGTH: 173
<212> TYPE: PRT
<213> ORGANISM: Artificial Sequence
<220> FEATURE:
<223> OTHER INFORMATION: recombinant ferritin subunit

<400> SEQUENCE: 70

Glu Ser Gln Val Arg Gln Gln Phe Ser Lys Asp Ile Glu Lys Leu Leu
```

```
                1               5                   10                  15
            Asn Glu Gln Val Asn Lys Glu Met Gln Ser Ser Asn Leu Tyr Met Ser
                                20                  25                  30

Met Ser Ser Trp Cys Tyr Thr His Ser Leu Asp Gly Ala Gly Leu Phe
                        35                  40                  45

Leu Phe Asp His Ala Ala Glu Glu Tyr Glu His Ala Lys Lys Leu Ile
                    50                  55                  60

Ile Phe Leu Asn Glu Asn Asn Val Pro Val Gln Leu Thr Ser Ile Ser
            65                  70                  75                  80

Ala Pro Glu His Lys Phe Glu Gly Leu Thr Gln Ile Phe Gln Lys Ala
                                85                  90                  95

Tyr Glu His Glu Gln His Ile Ser Glu Ser Ile Asn Asn Ile Val Asp
                        100                 105                 110

His Ala Ile Lys Ser Lys Asp His Ala Thr Phe Asn Phe Leu Gln Trp
                    115                 120                 125

Tyr Val Ala Glu Gln His Glu Glu Val Leu Phe Lys Asp Ile Leu
                    130                 135                 140

Asp Lys Ile Glu Leu Ile Gly Asn Glu Asn His Gly Leu Tyr Leu Ala
            145                 150                 155                 160

Asp Gln Tyr Val Lys Gly Ile Ala Lys Ser Arg Lys Ser
                                165                 170
```

<210> SEQ ID NO 71
<211> LENGTH: 265
<212> TYPE: PRT
<213> ORGANISM: Artificial Sequence
<220> FEATURE:
<223> OTHER INFORMATION: recombinant encapsulin subunit

<400> SEQUENCE: 71

```
            Met Glu Phe Leu Lys Arg Ser Phe Ala Pro Leu Thr Glu Lys Gln Trp
            1               5                   10                  15

Gln Glu Ile Asp Asn Arg Ala Arg Glu Ile Phe Lys Thr Gln Leu Tyr
                                20                  25                  30

Gly Arg Lys Phe Val Asp Val Glu Gly Pro Tyr Gly Trp Glu Tyr Ala
                        35                  40                  45

Ala His Pro Leu Gly Glu Val Glu Val Leu Ser Asp Glu Asn Glu Val
                    50                  55                  60

Val Lys Trp Gly Leu Arg Lys Ser Leu Pro Leu Ile Glu Leu Arg Ala
            65                  70                  75                  80

Thr Phe Thr Leu Asp Leu Trp Glu Leu Asp Asn Leu Glu Arg Gly Lys
                                85                  90                  95

Pro Asn Val Asp Leu Ser Ser Leu Glu Glu Thr Val Arg Lys Val Ala
                        100                 105                 110

Glu Phe Glu Asp Glu Val Ile Phe Arg Gly Cys Glu Lys Ser Gly Val
                    115                 120                 125

Lys Gly Leu Leu Ser Phe Glu Glu Arg Lys Ile Glu Cys Gly Ser Thr
                    130                 135                 140

Pro Lys Asp Leu Leu Glu Ala Ile Val Arg Ala Leu Ser Ile Phe Ser
            145                 150                 155                 160

Lys Asp Gly Ile Glu Gly Pro Tyr Thr Leu Val Ile Asn Thr Asp Arg
                                165                 170                 175

Trp Ile Asn Phe Leu Lys Glu Glu Ala Gly His Tyr Pro Leu Glu Lys
                        180                 185                 190

Arg Val Glu Glu Cys Leu Arg Gly Gly Lys Ile Ile Thr Thr Pro Arg
```

```
              195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265

<210> SEQ ID NO 72
<211> LENGTH: 265
<212> TYPE: PRT
<213> ORGANISM: Artificial Sequence
<220> FEATURE:
<223> OTHER INFORMATION: recombinant Sulfur Oxygenase Reductase subunit

<400> SEQUENCE: 72

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265

<210> SEQ ID NO 73
<211> LENGTH: 27
<212> TYPE: PRT
```

<213> ORGANISM: Artificial Sequence
<220> FEATURE:
<223> OTHER INFORMATION: Transmembrane domain

<400> SEQUENCE: 73

```
Lys Ile Phe Ile Met Ile Val Gly Gly Leu Ile Gly Leu Arg Ile Val
1               5                   10                  15

Phe Ala Val Leu Ser Val Ile His Arg Val Arg
            20                  25
```

<210> SEQ ID NO 74
<211> LENGTH: 23
<212> TYPE: PRT
<213> ORGANISM: Artificial Sequence
<220> FEATURE:
<223> OTHER INFORMATION: Transmembrane domain

<400> SEQUENCE: 74

```
Ile Leu Ala Ile Tyr Ser Thr Val Ala Ser Ser Leu Val Leu Leu Val
1               5                   10                  15

Ser Leu Gly Ala Ile Ser Phe
            20
```

<210> SEQ ID NO 75
<211> LENGTH: 29
<212> TYPE: PRT
<213> ORGANISM: Artificial Sequence
<220> FEATURE:
<223> OTHER INFORMATION: Transmembrane domain

<400> SEQUENCE: 75

```
Ile Ile Thr Ile Gly Ser Ile Cys Met Val Val Gly Ile Ile Ser Leu
1               5                   10                  15

Ile Leu Gln Ile Gly Asn Ile Ile Ser Ile Trp Val Ser
            20                  25
```

<210> SEQ ID NO 76
<211> LENGTH: 360
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 76

```
Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
            20                  25                  30

Arg Phe Gly Ile Val Ala Ser Arg Phe Asn His Ala Leu Val Asp Arg
        35                  40                  45

Leu Val Glu Gly Ala Ile Asp Ala Ile Val Arg His Gly Gly Arg Glu
    50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125
```

```
Pro Ile Thr Phe Gly Val Ile Thr Ala Asp Thr Leu Glu Gln Ala Ile
            130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Gly Ser
                165                 170                 175

Gly Gly Ser Gly Gly Ser Gly Ser Gly Gly Gly Asp Thr Ile Thr
            180                 185                 190

Leu Pro Cys Arg Pro Ala Pro Pro His Cys Ser Ser Asn Ile Thr
            195                 200                 205

Gly Leu Ile Leu Thr Arg Gln Gly Gly Tyr Ser Asn Asp Asn Thr Val
210                 215                 220

Ile Phe Arg Pro Ser Gly Gly Asp Trp Arg Asp Ile Ala Arg Cys Asn
225                 230                 235                 240

Ile Thr Gly Thr Val Val Ser Thr Gln Leu Phe Leu Asn Gly Ser Leu
                245                 250                 255

Ala Gly Asn Gly Thr Val Ile Arg Ser Glu Asn Phe Thr Asp Asn Ala
            260                 265                 270

Lys Ser Ile Cys Val Gln Leu Asn Thr Ser Val Glu Ile Asn Cys Thr
275                 280                 285

Gly Asn Gly Thr Cys Asn Ile Ser Arg Ala Lys Trp Asn Asn Thr Leu
            290                 295                 300

Lys Gln Ile Ala Ser Lys Leu Arg Glu Gln Tyr Gly Asn Lys Thr Ile
305                 310                 315                 320

Ile Phe Lys Pro Ser Ser Gly Gly Asp Pro Glu Phe Val Asn His Ser
                325                 330                 335

Phe Asn Cys Gly Asn Val Thr Phe Tyr Cys Asp Ser Thr Gln Leu Phe
            340                 345                 350

Asn Ser Thr Trp Phe Asn Ser Thr
            355                 360

<210> SEQ ID NO 77
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 77

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
                20                  25                  30

Asp Asn Thr Val Ile Phe Arg Pro Ser Gly Gly Asp Trp Arg Asp Ile
            35                  40                  45

Ala Arg Cys Gln Ile Ala Gly Thr Val Val Ser Thr Gln Leu Phe Leu
50                  55                  60

Asn Gly Ser Leu Ala Gly Asn Gly Thr Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125
```

```
Asn Lys Thr Ile Ile Phe Lys Pro Ser Ser Gly Gly Asp Pro Glu Phe
            130                 135                 140

Val Asn His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 78
<211> LENGTH: 5
<212> TYPE: PRT
<213> ORGANISM: Artificial Sequence
<220> FEATURE:
<223> OTHER INFORMATION: recombinant gp120 protein fragment

<400> SEQUENCE: 78

Gln Gln Tyr Glu Phe
1               5

<210> SEQ ID NO 79
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 79

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
            20                  25                  30

Asp Asn Thr Val Ile Phe Arg Pro Ser Gly Gly Asp Trp Arg Asp Ile
        35                  40                  45

Ala Arg Cys Gln Ile Ala Gly Asn Val Thr Ser Thr Gln Leu Phe Leu
    50                  55                  60

Asn Gly Ser Leu Ala Gly Asn Gly Thr Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Asn Val Thr Phe Tyr Cys Asp Ser
145                 150                 155                 160

Thr Gln Leu Phe Asn Ser Thr Trp Phe Asn Ser Thr
                165                 170

<210> SEQ ID NO 80
<211> LENGTH: 172
<212> TYPE: PRT
<213> ORGANISM: Artificial Sequence
<220> FEATURE:
<223> OTHER INFORMATION: recombinant gp120 protein

<400> SEQUENCE: 80

Asp Thr Ile Thr Leu Pro Cys Arg Pro Ala Pro Pro His Cys Ser
1               5                   10                  15

Ser Asn Ile Thr Gly Leu Ile Leu Thr Arg Gln Gly Gly Tyr Ser Asn
```

```
                    20                  25                  30
Asp Asn Thr Val Ile Phe Arg Pro Ser Gly Gly Asp Trp Arg Asp Ile
                35                  40                  45

Ala Arg Cys Gln Ile Ala Gly Asn Val Thr Ser Thr Gln Leu Phe Leu
     50                  55                  60

Asn Gly Ser Leu Ala Gly Glu Val Asn Gly Thr Ser Glu Asp Trp
 65                  70                  75                  80

Arg Asp Asn Ala Lys Ser Ile Cys Val Gln Leu Asn Thr Ser Val Glu
                 85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
            115                 120                 125

Asn Lys Thr Ile Ile Phe Lys Pro Ser Ser Gly Gly Asp Pro Glu Phe
            130                 135                 140

Val Asn His Ser Phe Asn Cys Gly Asn Val Thr Phe Tyr Cys Asp Ser
145                 150                 155                 160

Thr Gln Leu Phe Asn Ser Thr Trp Phe Asn Ser Thr
                165                 170

<210> SEQ ID NO 81
<211> LENGTH: 173
<212> TYPE: PRT
<213> ORGANISM: Artificial Sequence
<220> FEATURE:
<223> OTHER INFORMATION: recombinant gp120 protein

<400> SEQUENCE: 81

Asp Thr Ile Thr Leu Pro Cys Asn Gly Thr Gly Pro Pro His Cys
1               5                   10                  15

Ser Ser Asn Ile Thr Gly Leu Ile Leu Thr Arg Gln Gly Gly Tyr Ser
                 20                  25                  30

Asn Asp Asn Thr Val Ile Phe Arg Pro Ser Gly Gly Asp Trp Arg Asp
                35                  40                  45

Ile Ala Arg Cys Gln Ile Ala Gly Asn Val Thr Ser Thr Gln Leu Phe
     50                  55                  60

Leu Asn Gly Ser Leu Ala Asn Gly Thr Val Asn Gly Thr Ser Glu Asp
 65                  70                  75                  80

Trp Arg Asp Asn Ala Lys Ser Ile Cys Val Gln Leu Asn Thr Ser Val
                 85                  90                  95

Glu Ile Asn Cys Thr Gly Ala Gly His Cys Asn Ile Ser Arg Ala Lys
            100                 105                 110

Trp Asn Asn Thr Leu Lys Gln Ile Ala Ser Lys Leu Arg Glu Gln Tyr
            115                 120                 125

Gly Asn Lys Thr Ile Ile Phe Lys Pro Ser Ser Gly Gly Asp Pro Glu
            130                 135                 140

Phe Val Asn His Ser Phe Asn Cys Gly Asn Val Thr Phe Tyr Cys Asp
145                 150                 155                 160

Ser Thr Gln Leu Phe Asn Ser Thr Trp Phe Asn Ser Thr
                165                 170

<210> SEQ ID NO 82
<211> LENGTH: 172
<212> TYPE: PRT
<213> ORGANISM: Artificial Sequence
<220> FEATURE:
<223> OTHER INFORMATION: recombinant gp120 protein
```

<400> SEQUENCE: 82

Asp Thr Ile Thr Leu Pro Cys Arg Pro Ala Pro Pro Asn Cys Thr
1               5                   10                  15

Ser Asn Ile Thr Gly Leu Ile Leu Thr Arg Gln Gly Gly Tyr Ser Asn
            20                  25                  30

Asp Asn Thr Val Ile Phe Arg Pro Ser Gly Gly Asp Trp Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Gly Asn Gly Thr Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Asn Gly Thr Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Asn Val Thr Phe Tyr Cys Asp Ser
145                 150                 155                 160

Thr Gln Leu Phe Asn Ser Thr Trp Phe Asn Ser Thr
                165                 170

<210> SEQ ID NO 83
<211> LENGTH: 360
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 83

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
            20                  25                  30

Arg Phe Gly Ile Val Ala Ser Arg Phe Asn His Ala Leu Val Asp Arg
        35                  40                  45

Leu Val Glu Gly Ala Ile Asp Ala Ile Val Arg His Gly Gly Arg Glu
    50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
    130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Gly Ser
                165                 170                 175

```
Gly Gly Ser Gly Gly Ser Gly Gly Gly Asp Thr Ile Thr
            180             185             190

Leu Pro Cys Arg Pro Ala Pro Pro His Cys Ser Ser Asn Ile Thr
        195             200             205

Gly Leu Ile Leu Thr Arg Gln Gly Gly Tyr Ser Asn Asp Asn Thr Val
    210             215             220

Ile Phe Arg Pro Ser Gly Gly Asp Trp Arg Asp Ile Ala Arg Cys Gln
225             230             235             240

Ile Ala Gly Asn Val Thr Ser Thr Gln Leu Phe Leu Asn Gly Ser Leu
            245             250             255

Ala Gly Asn Gly Thr Val Ile Arg Ser Glu Asp Trp Arg Asp Asn Ala
        260             265             270

Lys Ser Ile Cys Val Gln Leu Asn Thr Ser Val Glu Ile Asn Cys Thr
    275             280             285

Gly Ala Gly His Cys Asn Ile Ser Arg Ala Lys Trp Asn Asn Thr Leu
    290             295             300

Lys Gln Ile Ala Ser Lys Leu Arg Glu Gln Tyr Gly Asn Lys Thr Ile
305             310             315             320

Ile Phe Lys Pro Ser Ser Gly Gly Asp Pro Glu Phe Val Asn His Ser
            325             330             335

Phe Asn Cys Gly Asn Val Thr Phe Tyr Cys Asp Ser Thr Gln Leu Phe
        340             345             350

Asn Ser Thr Trp Phe Asn Ser Thr
            355             360

<210> SEQ ID NO 84
<211> LENGTH: 360
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 84

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
            20                  25                  30

Arg Phe Gly Ile Val Ala Ser Arg Phe Asn His Ala Leu Val Asp Arg
        35                  40                  45

Leu Val Glu Gly Ala Ile Asp Ala Ile Val Arg His Gly Gly Arg Glu
    50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
    130                 135                 140

Glu Arg Ala Gly Thr Lys His Gly Asn Lys Gly Trp Glu Ala Ala Leu
145                 150                 155                 160

Ser Ala Ile Glu Met Ala Asn Leu Phe Lys Ser Leu Arg Gly Gly Ser
```

```
            165                 170                 175
Gly Gly Ser Gly Gly Ser Gly Gly Gly Asp Thr Ile Thr
            180                 185                 190

Leu Pro Cys Arg Pro Ala Pro Pro His Cys Ser Ser Asn Ile Thr
            195                 200                 205

Gly Leu Ile Leu Thr Arg Gln Gly Gly Tyr Ser Asn Asp Asn Thr Val
            210                 215                 220

Ile Phe Arg Pro Ser Gly Gly Asp Trp Arg Asp Ile Ala Arg Cys Gln
225                 230                 235                 240

Ile Ala Gly Asn Val Thr Ser Thr Gln Leu Phe Leu Asn Gly Ser Leu
                245                 250                 255

Ala Gly Gly Glu Val Asn Gly Thr Ser Glu Asp Trp Arg Asp Asn Ala
            260                 265                 270

Lys Ser Ile Cys Val Gln Leu Asn Thr Ser Val Glu Ile Asn Cys Thr
                275                 280                 285

Gly Ala Gly His Cys Asn Ile Ser Arg Ala Lys Trp Asn Asn Thr Leu
            290                 295                 300

Lys Gln Ile Ala Ser Lys Leu Arg Glu Gln Tyr Gly Asn Lys Thr Ile
305                 310                 315                 320

Ile Phe Lys Pro Ser Ser Gly Gly Asp Pro Glu Phe Val Asn His Ser
                325                 330                 335

Phe Asn Cys Gly Asn Val Thr Phe Tyr Cys Asp Ser Thr Gln Leu Phe
            340                 345                 350

Asn Ser Thr Trp Phe Asn Ser Thr
            355                 360

<210> SEQ ID NO 85
<211> LENGTH: 361
<212> TYPE: PRT
<213> ORGANISM: Artificial Sequence
<220> FEATURE:
<223> OTHER INFORMATION: recombinant gp120 lumazine synthase fusion
      protein

<400> SEQUENCE: 85

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
                20                  25                  30

Arg Phe Gly Ile Val Ala Ser Arg Phe Asn His Ala Leu Val Asp Arg
            35                  40                  45

Leu Val Glu Gly Ala Ile Asp Ala Ile Val Arg His Gly Gly Arg Glu
        50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
    130                 135                 140

Glu Arg Ala Gly Thr Lys His Gly Asn Lys Gly Trp Glu Ala Ala Leu
145                 150                 155                 160
```

Ser Ala Ile Glu Met Ala Asn Leu Phe Lys Ser Leu Arg Gly Gly Ser
            165                 170                 175

Gly Gly Ser Gly Gly Ser Gly Gly Gly Asp Thr Ile Thr
        180                 185                 190

Leu Pro Cys Asn Gly Thr Gly Pro Pro His Cys Ser Ser Asn Ile
            195                 200                 205

Thr Gly Leu Ile Leu Thr Arg Gln Gly Gly Tyr Ser Asn Asp Asn Thr
        210                 215                 220

Val Ile Phe Arg Pro Ser Gly Gly Asp Trp Arg Asp Ile Ala Arg Cys
225                 230                 235                 240

Gln Ile Ala Gly Asn Val Thr Ser Thr Gln Leu Phe Leu Asn Gly Ser
            245                 250                 255

Leu Ala Asn Gly Thr Val Asn Gly Thr Ser Glu Asp Trp Arg Asp Asn
        260                 265                 270

Ala Lys Ser Ile Cys Val Gln Leu Asn Thr Ser Val Glu Ile Asn Cys
        275                 280                 285

Thr Gly Ala Gly His Cys Asn Ile Ser Arg Ala Lys Trp Asn Asn Thr
        290                 295                 300

Leu Lys Gln Ile Ala Ser Lys Leu Arg Glu Gln Tyr Gly Asn Lys Thr
305                 310                 315                 320

Ile Ile Phe Lys Pro Ser Ser Gly Gly Asp Pro Glu Phe Val Asn His
                325                 330                 335

Ser Phe Asn Cys Gly Asn Val Thr Phe Tyr Cys Asp Ser Thr Gln Leu
            340                 345                 350

Phe Asn Ser Thr Trp Phe Asn Ser Thr
        355                 360

<210> SEQ ID NO 86
<211> LENGTH: 360
<212> TYPE: PRT
<213> ORGANISM: Artificial Sequence
<220> FEATURE:
<223> OTHER INFORMATION: recombinant gp120 lumazine synthase fusion
    protein

<400> SEQUENCE: 86

Met Gly Trp Ser Cys Ile Ile Leu Phe Leu Val Ala Thr Ala Thr Gly
1               5                   10                  15

Val His Ser Met Gln Ile Tyr Glu Gly Lys Leu Thr Ala Glu Gly Leu
            20                  25                  30

Arg Phe Gly Ile Val Ala Ser Arg Phe Asn His Ala Leu Val Asp Arg
        35                  40                  45

Leu Val Glu Gly Ala Ile Asp Ala Ile Val Arg His Gly Gly Arg Glu
    50                  55                  60

Glu Asp Ile Thr Leu Val Arg Val Pro Gly Ser Trp Glu Ile Pro Val
65                  70                  75                  80

Ala Ala Gly Glu Leu Ala Arg Lys Glu Asp Ile Asp Ala Val Ile Ala
                85                  90                  95

Ile Gly Val Leu Ile Arg Gly Ala Thr Pro His Phe Asp Tyr Ile Ala
            100                 105                 110

Ser Glu Val Ser Lys Gly Leu Ala Asp Leu Ser Leu Glu Leu Arg Lys
        115                 120                 125

Pro Ile Thr Phe Gly Val Ile Thr Ala Asp Thr Leu Glu Gln Ala Ile
    130                 135                 140

Glu Arg Ala Gly Thr Lys His Gly Asn Lys Gly Trp Glu Ala Ala Leu
145                 150                 155                 160

-continued

```
Ser Ala Ile Glu Met Ala Asn Leu Phe Lys Ser Leu Arg Gly Gly Ser
            165                 170                 175
Gly Gly Ser Gly Gly Ser Gly Gly Ser Gly Gly Gly Asp Thr Ile Thr
        180                 185                 190
Leu Pro Cys Arg Pro Ala Pro Pro Asn Cys Thr Ser Asn Ile Thr
        195                 200                 205
Gly Leu Ile Leu Thr Arg Gln Gly Gly Tyr Ser Asn Asp Asn Thr Val
    210                 215                 220
Ile Phe Arg Pro Ser Gly Gly Asp Trp Arg Asp Ile Ala Arg Cys Gln
225                 230                 235                 240
Ile Ala Gly Thr Val Val Ser Thr Gln Leu Phe Leu Asn Gly Ser Leu
                245                 250                 255
Ala Gly Asn Gly Thr Val Ile Arg Ser Glu Asp Trp Arg Asp Asn Ala
            260                 265                 270
Lys Ser Ile Cys Val Gln Leu Asn Thr Ser Val Glu Ile Asn Cys Thr
        275                 280                 285
Gly Asn Gly Thr Cys Asn Ile Ser Arg Ala Lys Trp Asn Asn Thr Leu
    290                 295                 300
Lys Gln Ile Ala Ser Lys Leu Arg Glu Gln Tyr Gly Asn Lys Thr Ile
305                 310                 315                 320
Ile Phe Lys Pro Ser Ser Gly Gly Asp Pro Glu Phe Val Asn His Ser
                325                 330                 335
Phe Asn Cys Gly Asn Val Thr Phe Tyr Cys Asp Ser Thr Gln Leu Phe
            340                 345                 350
Asn Ser Thr Trp Phe Asn Ser Thr
        355                 360
```

<210> SEQ ID NO 87
<211> LENGTH: 1104
<212> TYPE: DNA
<213> ORGANISM: Artificial Sequence
<220> FEATURE:
<223> OTHER INFORMATION: recombinant gp120 lumazine synthase fusion
      protein

<400> SEQUENCE: 87

```
atgcccatgg gcagcctgca gcccctggcc accctgtacc tgctgggcat gctggtggct    60
agcgtgctgg ccatgcagat ctacgaaggc aagctgaccg ccgaggggct gagattcgga   120
attgtggcaa gcaggtttaa ccacgcactg gtggaccgac tggtcgaagg agctatcgat   180
gcaattgtgc ggcatggcgg gagagaggaa gacatcacac tggtgagagt cccaggcagc   240
tgggagattc cagtggcagc tggagaactg gcacggaaag aggacatcga tgccgtgatc   300
gctattggcg tcctgattag aggggctact ccccacttcg actatatcgc atcagaagtg   360
agcaagggcc tggccgatct gtctctggag ctgcgaaaac ctatcacttt tggggtcatt   420
actgccgata ccctggaaca ggcaatcgag gcgccggca ccaagcatgg aaacaaaggc   480
tgggaagcag ccctgtccgc tattgagatg gcaaatctgt tcaagtctct gaggggaggc   540
tccggaggct ccggcggctc tggcggcagc ggcggaggcg acaccatcac actgccatgc   600
aacggaaccg gaccacctcc acactgtagc tccaatatca ccggactgat cctgacaagg   660
cagggaggct actccaacga taatacagtg atcttcagac catctggcgg cgactggagg   720
gatatcgcaa gatgcaatat caccggcaca gtggtgagca cccagctgtt tctgaacggc   780
tccctggccg gcaatggcac agtgatcagg tccgaggact ggcgcgataa cgccaagtct   840
```

| | |
|---|---|
| atctgcgtgc agctgaacac cagcgtggag atcaattgca caggcgccgg ccactgtaat | 900 |
| atctctaggg ccaagtggaa caatacctg aagcagatcg ccagcaagct gagagagcag | 960 |
| tacggcaaca agacaatcat cttcaagccc tctagcggcg gcgaccctga gttcgtgaac | 1020 |
| cacagcttta attgcggcgg cgagttcttt tattgtgatt ccacccagct gttcaactcc | 1080 |
| acctggttta attctacatg atga | 1104 |

<210> SEQ ID NO 88
<211> LENGTH: 1101
<212> TYPE: DNA
<213> ORGANISM: Artificial Sequence
<220> FEATURE:
<223> OTHER INFORMATION: recombinant gp120 lumazine synthase fusion protein

<400> SEQUENCE: 88

| | |
|---|---|
| atgcccatgg gcagcctgca gcccctggcc accctgtacc tgctgggcat gctggtggct | 60 |
| agcgtgctgg ccatgcagat ctacgaaggc aagctgaccg ccgaggggct gagattcgga | 120 |
| attgtggcaa gcaggtttaa ccacgcactg gtggaccgac tggtcgaagg agctatcgat | 180 |
| gcaattgtgc ggcatggcgg gagagaggaa gacatcacac tggtgagagt cccaggcagc | 240 |
| tgggagattc cagtggcagc tggagaactg gcacggaaag aggacatcga tgccgtgatc | 300 |
| gctattggcg tcctgattag aggggctact ccccacttcg actatatcgc atcagaagtg | 360 |
| agcaagggcc tggccgatct gtctctggag ctgcgaaaac ctatcacttt tggggtcatt | 420 |
| actgccgata ccctggaaca ggcaatcgag cgcgccggca ccaagcatgg aaacaaaggc | 480 |
| tgggaagcag ccctgtccgc tattgagatg gcaaatctgt tcaagtctct gaggggaggc | 540 |
| tccggaggct ctggcggcag cggcggctcc ggcggaggcg acaccatcac actgccatgc | 600 |
| aggcctgcac cacctccaaa ctgtacctct aatatcacag gactgatcct gaccaggcag | 660 |
| ggaggatact ctaacgataa tacagtgatc ttcagaccta gcggcggcga ctggagggat | 720 |
| atcgcaagat gcaatatcac cggcacagtg gtgtccaccc agctgtttct gaatggctct | 780 |
| ctggccggca acggcacagt gatcaggagc gaggactggc gcgataatgc aagagcatc | 840 |
| tgcgtgcagc tgaacacctc cgtggagatc aactgcaccg gcaatggcac atgtaacatc | 900 |
| agcagggcca gtggaacaa taccctgaag cagatcgcct ccaagctgcg cgagcagtac | 960 |
| ggcaataaga caatcatctt caagccaagc tccggcggcg accccgagtt cgtgaaccac | 1020 |
| tcctttaact gcggcaatgt gaccttttat tgtgattcta cacagctgtt caattctacc | 1080 |
| tggtttaaca gcacatgatg a | 1101 |

<210> SEQ ID NO 89
<211> LENGTH: 1104
<212> TYPE: DNA
<213> ORGANISM: Artificial Sequence
<220> FEATURE:
<223> OTHER INFORMATION: recombinant gp120 lumazine synthase fusion protein

<400> SEQUENCE: 89

| | |
|---|---|
| atgcccatgg gcagcctgca gcccctggcc accctgtacc tgctgggcat gctggtggct | 60 |
| agcgtgctgg ccatgcagat ctacgaaggc aagctgaccg ccgaggggct gagattcgga

```
gctattggcg tcctgattag aggggctact ccccacttcg actatatcgc atcagaagtg      360
agcaagggcc tggccgatct gtctctggag ctgcgaaaac ctatcacttt tggggtcatt      420
actgccgata ccctggaaca ggcaatcgag cgcgccggca ccaagcatgg aaacaaaggc      480
tgggaagcag ccctgtccgc tattgagatg caaatctgt tcaagtctct gaggggaggc       540
tccggaggct ccggcggctc tggcggcagc ggcggaggcg acaccatcac actgccatgc      600
aacggaaccg gaccacctcc acactgtagc tccaatatca ccggactgat cctgacaagg      660
cagggaggct actccaacga taatacagtg atcttcagac catctggcgg cgactggagg      720
gatatcgcaa gatgcaatat caccggcaca gtggtgagca cccagctgtt tctgaacggc      780
tccctggccg gcaatggcac agtgatcagg tccgaggact ggcgcgataa cgccaagtct      840
atctgcgtgc agctgaacac cagcgtggag atcaattgca caggcgccgg ccactgtaat      900
atctctaggg ccaagtggaa caatacccctg aagcagatcg ccagcaagct gagagagcag     960
tacggcaaca agacaatcat cttcaagccc tctagcggcg cgaccctga gttcgtgaac      1020 cacagcttta attgcggcaa cgtgaccttt tattgtgatt ccacccagct gttcaactcc     1080
acctggttta attctacatg atga                                             1104

<210> SEQ ID NO 90
<211> LENGTH: 525
<212> TYPE: DNA
<213> ORGANISM: Artificial Sequence
<220> FEATURE:
<223> OTHER INFORMATION: recombinant gp120 protein

<400> SEQUENCE: 90
gacaccatca cactgccatg caacggaacc ggaccacctc cacactgtag ctccaatatc       60
accggactga tcctgacaag gcagggaggc tactccaacg ataatacagt gatcttcaga      120
ccatctggcg cgactggagg gatatcgcaa gatgcaata tcaccggcac agtggtgagc       180
acccagctgt ttctgaacgg ctccctggcc ggcaatggca cagtgatcag gtccgaggac      240
tggcgcgata cgccaagtc tatctgcgtg cagctgaaca ccagcgtgga gatcaattgc       300
acaggcgccg ccactgtaa tatctctagg gccaagtgga acaataccct gaagcagatc       360
gccagcaagc tgagagagca gtacggcaac aagacaatca tcttcaagcc ctctagcggc      420
ggcgaccctg agttcgtgaa ccacagctt aattgcggcg cgagttctt ttattgtgat       480 tccacccagc tgttcaactc cacctggttt aattctacat gatga                      525

<210> SEQ ID NO 91
<211> LENGTH: 522
<212> TYPE: DNA
<213> ORGANISM: Artificial Sequence
<220> FEATURE:
<223> OTHER INFORMATION: recombinant gp120 protein

<400> SEQUENCE: 91
gacaccatca cactgccatg caggcctgca ccacctccaa actgtacctc taatatcaca       60
ggactgatcc tgaccaggca gggaggatac tctaacgata atacagtgat cttcagacct      120
agcggcggcg actggaggga tatcgcaaga tgcaatatca ccggcacagt ggtgtccacc      180
cagctgtttc tgaatggctc tctggccggc aacggcacag tgatcaggag cgaggactgg      240
cgcgataatg ccaagagcat ctgcgtgcag ctgaacacct ccgtggagat caactgcacc      300
ggcaatggca catgtaacat cagcagggcc aagtggaaca atacccctga agcagatcgcc     360
```

-continued

```
tccaagctgc gcgagcagta cggcaataag acaatcatct tcaagccaag ctccggcggc    420
gaccccgagt tcgtgaacca ctcctttaac tgcggcaatg tgaccttttta ttgtgattct    480 acacagctgt tcaattctac ctggtttaac agcacatgat ga                        522
```

<210> SEQ ID NO 92
<211> LENGTH: 525
<212> TYPE: DNA
<213> ORGANISM: Artificial Sequence
<220> FEATURE:
<223> OTHER INFORMATION: recombinant gp120 protein

<400> SEQUENCE: 92

```
gacaccatca cactgccatg caacggaacc ggaccacctc cacactgtag ctccaatatc     60
accggactga tcctgacaag gcagggaggc tactccaacg ataatacagt gatcttcaga    120
ccatctggcg gcgactggag ggatatcgca agatgcaata tcaccggcac agtggtgagc    180
acccagctgt ttctgaacgg ctccctggcc ggcaatggca cagtgatcag gtccgaggac    240
tggcgcgata cgccaagtc tatctgcgtg cagctgaaca ccagcgtgga gatcaattgc    300
acaggcgccg ccactgtaa tatctctagg gccaagtgga acaataccct gaagcagatc    360
gccagcaagc tgagagagca gtacggcaac aagacaatca tcttcaagcc ctctagcggc    420
ggcgaccctg agttcgtgaa ccacagcttt aattgcggca acgtgacctt ttattgtgat    480
tccacccagc tgttcaactc cacctggttt aattctacat gatga                    525
```

<210> SEQ ID NO 93
<211> LENGTH: 178
<212> TYPE: PRT
<213> ORGANISM: Artificial sequence
<220> FEATURE:
<223> OTHER INFORMATION: lumazine synthase nanoparticle sequence

<400> SEQUENCE: 93

```
Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
                20                  25                  30

Thr Ala Glu Gly Leu Arg Phe Gly Ile Val Ala Ser Arg Phe Asn His
            35                  40                  45

Ala Leu Val Asp Arg Leu Val Glu Gly Ala Ile Asp Ala Ile Val Arg
        50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
            100                 105                 110

Phe Asp Tyr Ile Ala Ser Glu Val Ser Lys Gly Leu Ala Asp Leu Ser
        115                 120                 125

Leu Glu Leu Arg Lys Pro Ile Thr Phe Gly Val Ile Thr Ala Asp Thr
    130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg
```

<210> SEQ ID NO 94
<211> LENGTH: 366
<212> TYPE: PRT
<213> ORGANISM: Artificial sequence
<220> FEATURE:
<223> OTHER INFORMATION: recombinant gp120 lumazine synthase fusion protein

<400> SEQUENCE: 94

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
            20                  25                  30

Thr Ala Glu Gly Leu Arg Phe Gly Ile Val Ala Ser Arg Phe Asn His
        35                  40                  45

Ala Leu Val Asp Arg Leu Val Glu Gly Ala Ile Asp Ala Ile Val Arg
50 55 60

His Gly Gly Arg Glu Glu Asp Ile Thr Leu Val Arg Val Pro Gly Ser
65 70 75 80

Trp Glu Ile Pro Val Ala Ala Gly Glu Leu Ala Arg Lys Glu Asp Ile
85 90 95

Asp Ala Val Ile Ala Ile Gly Val Leu Ile Arg Gly Ala Thr Pro His
100 105 110

Phe Asp Tyr Ile Ala Ser Glu Val Ser Lys Gly Leu Ala Asp Leu Ser
115 120 125

Leu Glu Leu Arg Lys Pro Ile Thr Phe Gly Val Ile Thr Ala Asp Thr
130 135 140

Leu Glu Gln Ala Ile Glu Arg Ala Gly Thr Lys His Gly Asn Lys Gly
145 150 155 160

Trp Glu Ala Ala Leu Ser Ala Ile Glu Met Ala Asn Leu Phe Lys Ser
165 170 175

Leu Arg Gly Gly Ser Gly Gly Ser Gly Gly Ser Gly Gly Ser Gly Gly
180 185 190

Gly Asp Thr Ile Thr Leu Pro Cys Asn Gly Thr Gly Pro Pro Pro His
195 200 205

Cys Ser Ser Asn Ile Thr Gly Leu Ile Leu Thr Arg Gln Gly Gly Tyr
210 215 220

Ser Asn Asp Asn Thr Val Ile Phe Arg Pro Ser Gly Gly Asp Trp Arg
225 230 235 240

Asp Ile Ala Arg Cys Asn Ile Thr Gly Thr Val Val Ser Thr Gln Leu
245 250 255

Phe Leu Asn Gly Ser Leu Ala Gly Asn Gly Thr Val Ile Arg Ser Glu
260 265 270

Asp Trp Arg Asp Asn Ala Lys Ser Ile Cys Val Gln Leu Asn Thr Ser
275 280 285

Val Glu Ile Asn Cys Thr Gly Ala Gly His Cys Asn Ile Ser Arg Ala
290 295 300

Lys Trp Asn Asn Thr Leu Lys Gln Ile Ala Ser Lys Leu Arg Glu Gln
305 310 315 320

Tyr Gly Asn Lys Thr Ile Ile Phe Lys Pro Ser Ser Gly Gly Asp Pro
325 330 335

Glu Phe Val Asn His Ser Phe Asn Cys Gly Gly Glu Phe Phe Tyr Cys
340 345 350

Asp Ser Thr Gln Leu Phe Asn Ser Thr Trp Phe Asn Ser Thr
355 360 365

<210> SEQ ID NO 95
<211> LENGTH: 365
<212> TYPE: PRT
<213> ORGANISM: Artificial sequence
<220> FEATURE:
<223> OTHER INFORMATION: recombinant gp120 lumazine synthase fusion protein

<400> SEQUENCE: 95

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
            20                  25                  30

Thr Ala Glu Gly Leu Arg Ph

<210> SEQ ID NO 96
<211> LENGTH: 365
<212> TYPE: PRT
<213> ORGANISM: Artificial sequence
<220> FEATURE:
<223> OTHER INFORMATION: recombinant gp120 lumazine synthase fusion protein

<400> SEQUENCE: 96

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
            20                  25                  30

Thr Ala Glu Gly Leu Arg Phe Gly Ile Val Ala Ser Arg Phe Asn His
        35                  40                  45

Ala Leu Val Asp Arg Leu Val Glu Gly Ala Ile Asp Ala Ile Val Arg
    50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
            100                 105                 110

Phe Asp Tyr Ile Ala Ser Glu Val Ser Lys Gly Leu Ala Asp Leu Ser
        115                 120                 125

Leu Glu Leu Arg Lys Pro Ile Thr Phe Gly Val Ile Thr Ala Asp Thr
130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
            180                 185                 190

Gly Asp Thr Ile Thr Leu Pro Cys Arg Pro Ala Pro Pro Asn Cys
        195                 200                 205

Thr Ser Asn Ile Thr Gly Leu Ile Leu Thr Arg Gln Gly Gly Tyr Ser
    210                 215                 220

Asn Asp Asn Thr Val Ile Phe Arg Pro Ser Gly Gly Asp Trp Arg Asp
225                 230                 235                 240

Ile Ala Arg Cys Asn Ile Thr Gly Thr Val Ser Thr Gln Leu Phe
                245                 250                 255

Leu Asn Gly Ser Leu Ala Gly Asn Gly Thr Val Ile Arg Ser Glu Asp
            260                 265                 270

Trp Arg Asp Asn Ala Lys Ser Ile Cys Val Gln Leu Asn Thr Ser Val
        275                 280                 285

Glu Ile Asn Cys Thr Gly Asn Gly Thr Cys Asn Ile Ser Arg Ala Lys
    290                 295                 300

Trp Asn Asn Thr Leu Lys Gln Ile Ala Ser Lys Leu Arg Glu Gln Tyr
305                 310                 315                 320

Gly Asn Lys Thr Ile Ile Phe Lys Pro Ser Ser Gly Gly Asp Pro Glu
                325                 330                 335

Phe Val Asn His Ser Phe Asn Cys Thr Gly Glu Phe Pro Tyr Cys Asp
            340                 345                 350

-continued

Ser Thr Gln Leu Phe Asn Ser Thr Trp Phe Asn Ser Thr
            355                 360                 365

<210> SEQ ID NO 97
<211> LENGTH: 365
<212> TYPE: PRT
<213> ORGANISM: Artificial sequence
<220> FEATURE:
<223> OTHER INFORMATION: recombinant gp120 lumazine synthase fusion
      protein

<400> SEQUENCE: 97

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
            20                  25                  30

Thr Ala Glu Gly Leu Arg Phe Gly Ile Val Ala Ser Arg Phe Asn His
        35                  40                  45

Ala Leu Val Asp Arg Leu Val Glu Gly Ala Ile Asp Ala Ile Val Arg
    50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
            100                 105                 110

Phe Asp Tyr Ile Ala Ser Glu Val Ser Lys Gly Leu Ala Asp Leu Ser
        115                 120                 125

Leu Glu Leu Arg Lys Pro Ile Thr Phe Gly Val Ile Thr Ala Asp Thr
130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
            180                 185                 190

Gly Asp Asn Ile Thr Leu Pro Cys Arg Pro Ala Pro Pro Asn Cys
        195                 200                 205

Thr Ser Asn Ile Thr Gly Leu Ile Leu Thr Arg Gln Gly Gly Tyr Ser
    210                 215                 220

Asn Asp Asn Thr Val Ile Phe Arg Pro Ser Gly Gly Asp Trp Arg Asp
225                 230                 235                 240

Ile Ala Arg Cys Asn Ile Thr Gly Asn Val Thr Ser Thr Gln Leu Phe
                245                 250                 255

Leu Asn Gly Ser Leu Ala Gly Asn Gly Thr Val Ile Arg Ser Glu Asp
            260                 265                 270

Trp Arg Asp Asn Ala Lys Ser Ile Cys Val Gln Leu Asn Thr Ser Val
        275                 280                 285

Glu Ile Asn Cys Thr Gly Ala Gly His Cys Asn Ile Ser Arg Ala Lys
    290                 295                 300

Trp Asn Asn Thr Leu Lys Gln Ile Ala Ser Lys Leu Arg Glu Gln Tyr
305                 310                 315                 320

Gly Asn Lys Thr Ile Ile Phe Lys Pro Ser Ser Gly Gly Asp Pro Glu
                325                 330                 335

Phe Val Asn His Ser Phe Asn Cys Thr Gly Glu Phe Phe Tyr Cys Asp
            340                 345                 350

Ser Thr Gln Leu Phe Asn Ser Thr Trp Phe Asn Ser Thr
        355                 360                 365

<210> SEQ ID NO 98
<211> LENGTH: 365
<212> TYPE: PRT
<213> ORGANISM: Artificial sequence
<220> FEATURE:
<223> OTHER INFORMATION: recombinant gp120 lumazine synthase fusion
      protein

<400> SEQUENCE: 98

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
            20                  25                  30

Thr Ala Glu Gly Leu Arg Phe Gly Ile Val Ala Ser Arg Phe Asn His
        35                  40                  45

Ala Leu Val Asp Arg Leu Val Glu Gly Ala Ile Asp Ala Ile Val Arg
    50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
            100                 105                 110

Phe Asp Tyr Ile Ala Ser Glu Val Ser Lys Gly Leu Ala Asp Leu Ser
        115                 120                 125

Leu Glu Leu Arg Lys Pro Ile Thr Phe Gly Val Ile Thr Ala Asp Thr
    130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
            180                 185                 190

Gly Asp Asn Ile Thr Leu Pro Cys Arg Pro Ala Pro Pro Asn Cys
        195                 200                 205

Thr Ser Asn Ile Thr Gly Leu Ile Leu Thr Arg Gln Gly Gly Tyr Ser
    210                 215                 220

Asn Asp Asn Thr Val Ile Phe Arg Pro Ser Gly Gly Asp Trp Arg Asp
225                 230                 235                 240

Ile Ala Arg Cys Gln Ile Ala Gly Thr Val Val Ser Thr Gln Leu Phe
                245                 250                 255

Leu Asn Gly Ser Leu Ala Asn Gly Thr Val Val Ile Arg Ser Glu Asp
            260                 265                 270

Trp Arg Asp Asn Ala Lys Ser Ile Cys Val Gln Leu Asn Thr Ser Val
        275                 280                 285

Glu Ile Asn Cys Thr Gly Asn Gly Thr Cys Asn Ile Ser Arg Ala Lys
    290                 295                 300

Trp Asn Asn Thr Leu Lys Gln Ile Ala Ser Lys Leu Arg Glu Gln Tyr
305                 310                 315                 320

Gly Asn Lys Thr Ile Ile Phe Lys Pro Ser Ser Gly Gly Asp Pro Glu
                325                 330                 335

Phe Val Asn His Ser Phe Asn Cys Thr Gly Glu Phe Phe Tyr Cys Asp

```
                    340                 345                 350
Ser Thr Gln Leu Phe Asn Ser Thr Trp Phe Asn Ser Thr
                355                 360                 365
```

<210> SEQ ID NO 99
<211> LENGTH: 366
<212> TYPE: PRT
<213> ORGANISM: Artificial sequence
<220> FEATURE:
<223> OTHER INFORMATION: recombinant gp120 lumazine synthase fusion
      protein

<400> SEQUENCE: 99

```
Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
                20                  25                  30

Thr Ala Glu Gly Leu Arg Phe Gly Ile Val Ala Ser Arg Phe Asn His
                35                  40                  45

Ala Leu Val Asp Arg Leu Val Glu Gly Ala Ile Asp Ala Ile Val Arg
            50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
                100                 105                 110

Phe Asp Tyr Ile Ala Ser Glu Val Ser Lys Gly Leu Ala Asp Leu Ser
            115                 120                 125

Leu Glu Leu Arg Lys Pro Ile Thr Phe Gly Val Ile Thr Ala Asp Thr
130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
                180                 185                 190

Gly Asp Thr Ile Thr Leu Pro Cys Asn Gly Thr Gly Pro Pro Pro Asn
            195                 200                 205

Cys Thr Ser Asn Ile Thr Gly Leu Ile Leu Thr Arg Gln Gly Gly Tyr
210                 215                 220

Ser Asn Asp Asn Thr Val Ile Phe Arg Pro Ser Gly Gly Asp Trp Arg
225                 230                 235                 240

Asp Ile Ala Arg Cys Asn Ile Thr Gly Thr Val Val Ser Thr Gln Leu
                245                 250                 255

Phe Leu Asn Gly Ser Leu Ala Asn Gly Thr Val Val Ile Arg Ser Glu
                260                 265                 270

Asp Trp Arg Asp Asn Ala Lys Ser Ile Cys Val Gln Leu Asn Thr Ser
            275                 280                 285

Val Glu Ile Asn Cys Thr Gly Asn Gly Thr Cys Asn Ile Ser Arg Ala
            290                 295                 300

Lys Trp Asn Asn Thr Leu Lys Gln Ile Ala Ser Lys Leu Arg Glu Gln
305                 310                 315                 320

Tyr Gly Asn Lys Thr Ile Ile Phe Lys Pro Ser Ser Gly Gly Asp Pro
                325                 330                 335
```

```
Glu Phe Val Asn His Ser Phe Asn Cys Gly Asn Val Thr Phe Tyr Cys
                340                 345                 350

Asp Ser Thr Gln Leu Phe Asn Ser Thr Trp Phe Asn Ser Thr
            355                 360                 365

<210> SEQ ID NO 100
<211> LENGTH: 365
<212> TYPE: PRT
<213> ORGANISM: Artificial sequence
<220> FEATURE:
<223> OTHER INFORMATION: recombinant gp120 lumazine synthase fusion
      protein

<400> SEQUENCE: 100

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
            20                  25                  30

Thr Ala Glu Gly Leu Arg Phe Gly Ile Val Ala Ser Arg Phe Asn His
        35                  40                  45

Ala Leu Val Asp Arg Leu Val Glu Gly Ala Ile Asp Ala Ile Val Arg
    50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
            100                 105                 110

Phe Asp Tyr Ile Ala Ser Glu Val Ser Lys Gly Leu Ala Asp Leu Ser
        115                 120                 125

Leu Glu Leu Arg Lys Pro Ile Thr Phe Gly Val Ile Thr Ala Asp Thr
    130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
            180                 185                 190

Gly Asp Thr Ile Thr Leu Pro Cys Arg Pro Ala Pro Pro His Cys
        195                 200                 205

Ser Ser Asn Ile Thr Gly Leu Ile Leu Thr Arg Gln Gly Gly Tyr Ser
    210                 215                 220

Asn Asp Asn Thr Val Ile Phe Arg Pro Ser Gly Gly Asp Trp Arg Asp
225                 230                 235                 240

Ile Ala Arg Cys Gln Ile Ala Gly Thr Val Val Ser Thr Gln Leu Phe
                245                 250                 255

Leu Asn Gly Ser Leu Ala Gly Asn Gly Thr Val Ile Arg Ser Glu Asp
            260                 265                 270

Trp Arg Asp Asn Ala Lys Ser Ile Cys Val Asn Leu Thr Thr Ser Val
        275                 280                 285

Glu Ile Asn Cys Thr Gly Asn Gly Thr Cys Asn Ile Ser Arg Ala Lys
    290                 295                 300

Trp Asn Asn Thr Leu Lys Gln Ile Ala Ser Lys Leu Arg Glu Gln Tyr
305                 310                 315                 320

Gly Asn Lys Thr Ile Ile Phe Lys Pro Ser Ser Gly Gly Asp Pro Glu
                325                 330                 335
```

Phe Val Asn His Ser Phe Asn Cys Gly Asn Val Thr Phe Tyr Cys Asp
            340                 345                 350

Ser Thr Gln Leu Phe Asn Ser Thr Trp Phe Asn Ser Thr
            355                 360                 365

<210> SEQ ID NO 101
<211> LENGTH: 365
<212> TYPE: PRT
<213> ORGANISM: Artificial sequence
<220> FEATURE:
<223> OTHER INFORMATION: recombinant gp120 lumazine synthase fusion
      protein

<400> SEQUENCE: 101

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
            20                  25                  30

Thr Ala Glu Gly Leu Arg Phe Gly Ile Val Ala Ser Arg Phe Asn His
        35                  40                  45

Ala Leu Val Asp Arg Leu Val Glu Gly Ala Ile Asp Ala Ile Val Arg
    50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
            100                 105                 110

Phe Asp Tyr Ile Ala Ser Glu Val Ser Lys Gly Leu Ala Asp Leu Ser
        115                 120                 125

Leu Glu Leu Arg Lys Pro Ile Thr Phe Gly Val Ile Thr Ala Asp Thr
130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
            180                 185                 190

Gly Asp Thr Ile Thr Leu Pro Cys Arg Pro Ala Pro Pro His Cys
        195                 200                 205

Ser Ser Asn Ile Thr Gly Leu Ile Leu Thr Arg Gln Gly Gly Tyr Ser
    210                 215                 220

Asn Asp Asn Thr Val Ile Phe Arg Pro Ser Gly Gly Asp Trp Arg Asp
225                 230                 235                 240

Ile Ala Arg Cys Asn Ile Thr Gly Thr Val Val Ser Thr Gln Leu Phe
                245                 250                 255

Leu Asn Gly Ser Leu Ala Gly Asn Gly Thr Val Ile Arg Ser Glu Asp
            260                 265                 270

Trp Arg Asp Asn Ala Lys Ser Ile Cys Val Gln Leu Asn Thr Ser Val
        275                 280                 285

Glu Ile Asn Cys Thr Gly Asn Gly Thr Cys Asn Ile Ser Arg Ala Lys
    290                 295                 300

Trp Asn Asn Thr Leu Lys Gln Ile Ala Ser Lys Leu Arg Glu Gln Tyr
305                 310                 315                 320

Gly Asn Lys Thr Ile Ile Phe Lys Pro Ser Ser Gly Gly Asp Pro Glu

```
                    325                 330                 335
Phe Val Asn His Ser Phe Asn Cys Gly Asn Val Thr Phe Tyr Cys Asp
                340                 345                 350
Ser Thr Gln Leu Phe Asn Ser Thr Trp Phe Asn Ser Thr
                355                 360                 365

<210> SEQ ID NO 102
<211> LENGTH: 365
<212> TYPE: PRT
<213> ORGANISM: Artificial sequence
<220> FEATURE:
<223> OTHER INFORMATION: recombinant gp120 lumazine synthase fusion
      protein

<400> SEQUENCE: 102

Met Pro Met Gly Ser Leu Gln Pro Leu Ala Thr Leu Tyr Leu Leu Gly
1               5                   10                  15
Met Leu Val Ala Ser Val Leu Ala Met Gln Ile Tyr Glu Gly Lys Leu
                20                  25                  30
Thr Ala Glu Gly Leu Arg Phe Gly Ile Val Ala Ser Arg Phe Asn His
                35                  40                  45
Ala Leu Val Asp Arg Leu Val Glu Gly Ala Ile Asp Ala Ile Val Arg
            50                  55                  60
His Gly Gly Arg Glu Glu Asp Ile Thr Leu Val Arg Val Pro Gly Ser
65                  70                  75                  80
Trp Glu Ile Pro Val Ala Ala Gly Glu Leu Ala Arg Lys Glu Asp Ile
                85                  90                  95
Asp Ala Val Ile Ala Ile Gly Val Leu Ile Arg Gly Ala Thr Pro His
                100                 105                 110
Phe Asp Tyr Ile Ala Ser Glu Val Ser Lys Gly Leu Ala Asp Leu Ser
                115                 120                 125
Leu Glu Leu Arg Lys Pro Ile Thr Phe Gly Val Ile Thr Ala Asp Thr
            130                 135                 140
Leu Glu Gln Ala Ile Glu Arg Ala Gly Thr Lys His Gly Asn Lys Gly
145                 150                 155                 160
Trp Glu Ala Ala Leu Ser Ala Ile Glu Met Ala Asn Leu Phe Lys Ser
                165                 170                 175
Leu Arg Gly Gly Ser Gly Gly Ser Gly Gly Ser Gly Gly Ser Gly Gly
                180                 185                 190
Gly Asp Thr Ile Thr Leu Pro Cys Arg Pro Ala Pro Pro His Cys
            195                 200                 205
Ser Ser Asn Ile Thr Gly Leu Ile Leu Thr Arg Gln Gly Gly Tyr Ser
            210                 215                 220
Asn Asp Asn Thr Val Ile Phe Arg Pro Ser Gly Gly Asp Trp Arg Asp
225                 230                 235                 240
Ile Ala Arg Cys Gln Ile Ala Gly Asn Val Thr Ser Thr Gln Leu Phe
                245                 250                 255
Leu Asn Gly Ser Leu Ala Gly Asn Gly Thr Val Ile Arg Ser Glu Asp
                260                 265                 270
Trp Arg Asp Asn Ala Lys Ser Ile Cys Val Gln Leu Asn Thr Ser Val
            275                 280                 285
Glu Ile Asn Cys Thr Gly Asn Gly Thr Cys Asn Ile Ser Arg Ala Lys
            290                 295                 300
Trp Asn Asn Thr Leu Lys Gln Ile Ala Ser Lys Leu Arg Glu Gln Tyr
305                 310                 315                 320
```

```
Gly Asn Lys Thr Ile Ile Phe Lys Pro Ser Ser Gly Gly Asp Pro Glu
            325                 330                 335

Phe Val Asn His Ser Phe Asn Cys Gly Asn Val Thr Phe Tyr Cys Asp
            340                 345                 350

Ser Thr Gln Leu Phe Asn Ser Thr Trp Phe Asn Ser Thr
            355                 360                 365

<210> SEQ ID NO 103
<211> LENGTH: 366
<212> TYPE: PRT
<213> ORGANISM: Artificial sequence
<220> FEATURE:
<223> OTHER INFORMATION: recombinant gp120 lumazine synthase fusion
      protein

<400> SEQUENCE: 103

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
            20                  25                  30

Thr Ala Glu Gly Leu Arg Phe Gly Ile Val Ala Ser Arg Phe Asn His
            35                  40                  45

Ala Leu Val Asp Arg Leu Val Glu Gly Ala Ile Asp Ala Ile Val Arg
        50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
            100                 105                 110

Phe Asp Tyr Ile Ala Ser Glu Val Ser Lys Gly Leu Ala Asp Leu Ser
        115                 120                 125

Leu Glu Leu Arg Lys Pro Ile Thr Phe Gly Val Ile Thr Ala Asp Thr
130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
            180                 185                 190

Gly Asp Thr Ile Thr Leu Pro Cys Asn Gly Thr Gly Pro Pro His
        195                 200                 205

Cys Ser Ser Asn Ile Thr Gly Leu Ile Leu Thr Arg Gln Gly Gly Tyr
210                 215                 220

Ser Asn Asp Asn Thr Val Ile Phe Arg Pro Ser Gly Gly Asp Trp Arg
225                 230                 235                 240

Asp Ile Ala Arg Cys Asn Ile Thr Gly Thr Val Val Ser Thr Gln Leu
                245                 250                 255

Phe Leu Asn Gly Ser Leu Ala Gly Asn Gly Thr Val Ile Arg Ser Glu
            260                 265                 270

Asp Trp Arg Asp Asn Ala Lys Ser Ile Cys Val Gln Leu Asn Thr Ser
        275                 280                 285

Val Glu Ile Asn Cys Thr Gly Ala Gly His Cys Asn Ile Ser Arg Ala
    290                 295                 300

Lys Trp Asn Asn Thr Leu Lys Gln Ile Ala Ser Lys Leu Arg Glu Gln
305                 310                 315                 320
```

Tyr Gly Asn Lys Thr Ile Ile Phe Lys Pro Ser Ser Gly Gly Asp Pro
                325                 330                 335

Glu Phe Val Asn His Ser Phe Asn Cys Gly Asn Val Thr Phe Tyr Cys
                340                 345                 350

Asp Ser Thr Gln Leu Phe Asn Ser Thr Trp Phe Asn Ser Thr
                355                 360                 365

<210> SEQ ID NO 104
<211> LENGTH: 366
<212> TYPE: PRT
<213> ORGANISM: Artificial sequence
<220> FEATURE:
<223> OTHER INFORMATION: recombinant gp120 lumazine synthase fusion
      protein

<400> SEQUENCE: 104

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
                20                  25                  30

Thr Ala Glu Gly Leu Arg Phe Gly Ile Val Ala Ser Arg Phe Asn His
            35                  40                  45

Ala Leu Val Asp Arg Leu Val Glu Gly Ala Ile Asp Ala Ile Val Arg
        50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
                100                 105                 110

Phe Asp Tyr Ile Ala Ser Glu Val Ser Lys Gly Leu Ala Asp Leu Ser
            115                 120                 125

Leu Glu Leu Arg Lys Pro Ile Thr Phe Gly Val Ile Thr Ala Asp Thr
        130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
                180                 185                 190

Gly Asp Asn Ile Thr Leu Pro Cys Asn Gly Thr Gly Pro Pro His
            195                 200                 205

Cys Ser Ser Asn Ile Thr Gly Leu Ile Leu Thr Arg Gln Gly Gly Tyr
        210                 215                 220

Ser Asn Asp Asn Thr Val Ile Phe Arg Pro Ser Gly Gly Asp Trp Arg
225                 230                 235                 240

Asp Ile Ala Arg Cys Asn Ile Thr Gly Thr Val Val Ser Thr Gln Leu
                245                 250                 255

Phe Leu Asn Gly Ser Leu Ala Gly Asn Gly Thr Val Ile Arg Ser Glu
                260                 265                 270

Asp Trp Arg Asp Asn Ala Lys Ser Ile Cys Val Gln Leu Asn Thr Ser
            275                 280                 285

Val Glu Ile Asn Cys Thr Gly Ala Gly His Cys Asn Ile Ser Arg Ala
        290                 295                 300

Lys Trp Asn Asn Thr Leu Lys Gln Ile Ala Ser Lys Leu Arg Glu Gln

```
                       305                 310                 315                 320
Tyr Gly Asn Lys Thr Ile Ile Phe Lys Pro Ser Ser Gly Gly Asp Pro
                325                 330                 335

Glu Phe Val Asn His Ser Phe Asn Cys Gly Asn Val Thr Phe Tyr Cys
                340                 345                 350

Asp Ser Thr Gln Leu Phe Asn Ser Thr Trp Phe Asn Ser Thr
                355                 360                 365

<210> SEQ ID NO 105
<211> LENGTH: 366
<212> TYPE: PRT
<213> ORGANISM: Artificial sequence
<220> FEATURE:
<223> OTHER INFORMATION: recombinant gp120 lumazine synthase fusion
      protein

<400> SEQUENCE: 105

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
                20                  25                  30

Thr Ala Glu Gly Leu Arg Phe Gly Ile Val Ala Ser Arg Phe Asn His
                35                  40                  45

Ala Leu Val Asp Arg Leu Val Glu Gly Ala Ile Asp Ala Ile Val Arg
        50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
                100                 105                 110

Phe Asp Tyr Ile Ala Ser Glu Val Ser Lys Gly Leu Ala Asp Leu Ser
            115                 120                 125

Leu Glu Leu Arg Lys Pro Ile Thr Phe Gly Val Ile Thr Ala Asp Thr
130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
                180                 185                 190

Gly Asp Asn Ile Thr Leu Pro Cys Asn Gly Thr Gly Pro Pro His
            195                 200                 205

Cys Ser Ser Asn Ile Thr Gly Leu Ile Leu Thr Arg Gln Gly Gly Tyr
210                 215                 220

Ser Asn Asp Asn Thr Val Ile Phe Arg Pro Ser Gly Gly Asp Trp Arg
225                 230                 235                 240

Asp Ile Ala Arg Cys Asn Ile Thr Gly Thr Val Val Ser Thr Gln Leu
                245                 250                 255

Phe Leu Asn Gly Ser Leu Ala Gly Asn Gly Thr Val Ile Arg Ser Glu
                260                 265                 270

Asp Trp Arg Asp Asn Ala Lys Ser Ile Cys Val Gln Leu Asn Thr Ser
            275                 280                 285

Val Glu Ile Asn Cys Thr Gly Ala Gly His Cys Asn Ile Ser Arg Ala
            290                 295                 300
```

```
Lys Trp Asn Asn Thr Leu Lys Gln Ile Ala Ser Lys Leu Arg Glu Gln
305                 310                 315                 320

Tyr Gly Asn Lys Thr Ile Ile Phe Lys Pro Ser Ser Gly Gly Asp Pro
            325                 330                 335

Glu Phe Val Asn His Ser Phe Asn Cys Gly Gly Glu Phe Phe Tyr Cys
            340                 345                 350

Asn Ser Thr Gln Leu Phe Asn Ser Thr Trp Phe Asn Ser Thr
            355                 360                 365

<210> SEQ ID NO 106
<211> LENGTH: 366
<212> TYPE: PRT
<213> ORGANISM: Artificial sequence
<220> FEATURE:
<223> OTHER INFORMATION: recombinant gp120 lumazine synthase fusion
      protein

<400> SEQUENCE: 106

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
            20                  25                  30

Thr Ala Glu Gly Leu Arg Phe Gly Ile Val Ala Ser Arg Phe Asn His
        35                  40                  45

Ala Leu Val Asp Arg Leu Val Glu Gly Ala Ile Asp Ala Ile Val Arg
    50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
            100                 105                 110

Phe Asp Tyr Ile Ala Ser Glu Val Ser Lys Gly Leu Ala Asp Leu Ser
        115                 120                 125

Leu Glu Leu Arg Lys Pro Ile Thr Phe Gly Val Ile Thr Ala Asp Thr
130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
            180                 185                 190

Gly Asp Thr Ile Thr Leu Pro Cys Asn Gly Thr Gly Pro Pro His
        195                 200                 205

Cys Ser Ser Asn Ile Thr Gly Leu Ile Leu Thr Arg Gln Gly Gly Tyr
    210                 215                 220

Ser Asn Asp Asn Thr Val Ile Phe Arg Pro Ser Gly Gly Asp Trp Arg
225                 230                 235                 240

Asp Ile Ala Arg Cys Asn Ile Thr Gly Thr Val Val Ser Thr Gln Leu
                245                 250                 255

Phe Leu Asn Gly Ser Leu Ala Gly Asn Gly Thr Val Ile Arg Ser Glu
            260                 265                 270

Asp Trp Arg Asp Asn Ala Lys Ser Ile Cys Val Gln Leu Asn Thr Ser
        275                 280                 285

Val Glu Ile Asn Cys Thr Gly Asn Gly Thr Cys Asn Ile Ser Arg Ala
290                 295                 300
```

Lys Trp Asn Asn Thr Leu Lys Gln Ile Ala Ser Lys Leu Arg Glu Gln
305                 310                 315                 320

Tyr Gly Asn Lys Thr Ile Ile Phe Lys Pro Ser Ser Gly Gly Asp Pro
                325                 330                 335

Glu Phe Val Asn His Ser Phe Asn Cys Gly Asn Val Thr Phe Tyr Cys
                340                 345                 350

Asp Ser Thr Gln Leu Phe Asn Ser Thr Trp Phe Asn Ser Thr
                355                 360                 365

<210> SEQ ID NO 107
<211> LENGTH: 366
<212> TYPE: PRT
<213> ORGANISM: Artificial sequence
<220> FEATURE:
<223> OTHER INFORMATION: recombinant gp120 lumazine synthase fusion
      protein

<400> SEQUENCE: 107

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
                20                  25                  30

Thr Ala Glu Gly Leu Arg Phe Gly Ile Val Ala Ser Arg Phe Asn His
            35                  40                  45

Ala Leu Val Asp Arg Leu Val Glu Gly Ala Ile Asp Ala Ile Val Arg
        50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
                100                 105                 110

Phe Asp Tyr Ile Ala Ser Glu Val Ser Lys Gly Leu Ala Asp Leu Ser
            115                 120                 125

Leu Glu Leu Arg Lys Pro Ile Thr Phe Gly Val Ile Thr Ala Asp Thr
130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
            180                 185                 190

Gly Asp Thr Ile Thr Leu Pro Cys Asn Gly Thr Gly Pro Pro His
            195                 200                 205

Cys Ser Ser Asn Ile Thr Gly Leu Ile Leu Thr Arg Gln Gly Gly Tyr
210                 215                 220

Ser Asn Asp Asn Thr Val Ile Phe Arg Pro Ser Gly Gly Asp Trp Arg
225                 230                 235                 240

Asp Ile Ala Arg Cys Asn Ile Thr Gly Thr Val Val Ser Thr Gln Leu
                245                 250                 255

Phe Leu Asn Gly Ser Leu Ala Gly Asn Gly Thr Val Ile Arg Ser Glu
                260                 265                 270

Asp Trp Arg Asp Asn Ala Lys Ser Ile Cys Val Gln Leu Asn Thr Ser
            275                 280                 285

Val Glu Ile Asn Cys Thr Gly Ala Gly His Cys Asn Ile Ser Arg Ala

```
            290                 295                 300
Lys Trp Asn Asn Thr Leu Lys Gln Ile Ala Ser Lys Leu Arg Glu Gln
305                 310                 315                 320

Tyr Gly Asn Lys Thr Ile Ile Phe Lys Pro Ser Ser Gly Gly Asp Pro
                325                 330                 335

Glu Phe Val Asn His Ser Phe Asn Cys Gly Asn Val Thr Phe Tyr Cys
                340                 345                 350

Asn Ser Thr Gln Leu Phe Asn Ser Thr Trp Phe Asn Ser Thr
                355                 360                 365
```

<210> SEQ ID NO 108
<211> LENGTH: 366
<212> TYPE: PRT
<213> ORGANISM: Artificial sequence
<220> FEATURE:
<223> OTHER INFORMATION: recombinant gp120 lumazine synthase fusion protein

<400> SEQUENCE: 108

```
Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
                20                  25                  30

Thr Ala Glu Gly Leu Arg Phe Gly Ile Val Ala Ser Ar

```
Val Glu Ile Asn Cys Thr Gly Asn Gly Thr Cys Asn Ile Ser Arg Ala
    290                 295                 300

Lys Trp Asn Asn Thr Leu Lys Gln Ile Ala Ser Lys Leu Arg Glu Gln
305                 310                 315                 320

Tyr Gly Asn Lys Thr Ile Ile Phe Lys Pro Ser Ser Gly Gly Asp Pro
                325                 330                 335

Glu Phe Val Asn His Ser Phe Asn Cys Gly Gly Glu Phe Phe Tyr Cys
                340                 345                 350

Asn Ser Thr Gln Leu Phe Asn Ser Thr Trp Phe Asn Ser Thr
            355                 360                 365
```

<210> SEQ ID NO 109
<211> LENGTH: 365
<212> TYPE: PRT
<213> ORGANISM: Artificial sequence
<220> FEATURE:
<223> OTHER INFORMATION: recombinant gp120 lumazine synthase fusion protein

<400> SEQUENCE: 109

```
Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
                20                  25                  30

Thr Ala Glu Gly Leu Arg Phe Gly Ile Val Ala Ser Arg Phe Asn His
            35                  40                  45

Ala Leu Val Asp Arg Leu Val Glu Gly Ala Ile Asp Ala Ile Val Arg
50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
                100                 105                 110

Phe Asp Tyr Ile Ala Ser Glu Val Ser Lys Gly Leu Ala Asp Leu Ser
            115                 120                 125

Leu Glu Leu Arg Lys Pro Ile Thr Phe Gly Val Ile Thr Ala Asp Thr
130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
            180                 185                 190

Gly Asp Thr Ile Thr Leu Pro Cys Arg Pro Ala Pro Pro His Cys
            195                 200                 205

Ser Ser Asn Ile Thr Gly Leu Ile Leu Thr Arg Gln Gly Gly Tyr Ser
            210                 215                 220

Asn Asp Asn Thr Val Ile Phe Arg Pro Ser Gly Gly Asp Trp Arg Asp
225                 230                 235                 240

Ile Ala Arg Cys Asn Ile Thr Gly Thr Val Val Ser Thr Gln Leu Phe
                245                 250                 255

Leu Asn Gly Ser Leu Ala Gly Asn Gly Thr Val Ile Arg Ser Glu Asn
            260                 265                 270

Phe Thr Asp Asn Ala Lys Ser Ile Cys Val Gln Leu Asn Thr Ser Val
            275                 280                 285
```

```
Glu Ile Asn Cys Thr Gly Asn Gly Thr Cys Asn Ile Ser Arg Ala Lys
            290                 295                 300

Trp Asn Asn Thr Leu Lys Gln Ile Ala Ser Lys Leu Arg Glu Gln Tyr
305                 310                 315                 320

Gly Asn Lys Thr Ile Ile Phe Lys Pro Ser Gly Gly Asp Pro Glu
                325                 330                 335

Phe Val Asn His Ser Phe Asn Cys Gly Asn Val Thr Phe Tyr Cys Asp
            340                 345                 350

Ser Thr Gln Leu Phe Asn Ser Thr Trp Phe Asn Ser Thr
            355                 360                 365

<210> SEQ ID NO 110
<211> LENGTH: 365
<212> TYPE: PRT
<213> ORGANISM: Artificial sequence
<220> FEATURE:
<223> OTHER INFORMATION: recombinant gp120 lumazine synthase fusion
      protein

<400> SEQUENCE: 110

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
            20                  25                  30

Thr Ala Glu Gly Leu Arg Phe Gly Ile Val Ala Ser Arg Phe Asn His
        35                  40                  45

Ala Leu Val Asp Arg Leu Val Glu Gly Ala Ile Asp Ala Ile Val Arg
    50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
            100                 105                 110

Phe Asp Tyr Ile Ala Ser Glu Val Ser Lys Gly Leu Ala Asp Leu Ser
        115                 120                 125

Leu Glu Leu Arg Lys Pro Ile Thr Phe Gly Val Ile Thr Ala Asp Thr
130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
            180                 185                 190

Gly Asp Thr Ile Thr Leu Pro Cys Arg Pro Ala Pro Pro His Cys
        195                 200                 205

Ser Ser Asn Ile Thr Gly Leu Ile Leu Thr Arg Gln Gly Gly Tyr Ser
    210                 215                 220

Asn Asp Asn Thr Val Ile Phe Arg Pro Ser Gly Gly Asp Trp Arg Asp
225                 230                 235                 240

Ile Ala Arg Cys Gln Ile Ala Gly Asn Val Thr Ser Thr Gln Leu Phe
                245                 250                 255

Leu Asn Gly Ser Leu Ala Gly Asn Gly Thr Val Ile Arg Ser Glu Asp
            260                 265                 270

Trp Arg Asp Asn Ala Lys Ser Ile Cys Val Gln Leu Asn Thr Ser Val
```

```
                275                 280                 285
Glu Ile Asn Cys Thr Gly Ala Gly His Cys Asn Ile Ser Arg Ala Lys
    290                 295                 300

Trp Asn Asn Thr Leu Lys Gln Ile Ala Ser Lys Leu Arg Glu Gln Tyr
305                 310                 315                 320

Gly Asn Lys Thr Ile Ile Phe Lys Pro Ser Ser Gly Gly Asp Pro Glu
                325                 330                 335

Phe Val Asn His Ser Phe Asn Cys Gly Asn Val Thr Phe Tyr Cys Asp
                340                 345                 350

Ser Thr Gln Leu Phe Asn Ser Thr Trp Phe Asn Ser Thr
                355                 360                 365

<210> SEQ ID NO 111
<211> LENGTH: 365
<212> TYPE: PRT
<213> ORGANISM: Artificial sequence
<220> FEATURE:
<223> OTHER INFORMATION: recombinant gp120 lumazine synthase fusion
      protein

<400> SEQUENCE: 111

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
                20                  25                  30

Thr Ala Glu Gly Leu Arg Phe Gly Ile Val Ala Ser Arg Phe Asn His
                35                  40                  45

Ala Leu Val Asp Arg Leu Val Glu Gly Ala Ile Asp Ala Ile Val Arg
    50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
                100                 105                 110

Phe Asp Tyr Ile Ala Ser Glu Val Ser Lys Gly Leu Ala Asp Leu Ser
            115                 120                 125

Leu Glu Leu Arg Lys Pro Ile Thr Phe Gly Val Ile Thr Ala Asp Thr
130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
                180                 185                 190

Gly Asp Thr Ile Thr Leu Pro Cys Arg Pro Ala Pro Pro His Cys
                195                 200                 205

Ser Ser Asn Ile Thr Gly Leu Ile Leu Thr Arg Gln Gly Gly Tyr Ser
    210                 215                 220

Asn Asp Asn Thr Val Ile Phe Arg Pro Ser Gly Gly Asp Trp Arg Asp
225                 230                 235                 240

Ile Ala Arg Cys Gln Ile Ala Gly Asn Val Thr Ser Thr Gln Leu Phe
                245                 250                 255

Leu Asn Gly Ser Leu Ala Gly Gly Glu Val Asn Gly Thr Ser Glu Asp
                260                 265                 270
```

```
Trp Arg Asp Asn Ala Lys Ser Ile Cys Val Gln Leu Asn Thr Ser Val
            275                 280                 285

Glu Ile Asn Cys Thr Gly Ala Gly His Cys Asn Ile Ser Arg Ala Lys
        290                 295                 300

Trp Asn Asn Thr Leu Lys Gln Ile Ala Ser Lys Leu Arg Glu Gln Tyr
305                 310                 315                 320

Gly Asn Lys Thr Ile Ile Phe Lys Pro Ser Ser Gly Gly Asp Pro Glu
                325                 330                 335

Phe Val Asn His Ser Phe Asn Cys Gly Asn Val Thr Phe Tyr Cys Asp
            340                 345                 350

Ser Thr Gln Leu Phe Asn Ser Thr Trp Phe Asn Ser Thr
        355                 360                 365
```

<210> SEQ ID NO 112
<211> LENGTH: 366
<212> TYPE: PRT
<213> ORGANISM: Artificial sequence
<220> FEATURE:
<223> OTHER INFORMATION: recombinant gp120 lumazine synthase fusion protein

<400> SEQUENCE: 112

```
Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
            20                  25                  30

Thr Ala Glu Gly Leu Arg Phe Gly Ile Val Ala Ser Arg Phe Asn His
        35                  40                  45

Ala Leu Val Asp Arg Leu Val Glu Gly Ala Ile Asp Ala Ile Val Arg
    50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
            100                 105                 110

Phe Asp Tyr Ile Ala Ser Glu Val Ser Lys Gly Leu Ala Asp Leu Ser
        115                 120                 125

Leu Glu Leu Arg Lys Pro Ile Thr Phe Gly Val Ile Thr Ala Asp Thr
    130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
            180                 185                 190

Gly Asp Thr Ile Thr Leu Pro Cys Asn Gly Thr Gly Pro Pro His
        195                 200                 205

Cys Ser Ser Asn Ile Thr Gly Leu Ile Leu Thr Arg Gln Gly Gly Tyr
    210                 215                 220

Ser Asn Asp Asn Thr Val Ile Phe Arg Pro Ser Gly Gly Asp Trp Arg
225                 230                 235                 240

Asp Ile Ala Arg Cys Gln Ile Ala Gly Asn Val Thr Ser Thr Gln Leu
                245                 250                 255

Phe Leu Asn Gly Ser Leu Ala Asn Gly Thr Val Asn Gly Thr Ser Glu
            260                 265                 270
```

```
Asp Trp Arg Asp Asn Ala Lys Ser Ile Cys Val Gln Leu Asn Thr Ser
        275                 280                 285

Val Glu Ile Asn Cys Thr Gly Ala Gly His Cys Asn Ile Ser Arg Ala
    290                 295                 300

Lys Trp Asn Asn Thr Leu Lys Gln Ile Ala Ser Lys Leu Arg Glu Gln
305                 310                 315                 320

Tyr Gly Asn Lys Thr Ile Ile Phe Lys Pro Ser Ser Gly Gly Asp Pro
                325                 330                 335

Glu Phe Val Asn His Ser Phe Asn Cys Gly Asn Val Thr Phe Tyr Cys
                340                 345                 350

Asp Ser Thr Gln Leu Phe Asn Ser Thr Trp Phe Asn Ser Thr
                355                 360                 365

<210> SEQ ID NO 113
<211> LENGTH: 365
<212> TYPE: PRT
<213> ORGANISM: Artificial sequence
<220> FEATURE:
<223> OTHER INFORMATION: recombinant gp120 lumazine synthase fusion
      protein

<400> SEQUENCE: 113

Met Pro Met Gly Ser Leu Gln Pro Leu Ala Thr Leu Tyr Leu Leu Gly
1               5                   10                  15

Met Leu Val Ala Ser Val Leu Ala Met Gln Ile Tyr Glu Gly Lys Leu
            20                  25                  30

Thr Ala Glu Gly Leu Arg Phe Gly Ile Val Ala Ser Arg Phe Asn His
        35                  40                  45

Ala Leu Val Asp Arg Leu Val Glu Gly Ala Ile Asp Ala Ile Val Arg
    50                  55                  60

His Gly Gly Arg Glu Glu Asp Ile Thr Leu Val Arg Val Pro Gly Ser
65                  70                  75                  80

Trp Glu Ile Pro Val Ala Ala Gly Glu Leu Ala Arg Lys Glu Asp Ile
                85                  90                  95

Asp Ala Val Ile Ala Ile Gly Val Leu Ile Arg Gly Ala Thr Pro His
                100                 105                 110

Phe Asp Tyr Ile Ala Ser Glu Val Ser Lys Gly Leu Ala Asp Leu Ser
        115                 120                 125

Leu Glu Leu Arg Lys Pro Ile Thr Phe Gly Val Ile Thr Ala Asp Thr
130                 135                 140

Leu Glu Gln Ala Ile Glu Arg Ala Gly Thr Lys His Gly Asn Lys Gly
145                 150                 155                 160

Trp Glu Ala Ala Leu Ser Ala Ile Glu Met Ala Asn Leu Phe Lys Ser
                165                 170                 175

Leu Arg Gly Gly Ser Gly Gly Ser Gly Gly Ser Gly Gly Ser Gly Gly
                180                 185                 190

Gly Asp Thr Ile Thr Leu Pro Cys Arg Pro Ala Pro Pro Asn Cys
        195                 200                 205

Thr Ser Asn Ile Thr Gly Leu Ile Leu Thr Arg Gln Gly Gly Tyr Ser
    210                 215                 220

Asn Asp Asn Thr Val Ile Phe Arg Pro Ser Gly Gly Asp Trp Arg Asp
225                 230                 235                 240

Ile Ala Arg Cys Gln Ile Ala Gly Thr Val Ser Thr Gln Leu Phe
                245                 250                 255

Leu Asn Gly Ser Le

-continued

```
              260                 265                 270
Trp Arg Asp Asn Ala Lys Ser Ile Cys Val Gln Leu Asn Thr Ser Val
            275                 280                 285

Glu Ile Asn Cys Thr Gly Asn Gly Thr Cys Asn Ile Ser Arg Ala Lys
            290                 295                 300

Trp Asn Asn Thr Leu Lys Gln Ile Ala Ser Lys Leu Arg Glu Gln Tyr
305                 310                 315                 320

Gly Asn Lys Thr Ile Ile Phe Lys Pro Ser Ser Gly Gly Asp Pro Glu
                325                 330                 335

Phe Val Asn His Ser Phe Asn Cys Gly Asn Val Thr Phe Tyr Cys Asp
            340                 345                 350

Ser Thr Gln Leu Phe Asn Ser Thr Trp Phe Asn Ser Thr
            355                 360                 365
```

GLYCAN-MASKED ENGINEERED OUTER DOMAINS OF HIV-1 gp120 AND THEIR USE

CROSS REFERENCE TO RELATED APPLICATIONS

This application is a continuation of U.S. Non-Provisional application Ser. No. 16/496,912, filed Sep. 23, 2019, which is the U.S. National Stage of International Application No. PCT/US2018/024330, filed Mar. 26, 2018, which was published in English under PCT Article 21(2), which in turn claims the benefit of U.S. Provisional Application No. 62/476,397, filed Mar. 24, 2017. Each of the above-listed applications is herein incorporated by reference in its entirety.

FIELD

This disclosure relates to immunogens comprising an engineered outer domain of human immunodeficiency virus type 1 (HIV-1) gp120 and their use to induce an immune response in a subject.

BACKGROUND

Millions of people are infected with HIV-1 worldwide, and 2.5 to 3 million new infections have been estimated to occur yearly. Although effective antiretroviral therapies are available, millions succumb to AIDS every year, especially in sub-Saharan Africa, underscoring the need to develop measures to prevent the spread of this disease.

An enveloped virus, HIV-1 hides from humoral recognition behind a wide array of protective mechanisms. The major envelope protein of HIV-1 is a glycoprotein of approximately 160 kD (gp160). During infection, proteases of the host cell cleave gp160 into gp120 and gp41. Gp41 is an integral membrane protein, while gp120 protrudes from the mature virus. Together gp120 and gp41 make up the HIV-1 Envelope protein (Env) spike, which is a target for neutralizing antibodies. For example, broadly neutralizing antibodies (bnAbs) that bind to gp120 have been identified, including VRC01-class antibodies (such as VRC01), which specifically binds to the CD4-binding site (CD4bs) on the outer domain of gp120 and can neutralize a high percentage of HIV-1 strains.

One challenge for elicitation of protective immune response to HIV-1 is that most broadly neutralizing antibodies to HIV-1 undergo extensive somatic mutation following germline recombination. In many instances, such as with VRC01, the putative germline precursor antibody binds poorly or fails to bind to the viral antigen. Development of immunogens that can prime a subdominant antibody response that ultimately leads to a neutralizing response targeting the viral antigen in a reproducible manner has been difficult. Further, available "germline-targeting" immunogens are often heavily mutated forms of a native viral antigen that can produce a substantial off-target and unintended immune response when administered to a subject.

Thus, there is a need for immunogens that are capable of inducing an immune response that activates relatively rare precursors of bnAbs (such as VRC01-class antibodies), but that are also immune-focused to reduce off-target immune activation.

SUMMARY

Provided herein are engineered HIV-1 gp120 outer domain (eOD) immunogens that have been modified to activate precursors of VRC01-class bnAbs, and also include selective glycosylation to reduce production of an off-target immune response. The disclosed immunogens provide a substantially more focused immune response compared to prior eOD immunogens for induction of VRC01-class precursor antibodies.

In some embodiments, the immunogen comprises an eOD comprising an amino acid sequence according to SEQ ID NO: 1 further comprising amino acid substitutions, insertions, and/or deletions as follows: (a) amino acid substitutions to introduce N-linked glycan sequons beginning at residues 52 and 70, or residues 52 and 71 with a E70G substitution, of SEQ ID NO: 1; (b) amino acid substitutions to introduce N-linked glycan sequons beginning at one or more of residues 8, 14, 102, 153, and 159 of SEQ ID NO: 1, wherein a glycine insertion is introduced between residues 10 and 11 if the N-linked glycan sequon beginning at residue 8 is introduced; and (c) optionally one or more additional amino acid substitutions, insertions, or deletions. The eOD also comprises N-linked glycan sequons beginning at residues corresponding to residues 18, 65, 92, 98, 106, 113, 129, 146, 165, and 170 of SEQ ID NO: 1, one or more of which (such as all) may be glycosylated. Further, the residues of the eOD corresponding to residues 25-45, 79-85, and 126-145 of SEQ ID NO: 1 are identical to SEQ ID NO: 1. Additionally, the remaining residues of the eOD comprise an amino acid sequence at least 90% identical to the corresponding residues of SEQ ID NO: 1. The eOD specifically binds to VRC01-class bnAbs and their inferred germline revertants.

In some embodiments, the immunogen comprises an eOD comprising an amino acid sequence according to SEQ ID NO: 1 further comprising amino acid substitutions, insertions, and/or deletions as follows: (a) amino acid substitutions to N-linked glycan sequons beginning at one or more of residues 8, 14, 56, 70, 71, 74, 102, and 153 of SEQ ID NO: 1, wherein a glycine insertion is introduced between residues 10 and 11 if the N-linked glycan sequon beginning at residue 8 is introduced, and an E70G substitution is introduced if the N-linked glycan sequon beginning at residue 71 is introduced; (b) optionally a GG substitution for the residues at positions corresponding to positions 70 and 71 of SEQ ID NO: 1 if N-linked glycan sequons beginning at residue 70 or 71 are not introduced; and (c) optionally one or more additional amino acid substitutions, insertions, or deletions. The eOD also comprises N-linked glycan sequons beginning at residues corresponding to residues 18, 65, 92, 98, 106, 113, 129, 146, 165, and 170 of SEQ ID NO: 1, one or more of which (such as all) may be glycosylated. Further, the residues of the eOD corresponding to residues 25-45, 79-85, and 126-145 of SEQ ID NO: 1 are identical to SEQ ID NO: 1. Additionally, the remaining residues of the eOD comprise an amino acid sequence at least 90% identical to the corresponding residues of SEQ ID NO: 1. The eOD specifically binds to VRC01-class bnAbs and their inferred germline revertants.

In some embodiments, the immunogen comprises an eOD comprising an amino acid sequence set forth as any one of SEQ ID NOs: 15 (Mut15), 16 (Mut16), 17 (Mut17), 18 (Mut18), 19 (Mut19), 21 (Mut21), 27 (Mut27), 28 (Mut28), 29 (Mut29), 33 (Mut33), 34 (Mut34), 35 (Mut35), 36 (Mut36), 37 (Mut37), 38 (Mut38), 47 (Mut47), 79 (Mut49), 80 (Mut50), 81 (Mut51), or 82 (Mut52).

In some embodiments, the eOD is linked to a subunit of a self-assembling protein nanoparticle (such as a lumazine synthase subunit) by a peptide linker, or is directly linked to the subunit of the self-assembling protein nanoparticle. The eOD linked to the subunit of the self-assembling protein nanoparticle can be expressed under conditions for self-assembly into a globular protein nanoparticle (such as a lumazine synthase 60mer). In some embodiments, the eOD linked to the subunit of the self-assembling protein nanoparticle comprises an amino acid sequence set forth as residues 20-361 of any one of SEQ ID NOs: 51 (Mut15), 56 (Mut21), 60 (Mut33), 61 (Mut34), 62 (Mut35), 63 (Mut36), 64 (Mut37), 65 (Mut38), or 85 (Mut51); or residues 20-360 of any one of SEQ ID NOs: 52 (Mut16), 53 (Mut17), 54 (Mut18), 55 (Mut19), 57 (Mut27), 58 (Mut28), 59 (Mut29), 76 (Mut47), 83 (Mut49), 84 (Mut50), 86 (Mut52).

When administered to a subject, the immunogen induces an immune response that targets the CD4 binding site (CD4bs) of gp120. For example, the immunogen can be used to prime an immune response to the CD4 binding site of gp120. In some embodiments, the immune response activates memory B cells that bind to the eOD, wherein at least 50% of the memory B cells that bind to the eOD bind to a CD4 binding site on the eOD. In some embodiments, the immune response comprises production of IGHV1-2*02 containing antibodies that bind to the CD4bs on the eOD of the immunogen.

Nucleic acid molecules encoding the disclosed immunogens and expression vectors (such as an inactivated or attenuated viral vector) including the nucleic acid molecules are also provided.

Compositions including the disclosed immunogens are also provided. The composition may be a pharmaceutical composition suitable for administration to a subject, and may also be contained in a unit dosage form. The compositions can further include an adjuvant. The immunogen can be further conjugated to a carrier to facilitate presentation to the immune system.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1D. Immune focusing of the eOD-GT8 immunogen by addition of N-linked glycans to mask non-CD4bs epitopes. eOD-GT8 is a fusion protein including an eOD fused (via a peptide linker) to a single subunit of an *Aquifex aeolicus* lumazine synthase nanoparticle, that self-assembles into a spherical 60mer nanoparticle with the eOD extending radially outward from the nanoparticle surface. (FIG. 1A) Flow chart illustrating the strategy employed for adding new glycans to non-CD4bs surfaces of eOD-GT8. Diamonds indicate queries for surface residues; an affirmative answer results in progress to the next step. Rectangles indicate consecutive steps in the strategy. (FIG. 1B) Summary of added N-linked glycan positions on single mutants eOD-GT8-mut1-12 and 23 and multiple mutants eOD-GT8-mut15, -mut16, -mut21, and -mut33. Hxbc2 residue numbering and wildtype amino acid sequences and mutated amino acid sequences were shown. Mutant residues are shown in bold text. Each glycan was introduced by mutating the target sequence to include an NxT sequon. For labeling simplicity, the eOD-GT8 mutants are referred to by Mut # in this panel and subsequent figures. Sequences shown include EEEV (residues 70-73 of SEQ ID NO: 1). (FIG. 1C) Surface representations of the eOD portion of eOD-GT8 showing the locations of predicted native glycans (light grey) and all 13 additional glycans modeled together (medium grey). The lower panels are rotated 180 degrees along the Y-axis from the top panels to provide a view of the opposite side of eOD-GT8. (FIG. 1D) Examples of combinations of glycan additions from four selected designs modeled on eOD-GT8 with design numbers listed below each model. All models in FIGS. 1C and 1D were based on the published eOD-GT8 structure (protein data bank (PDB) entry 5IES).

(FIG. 2A) Heatmaps illustrating results of antigenic analysis by ELISA of 48 different eOD-GT8 60mer mutants. Shading indicates the OD450 of binding. Glycan mutants eOD-GT8-mut1-48 60mer, the parental eOD-GT8 60mer, and its CD4bs-knock out mutant (KO) were assayed for binding to two panels of antibodies. One panel included three CD4bs-specific monoclonal antibodies and the other panel included four non-CD4bs, eOD-GT8-reactive monoclonal antibodies X1A2, X1C6, mA9 and mE4 as well as polyclonal rabbit anti-gp120 serum. Four mutants, eOD-GT8-mut15, -mut16, -mut21, and -mut33 60mer (marked by stars) bound with lowest affinity to non-CD4bs antibodies while retaining high affinity for CD4bs-specific mAbs. An "X" indicates "assay not performed". See FIG. 11 for mutation information. (FIG. 2B) Heatmap displaying area under the curve (AUC) for ELISA of eOD-GT8 (eOD8), its CD4bs-KO mutant (KO), and the glycan mutants eOD-GT8-mut15, -mut16, -mut21, and -mut33 60mer to an expanded panel of CD4bs-specific VRC01-class antibodies and germline revertant antibodies, as well as 25 published human VRC01-class IgG precursors (HuGL1-25) isolated from naïve human peripheral blood mononuclear cells (PBMCs) using eOD-GT8 as a sorting probe. High affinity binders ($K_D$ to eOD-GT8 less than 3 µM) are marked with stars. Polyclonal rabbit-anti-gp120 serum and two non-CD4bs mAbs were used as controls for comparison. (FIG. 2C) Scatter plot showing $K_D$ values for the recognition of eOD-GT8 60mer and eOD-GT8-mut15, -mut16, and -mut33 60mer by 19 human VRC01-class IgG precursors (from HuGL1-25), obtained by surface plasmon resonance (SPR). The X-axis indicates the nanoparticle immunogens tested, and Y-axis indicates $K_D$ values of these antigens to 19 HuGL Fabs. The results shown represent one of two independent experiments with similar results. Average $K_D$ values for the binding of eOD-GT8 60mer, eOD-GT8-mut15, -mut16, and -mut33 60mer to 19 HuGL Fabs are shown in the bottom of Y-axis. (FIG. 2D) Plot illustrating the increase in eOD-GT8 mutant $K_D$s relative to eOD-GT8 for 19 HuGL Fabs. $K_D$s were from FIG. 2C. The X-axis indicates the individual HuGL Fabs tested, and the Y-axis indicates the ratio of eOD-GT8 mutant $K_D$s to parental eOD-GT8 $K_D$s for each HuGL Fab tested. Dashed line in D indicates a ratio of 1.0 for eOD-GT8.

(FIG. 3A) Typical 2D-averaged negative-stained electron microscopy images of the parental and the indicated glycan mutant eOD-GT8 60mer nanoparticles. Average dimensions are shown with standard deviations. (FIGS. 3B-3C) The glycan occupancy bar graphs for parental and mutant eOD-GT8s as detected by LC-MS. The X-axis indicates the amino acid positions circularly permutated eOD-GT8 immunogen. The native and added ("*") N-linked glycans are each labeled with HxBc2 residue positions. The Y-axis indicates the percentage glycan occupancy for each of the glycosylated positions. Locations of predicted, but unoccupied N-linked glycans (Hxbc2 positions 339 and 356 respectively) were marked with black dots on the X-axis.

FIGS. 4A-4G. Glycan-masking of eOD-GT8 60mer immunogens improved the CD4bs-specific antibody response. (FIG. 4A) Immunization scheme. Three or five mice per group were immunized once as indicated. (FIG. 4B) ELISA plots showing recognition of eOD-GT8 (solid lines) and eOD-GT8 KO (dashed lines) proteins by sera collected two or three weeks after immunization of the five indicated groups. Mean±SEM are shown for each group. (FIG. 4C) Quantification of ELISA data from FIG. 4B showing the $ED_{50}$ (dilution factor) of total antigen-specific (based on eOD-GT8 binding curves), non-CD4bs-specific (based on eOD-GT8 KO binding curves) and CD4bs-specific ("total" minus "non-CD4bs") responses, and the percentages of non-CD4bs-specific and CD4bs-specific responses in the sera. (FIG. 4D) Representative flow cytometry plots for IgG$^+$ B cells collected from IGHV1-2*02 KI mice immunized with eOD-GT8 or eOD-GT8-mut15, 16, 21 or 33 60mer three weeks after immunization. IgG$^+$ B-cells were identified as reactive with eOD-GT8, eOD-GT8 KO or both. The lower right quadrant of each plot indicates the number of CD4bs-specific IgG$^+$ B cells in total eOD-GT8 reactive B cell populations (eOD-GT8$^+$eOD-GT8 KO$^-$), and the upper right quadrants shows the number of non-CD4bs B cells (eOD-GT8$^+$eOD-GT8 KO$^+$ double positive). (FIG. 4E) Scatter plots quantifying the percentages (mean±SEM) of CD4bs-specific (left) and non-CD4bs (right) IgG$^+$ B cells within total IgG$^+$ populations from immunized mice. CD4bs-specific B cells were defined as those binding to eOD-GT8 but not to the CD4bs KO version of eOD-GT8, whereas the non-CD4bs-specific B cells binding to both oOD-GT8 and its CD4bs KO mutant. (FIG. 4F) Scatter plot of relative percentages of CD4bs-specific B cells within the total antigen-specific populations from immunized mice are shown with mean±SEM. Relative percentages of CD4bs-specific B cells are calculated by dividing the percentages of CD4bs-specific B cells with the total percentages of antigen-specific B cells in total IgG$^+$ population. Antigen-specific B cells are the sum of the CD4bs-specific B cells and non-CD4bs B cells shown in FIG. 4D. (FIG. 4G) Tabulated values for the frequencies of VRC01-class antibodies among total amplified K chains from CD4bs-specific B cells elicited by eOD-GT8 or eOD-GT8 glycan-masked mutants. Frequencies of VRC01-class antibodies among amplified K chains were calculated by dividing the total numbers of isolated VRC01-class antibodies in each group by the total numbers of amplified kappa chains in each group. See also FIGS. 9 and 12.

FIGS. 5A-5D. Investigation of additional immunization regimens confirmed that glycan-masking of eOD-GT8 improves the CD4bs-specific antibody response. (FIG. 5A) Immunization schemes. Three mice per group were immunized once or twice adjuvanted with Ribi or Poly I:C as indicated with a 4 week interval. (FIG. 5B) Scatter plots of serum ELISA results showing percentages (mean±SEM) of CD4bs-specific serum responses ($ED_{50}$ of eOD-GT8 minus $ED_{50}$ of eOD-GT8 KO) relative to the total eOD-GT8 response ($ED_{50}$ of eOD-GT8). (FIG. 5C) Scatter plots showing percentages (mean±SEM) of CD4bs-specific B cells relative to the total antigen-specific populations calculated with the same method described in FIG. 4F. (FIG. 5D) Tabulated values for the frequencies of VRC01-class antibodies among total amplified K chains from CD4bs-specific B cells elicited by eOD-GT8 or eOD-GT8 glycan-masked mutants. Frequencies of VRC01-class antibodies among amplified K chains were calculated by dividing the total numbers of isolated VRC01-class antibodies in each group with total numbers of amplified kappa chains in each group. See also FIGS. 13 and 14.

(FIG. 6A) Scatter plots showing the percent CD4bs-specific serum response (Y axis) for each mouse immunized with the indicated immunogen (X axis). CD4bs-specific serum responses were calculated as $ED_{50}$ of eOD-GT8 minus ED50 of eOD-GT8 KO divided by the total eOD-GT8 response ($ED_{50}$). (FIG. 6B) Scatter plots showing percent (Y axis) CD4bs-specific B cells relative to the total antigen-specific B cell populations elicited in each individual mouse immunized with the indicated immunogens (X axis). For FIGS. 6A and 6B, each dot represents a mouse, the mean±SEM is indicated for each immunogen group and P-values (unpaired Mann-Whitney) less than 0.05 are shown after confirming an overall nonparametric ANOVA Krustal-Wallis test gave a p-value of less than 0.0001. (FIG. 6C) The frequencies of VRC01-class antibodies elicited by eOD-GT8 60mer and eOD-GT8 60mer glycan-masked mutants. Frequencies of VRC01-class antibodies among amplified K chains were calculated by dividing the total numbers of isolated VRC01-class antibodies in each mouse with total numbers of amplified K chains in each mouse. Each dot represents a mouse, the mean is indicated by the top of the gray bar, ±SEM error is shown for each mean and P-values (unpaired Mann-Whitney) less than 0.05 are shown after confirming an overall nonparametric ANOVA Krustal-Wallis test gave a p-value of less than 0.0001. Fractional values above each bar provide the number of VRC01-class antibodies identified over the total number of amplified K chains for each respective immunogen. (FIG. 6D) Scatter plot comparing the frequencies of VRC01-class antibodies elicited by eOD-GT8 60mer and by eOD-GT8 60mer glycan-masked mutants. Each dot represents an immunization group. Frequencies of VRC01-class antibodies among amplified K chains were calculated by dividing the total numbers of isolated VRC01-class antibodies in each group with total numbers of amplified K chains in each group. The mean for each set is indicated numerically above the X axis. (FIG. 6E) Sequence conservation of five amino acid CDRL3 loops from elicited VRC01-class antibodies. The top line indicates the residue positions in the CDRL3, the following rows indicates the CDRL3 sequences for VRC01 and VRC01-class antibodies. X refers to any amino acid and Φ refers to hydrophobic residues. The lower rows shows Sequence Logo representations of the distributions of amino acids at each position in the 5-amino acid CDRL3 of VRC01-class antibodies elicited by eOD-GT8 60mer and eOD-GT8 60mer glycan-masked mutants. The images were created using WebLogo (weblogo.berkeley.edu/logo.cgi). The height of each amino acid letter denotes the frequency for observing that amino acid at that position. VRC01-class antibodies elicited from eOD-GT8-mut18 or Mut33 60mer are not shown due to low sequence numbers isolated (2 and 3 respectively). CDRL3 sequences of eOD-GT8 60mer-elicited antibodies are from 7 antibodies in this study and 17 antibodies from previous published study in the same VH1-2*02 KI mice immunized with eOD-GT8 60mer at 30 or 60 μg once with Poly I:C adjuvant (Tian et al., Cell 166: 1471-1484 e1418, 2016). Sequences shown include QQYEF (SEQ ID NO: 78).

(FIG. 7A) Molecular models showing surface representations of eOD-GT8 (left panel, from PDB 5IES) and its CD4bs-knock out mutant eOD-GT8

KO (right panel) with two point mutations D279K/D368R. (FIGS. 7B and 7C) ELISA of eOD-GT8 and eOD-GT KO with mature VRC01-class Abs (FIG. 7B), germline-reverted VRC01-class antibodies (FIG. 7C) and a non-CD4bs mAb X1C6 (boxed).

FIGS. 8A-8C. Purification of eOD-GT8 60mer and select mutants. Selected glycan mutants with preferable antigenic profiles were expressed in transiently transfected Expi293 cells and purified by affinity and gel filtration chromatography. (FIG. 8A) A representative gel-filtration elution curve showing eOD-GT8-mut16 60mer on Superdex200 10/300GL column. The shaded fractions were collected for physical analysis immunization studies. (FIG. 8B) SDS-PAGE of purified wild type eOD-GT8 60mer (WT) and the. MW, molecular weight standards with sizes noted on the left in values of kDa. (FIG. 8C) Protein production yields of eOD-GT8 and the selected glycan mutants after gel filtration.

(FIG. 9A) Agarose gel showing genotyping results of IGHV1-2*02 transgenic mice after breeding. M, DNA marker. NC, no template negative control. Vector, positive control using wildtype and knock-in plasmid DNA as PCR template. K, homozygous transgenic mouse genomic DNA as the template. H, heterozygous transgenic mouse genomic DNA as the template. WT, wildtype littermate genomic DNA as the template. (FIG. 9B) FACS analysis showing expression of B cells and T cells in splenocytes of wild type (WT) littermate and the IGHV1-2*02 knock-in mice (IGHV1-2*02 KI). (FIG. 9C) Scatter plot showing expression (as percentage of total B cells) on the Y axis of expression of IgG and IgM positive B cells in wild type (WT) littermates and homozygous knock-in mouse (Vh1-2 KI) or C57BL/6 mouse.

FIG. 10. Surface representation of eOD-GT8 showing the locations of two clusters of added glycans which focus the antibody response to the CD4bs. Three orientations rotated around the Y axis are shown. PDB entry 5IES was used as a model for all three panels.

FIGS. 11A-11C. Summary of added and native N-linked glycan positions on eOD-GT8 mutants 1-52 to mask non-CD4bs surfaces from the immune system. Grey shading indicates sequons that are present in the parent eOD-GT8 sequence. The HXB2 positions indicate the HXB2 amino acid number for the asparagine of the N-linked glycan. Note that introduction of the glycan sequon at HXB2 419 was combined with a C-terminal "G" insertion between HXB2 positions 421 and 422. The glycan addition at HXB2 position 268 was combined with an E267G mutation just N-terminal to the glycan sequon. The glycan addition at HXB2 position 287 abrogates the native glycan at HXB2 position 289. Mut22, Mut23, and Mut50 have two additional mutations (E267G, E268G). Mut40, Mut41, and Mut45 have two additional mutations for added stability (I477L, D478N). Sequences shown in FIGS. 11A-11C include EEEV (residues 70-73 of SEQ ID NO: 1), NGTG (residues 8-11 of SEQ ID NO: 11), and GNGT (residues 101-104 of SEQ ID NO: 10).

FIG. 12. Quantification of VRC01-class antibodies amplified from class-switched B cells of mice immunized once with 60 μg eOD-GT8 60mer or eOD-GT8 60mer mutant immunogens adjuvanted with Poly I:C.

FIG. 13. Quantification of VRC01-class antibodies amplified from class-switched B cells of mice immunized once with 30 μg eOD-GT8 or eOD-GT8 60mer mutant immunogens adjuvanted with Poly I:C.

FIG. 14. Quantification of VRC01-class antibodies amplified from class-switched B cells of mice immunized twice with 30 μg eOD-GT8 60mer or eOD-GT8 60mer mutant immunogens adjuvanted with ribi.

SEQUENCES

Figure 1C:
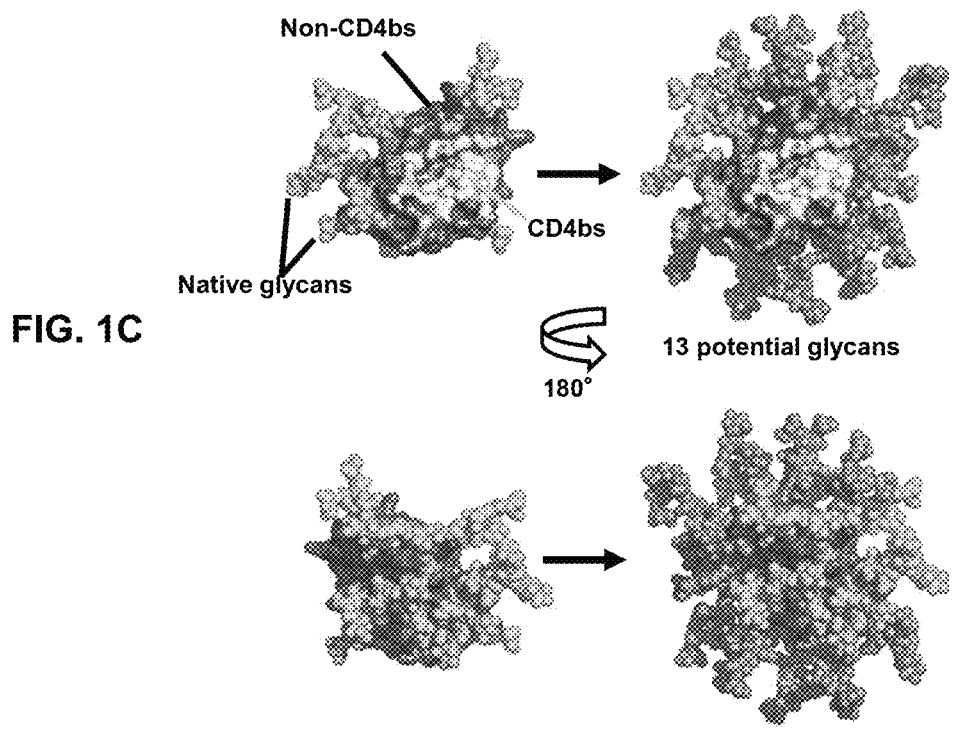

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~240 kb), which was created on Jan. 28, 2022, which is incorporated by reference herein.

DETAILED DESCRIPTION

The elicitation of protective antibodies against HIV-1 remains a major scientific challenge. While animal models have demonstrated that passive administration of HIV-1 specific neutralizing antibodies can fully protect against infection, the induction of such antibodies via immunization has not yet been achieved. Multiple broadly neutralizing antibodies (bNAbs) targeting the CD4-binding site (CD4bs) of HIV-1 Env gp120, including VRC01, NIH45-46, VRC-PG04, 3BNC117 and N6, have been isolated from HIV-1 infected individuals and can potently neutralize diverse strains of HIV-1. Many of these CD4bs-directed human bNAbs share three common characteristics typified by the prototype antibody VRC01 and are termed VRC01-class antibodies (Jardine et al., *PLoS Pathog.*, 12, e1005815, 2016b; Kwong and Mascola, *Immunity*, 37, 412-425, 2012; Scheid et al., *Science*, 333, 1633-1637, 2011; West et al., *Proc Natl Acad Sci USA*, 109, E2083-2090, 2012; Wu et al., *Science*, 329: 856-861, 2010; Wu et al., *Science*, 333: 1593-1602, 2011; Zhou et al., *Immunity*, 39, 245-258, 2013): 1) IGHV1-2 is used exclusively for heavy chains, 2) an unusually short 5 amino acid light chain complementarity-determining region 3 (CDRL3) loop, and 3) high somatic hypermutation (SHM) in the variable region.

In contrast to the broad and potent neutralization activity of mature VRC01-class antibodies, inferred VRC01-class unmutated common ancestors (UCA) or germline revertants show little or no detectable interaction with gp120 monomers or native envelope (Env) trimers (Hoot et al., *PLoS Pathog*, 9, e1003106, 2013; McGuire et al., *Nat Commun.*, 7, 10618, 2016; McGuire et al., *J Exp Med*, 210, 655-663, 2013; Scharf et al., *Proc Natl Acad Sci USA*, 110: 6049-6054, 2013; Zhou et al., *Science*, 329, 811-817, 2010). Thus, one challenge for rational vaccine design is to understand how to prime naturally subdominant antibody responses in a reproducible manner. Germline-targeting offers one strategy to achieve this goal.

Specifically engineered gp120 Env or their outer domains (eOD) derived from various HIV-1 strains have been reported to bind VRC01-class germline precursors as well as to activate B cells expressing them in vitro or in vivo (Jardine et al., *Science*, 340: 711-716, 2013; Jardine et al., *Science*, 351: 1458-1463, 2016; McGuire et al., *J Exp Med*, 210, 655-663, 2013). One such construct, eOD-GT8 60mer, an engineered, circularly permutated OD genetically fused to a 60 subunit self-assembling nanoparticle, demonstrates high binding affinity to VRC01-class precursors (Jardine et al., *Science*, 351: 1458-1463, 2016) and has been shown to elicit VRC01-class germline precursors with a 5-amino acid CDRL3 in various IGHV1-2 knock-in mouse models or in Ig-humanized mice (Jardine et al., *Science,* 349: 156-161, 2015; Sok et al., *Science,* 353, 1557-1560, 2016; Tian et al., *Cell* 166: 1471-1484 e1418, 2016). However, eOD-GT8 also elicits significant off-target immunogenicity demonstrated by a high titer of immune serum binding to the CD4bs-knock out (KO) eOD-GT8 variant and by a high percentage of antigen-specific B cells reacting to the CD4bs-KO protein (Sok et al., *Science,* 353, 1557-1560, 2016; Tian et al., *Cell* 166: 1471-1484 e1418, 2016). This off-target immune response undermines the effectiveness of the eOD-GT8 60mer in eliciting VRC01-class bnAb precursors.

As disclosed herein, specific mutations of the eOD on the eOD-GT8 60mer were designed to introduce multiple N-linked glycosylation sites on the non-CD4bs surfaces of the eOD that mask non-CD4bs epitopes. Of approximately 50 tested mutants that were designed and screened, a few glycan additions were identified that confer surprisingly reduced binding to non-CD4bs antibodies yet retain strong binding to VRC01-class germline precursor antibodies. In particular, the introduction of glycan sequons at positions 52 and 70 or positions 52 and 71 (with a E70G substitution) of the eOD, optionally in combination with introduction of one or more additional glycan sequons, provides a substantial reduction in the antigenicity and immunogenicity of the eOD for off-target (non-CD4bs) antibodies, while maintaining the antigenicity and immunogenicity of the eOD for CD4bs antibodies. Antibody binding data from FIG. 2A indicates that various other combinations of glycans at residues 8, 52, 56, 70/71, 74 or 153 would cause a similar reduction in the antigenicity and immunogenicity of the eOD for off-target (non-CD4bs) antibodies. This "glycan-masking" enables significantly better performance as germline-targeting immunogens than the parent eOD from eOD-GT8. As discussed in the examples, remarkably, it was observed that selected glycan masked eOD-GT8 60mer mutants elicited an increase in CD4bs-specific B cell frequency among all antigen-specific B cells from ~30% for the parent eOD-GT8 60mer to ~90% for glycan masked eOD-GT8 60mer mutants in in vivo immunogenicity assays.

Accordingly, the disclosed eOD-GT8 variants are immune-focused for elicitation of antibodies to the CD4bs of gp120, and have utility as both vaccines for HIV-1 (for example, to prime an immune response to gp120) and as probes for CD4bs-directed antibodies (for example, to detect and quantify target antibodies in a polyclonal serum response).

I. Summary of Terms

Unless otherwise noted, technical terms are used according to conventional usage. Definitions of many common terms in molecular biology may be found in Krebs et al. (eds.), *Lewin's genes XII,* published by Jones & Bartlett Learning, 2017. As used herein, the singular forms "a," "an," and "the," refer to both the singular as well as plural, unless the context clearly indicates otherwise. For example, the term "an antigen" includes singular or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Adjuvant: A vehicle used to enhance antigenicity. In some embodiments, an adjuvant can include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-$\alpha$, IFN-$\gamma$, G-CSF, LFA-3, CD72, B7-1, B7-2, OX-40L, 4-1BBL and toll-like receptor (TLR) agonists, such as TLR-9 agonists. See, for example, Singh (ed.) Vaccine Adjuvants and Delivery Systems, Wiley-Interscience, 2007. Adjuvants can be used in combination with the disclosed immunogens.

Administration: The introduction of a composition into a subject by a chosen route. Administration can be local or systemic. For example, if the chosen route is intravenous, the composition (such as a composition including a disclosed immunogen) is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Antibody: An immunoglobulin, antigen-binding fragment, or derivative thereof, that specifically binds and recognizes an analyte (antigen), such as HIV-1 Env. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010). Light and heavy chain variable regions contain a "framework" region interrupted by three hypervariable regions, also called "complementarity-determining regions" or "CDRs" (see, e.g., Kabat et al., *Sequences of Proteins of Immunological Interest,* U.S. Department of Health and Human Services, 1991). The framework region of an antibody, that is the combined framework regions of the constituent light and heavy chains, serves to position and align the CDRs in three-dimensional space. The CDRs are primarily responsible for binding to an epitope of an antigen.

Carrier: An immunogenic molecule to which an antigen (such as an eOD as described herein) can be linked. When linked to a carrier, the antigen may become more immunogenic. Carriers are chosen to increase the immunogenicity of the antigen and/or to elicit antibodies against the carrier which are diagnostically, analytically, and/or therapeutically beneficial. Useful carriers include polymeric carriers, which can be natural (for example, proteins from bacteria or viruses), semi-synthetic or synthetic materials containing one or more functional groups to which a reactant moiety can be attached.

CD4: Cluster of differentiation factor 4 polypeptide; a T-cell surface protein that mediates interaction with the MHC class II molecule. CD4 also serves as the primary receptor site for HIV-1 on T-cells during HIV-1 infection. CD4 is known to bind to gp120 from HIV-1. The known sequence of the CD4 precursor has a hydrophobic signal peptide, an extracellular region of approximately 370 amino acids, a highly hydrophobic stretch with significant identity to the membrane-spanning domain of the class II MHC beta chain, and a highly charged intracellular sequence of 40 resides (Maddon, *Cell* 42:93, 1985).

Conjugate: A composition composed of two heterologous molecules (such as an eOD and a carrier, such as a protein carrier) linked together useful for stimulating or eliciting a specific immune response in a vertebrate. In some embodiments, the immune response is protective in that it enables the vertebrate animal to better resist infection from the organism against which the immunogenic conjugate is directed. One specific example of a type of immunogenic conjugate is a vaccine, such as a conjugate vaccine.

Control: A reference standard. In some embodiments, the control is a negative control sample obtained from a healthy patient. In other embodiments, the control is a positive control sample obtained from a patient diagnosed with HIV-1 infection. In still other embodiments, the control is a historical control or standard reference value or range of values (such as a previously tested control sample, such as a group of HIV-1 patients with known prognosis or outcome, or group of samples that represent baseline or normal values).

A difference between a test sample and a control can be an increase or conversely a decrease. The difference can be a qualitative difference or a quantitative difference, for example, a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Covalent bond: An interatomic bond between two atoms, characterized by the sharing of one or more pairs of electrons by the atoms. The terms "covalently bound" or "covalently linked" refer to making two separate molecules into one contiguous molecule. The terms include reference to joining an antigen (such as a disclosed eOD, for example Mut15, Mut16, Mut21, Mut33, Mut49, Mut50, Mut51, or Mut52) either directly or indirectly to a carrier molecule, for example indirectly with an intervening linker molecule, such as a peptide or non-peptide linker.

Degenerate variant: In the context of the present disclosure, a "degenerate variant" refers to a polynucleotide encoding a polypeptide (such as a disclosed immunogen) that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Detecting: To identify the existence, presence, or fact of something.

Effective amount: An amount of agent, such as an immunogen, that is sufficient to generate a desired response, such as an immune response in a subject. It is understood that to obtain a protective immune response against an antigen of interest can require multiple administrations of a disclosed immunogen, and/or administration of a disclosed immunogen as the "prime" in a prime boost protocol wherein the boost immunogen can be different from the prime immunogen. Accordingly, an effective amount of a disclosed immunogen can be the amount of the immunogen sufficient to elicit a priming immune response in a subject that can be subsequently boosted with the same or a different immunogen to generate a protective immune response.

Engineered gp120 outer domain (eOD): A recombinant protein including modified sequence of the outer domain of HIV-1 gp120 that is circularly permutated. In several embodiments, the eODs described herein can specifically bind to VRC01 bnAb and germline precursors of this antibody. In several embodiments, the eODs described herein are modified forms of the eOD-GT8 eOD described in PCT Pub. No. WO 2016/205704A2 (which is incorporated by reference herein) with improved antigenic and immunogenic characteristics.

eOD-GT8: An eOD fused to a lumazine synthase subunit as described in Jardine, J. G., et al., *Science* 351, 1458 (2016) and PCT Pub. WO2016205704, the amino acid sequence of the eOD of eOD-GT8 of which is provided herein as SEQ ID NO: 1.

Expression: Transcription or translation of a nucleic acid sequence. For example, an encoding nucleic acid sequence (such as a gene) can be expressed when its DNA is transcribed into RNA or an RNA fragment, which in some examples is processed to become mRNA. An encoding nucleic acid sequence (such as a gene) may also be expressed when its mRNA is translated into an amino acid sequence, such as a protein or a protein fragment. In a particular example, a heterologous gene is expressed when it is transcribed into RNA. In another example, a heterologous gene is expressed when its RNA is translated into an amino acid sequence. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcriptional terminators, a start codon (ATG) in front of a protein-encoding gene, splice signals for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Heterologous: Originating from a different genetic source. A nucleic acid molecule that is heterologous to a cell originated from a genetic source other than the cell in which it is expressed. Methods for introducing a heterologous nucleic acid molecule in a cell or organism are well known in the art, for example, transformation with a nucleic acid, including electroporation, lipofection, particle gun acceleration, and homologous recombination.

Human Immunodeficiency Virus Type 1 (HIV-1): A retrovirus that causes immunosuppression in humans (HIV-1 disease), and leads to a disease complex known as the acquired immunodeficiency syndrome (AIDS). "HIV-1 disease" refers to a well-recognized constellation of signs and symptoms (including the development of opportunistic infections) in persons who are infected by an HIV-1 virus, as determined by antibody or western blot studies. Laboratory findings associated with this disease include a progressive decline in T cells. Related viruses that are used as animal models include simian immunodeficiency virus (SIV), and feline immunodeficiency virus (FIV). Treatment of HIV-1 with HAART has been effective in reducing the viral burden and ameliorating the effects of HIV-1 infection in infected individuals.

HIV-1 envelope protein (Env): The HIV-1 Env protein is initially synthesized as a precursor protein of 845-870 amino acids in size. Individual precursor polypeptides form a homotrimer and undergo glycosylation within the Golgi apparatus as well as processing to remove the signal peptide, and cleavage by a cellular protease between approximately positions 511/512 to generate separate gp120 and gp41 polypeptide chains, which remain associated as gp120-gp41 protomers within the homotrimer.

Mature gp120 includes approximately HIV-1 Env residues 31-511, contains most of the external, surface-exposed, domains of the HIV-1 Env trimer, and it is gp120 which binds both to cellular CD4 receptors and to cellular chemokine receptors (such as CCR5). The mature gp120 wild-type polypeptide is heavily N-glycosylated, giving rise to an apparent molecular weight of 120 kD. Native gp120 includes five conserved regions (C1-C5) and five regions of high variability (V1-V5).

The gp120 core has a molecular structure, which includes two domains: an "inner" domain (which faces gp41) and an "outer" domain (which is mostly exposed on the surface of the oligomeric envelope glycoprotein complex). The two gp120 domains are separated by a "bridging sheet" that is not part of either domain.

A standardized numbering scheme for referred to HIV-1 Env proteins (the HXB2 numbering scheme) is set forth in *Numbering Positions in HIV Relative to HXB2CG* Bette Korber et al., Human Retroviruses and AIDS 1998: A Compilation and Analysis of Nucleic Acid and Amino Acid Sequences. Korber et al., Eds. Theoretical Biology and Biophysics Group, Los Alamos National Laboratory, Los Alamos, NM, which is incorporated by reference herein in its entirety. For reference, the amino acid sequence of HIV-1 Env of HXB2 is set forth as SEQ ID NO: 66 (GENBANK® GI: 1906382, incorporated by reference herein).

```
HXB2 (Cade B, SEQ ID NO: 66):
MRVKEKYQHLWRWGWRWGTMLLGMLMICSATEKLW

VTVYYGVPVWKEATTTLFCASDAKAYDTEVHNVWA

THACVPTDPNPQEVVLVNVTENFNMWKNDMVEQMH

EDIISLWDQSLKPCVKLTPLCVSLKCTDLKNDTNT

NSSSGRMIMEKGEIKNCSFNISTSIRGKVQKEYAF

FYKLDIIPIDNDTTSYKLTSCNTSVITQACPKVSF

EPIPIHYCAPAGFAILKCNNKTFNGTGPCTNVSTV

QCTHGIRPVVSTQLLLNGSLAEEEVVIRSVNFTDN

AKTIIVQLNTSVEINCTRPNNNTRKRIRIQRGPGR

AFVTIGKIGNMRQAHCNISRAKWNNTLKQIASKLR

EQFGNNKTIIFKQSSGGDPEIVTHSFNCGGEFFYC

NSTQLFNSTWFNSTWSTEGSNNTEGSDTITLPCRI

KQIINMWQKVGKAMYAPPISGQIRCSSNITGLLLT

RDGGNSNNESEIFRPGGGDMRDNWRSELYKYKVVK

IEPLGVAPTKAKRRVVQREKRAVGIGALFLGFLGA

AGSTMGAASMTLTVQARQLLSGIVQQQNNLLRAIE

AQQHLLQLTVWGIKQLQARILAVERYLKDQQLLGI

WGCSGKLICTTAVPWNASWSNKSLEQIWNHTTWME
```

-continued

WDREINNYTSLIHSLIEESQNQQEKNEQELLELDK

WASLWNWFNITNWLWYIKLFIMIVGGLVGLRIVFA

VLSIVNRVRQGYSPLSFQTHLPTPRGPDRPEGIEE

EGGERDRDRSIRLVNGSLALIWDDLRSLCLFSYHR

LRDLLLIVTRIVELLGRRGWEALKYWWNLLQYWSQ

ELKNSAVSLLNATAIAVAEGTDRVIEVVQGACRAI

RHIPRRIRQGLERILL

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. "Priming an immune response" refers to treatment of a subject with a "prime" immunogen to induce an immune response that is subsequently "boosted" with a boost immunogen. Together, the prime and boost immunizations produce the desired immune response in the subject. "Enhancing an immune response" refers to co-administration of an adjuvant and an immunogenic agent, wherein the adjuvant increases the desired immune response to the immunogenic agent compared to administration of the immunogenic agent to the subject in the absence of the adjuvant.

Immunogen: A protein or a portion thereof that is capable of inducing an immune response in a mammal, such as a mammal infected or at risk of infection with a pathogen.

Immunogenic composition: A composition comprising a disclosed immunogen, or a nucleic acid molecule or vector encoding a disclosed immunogen, that elicits a measurable CTL response against the immunogen, or elicits a measurable B cell response (such as production of antibodies) against the immunogen, when administered to a subject. It further refers to isolated nucleic acids encoding an immunogen, such as a nucleic acid that can be used to express the immunogen (and thus be used to elicit an immune response against this immunogen). For in vivo use, the immunogenic composition will typically include the protein or nucleic acid molecule in a pharmaceutically acceptable carrier and may also include other agents, such as an adjuvant.

Inhibiting or treating a disease: Inhibiting the full development of a disease or condition, for example, in a subject who is at risk for a disease such as acquired immunodeficiency syndrome (AIDS). "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. Inhibiting a disease can include preventing or reducing the risk of the disease, such as preventing or reducing the risk of viral infection. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% isolated, such as at least 75%, 80%, 90%, 95%, 98%, 99%, or even 99.9% isolated.

Linked: The term "linked" means joined together, either directly or indirectly. For example, a first moiety may be covalently or noncovalently (e.g., electrostatically) linked to a second moiety. This includes, but is not limited to, covalently bonding one molecule to another molecule, noncovalently bonding one molecule to another (e.g. electrostatically bonding), non-covalently bonding one molecule to another molecule by hydrogen bonding, non-covalently bonding one molecule to another molecule by van der Waals forces, and any and all combinations of such couplings. Indirect attachment is possible, such as by using a "linker" (a molecule or group of atoms positioned between two moieties). In several embodiments, linked components are associated in a chemical or physical manner so that the components are not freely dispersible from one another, at least until contacting a cell, such as an immune cell.

Linker: A molecule or group of atoms positioned between two moieties. Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker. In several embodiments, a peptide linker can be used to link the C-terminus of a first protein to the N-terminus of a second protein. Non-limiting examples of peptide linkers include glycine-serine peptide linkers, which are typically not more than 30 amino acids in length. Typically, such linkage is accomplished using molecular biology techniques to genetically manipulate DNA encoding the first polypeptide linked to the second polypeptide by the peptide linker.

N-linked glycan sequon: A triplet sequence of NX(S/T) of a protein, in which N is asparagine, X is any residue except proline, and (S/T) is a serine or threonine residue. Reference to an N-linked glycan sequon that begins at a particular residue position of a protein means that the asparagine of the sequon begins at that position.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Pharmaceutically acceptable carriers: The pharmaceutically acceptable carriers of use are conventional. *Remington: The Science and Practice of Pharmacy, 22$^{nd}$ ed.*, London, UK: Pharmaceutical Press, 2013, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate. In particular embodiments, suitable for administration to a subject the carrier may be sterile, and/or suspended or otherwise contained in a unit dosage form containing one or more measured doses of the composition suitable to elicit the desired anti-HIV-1 immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide and protein: Any chain of amino acids, regardless of length or post-translational modification (e.g., glycosylation or phosphorylation). "Polypeptide" apply to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Prime-boost vaccination: An immunotherapy including administration of a first immunogenic composition (the prime immunogen) followed by administration of a second immunogenic composition (the boost immunogen) to a subject to elicit an immune response. A suitable time interval between administration of the primer vaccine and the booster vaccine can be used. In some embodiments, the prime immunogen, the boost immunogen, or both prime immunogen and the boost immunogen are administered to the subject with an adjuvant to enhance the immune response. In one non-limiting example, the prime immunogen comprises an eOD as described herein (for example, a lumazine synthase 60mer nanoparticle comprising Mut15, Mut16, Mut21, Mut33, Mut49, Mut50, Mut51, or Mut52), and the boost immunogen is a trimeric HIV-1 Env ectodomain, for example, as described in PCT. Pub. WO2016/037154, which is incorporated by reference herein.

Protein nanoparticle: A multi-subunit, protein-based polyhedron shaped structure. The subunits are each composed of proteins or polypeptides (for example a glycosylated polypeptide), and, optionally of single or multiple features of the following: nucleic acids, prosthetic groups, organic and inorganic compounds. Non-limiting examples of protein nanoparticles include ferritin nanoparticles (see, e.g., Zhang, Y. *Int. J. Mol. Sci.*, 12:5406-5421, 2011, incorporated by reference herein), encapsulin nanoparticles (see, e.g., Sutter et al., *Nature Struct. and Mol. Biol.*, 15:939-947, 2008, incorporated by reference herein), Sulfur Oxygenase Reductase (SOR) nanoparticles (see, e.g., Urich et al., *Science*, 311:996-1000, 2006, incorporated by reference herein), lumazine synthase nanoparticles (see, e.g., Zhang et al., *J. Mol. Biol.*, 306: 1099-1114, 2001) or pyruvate dehydrogenase nanoparticles (see, e.g., Izard et al., *PNAS* 96: 1240-1245, 1999, incorporated by reference herein). Ferritin, encapsulin, SOR, lumazine synthase, and pyruvate dehydrogenase are monomeric proteins that self-assemble into a globular protein complexes that in some cases consists of 24, 60, 24, 60, and 60 protein subunits, respectively. In some examples, ferritin, encapsulin, SOR, lumazine synthase, or pyruvate dehydrogenase monomers are linked to a disclosed eOD (for example, Mut15, Mut16, Mut21, Mut33, Mut49, Mut50, Mut51, or Mut52) and self-assembled into a protein nanoparticle presenting the disclosed antigens on its surface, which can be administered to a subject to stimulate an immune response to the antigen.

Recombinant: A recombinant nucleic acid is one that has a sequence that is not naturally occurring or has a sequence that is made by an artificial combination of two otherwise separated segments of sequence. This artificial combination can be accomplished, for example, the artificial manipulation of isolated segments of nucleic acids, for example, using genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid sequences is expressed in terms of the similarity between the sequences, otherwise referred to as sequence identity. Sequence identity is frequently measured in terms of percentage identity; the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2(4):482-489, 1981; Needleman and Wunsch, *J. Mol.*

*Biol.* 48(3):443-453, 1970; Pearson and Lipman, *Proc. Nat. Acad. Sci. U.S.A.* 85(8):2444-2448, 1988; Higgins and Sharp, *Gene,* 73(1):237-244, 1988; Higgins and Sharp, *Bioinformatics,* 5(2):151-3, 1989; Corpet, *Nucleic Acids Res.* 16(22):10881-10890, 1988; Huang et al. *Bioinformatics,* 8(2):155-165, 1992; and Pearson, *Methods Mol. Biol.* 24:307-331, 1994. Altschul et al., *J. Mol. Biol.* 215(3):403-410, 1990, presents a detailed consideration of sequence alignment methods and homology calculations. The NCBI Basic Local Alignment Search Tool (BLAST) (Altschul et al., *J. Mol. Biol.* 215(3):403-410, 1990) is available from several sources, including the National Center for Biological Information and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

Variants of a polypeptide are typically characterized by possession of at least about 75%, for example, at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet.

As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Signal Peptide: A short amino acid sequence (e.g., approximately 18-30 amino acids in length) that directs newly synthesized secretory or membrane proteins to and through membranes (for example, the endoplasmic reticulum membrane). Signal peptides are typically located at the N-terminus of a polypeptide and are removed by signal peptidases after the polypeptide has crossed the membrane. Signal peptide sequences typically contain three common structural features: an N-terminal polar basic region (n-region), a hydrophobic core, and a hydrophilic c-region). An exemplary signal peptide sequence is set forth as residues 1-19 of SEQ ID NO: 49.

Specifically bind: When referring to the formation of an antibody:antigen protein complex, or a protein:protein complex, refers to a binding reaction which determines the presence of a target protein, peptide, or polysaccharide (for example, a glycoprotein), in the presence of a heterogeneous population of proteins and other biologics. Thus, under designated conditions, a particular antibody or protein binds preferentially to a particular target protein, peptide or polysaccharide (such as an antigen present on the surface of a pathogen, for example, gp120) and does not bind in a significant amount to other proteins or polysaccharides present in the sample or subject. Specific binding can be determined by methods known in the art. A first protein or antibody specifically binds to a target protein when the interaction has a $K_D$ of less than $10^{-6}$ Molar, such as less than $10^{-7}$ Molar, less than $10^{-8}$ Molar, less than $10^{-9}$, or even less than $10^{-10}$ Molar.

Subject: Living multi-cellular vertebrate organisms, a category that includes human and non-human mammals. In an example, a subject is a human. In a particular example, the subject is a newborn infant. In an additional example, a subject is selected that is in need of inhibiting of an HIV-1 infection. For example, the subject is either uninfected and at risk of HIV-1 infection or is infected in need of treatment.

Transmembrane domain: An amino acid sequence that inserts into a lipid bilayer, such as the lipid bilayer of a cell or virus or virus-like particle. A transmembrane domain can be used to anchor an antigen to a membrane.

Under conditions sufficient for: A phrase that is used to describe any environment that permits a desired activity.

Vaccine: A pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In one specific, non-limiting example, a vaccine reduces the severity of the symptoms associated with HIV-1 infection and/or decreases the viral load compared to a control. In another non-limiting example, a vaccine reduces HIV-1 infection compared to a control.

Vector: An entity containing a nucleic acid molecule (such as a DNA or RNA molecule) molecule bearing a promoter(s) that is operationally linked to the coding sequence of an immunogenic protein of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements. Viral vectors are recombinant nucleic acid vectors having at least some nucleic acid sequences derived from one or more viruses.

A non-limiting example of a DNA-based expression vector is pCDNA3.1, which can include includes a mammalian expression enhancer and promoter (such as a CMV promoter). Non-limiting examples of viral vectors include adeno-associated virus (AAV) vectors as well as Poxvirus vector (e.g., Vaccinia, MVA, avian Pox, or Adenovirus).

Virus-like particle (VLP): A non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. The presence of VLPs following recombinant expression of viral proteins are typically detected using conventional techniques, such as by electron microscopy, biophysical characterization, and the like. Further, VLPs can be isolated by known techniques, e.g., density gradient centrifugation and identified by characteristic density banding. See, for example, Baker et al. (1991) *Biophys. J.* 60:1445-1456; and Hagensee et al. (1994) *J. Virol.* 68:4503-4505; Vincente, *J Invertebr Pathol.*, 2011; Schneider-Ohrum and Ross, *Curr. Top. Microbiol. Immunol.*, 354: 53073, 2012).

VRC01: A broadly neutralizing monoclonal antibody that specifically binds to the CD4 binding site on HIV-1 Env and can inhibit HIV-1 infection of target cells. The VRC01 mAb and with methods of its use and production are known (see, for example, Wu et al., *Science*, 329(5993):856-861, 2010, and PCT publication WO2012/154312, each of which is incorporated by reference herein). The amino acid sequences of the heavy and light variable regions of the VRC01 mAb are known and have been deposited in GenBank as Nos. ADF47181.1 (VRC01 $V_H$) and ADF47184.1 (VRC01 $V_L$), each of which is incorporated by reference herein.

VRC01gHvgLv: A modified VRC01 antibody having heavy and light chain variable regions where the sequences of the variable regions corresponding to heavy and light chain V-gene sequence is mutated to the relevant germline sequence. The amino acid sequences of the heavy and light variable regions of the VRC01gHvgLv mAb are known and are described in Wu, X., et al., *Science* 333, 1593 (2011); Georgiev, I. V. et al (2014) *J. Immunol.* 192(3) 1100-1106, which is incorporated by reference herein.

VRC01-class antibody: A class of antibodies that bind to the CD4bs on gp120 and can neutralize HIV-1. The prototypical member of the VRC01-class of antibodies—VRC01—can neutralize over 90% of circulating HIV-1 isolates with an average 50% inhibitory concentration ($IC_{50}$) of ~0.3 μg/ml. Despite overall sequence differences between VRC01-class antibodies, antibody-gp120 co-crystal structures revealed VRC01-class recognition of gp120 to be consistent across the class. Three-dimensional structure analysis of HIV-1 gp120 from different HIV-1 clades in complexes with different VRC01-class antibodies from multiple donors show that the VRC01-class antibodies share striking similarity in physical structure, and revealed several antibody features that contribute to gp120 binding and HIV-1 neutralization. The substantial structural and ontogenetic characterization of VRC01-class of antibodies allows recognition of the members of this class by interrogation of antibody sequence.

For example, the $V_H$ of a VRC01-class antibody has a IGHV1-2*02 germline origin, wherein the VRC01-class $V_H$ encoding sequence is from 20-35% (such as 25-30%) divergent from the corresponding germline gene sequence. The VRC01-class $V_H$ includes a tryptophan residue at kabat position 50 ($V_H$ $Trp_{50}$), an asparagine residue at kabat position 58 ($V_H$ $Asn_{58}$), and an arginine residue at kabat position 71 ($V_H$ $Arg_{71}$). These residues form specific interactions with amino acids on gp120 that contribute to the VRC01-class specificity and neutralization properties. When a VRC01-class antibody is bound to gp120, $V_H$ $Trp_{50}$ forms a hydrogen bond with gp120 $Asn_{280}$, $V_H$ $Asp_{58}$ forms hydrogen bonds with gp120 $Arg_{456}$ and $Gly_{458}$, $V_H$ $Arg_{71}$ forms salt bridges with gp120 $Asp_{368}$, and $V_H$ Trp100B forms a hydrogen bond with gp120 $Asn_{279}$.

Further, the $V_L$ of a VRC01-class antibody has an IGKV1-33, IGKV3-11, IGKV3-15, IGKV3-20, IGLV2-14 germline origin, wherein the VRC01-class $V_L$ encoding sequence is from 15-35% (such as 25-30%) divergent from the corresponding germline gene sequence. The VRC01-class $V_L$ includes either a LCDR1 (kabat positioning) with a 2-6 amino acid deletion, or a LCDR1 with glycine residues at kabat positions 28 and 30. The deletion or the presence of the glycine residues provides flexibility that allows the LCDR1 to avoid structural clash with the D loop of gp120 when the antibody is bound to the CD4bs. Further, the VRC01-class $V_L$ includes an LCDR3 that is five amino acids in length (according to kabat positioning) and includes a hydrophobic residue (such as leucine or tyrosine) at kabat position 91, deletion of kabat positions 92-95, and a glutamate or glutamine residue at kabat position 96. The hydrophobic residue at position 91 packs against the backbone of gp120 loop D, and the glutamate or glutamine residue at kabat position 96 interacts with a conserved electropositive region on the base of the gp120 V5 domain.

Non-limiting examples of antibodies that fall within the VRC01-class include the VRC01, VRC03, VRC07, VRC07-523, VRC13, 3BCN117, 12A12, 12A21, VRC-PG04, NIH45-46, VRC23, VRC-CH30, VRC-CH31, and VRC-PG20 antibodies. Description, characterization, and productions of these antibodies, as well as the VRC01-class of antibodies is available (see, e.g., Diskin et al., *Science*, 334(6060):1289-93, 2011; Kwong and Mascola, *Immunity*, 37, 412-425, 2012; Li et al., *J. Virol.*, 85, 8954-8967, 2011; Rudicell et al., *J. Virol.*, 88, 12669-12682, 2012; Scheid et al., *Science*, 333(6049):1633-1637, 2011; West et al., *PNAS*, 109:E2083-2090, 2012; Wu et al., *Science*, 329(5993):856-861, 2010; Wu et al., *Science*, 333(6049):1593-1602, 2011; Zhou et al., *Immunity*, 39:245-258, 2013; Georgiev et al., *Science*, 340:751-756, 2013; Zhu et al., *PNAS*, 110, E4088-E4097, 2013; and WIPO Pub. Nos. WO 2012/158948, WO2011038290, WO2012154312, WO2013142324, and WO2013016468, each of which is incorporated by reference herein in its entirety).

VRC01-class germline precursor: Antibodies are encoded by the rearrangement of variable (V), diversity (D), and joining (J) gene segments into recombined genes that encode a large but ultimately finite number of unmutated antibody structures, known as the germline repertoire. Following recombination of the V, D, and J genes, maturation of the antibody proceeds by somatic mutation. The "germline precursor" of a mature antibody is an antibody with heavy and light chain variable regions comprising sequences corresponding to the recombined V, D, and J gene segments of the mature antibody prior to somatic mutation. Thus, a VRC01-class germline precursor is an antibody with heavy and light chain variable regions comprising sequences corresponding to the recombined V, D, and J gene segments of a VRC01-class antibody (such as VRC01) prior to somatic mutation. Examples of VRC01-class germline precursor antibodies are disclosed, for example, in Jardine et al., "Rational HIV Immunogen design to target specific germline B cell receptors," *Science*, 340:6122:711-716, 2013, which is incorporated by reference herein.

II. Immunogens

Embodiments of immunogens comprising an eOD as disclosed herein and methods of their use and production are provided. The immunogen specifically binds to precursors of VRC01-class bnAbs, such as VRC01gHvgLv, and has substantially reduced binding (relative to the eOD of eOD- GT8) to off-target antibodies that do not bind to the VRC01 binding site. In several embodiments, the immunogens can be used to prime a neutralizing immune response to HIV-1 in a subject (such as an immune response that targets the VRC01 binding site of gp120), for example, to treat or prevent an HIV-1 infection in the subject.

Engineered Gp120 Outer Domains

The disclosed eODs are modified forms of the eOD-GT8 eOD disclosed in PCT. Pub. WO2016/205704, the sequence of which is provided herein as SEQ ID NO: 1. The modifications to the eOD-GT8 eOD include amino acid substitutions to introduce of glycan sequons. As discussed in the examples, the additional glycans on the eOD lead to surprising improvements in immunogen antigenicity and immunogenicity.

In some embodiments, the immunogen comprises an eOD comprising an amino acid sequence according to SEQ ID NO: 1 that further comprises amino acid substitutions, insertions, and/or deletions as follows:

(a) amino acid substitutions to introduce N-linked glycan sequons beginning at residues 52 and 70, or residues 52 and 71 with a E70G substitution, of SEQ ID NO: 1;

(b) amino acid substitutions to introduce N-linked glycan sequons beginning at one or more of residues 8, 14, 102, 153, and 159 of SEQ ID NO: 1, wherein a glycine insertion is introduced between residues 10 and 11 if the N-linked glycan sequon beginning at residue 8 is introduced; and (c) optionally one or more additional amino acid substitutions, insertions, or deletions.

In these embodiments, the amino acid sequence of the eOD also comprises N-linked glycan sequons beginning at residues corresponding to residues 18, 65, 92, 98, 106, 113, 129, 146, 165, and 170 of SEQ ID NO: 1, and the remaining residues of the eOD comprise an amino acid sequence at least 90% (such as at least 95%, at least 96%, at least 97%, at least 98%, at least 99%, or even 100%) identical to the corresponding residues of SEQ ID NO: 1. In several embodiments, the amino acid sequence of the residues of the eOD corresponding to residues 25-45, 79-85, and 126-145 of SEQ ID NO: 1 are identical to SEQ ID NO: 1. These residues are believed to be involved in HIV-1 Env binding VRC01 and VRC01-germline precursor antibodies. The eOD specifically binds to VRC01 and VRC01gHvgLv antibodies.

In some embodiments, the eOD comprises the amino acid substitutions to introduce N-linked glycan sequons beginning at residues 52 and 70. In some embodiments, the eOD comprises the amino acid substitutions to introduce N-linked glycan sequons beginning at residues 52 and 71, and also comprises the E70G substitution.

In some embodiments, the immunogen comprises an eOD comprising an amino acid sequence according to SEQ ID NO: 1 that further comprises amino acid substitutions, insertions, and/or deletions as follows:

(a) amino acid substitutions to introduce N-linked glycan sequons beginning at one or more of residues 8, 14, 56, 70, 71, 74, 102, and 153 of SEQ ID NO: 1, wherein a glycine insertion is introduced between residues 10 and 11 if the N-linked glycan sequon beginning at residue 8 is introduced, and an E70G substitution is introduced if the N-linked glycan sequon beginning at residue 71 is introduced;

(b) optionally a GG substitution for the residues at positions corresponding to positions 70 and 71 of SEQ ID NO: 1 if N-linked glycan sequons beginning at residue 70 or 71 are not introduced; and (c) optionally one or more additional amino acid substitutions, insertions, or deletions; and In these embodiments, the amino acid sequence of the eOD also comprises N-linked glycan sequons beginning at residues corresponding to residues 18, 65, 92, 98, 106, 113, 129, 146, 165, and 170 of SEQ ID NO: 1, and the remaining residues of the eOD comprise an amino acid sequence at least 90% (such as at least 95%, at least 96%, at least 97%, at least 98%, at least 99%, or even 100%) identical to the corresponding residues of SEQ ID NO: 1. In several embodiments, the amino acid sequence of the residues of the eOD corresponding to residues 25-45, 79-85, and 126-145 of SEQ ID NO: 1 are identical to SEQ ID NO: 1. These residues are believed to be involved in HIV-1 Env binding VRC01 and VRC01-germline precursor antibodies. The eOD specifically binds to VRC01 and VRC01gHvgLv antibodies.

In some embodiments, the residues of the eOD corresponding to residues 11-13 of SEQ ID NO: 1 are identical to SEQ ID NO: 1. These residues (PPP) provide a proline linker between HXB2 positions 420 and 445 of the eOD.

In some embodiments, the eOD comprises, consists essentially of, or consists of the amino acid sequence set forth as any one of SEQ ID NOs: 15 (Mut15), 16 (Mut16), 17 (Mut17), 18 (Mut18), 19 (Mut19), 21 (Mut21), 27 (Mut27), 28 (Mut28), 29 (Mut29), 33 (Mut33), 34 (Mut34), 35 (Mut35), 36 (Mut36), 37 (Mut37), 38 (Mut38), or 47 (Mut47). In some embodiments, the eOD comprises, consists essentially of, or consists of the amino acid sequence set forth as any one of SEQ ID NOs: 79 (Mut49), 80 (Mut50), 81 (Mut51), or 82 (Mut52).

Several embodiments include a multimer of a disclosed eOD, for example, a multimer including 2, 3, 4, 5, 6, 7, 8, 9, 10, or 24, or 60, or more of the eOD.

In several embodiments, an immunogen comprising the eOD can be used to prime a neutralizing immune response to HIV-1 in a subject (such as an immune response that targets the VRC01 binding site of gp120), for example, to treat or prevent an HIV-1 infection in the subject. As discussed in the examples, embodiments of immunogens comprising the disclosed eODs produced an immune response in an animal model that activated memory B cells that bind to the eOD. In some embodiments, an immunogen comprising the eOD (such as a lumazine synthase nanoparticle, discussed below) induces an immune response that includes activation of memory B cells targeting the eOD, wherein at least 50% (such as at least 60%, at least 70%, or at least 80%) of the activated memory B cells bind to the VRC01 binding site on the eOD. In some embodiments, an immunogen comprising the eOD (such as a lumazine synthase nanoparticle, discussed below) induces an immune response comprises production of IGHV1-2*02 antibodies (e.g., germline precursors of VRC01-class antibodies) that bind to the VRC01 binding site on the eOD of the immunogen.

It is understood in the art that some variations can be made in the amino acid sequence of a protein without affecting the activity of the protein. Such variations include insertion of amino acid residues, deletions of amino acid residues, and substitutions of amino acid residues. These variations in sequence can be naturally occurring variations or they can be engineered through the use of genetic engineering technique. Examples of such techniques are found in see, e.g., Sambrook et al. (Molecular Cloning: A Laboratory Manual, 4$^{th}$ ed, Cold Spring Harbor, New York, 2012) and Ausubel et al. (In Current Protocols in Molecular Biology, John Wiley & Sons, New York, through supplement 104, 2013, both of which are incorporated herein by reference in their entirety.

The disclosed eODs can be derivatized or linked to another molecule (such as another peptide or protein). In general, the disclosed eODs are derivatized such that the binding to VRC01-class precursor antibodies is not affected adversely by the derivatization or labeling. For example, the disclosed eODs can be functionally linked (by chemical coupling, genetic fusion, noncovalent association or otherwise) to one or more other molecular entities, such as an antibody or protein or detection tag.

Protein Nanoparticles

In some embodiments, a self-assembled protein nanoparticle is provided that includes multiple copies of a disclosed eOD (for example, Mut15, Mut16, Mut21, Mut33, Mut49, Mut50, Mut51, or Mut52) displayed on the surface of the nanoparticle. Non-limiting examples of such nanoparticles include ferritin, encapsulin, Sulfur Oxygenase Reductase (SOR), and lumazine synthase nanoparticles, which are comprised of an assembly of monomeric subunits including ferritin, encapsulin proteins, SOR proteins, and lumazine synthase proteins, respectively (see, e.g., Lopez-Sagaseta et al., "Self-assembling protein nanoparticles in the design of vaccines," *Comp. and Struct. Biotechnol.*, 14, 58-68, 2016). To construct such protein nanoparticles the eOD can be linked (directly, or indirectly via a peptide linker) to the N- or C-terminus of a subunit of the protein nanoparticle (such as a ferritin protein, an encapsulin protein, a SOR protein, or a lumazine synthase protein) and expressed in cells under appropriate conditions. The resulting fusion proteins self-assemble into a multimeric nanoparticle and can be purified.

In some embodiments, a disclosed eOD (for example, Mut15, Mut16, Mut21, Mut33, Mut49, Mut50, Mut51, or Mut52) can be linked to an *Aquifex aeolicus* lumazine synthase subunit to construct a lumazine synthase nanoparticle. The globular form of lumazine synthase nanoparticle is made up of monomeric subunits; an example of the sequence of one such lumazine synthase subunit is provides as the amino acid sequence set forth as:

```
                      (residues 20-173 of SEQ ID NO: 49)
MQIYEGKLTAEGLRFGIVASRFNHALVDRLVEGAI

DAIVRHGGREEDITLVRVPGSWEIPVAAGELARKE

DIDAVIAIGVLIRGATPHFDYIASEVSKGLADLSL

ELRKPITFGVITADTLEQAIERAGTKHGNKGWEAA

LSAIEMANLFKSLR
```

In some embodiments, the lumazine synthase subunit can contain one or more mutations to inhibit lumazine synthase activity, such as F22A, H88S, and/or R127A substitutions. Introduction of these mutations blocks lumazine synthase activity without reducing the multimerization of the lumazine synthase 60mer. Exemplary sequences are provided below.

```
Lumazine synthase with R127A
                                  (SEQ ID NO: 67)
MQIYEGKLTAEGLRFGIVASRFNHALVDRLVEGAI

DAIVRHGGREEDITLVRVPGSWEIPVAAGELARKE

DIDAVIAIGVLIRGATPHFDYIASEVSKGLADLSL

ELRKPITFGVITADTLEQAIEAAGTKHGNKGWEAA

LSAIEMANLFKSLR
```

```
Lumazine synthase with H88S and R127A
                                  (SEQ ID NO: 68)
MQIYEGKLTAEGLRFGIVASRFNHALVDRLVEGAI

DAIVRHGGREEDITLVRVPGSWEIPVAAGELARKE

DIDAVIAIGVLIRGATPSFDYIASEVSKGLADLSL

ELRKPITFGVITADTLEQAIEAAGTKHGNKGWEAA

LSAIEMANLFKSLR
```

```
Lumazine synthase with F22A, H88S,
and R127A
                                  (SEQ ID NO: 69)
MQIYEGKLTAEGLRFGIVASRANHALVDRLVEGAI

DAIVRHGGREEDITLVRVPGSWEIPVAAGELARKE

DIDAVIAIGVLIRGATPSFDYIASEVSKGLADLSL

ELRKPITFGVITADTLEQAIEAAGTKHGNKGWEAA

LSAIEMANLFKSLR
```

In some embodiments, the lumazine synthase subunit fused to the eOD comprises an N102D substitution to remove a potential N-linked glycosylation site at the 5-fold symmetry axis of the lumazine synthase nanoparticle. The lumazine synthase subunit sequences set forth above as SEQ ID NOs: 49 and 67-69 all include the N102D substitution.

In some embodiments, a disclosed eOD (for example, Mut15, Mut16, Mut21, Mut33, Mut49, Mut50, Mut51, or Mut52) can be linked to a lumazine synthase subunit including an amino acid sequence at least 80% (such as at least 85%, at least 90%, at least 95%, or at least 97%) identical to amino acid sequence set forth as any one of SEQ ID NOs: 49 or 67-70.

In some embodiments, the eOD linked to the lumazine synthase subunit comprises, consists essentially of, of consists of an amino acid sequence set forth as residues 20-361 of any one of SEQ ID NOs: 51 (Mut15), 56 (Mut21), 60 (Mut33), 61 (Mut34), 62 (Mut35), 63 (Mut36), 64 (Mut37), or 65 (Mut38); or residues 20-360 of any one of SEQ ID NOs: 52 (Mut16), 53 (Mut17), 54 (Mut18), 55 (Mut19), 57 (Mut27), 58 (Mut28), 59 (Mut29), or 76 (Mut47).

In some embodiments, the eOD linked to the lumazine synthase subunit comprises, consists essentially of, of consists of an amino acid sequence set forth as residues 20-360 of any one of SEQ ID NOs: 83 (Mut49), 84 (Mut50), or 86 (Mut52). In some embodiments, the eOD linked to the lumazine synthase subunit comprises, consists essentially of, of consists of an amino acid sequence set forth as residues 20-361 of SEQ ID NO: 85 (Mut51).

Following synthesis, the monomeric subunit proteins self-assemble into the globular lumazine synthase 60mer. In some embodiments, the lumazine synthase-eOD fusion can be co-expressed with a corresponding lumazine synthase subunit that lacks the eOD. Such co-expression protocols have been shown to increase formation of 60mer particles. Methods of constructing lumazine synthase protein nanoparticles that display a heterologous antigen are known and are further described herein (see, e.g., Jardine et al., *Science*, 340(6133): 711-716, 3013, and PCT Pub. WO2016/205704, each of which is incorporated by reference herein).

In some embodiments, a disclosed eOD (for example, Mut15, Mut16, Mut21, Mut33, Mut49, Mut50, Mut51, or Mut52) can be linked to a ferritin subunit to construct a ferritin nanoparticle. Ferritin nanoparticles that display a heterologous antigen and their use for immunization purposes (e.g., for immunization against influenza antigens) have been disclosed in the art (see, e.g., Kanekiyo et al., Nature, 499:102-106, 2013, incorporated by reference herein in its entirety). Ferritin is a globular protein that is found in all animals, bacteria, and plants, and which acts primarily to control the rate and location of polynuclear Fe(III)$_2$O$_3$ formation through the transportation of hydrated iron ions and protons to and from a mineralized core. The globular form of the ferritin nanoparticle is made up of monomeric subunits, which are polypeptides having a molecule weight of approximately 17-20 kDa. An example of the amino acid sequence of one such ferritin subunit is represented by:

(SEQ ID NO: 70)
ESQVRQQFSKDIEKLLNEQVNKEMQSSNLYMSMSS

WCYTHSLDGAGLFLFDHAAEEYEHAKKLIIFLNEN

NVPVQLTSISAPEHKFEGLTQIFQKAYEHEQHISE

SINNIVDHAIKSKDHATFNFLQWYVAEQHEEEVLF

KDILDKIELIGNENHGLYLADQYVKGIAKSRKS

In some embodiments, a disclosed eOD can be linked to a ferritin subunit including an amino acid sequence at least 80% (such as at least 85%, at least 90%, at least 95%, or at least 97%) identical to amino acid sequence set forth as SEQ ID NO: 70.

Following synthesis, these monomeric subunit proteins self-assemble into the globular ferritin protein, which has 24 monomeric subunit proteins, and a capsid-like structure having 432 symmetry. Methods of constructing ferritin nanoparticles that display a heterologous antigen are known (see, e.g., Zhang, Int. J. Mol. Sci., 12:5406-5421, 2011, which is incorporated herein by reference in its entirety).

In some embodiments, a disclosed eOD (for example, Mut15, Mut16, Mut21, Mut33, Mut49, Mut50, Mut51, or Mut52) can be linked to an encapsulin nanoparticle subunit to construct an encapsulin nanoparticle. The globular form of the encapsulin nanoparticle is made up of monomeric subunits; an example of the sequence of one such encapsulin subunit is provides as the amino acid sequence set forth as (SEQ ID NO: 71)
MEFLKRSFAPLTEKQWQEIDNRAREIFKTQLYGRK

FVDVEGPYGWEYAAHPLGEVEVLSDENEVVKWGLR

KSLPLIELRATFTLDLWELDNLERGKPNVDLSSLE

ETVRKVAEFEDEVIFRGCEKSGVKGLLSFEERKIE

CGSTPKDLLEAIVRALSIFSKDGIEGPYTLVINTD

RWINFLKEEAGHYPLEKRVEECLRGGKIITTPRIE

DALVVSERGGDFKLILGQDLSIGYEDREKDAVRLF

ITETFTFQVVNPEALILLKF

In some embodiments, a disclosed eOD can be linked to an encapsulin subunit including an amino acid sequence at least 80% (such as at least 85%, at least 90%, at least 95%, or at least 97%) identical to amino acid sequence set forth as SEQ ID NO: 71.

Following synthesis, the monomeric subunits self-assemble into the globular encapsulin assembly including 60, or in some cases, 180 monomeric subunits. Methods of constructing encapsulin nanoparticles that display a heterologous antigen are known (see, for example, Sutter et al., Nature Struct. and Mol. Biol., 15:939-947, 2008, which is incorporated by reference herein in its entirety). In specific examples, the encapsulin polypeptide is bacterial encapsulin, such as Thermotoga maritime or Pyrococcus furiosus or Rhodococcus erythropolis or Myxococcus xanthus encapsulin.

In some embodiments, a disclosed eOD (for example, Mut15, Mut16, Mut21, Mut33, Mut49, Mut50, Mut51, or Mut52) can be linked to a Sulfur Oxygenase Reductase (SOR) subunit to construct a recombinant SOR nanoparticle. In some embodiments, the SOR subunit can include the amino acid sequence set forth as (SEQ ID NO: 72)
MEFLKRSFAPLTEKQWQEIDNRAREIFKTQLYGRK

FVDVEGPYGWEYAAHPLGEVEVLSDENEVVKWGLR

KSLPLIELRATFTLDLWELDNLERGKPNVDLSSLE

ETVRKVAEFEDEVIFRGCEKSGVKGLLSFEERKIE

CGSTPKDLLEAIVRALSIFSKDGIEGPYTLVINTD

RWINFLKEEAGHYPLEKRVEECLRGGKIITTPRIE

DALVVSERGGDFKLILGQDLSIGYEDREKDAVRLF

ITETFTFQVVNPEALILLKF

In some embodiments, a disclosed eOD can be linked to a SOR subunit including an amino acid sequence at least 80% (such as at least 85%, at least 90%, at least 95%, or at least 97%) identical to amino acid sequence set forth as SEQ ID NO: 72.

SOR proteins are microbial proteins (for example from the thermoacidophilic archaeon Acidianus ambivalens that form 24 subunit protein assemblies. Methods of constructing SOR nanoparticles that display a heterologous antigen are known (see, e.g., Urich et al., Science, 311:996-1000, 2006, which is incorporated by reference herein in its entirety). An example of an amino acid sequence of a SOR protein for use to make SOR nanoparticles is set forth in Urich et al., Science, 311:996-1000, 2006, which is incorporated by reference herein in its entirety.

For production purposes, the eOD linked to the nanoparticle subunit can include an N-terminal signal peptide that is cleaved during cellular processing. The protein nanoparticles can be expressed in appropriate cells (e.g., HEK 293 Freestyle cells) and fusion proteins are secreted from the cells self-assembled into nanoparticles. The nanoparticles can be purified using known techniques, for example by a few different chromatography procedures, e.g. Mono Q (anion exchange) followed by size exclusion (SUPEROSE® 6) chromatography. The monomers of the protein nanoparticle can include various tags and sequences for production and purification of the epitope scaffold protein. Typically such protein tags are linked to the C-terminus of the monomer and are ultimately removed (for example by selective protease cleave) from the monomer.

Carrier Proteins

In some embodiments, the eOD (e.g., Mut15, Mut16, Mut21, Mut33, Mut49, Mut50, Mut51, or Mut52) can be linked to a carrier protein by a linker (such as a peptide linker) or can be directly linked to the carrier protein (for example, by conjugation, or synthesis as a fusion protein).

Suitable linkers are available and include, but are not limited to, straight or branched-chain carbon linkers, heterocyclic carbon linkers or peptide linkers. For an immunogenic conjugate from two or more constituents, each of the constituents typically contains the necessary reactive groups. Representative combinations of such groups are amino with carboxyl to form amide linkages or carboxy with hydroxyl to form ester linkages or amino with alkyl halides to form alkylamino linkages or thiols with thiols to form disulfides or thiols with maleimides or alkylhalides to form thioethers. Hydroxyl, carboxyl, amino and other functionalities, where not present may be introduced by known methods. Likewise, a wide variety of linking groups may be employed. In some cases, the linking group can be designed to be either hydrophilic or hydrophobic in order to enhance the desired binding characteristics of the eOD and the carrier. The covalent linkages should be stable relative to the solution conditions under which the conjugate is subjected.

In some embodiments, the linkers may be joined to the constituent amino acids through their side groups (such as through a disulfide linkage to cysteine) or to the alpha carbon amino and carboxyl groups of the terminal amino acids. In some embodiments, the linker, the eOD, and the carrier can be encoded as a single fusion polypeptide such that the eOD and the carrier are joined by peptide bonds.

The procedure for attaching a molecule to a polypeptide varies according to the chemical structure of the molecule. Polypeptides typically contain a variety of functional groups; for example, carboxylic acid (COOH), free amine ($-NH_2$) or sulfhydryl ($-SH$) groups, which are available for reaction with a suitable functional group on a polypeptide. Alternatively, the polypeptide is derivatized to expose or attach additional reactive functional groups. The derivatization may involve attachment of any of a number of linker molecules such as those available from Pierce Chemical Company, Rockford, IL.

It can be advantageous to produce conjugates in which more than one eOD is conjugated to a single carrier protein. In several embodiments, the conjugation of multiple eODs to a single carrier protein is possible because the carrier protein has multiple lysine or cysteine side-chains that can serve as sites of attachment. The amount of eOD reacted with the amount of carrier may vary depending upon the specific eOD and the carrier protein. However, the respective amounts should be sufficient to introduce from 1-30 chains of eOD onto the carrier protein. The resulting number of eOD linked to a single carrier molecule may vary depending upon the specific eOD and the carrier protein. In some embodiments, from 1 to 30, such as about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 eODs can be linked to each carrier protein molecule. "About" in this context refers to plus or minus 5% when measuring an average number of eODs per carrier molecule in the conjugate. Thus, in some embodiments, the average ratio of eOD to carrier protein molecules is between about 1:1 and about 30:1, such as about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1, about 21:1, about 22:1, about 23:1, about 24:1, about 25:1, about 26:1, about 27:1, about 28:1, about 29:1, or about 30:1, for example, between about 1:1 and about 15:1, between about 5:1 and about 20:1, or between about 10:1 and about 30:1.

In some embodiments (such as when KLH is used as a carrier), from 1 to 1000, such as about 50, about 100, about 200, about 300, about 400, about 500, about 700, about 1000, about 9, about 10, about 11, about 12, about 13, about 14, about 15, about 16, about 17, about 18, or about 19 eOD molecules can be linked to each carrier protein. "About" in this context refers to plus or minus 5% when measuring an average number of eOD molecules per carrier molecule in the conjugate. Thus, in some embodiments, the average ratio of eOD molecule to carrier protein is between about 1:1 and about 1000:1, such as between about 100:1 and about 500:1, between about 500:1 and about 10000:1, or between about 250:1 and about 750:1.

Examples of suitable carriers are those that can increase the immunogenicity of the conjugate and/or elicit antibodies against the carrier which are diagnostically, analytically, and/or therapeutically beneficial. Useful carriers include polymeric carriers, which can be natural, recombinantly produced, semi-synthetic or synthetic materials containing one or more amino groups, such as those present in a lysine amino acid residue present in the carrier, to which a reactant moiety can be attached. Carriers that fulfill these criteria are generally known in the art (see, for example, Fattom et al., *Infect. Immun.* 58:2309-12, 1990; Devi et al., *PNAS* 88:7175-79, 1991; Szu et al., *Infect. Immun.* 59:4555-61, 1991; Szu et al., *J. Exp. Med.* 166:1510-24, 1987; and Pavliakova et al., *Infect. Immun.* 68:2161-66, 2000). A carrier can be useful even if the antibody that it elicits is not of benefit by itself.

Specific, non-limiting examples of suitable polypeptide carriers include, but are not limited to, natural, semi-synthetic or synthetic polypeptides or proteins from bacteria or viruses. In one embodiment, bacterial products for use as carriers include bacterial toxins. Bacterial toxins include bacterial products that mediate toxic effects, inflammatory responses, stress, shock, chronic sequelae, or mortality in a susceptible host. Specific, non-limiting examples of bacterial toxins include, but are not limited to: *B. anthracis* PA (for example, as encoded by bases 143779 to 146073 of GENBANK® Accession No. NC 007322); *B. anthracis* LF (for example, as encoded by the complement of bases 149357 to 151786 of GENBANK® Accession No. NC 007322); bacterial toxins and toxoids, such as tetanus toxin/toxoid (for example, as described in U.S. Pat. Nos. 5,601,826 and 6,696,065); diphtheria toxin/toxoid (for example, as described in U.S. Pat. Nos. 4,709,017 and 6,696,065), such as tetanus toxin heavy chain C fragment; *P. aeruginosa* exotoxin/toxoid (for example, as described in U.S. Pat. Nos. 4,428,931, 4,488,991 and 5,602,095); pertussis toxin/toxoid (for example, as described in U.S. Pat. Nos. 4,997,915, 6,399,076 and 6,696,065); and *C. perfringens* exotoxin/toxoid (for example, as described in U.S. Pat. Nos. 5,817,317 and 6,403,094) *C. difficile* toxin B or A, or analogs or mimetics of and combinations of two or more thereof. Viral proteins, such as hepatitis B surface antigen (for example, as described in U.S. Pat. Nos. 5,151,023 and 6,013,264) and core antigen (for example, as described in U.S. Pat. Nos. 4,547,367 and 4,547,368) can also be used as carriers, as well as proteins from higher organisms such as keyhole limpet hemocyanin (KLH), horseshoe crab hemocyanin, Concholepas Hemocyanin (CCH), Ovalbumin (OVA), edestin, mammalian serum albumins (such as bovine serum albumin), and mammalian immunoglobulins. In some examples, the carrier is bovine serum albumin.

In some embodiments, the carrier is selected from one of: Keyhole Limpet Hemocyanin (KLH), tetanus toxoid, tetanus toxin heavy chain C fragment, diphtheria toxoid, diphtheria toxin variant CRM197, or H influenza protein D (HiD). CRM197 is a genetically detoxified form of diphtheria toxin; a single mutation at position 52, substituting glutamic acid for glycine, causes the ADP-ribosyltransferase activity of the native diphtheria toxin to be lost. For description of protein carriers for vaccines, see Pichichero, Protein carriers of conjugate vaccines: characteristics, development, and clinical trials, Hum Vaccin Immunother., 9: 2505-2523, 2013, which is incorporated by reference herein in its entirety).

Following conjugation of the eOD to the carrier protein, the conjugate can be purified by a variety of techniques. One goal of the purification step is to separate the unconjugated eOD or carrier from the conjugate. The conjugates can be purified away from unconjugated eOD or carrier by any number of standard techniques including, for example, size exclusion chromatography, density gradient centrifugation, hydrophobic interaction chromatography, or ammonium sulfate fractionation. See, for example, Anderson et al., *J. Immunol.* 137:1181-86, 1986 and Jennings & Lugowski, *J. Immunol.* 127:1011-18, 1981. The compositions and purity of the conjugates can be determined by GLC-MS and MALDI-TOF spectrometry, for example.

In several embodiments, the disclosed immunogenic conjugates can be formulated into immunogenic composition (such as vaccines), for example by the addition of a pharmaceutically acceptable carrier and/or adjuvant.

eOD Linked to a Transmembrane Domain

In some embodiments, the eOD (e.g., Mut15, Mut16, Mut21, Mut33, Mut49, Mut50, Mut51, or Mut52) can be membrane anchored, for example, the eOD can be linked to a transmembrane domain and expressed from a viral vector, or a RNA expression vector for immunization purposes. Typically, the transmembrane domain is linked to the N-terminal residue the eOD, although a C-terminal linkage can also be sued. One or more peptide linkers (such as a gly-ser linker, for example, a 10 amino acid glycine-serine peptide linker, such as a peptide linker comprising the amino acid sequence set forth as SEQ ID NO: 50 (GGSGGSGGSGGSGGG) can be used to link the transmembrane domain and gp41 ectodomain. In some embodiments a native HIV-1 Env MPER sequence can be used to link the transmembrane domain and the gp41 protein.

Non-limiting examples of transmembrane domains for use with the disclosed embodiments include the BG505 TM domain (KIFIMIVGGLIGLRIVFAVLSVIHRVR, SEQ ID NO: 73), the Influenza A Hemagglutinin TM domain (ILAIYSTVASSLVLLVSLGAISF, SEQ ID NO: 74), and the Influenza A Neuraminidase TM domain (IITIGSICMVVGIISLILQIGNIISIWVS, SEQ ID NO: 75).

III. Polynucleotides and Expression

Polynucleotides encoding a disclosed immunogen are also provided. These polynucleotides include DNA, cDNA and RNA sequences which encode the antigen. The genetic code can be used to construct a variety of functionally equivalent nucleic acids, such as nucleic acids which differ in sequence but which encode the same protein sequence, or encode a conjugate or fusion protein including the nucleic acid sequence. Exemplary sequences include:

```
Mut15 with lumazine synthase
                                    (SEQ ID NO: 87)
atgcccatgggcagcctgcagcccctggccaccct gtacctgctgggcatgctggtggctagcgtgctgg
```

-continued

```
ccatgcagatctacgaaggcaagctgaccgccgag gggctgagattcggaattgtggcaagcaggtttaa ccacgcactggtggaccgactggtcgaaggagcta tcgatgcaattgtgcggcatggcgggagagaggaa gacatcacactggtgagagtcccaggcagctggga gattccagtggcagctggagaactggcacggaaag aggacatcgatgccgtgatcgctattggcgtcctg attagaggggctactccccacttcgactatatcgc atcagaagtgagcaagggcctggccgatctgtctc tggagctgcgaaaacctatcacttttggggtcatt actgccgataccctggaacaggcaatcgagcgcgc cggcaccaagcatggaaacaaaggctgggaagcag ccctgtccgctattgagatggcaaatctgttcaag tctctgaggggaggctccggaggctccggcggctc tggcggcagcggcggaggcgacaccatcacactgc catgcaacggaaccggaccacctccacactgtagc tccaatatcaccggactgatcctgacaaggcaggg aggctactccaacgataatacagtgatcttcagac catctggcggcgactggagggatatcgcaagatgc aatatcaccggcacagtggtgagcacccagctgtt tctgaacggctccctggccggcaatggcacagtga tcaggtccgaggactggcgcgataacgccaagtct atctgcgtgcagctgaacaccagcgtggagatcaa ttgcacaggcgccggccactgtaatatctctaggg ccaagtggaacaataccctgaagcagatcgccagc aagctgagagagcagtacggcaacaagacaatcat cttcaagccctctagcggcggcgaccctgagttcg tgaaccacagctttaattgcggcggcgagttcttt tattgtgattccacccagctgttcaactccacctg gtttaattctacatgatga
```

```
Mut16 with lumazine synthase
                                    (SEQ ID NO: 88)
atgcccatgggcagcctgcagcccctggccaccct gtacctgctgggcatgctggtggctagcgtgctgg ccatgcagatctacgaaggcaagctgaccgccgag gggctgagattcggaattgtggcaagcaggtttaa ccacgcactggtggaccgactggtcgaaggagcta tcgatgcaattgtgcggcatggcgggagagaggaa gacatcacactggtgagagtcccaggcagctggga gattccagtggcagctggagaactggcacggaaag aggacatcgatgccgtgatcgctattggcgtcctg attagaggggctactccccacttcgactatatcgc
```

-continued

```
atcagaagtgagcaagggcctggccgatctgtctc tggagctgcgaaaacctatcacttttggggtcatt actgccgatacctggaacaggcaatcgagcgcgc cggcaccaagcatggaaacaaaggctgggaagcag ccctgtccgctattgagatggcaaatctgttcaag tctctgaggggaggctccggaggctctggcggcag cggcggctccggcggaggcgacaccatcacactgc catgcaggcctgcaccacctccaaactgtacctct aatatcacaggactgatcctgaccaggcagggagg atactctaacgataatacagtgatcttcagaccta gcggcggcgactggagggatatcgcaagatgcaat atcaccggcacagtggtgtccacccagctgtttct gaatggctctctggccggcaacggcacagtgatca ggagcgaggactggcgcgataatgccaagagcatc tgcgtgcagctgaacacctccgtggagatcaactg caccggcaatggcacatgtaacatcagcagggcca agtggaacaatacccctgaagcagatcgcctccaag ctgcgcgagcagtacggcaataagacaatcatctt caagccaagctccggcggcgaccccgagttcgtga accactcctttaactgcggcaatgtgaccttttat tgtgattctacacagctgttcaattctacctggtt taacagcacatgatga
```

Mut33 with lumazine synthase
(SEQ ID NO: 89)

```
atgcccatgggcagcctgcagcccctggccaccct gtacctgctgggcatgctggtggctagcgtgctgg ccatgcagatctacgaaggcaagctgaccgccgag gggctgagattcggaattgtggcaagcaggtttaa ccacgcactggtggaccgactggtcgaaggagcta tcgatgcaattgtgcggcatggcgggagagaggaa gacatcacactggtgagagtcccaggcagctggga gattccagtggcagctggagaactggcacggaaag aggacatcgatgccgtgatcgctattggcgtcctg attagaggggctactcccccacttcgactatatcgc atcagaagtgagcaagggcctggccgatctgtctc tggagctgcgaaaacctatcacttttggggtcatt actgccgatacctggaacaggcaatcgagcgcgc cggcaccaagcatggaaacaaaggctgggaagcag ccctgtccgctattgagatggcaaatctgttcaag tctctgaggggaggctccggaggctccgcggctc tggcggcagcggcggaggcgacaccatcacactgc
```

```
catgcaacggaaccggaccacctccacactgtagc tccaatatcaccggactgatcctgacaaggcaggg aggctactccaacgataatacagtgatcttcagac catctggcggcgactggagggatatcgcaagatgc aatatcaccggcacagtggtgagcacccagctgtt tctgaacggctccctggccggcaatggcacagtga tcaggtccgaggactggcgcgataacgccaagtct atctgcgtgcagctgaacaccagcgtggagatcaa ttgcacaggcgccggccactgtaatatctctaggg ccaagtggaacaataccctgaagcagatcgccagc aagctgagagagcagtacggcaacaagacaatcat cttcaagccctctagcggcggcgaccctgagttcg tgaaccacagctttaattgcggcaacgtgaccttt tattgtgattccacccagctgttcaactccacctg gtttaattctacatgatga
```

Mut15 without lumazine synthase
(SEQ ID NO: 90

```
gacaccatcacactgccatgcaacggaaccggacc acctccacactgtagctccaatatcaccggactga tcctgacaaggcaggaggctactccaacgataat acagtgatcttcagaccatctggcggcgactggag ggatatcgcaagatgcaatatcaccggcacagtgg tgagcacccagctgtttctgaacggctccctggcc ggcaatggcacagtgatcaggtccgaggactggcg cgataacgccaagtctatctgcgtgcagctgaaca ccagcgtggagatcaattgcacaggcgccggccac tgtaatatctctagggccaagtggaacaataccct gaagcagatcgccagcaagctgagagagcagtacg gcaacaagacaatcatcttcaagccctctagcggc ggcgaccctgagttcgtgaaccacagctttaattg cggcggcgagttctttttattgtgattccacccagc tgttcaactccacctggtttaattctacatgatga
```

Mut16 without lumazine synthase
(SEQ ID NO: 91)

```
gacaccatcacactgccatgcaggcctgcaccacc tccaaactgtacctctaatatcacaggactgatcc tgaccaggcagggaggatactctaacgataataca gtgatcttcagacctagcggcggcgactggaggga tatcgcaagatgcaatatcaccggcacagtggtgt ccacccagctgtttctgaatggctctctggccggc aacggcacagtgatcaggagcgaggactggcgcga taatgccaagagcatctgcgtgcagctgaacacct ccgtggagatcaactgcaccggcaatggcacatgt
```

-continued

```
aacatcagcagggccaagtggaacaataccctgaa gcagatcgcctccaagctgcgcgagcagtacggca ataagacaatcatcttcaagccaagctccggcggc gaccccgagttcgtgaaccactcctttaactgcgg caatgtgacctttattgtgattctacacagctgt tcaattctacctggtttaacagcacatgatga Mut33 without lumazine synthase
                              (SEQ ID NO: 92)
gacaccatcacactgccatgcaacggaaccggacc acctccacactgtagctccaatatcaccggactga tcctgacaaggcagggaggctactccaacgataat acagtgatcttcagaccatctggcggcgactggag ggatatcgcaagatgcaatatcaccggcacagtgg tgagcacccagctgtttctgaacggctccctggcc ggcaatggcacagtgatcaggtccgaggactggcg cgataacgccaagtctatctgcgtgcagctgaaca ccagcgtggagatcaattgcacaggcgccggccac tgtaatatctctagggccaagtggaacaataccct gaagcagatcgccagcaagctgagagagcagtacg gcaacaagacaatcatcttcaagccctctagcggc ggcgaccctgagttcgtgaaccacagctttaattg cggcaacgtgacctttattgtgattccacccagc tgttcaactccacctggtttaattctacatgatga
```

In several embodiments, the nucleic acid molecule encodes a precursor of a disclosed immunogen, such as a disclosed eOD linked to a lumazine synthase 60mer subunit, that, when expressed in cells under appropriate conditions, is processed into the active form of the immunogen. For example, the nucleic acid molecule can encode a eOD linked to a lumazine synthase 60mer subunit including a N-terminal signal sequence for entry into the cellular secretory system that is proteolytically cleaved in the during processing of the eOD linked to a lumazine synthase 60mer subunit.

Exemplary nucleic acids can be prepared by cloning techniques. Examples of appropriate cloning and sequencing techniques, and instructions sufficient for many cloning exercises are known (see, e.g., Sambrook et al. (Molecular Cloning: A Laboratory Manual, 4$^{th}$ ed, Cold Spring Harbor, New York, 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, MO), R&D Systems (Minneapolis, MN), Pharmacia Amersham (Piscataway, NJ), CLONTECH Laboratories, Inc. (Palo Alto, CA), Chem Genes Corp., Aldrich Chemical Company (Milwaukee, WI), Glen Research, Inc., GIBCO BRL Life Technologies, Inc. (Gaithersburg, MD), Fluka Chemica-Biochemika Analytika (Fluka Chemie AG, Buchs, Switzerland), Invitrogen (Carlsbad, CA), and Applied Biosystems (Foster City, CA), as well as many other commercial sources.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are known.

The polynucleotides encoding a disclosed immunogen can include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a disclosed immunogen can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

DNA sequences encoding the disclosed immunogen can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), 4$^{th}$ Ed., Humana Press). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as GnTI$^{-/-}$ cells (ATCC® No. CRL-3022), or HEK-293F cells.

Transformation of a host cell with recombinant DNA is typically carried out by conventional techniques. Where the host is prokaryotic, such as, but not limited to, *E. coli*, competent cells which are capable of DNA uptake can be prepared from cells harvested after exponential growth phase and subsequently treated by the CaCl$_2$ method using procedures well known in the art. Alternatively, MgCl$_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

In one non-limiting example, a disclosed immunogen is expressed using the pVRC8400 vector (described in Barouch et al., *J. Virol*, 79, 8828-8834, 2005, which is incorporated by reference herein).

Modifications can be made to a nucleic acid encoding a disclosed immunogen without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

IV. Viral Vectors

A nucleic acid molecule encoding a disclosed immunogen can be included in a viral vector, for example, for expression of the immunogen in a host cell, or for immunization of a subject. In some embodiments, the viral vectors are administered to a subject as part of a prime-boost vaccination. In several embodiments, the viral vectors are included in a vaccine, such as a primer vaccine or a booster vaccine for use in a prime-boost vaccination.

In several examples, the viral vector can be replication-competent. For example, the viral vector can have a mutation in the viral genome that does not inhibit viral replication in host cells. The viral vector also can be conditionally replication-competent. In other examples, the viral vector is replication-deficient in host cells.

A number of viral vectors have been constructed, that can be used to express the disclosed antigens, including polyoma, i.e., SV40 (Madzak et al., 1992, *J. Gen. Virol.*, 73:15331536), adenovirus (Berkner, 1992, *Cur. Top. Microbiol. Immunol.*, 158:39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256), vaccinia virus (Mackett et al., 1992, *Biotechnology*, 24:495-499), adeno-associated virus (Muzyczka, 1992, *Curr. Top. Microbiol. Immunol.*, 158:91-123; On et al., 1990, *Gene*, 89:279-282), herpes viruses including HSV and EBV (Margolskee, 1992, *Curr. Top. Microbiol. Immunol.*, 158: 67-90; Johnson et al., 1992, *J. Virol.*, 66:29522965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199), Sindbis viruses (H. Herweijer et al., 1995, *Human Gene Therapy* 6:1161-1167; U.S. Pat. Nos. 5,091,309 and 5,2217,879), alphaviruses (S. Schlesinger, 1993, *Trends Biotechnol.* 11:18-22; I. Frolov et al., 1996, *Proc. Natl. Acad. Sci.* USA 93:11371-11377) and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In several embodiments, the viral vector can include an adenoviral vector that expresses a disclosed immunogen. Adenovirus from various origins, subtypes, or mixture of subtypes can be used as the source of the viral genome for the adenoviral vector. Non-human adenovirus (e.g., simian, chimpanzee, gorilla, avian, canine, ovine, or bovine adenoviruses) can be used to generate the adenoviral vector. For example, a simian adenovirus can be used as the source of the viral genome of the adenoviral vector. A simian adenovirus can be of serotype 1, 3, 7, 11, 16, 18, 19, 20, 27, 33, 38, 39, 48, 49, 50, or any other simian adenoviral serotype. A simian adenovirus can be referred to by using any suitable abbreviation known in the art, such as, for example, SV, SAdV, SAV or sAV. In some examples, a simian adenoviral vector is a simian adenoviral vector of serotype 3, 7, 11, 16, 18, 19, 20, 27, 33, 38, or 39. In one example, a chimpanzee serotype C Ad3 vector is used (see, e.g., Peruzzi et al., Vaccine, 27:1293-1300, 2009). Human adenovirus can be used as the source of the viral genome for the adenoviral vector. Human adenovirus can be of various subgroups or serotypes. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22, 23, 24, 25, 26, 27, 28, 29, 30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. The person of ordinary skill in the art is familiar with replication competent and deficient adenoviral vectors (including singly and multiply replication deficient adenoviral vectors). Examples of replication-deficient adenoviral vectors, including multiply replication-deficient adenoviral vectors, are disclosed in U.S. Pat. Nos. 5,837,511; 5,851,806; 5,994, 106; 6,127,175; 6,482,616; and 7,195,896, and International Patent Application Nos. WO 94/28152, WO 95/02697, WO 95/16772, WO 95/34671, WO 96/22378, WO 97/12986, WO 97/21826, and WO 03/02231 1.

V. Virus-Like Particles

In some embodiments, a virus-like particle (VLP) is provided that includes a disclosed immunogen. VLPs lack the viral components that are required for virus replication and thus represent a highly attenuated, replication-incompetent form of a virus. However, the VLP can display a polypeptide (e.g., a disclosed eOD, such as Mut15, Mut16, Mut 21, or Mut33) that is analogous to that expressed on infectious virus particles and should be equally capable of eliciting an immune response to HIV-1 when administered to a subject. Virus like particles and methods of their production are known, and viral proteins from several viruses are known to form VLPs, including human papillomavirus, HIV (Kang et al., *Biol. Chem.* 380: 353-64 (1999)), Semliki-Forest virus (Notka et al., *Biol. Chem.* 380: 341-52 (1999)), human polyomavirus (Goldmann et al., J. Virol. 73: 4465-9 (1999)), rotavirus (Jiang et al., *Vaccine* 17: 1005-13 (1999)), parvovirus (Casal, Biotechnology and Applied Biochemistry, Vol 29, Part 2, pp 141-150 (1999)), canine parvovirus (Hurtado et al., *J. Virol.* 70: 5422-9 (1996)), hepatitis E virus (Li et al., *J. Virol.* 71: 7207-13 (1997)), and Newcastle disease virus. The formation of such VLPs can be detected by any suitable technique. Examples of suitable techniques known in the art for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

VI. Pharmaceutical Compositions

Immunogenic compositions comprising a disclosed immunogen and a pharmaceutically acceptable carrier are also provided. Such pharmaceutical compositions can be administered to subjects by a variety of administration modes known to the person of ordinary skill in the art, for example, intramuscular, subcutaneous, intravenous, intra-arterial, intra-articular, intraperitoneal, or parenteral routes. In several embodiments, pharmaceutical compositions including one or more of the disclosed immunogens are immunogenic compositions. Actual methods for preparing administrable compositions will be known or apparent to those skilled in the art and are described in more detail in such publications as *Remingtons Pharmaceutical Sciences*, 19$^{th}$ Ed., Mack Publishing Company, Easton, Pennsylvania, 1995.

Thus, an immunogen described herein can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually ≤1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The pharmaceutical compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The pharmaceutical composition may optionally include an adjuvant to enhance an immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, IN) and IL-12 (Genetics Institute, Cambridge, MA), among many other suitable adjuvants well known in the art, may be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some embodiments, the composition can be provided as a sterile composition. The pharmaceutical composition typically contains an effective amount of a disclosed immunogen and can be prepared by conventional techniques. Typically, the amount of immunogen in each dose of the immunogenic composition is selected as an amount which elicits an immune response without significant, adverse side effects. In some embodiments, the composition can be provided in unit dosage form for use to elicit an immune response in a subject, for example, to prevent HIV-1 infection in the subject. A unit dosage form contains a suitable single preselected dosage for administration to a subject, or suitable marked or measured multiples of two or more preselected unit dosages, and/or a metering mechanism for administering the unit dose or multiples thereof. In other embodiments, the composition further includes an adjuvant.

VII. Methods of Inducing an Immune Response

The disclosed immunogens (e.g., Mut15, Mut16, Mut21, Mut33, Mut49, Mut50, Mut51, or Mut52, or a lumazine synthase protein nanoparticle comprising Mut15, Mut16, Mut21, Mut33, Mut49, Mut50, Mut51, or Mut52), polynucleotides and vectors encoding the disclosed immunogens, and compositions including same, can be used in methods of inducing an immune response to HIV-1 to prevent, inhibit, and/or treat an HIV-1 infection.

When inhibiting, treating, or preventing HIV-1 infection, the methods can be used either to avoid infection in an HIV-1 seronegative subject (e.g., by inducing an immune response that protects against HIV-1 infection), or to treat existing infection in an HIV-1 seropositive subject. The HIV-1 seropositive subject may or may not carry a diagnosis of AIDS. Hence in some embodiments the methods involve selecting a subject at risk for contracting HIV-1 infection, or a subject at risk of developing AIDS (such as a subject with HIV-1 infection), and administering a disclosed immunogen to the subject to elicit an immune response to HIV-1 in the subject.

To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize HIV-1 infection. These and other routine methods allow the clinician to select patients in need of therapy using the methods and pharmaceutical compositions of the disclosure. In accordance with these methods and principles, a composition can be administered according to the teachings herein, or other conventional methods, as an independent prophylaxis or treatment program, or as a follow-up, adjunct or coordinate treatment regimen to other treatments.

The disclosed immunogens can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-HIV-1 immune response, such as an immune response to HIV-1 Env protein. Separate immunogenic compositions that elicit the anti-HIV-1 immune response can be combined in a polyvalent immunogenic composition administered to a subject in a single immunization step, or they can be administered separately (in monovalent immunogenic compositions) in a coordinate immunization protocol.

In one embodiment, a suitable immunization regimen includes at least two separate inoculations with one or more immunogenic compositions including a disclosed immunogen, with a second inoculation being administered more than about two, about three to eight, or about four, weeks following the first inoculation. A third inoculation can be administered several months after the second inoculation, and in specific embodiments, more than about five months after the first inoculation, more than about six months to about two years after the first inoculation, or about eight months to about one year after the first inoculation. Periodic inoculations beyond the third are also desirable to enhance the subject's "immune memory." The adequacy of the vaccination parameters chosen, e.g., formulation, dose, regimen and the like, can be determined by taking aliquots of serum from the subject and assaying antibody titers during the course of the immunization program. Alternatively, the T cell populations can be monitored by conventional methods. In addition, the clinical condition of the subject can be monitored for the desired effect, e.g., prevention of HIV-1 infection or progression to AIDS, improvement in disease state (e.g., reduction in viral load), or reduction in transmission frequency to an uninfected partner. If such monitoring indicates that vaccination is sub-optimal, the subject can be boosted with an additional dose of immunogenic composition, and the vaccination parameters can be modified in a fashion expected to potentiate the immune response. Thus, for example, a dose of a disclosed immunogen can be increased or the route of administration can be changed.

The prime and the boost can be administered as a single dose or multiple doses, for example, two doses, three doses, four doses, five doses, six doses or more can be administered to a subject over days, weeks or months. Multiple boosts can also be given, such one to five, or more. Different dosages can be used in a series of sequential inoculations. For example, a relatively large dose in a primary inoculation and then a boost with relatively smaller doses. The immune response against the selected antigenic surface can be generated by one or more inoculations of a subject.

In some embodiments, the prime comprises administration of an immunogen comprising an eOD as described herein (for example, Mut15, Mut16, Mut21, Mut33, Mut49, Mut50, Mut51, or Mut52, such as a lumazine synthase 60mer comprising Mut15, Mut16, Mut21, Mut33, Mut49, Mut50, Mut51, or Mut52), and the boost (or boosts) comprises administration of a recombinant HIV-1 Env ectodomain trimer that is stabilized in a prefusion mature closed conformation as described in PCT App. No. PCT/US2015/048729 (incorporated by reference herein in its entirety).

In several embodiments, a disclosed immunogen can be administered to the subject simultaneously with the administration of an adjuvant. In other embodiments, the immunogen can be administered to the subject after the administration of an adjuvant and within a sufficient amount of time to elicit the immune response.

Determination of effective dosages in this context is typically based on animal model studies followed up by human clinical trials and is guided by administration protocols that significantly reduce the occurrence or severity of targeted disease symptoms or conditions in the subject, or that elicit a desired response in the subject (such as a neutralizing immune response). Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes.

Dosage can be varied by the attending clinician to maintain a desired concentration at a target site (for example, systemic circulation). Higher or lower concentrations can be selected based on the mode of delivery, for example, transepidermal, rectal, oral, pulmonary, or intranasal delivery versus intravenous or subcutaneous delivery. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

A non-limiting range for a therapeutically effective amount of the disclosed immunogen within the methods and immunogenic compositions of the disclosure is about 0.0001 mg/kg body weight to about 10 mg/kg body weight, such as about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 4 mg/kg, about 5 mg/kg, or about 10 mg/kg, for example, 0.01 mg/kg to about 1 mg/kg body weight, about 0.05 mg/kg to about 5 mg/kg body weight, about 0.2 mg/kg to about 2 mg/kg body weight, or about 1.0 mg/kg to about 10 mg/kg body weight. In some embodiments, the dosage includes a set amount of a disclosed immunogen such as from about 1-300 µg, for example, a dosage of about 1, 2, 3, 4, 5, 6, 7, 8, 9, 10, 15, 20, 30, 40, 50, 60, 70, 80, 90, 100, 150, 200, 250, or about 300 µg.

HIV-1 infection does not need to be completely inhibited for the methods to be effective. For example, elicitation of an immune response to HIV-1 with one or more of the disclosed immunogens can reduce or inhibit HIV-1 infection by a desired amount, for example, by at least 10%, at least 20%, at least 50%, at least 60%, at least 70%, at least 80%, at least 90%, at least 95%, at least 98%, or even at least 100% (elimination or prevention of detectable HIV-1 infected cells), as compared to HIV-1 infection in the absence of the therapeutic agent.

Following immunization of a subject, serum can be collected from the subject at appropriate time points, frozen, and stored for neutralization testing. Methods to assay for neutralization activity include, but are not limited to, plaque reduction neutralization (PRNT) assays, microneutralization assays, flow cytometry based assays, single-cycle infection assays (e.g., as described in Martin et al. (2003) *Nature Biotechnology* 21:71-76), and pseudovirus neutralization assays (e.g., as described in Georgiev et al. (*Science*, 340, 751-756, 2013), Seaman et al. (*J. Virol.*, 84, 1439-1452, 2005), and Mascola et al. (*J. Virol.*, 79, 10103-10107, 2005), each of which is incorporated by reference herein in its entirety. In some embodiments, the serum neutralization activity can be assayed using a panel of HIV-1 pseudoviruses as described in Georgiev et al., *Science*, 340, 751-756, 2013 or Seaman et al. *J. Virol.*, 84, 1439-1452, 2005. Briefly, pseudovirus stocks are prepared by co-transfection of 293T cells with an HIV-1 Env-deficient backbone and an expression plasmid encoding the Env gene of interest. The serum to be assayed is diluted in Dulbecco's modified Eagle medium-10% FCS (Gibco) and mixed with pseudovirus. After 30 min, 10,000 TZM-bl cells are added, and the plates are incubated for 48 hours. Assays are developed with a luciferase assay system (Promega, Madison, WI), and the relative light units (RLU) are read on a luminometer (Perkin-Elmer, Waltham, MA). To account for background, a cutoff of $ID_{50} \geq 40$ can be used as a criterion for the presence of serum neutralization activity against a given pseudovirus.

One approach to administration of nucleic acids is direct immunization with plasmid DNA, such as with a mammalian expression plasmid. Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 µg encapsulated in ISCOMS™ have been found to produce Class I mediated CTL responses (Takahashi et al., *Nature* 344:873, 1990).

In some embodiments, a plasmid DNA vaccine is used to express a disclosed immunogen in a subject. For example, a nucleic acid molecule encoding a disclosed immunogen can be administered to a subject to elicit an immune response to HIV-1 gp120. In some embodiments, the nucleic acid molecule can be included on a plasmid vector for DNA immunization, such as the pVRC8400 vector (described in Barouch et al., *J. Virol*, 79, 8828-8834, 2005, which is incorporated by reference herein).

In another approach to using nucleic acids for immunization, a disclosed eOD can be expressed by attenuated viral hosts or vectors or bacterial vectors. Recombinant vaccinia virus, adeno-associated virus (AAV), herpes virus, retrovirus, cytogmeglo virus or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991).

In one embodiment, a nucleic acid encoding a disclosed eOD is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

EXAMPLES

The following examples are provided to illustrate particular features of certain embodiments, but the scope of the claims should not be limited to those features exemplified.

Example 1

Glycan-Masking Focuses Immune Responses to the HIV-1 CD4-Binding Site and Enhances Elicitation of VRC01-Class Precursor Antibodies The VRC01-class of potent bnAbs targets the conserved CD4bs of HIV-1 Env and has been a major target of HIV-vaccine design. A proposed immunogen to engage the VRC01-class germline precursors is the eOD-GT8 60mer, which has been shown to elicit VRC01-class precursors in transgenic mouse models. However, a large proportion of the antibodies elicited by eOD-GT8 60mer are non-CD4bs "off-target" antibodies (reported in Tian, M. et al., *Cell* 166, 1471 (2016)). This off-target immune response undermines the effectiveness of the eOD-GT8 immunogen in eliciting VRC01-class bnAb precursors.

This example describes design, production, and analysis of modified eOD constructs that provide improved selectivity for CD4bs antibodies and which produce improved serum responses relative to eOD-GT8 60mer nanoparticle.

To focus the immune responses to the CD4bs neutralization epitope, structural information was used to introduce sequons for N-linked glycans at 13 different locations on the non-CD4bs surface of the eOD of eOD-GT8. The antigenic integrity of these glycan-masked variants was verified with VRC01-class bNAbs, their germline revertants and non-CD4bs-specific antibodies. Glycan mutants with high binding to CD4bs-specific antibodies, but reduced binding to non-CD4bs-specific antibodies, were selected and further tested in an IGHV1-2*02 knock-in mouse model. In this model, the knock-in germline human IGHV1-2*02 heavy chain gene segment recombines with mouse $D_H$ and $J_H$ gene segments to generate a diverse repertoire of CDRH3s (Tian et al., *Cell* 166: 1471-1484 e1418, 2016) and pairs with the full repertoire of mouse Ig light chains.

Of approximately 50 tested mutants that were designed and screened, a few mutations were identified that confer remarkably reduced binding to non-CD4bs antibodies yet retain strong binding to VRC01-class germline precursor antibodies. The identified eOD-GT8 mutants also outperformed the original eOD-GT8 60mer in eliciting VRC01-class precursors in the IGHV1-2*02 knock-in mouse model after a one-dose immunization, as shown by $V_H V_L$-paired-IgG-deep-sequencing. The serological analysis and antigen-specific memory B-cell sorting demonstrated that the glycan-masking mutants induced considerably lower titers of non-CD4bs-speclflc antibodies and overall a significantly higher proportion of CD4bs-speclflc antibodies than the unmutated eOD-GT8 60mer. As discussed below, it was remarkably found that selected glycan masked eOD-GT8 60mer mutants elicited an increase in CD4bs-specific B cell frequency among all antigen-specific B cells from ~30% for the parent eOD-GT8 60mer to ~90% for glycan masked eOD-GT8 60mer mutants in in vivo immunogenicity assays.

It is believed that the ability of an immunogen to elicit a high proportion of CD4bs-specific antibody/B cell precursors is important to eliciting VRC01-class bnAbs. It is demonstrated herein that selected glycan-masking of the non-CD4bs surface of eOD-GT8 reduces off-target immune responses and facilitates the elicitation of VRC01-class precursor antibodies.

Results
Design of eOD Glycan-Masking Mutants.

eOD of eOD-GT8 monomer contains 10 predicted native N-linked glycans. Despite this surface coverage, a considerable area of protein surface outside the CD4bs is exposed. To reduce off-target immunogenicity, non-CD4bs regions were masked from the humoral immune system by introducing N-linked glycans onto the eOD portion of the eOD-GT8 60mer surface. To select new glycan sites the crystal structure of the eOD-GT8 monomer (PDB ID NO. 5IES; Jardine et al., *Science* 351, 1458-1463, 2016) was used as a model. Thirteen potential sites for the introduction of NxT sequons were identified by using the following criteria: 1) surface residues at least 5 Å from the CD4bs, 2) not adjacent to native glycans, 3) NxT mutations not expected to disrupt the eOD structure, and 4) high probability of glycosylation as determined from the sequence using NetNGlyc (cbs.dtu.dk/services/NetOGlyc/) (FIG. 1A). Each glycan was introduced by mutating the target sequence to include an Asn-X-Thr sequon, though an Asn-X-Ser sequon could also be effective. Some reports indicate that NxT sequons are glycosylated more efficiently than NxS sequons. Thirteen single glycan mutants, each containing one added glycan, were created for individual evaluation (eOD-GT8-mut1-12 and eOD-GT8-mut23; FIG. 1B and FIG. 11). Structural modeling of the additional glycans provided an indication of the extensive non-CD4bs surface that could potentially be covered by these glycan additions (FIG. 1C).

To maximize the masking area while ensuring protein stability, 39 multi-glycan mutants were designed, each containing 2 to 6 of the 13 new glycans (eOD-GT8-mut13-22 and eOD-GT8-mut24-52 in FIG. 11). Since previous studies have suggested that protruding loops on protein surfaces tend to be immunogenic, regions of the non-CD4bs surface of eOD-GT8 were focused on as potential immunogenic hotspots when creating the groupings for glycan-masking. Examination of the eOD-GT8 monomer crystal structure indicated that the glycans from eOD-GT8-mut1, -mut2, -mut3, -mut7, -mut10, and -mut11 were each located on protruding loops. Additionally, in three mutants (eOD-GT8-mut24, -mut27, and -mut39), the native glycan at 289 was moved to position 287 to improve glycan coverage. Furthermore, to construct a potential boosting immunogen that could drive affinity maturation of VRC01-class germline precursors to accommodate the conserved N276 and N463 glycans existing in over 90% of HIV-1 strains, an additional N276 or N463 glycan was also incorporated in eOD-GT8-mut42, -mut43, -mut44, -mut45, -mut46, -mut47, and -mut48 (FIG. 11).

In total, 52 eOD-GT8 mutants were designed including 13 single glycan mutants and 39 glycan combinations. The sequences of the eOD mutants is provided below:

For reference, the eOD sequence of eOD-GT8 is as follows:

```
                                        (SEQ ID NO: 1)
DTITLPCRPAPPPHCSSNITGLILTRQGGYSNDNT

VIFRPSGGDWRDIARCQIAGTVVSTQLFLNGSLAE

EEVVIRSEDWRDNAKSICVQLNTSVEINCTGAGHC

NISRAKWNNTLKQIASKLREQYGNKTIIFKPSSGG

DPEFVNHSFNCGGEFFYCDSTQLFNSTWFNST
```

The 52 eOD variants are as follows (mutation numbers in parentheses indicate the residue positions in Hxbc2 numbering where glycans were added):

```
Mut1 (268)
                                       (SEQ ID NO: 77)
DTITLPCRPAPPPHCSSNITGLILTRQGGYSNDNT

VIFRPSGGDWRDIARCQIAGTVVSTQLFLNGSLAG

NGTVIRSEDWRDNAKSICVQLNTSVEINCTGAGHC

NISRAKWNNTLKQIASKLREQYGNKTIIFKPSSGG

DPEFVNHSFNCGGEFFYCDSTQLFNSTWFNST

Mut2 (267)
                                        (SEQ ID NO: 2)
DTITLPCRPAPPPHCSSNITGLILTRQGGYSNDNT

VIFRPSGGDWRDIARCQIAGTVVSTQLFLNGSLAN

GTVVIRSEDWRDNAKSICVQLNTSVEINCTGAGHC

NISRAKWNNTLKQIASKLREQYGNKTIIFKPSSGG

DPEFVNHSFNCGGEFFYCDSTQLFNSTWFNST

Mut3 (444)
                                        (SEQ ID NO: 3)
DTITLPCRPAPPPNCTSNITGLILTRQGGYSNDNT

VIFRPSGGDWRDIARCQIAGTVVSTQLFLNGSLAE

EEVVIRSEDWRDNAKSICVQLNTSVEINCTGAGHC
```

```
Mut4 (482)
                            (SEQ ID NO: 4)
DTITLPCRPAPPPHCSSNITGLILTRQGGYSNDNT
VIFRPSGGDWRDIARCNITGTVVSTQLFLNGSLAE
EEVVIRSEDWRDNAKSICVQLNTSVEINCTGAGHC
NISRAKWNNTLKQIASKLREQYGNKTIIFKPSSGG
DPEFVNHSFNCGGEFFYCDSTQLFNSTWFNST

Mut5 (253)
                            (SEQ ID NO: 5)
DTITLPCRPAPPPHCSSNITGLILTRQGGYSNDNT
VIFRPSGGDWRDIARCQIAGNVTSTQLFLNGSLAE
EEVVIRSEDWRDNAKSICVQLNTSVEINCTGAGHC
NISRAKWNNTLKQIASKLREQYGNKTIIFKPSSGG
DPEFVNHSFNCGGEFFYCDSTQLFNSTWFNST

Mut6 (377)
                            (SEQ ID NO: 6)
DTITLPCRPAPPPHCSSNITGLILTRQGGYSNDNT
VIFRPSGGDWRDIARCQIAGTVVSTQLFLNGSLAE
EEVVIRSEDWRDNAKSICVQLNTSVEINCTGAGHC
NISRAKWNNTLKQIASKLREQYGNKTIIFKPSSGG
DPEFVNHSFNCTGEFFYCDSTQLFNSTWFNST

Mut7 (380)
                            (SEQ ID NO: 7)
DTITLPCRPAPPPHCSSNITGLILTRQGGYSNDNT
VIFRPSGGDWRDIARCQIAGTVVSTQLFLNGSLAE
EEVVIRSEDWRDNAKSICVQLNTSVEINCTGAGHC
NISRAKWNNTLKQIASKLREQYGNKTIIFKPSSGG
DPEFVNHSFNCGNVTFYCDSTQLFNSTWFNST

Mut8 (413)
                            (SEQ ID NO: 8)
DNITLPCRPAPPPHCSSNITGLILTRQGGYSNDNT
VIFRPSGGDWRDIARCQIAGTVVSTQLFLNGSLAE
EEVVIRSEDWRDNAKSICVQLNTSVEINCTGAGHC
NISRAKWNNTLKQIASKLREQYGNKTIIFKPSSGG
DPEFVNHSFNCGGEFFYCDSTQLFNSTWFNST

Mut9 (347)
                            (SEQ ID NO: 9)
DTITLPCRPAPPPHCSSNITGLILTRQGGYSNDNT
VIFRPSGGDWRDIARCQIAGTVVSTQLFLNGSLAE
EEVVIRSEDWRDNAKSICVQLNTSVEINCTGAGHC
NISRAKWNNTLKQIANKTREQYGNKTIIFKPSSGG
DPEFVNHSFNCGGEFFYCDSTQLFNSTWFNST

Mut10 (299)
                            (SEQ ID NO: 10)
DTITLPCRPAPPPHCSSNITGLILTRQGGYSNDNT
VIFRPSGGDWRDIARCQIAGTVVSTQLFLNGSLAE
EEVVIRSEDWRDNAKSICVQLNTSVEINCTGNGTC
NISRAKWNNTLKQIASKLREQYGNKTIIFKPSSGG
DPEFVNHSFNCGGEFFYCDSTQLFNSTWFNST

Mut11 (419)
                            (SEQ ID NO: 11)
DTITLPCNGTGPPPHCSSNITGLILTRQGGYSNDN
TVIFRPSGGDWRDIARCQIAGTVVSTQLFLNGSLA
EEEVVIRSEDWRDNAKSICVQLNTSVEINCTGAGH
CNISRAKWNNTLKQIASKLREQYGNKTIIFKPSSG
GDPEFVNHSFNCGGEFFYCDSTQLFNSTWFNST

Mut12 (386)
                            (SEQ ID NO: 12)
DTITLPCRPAPPPHCSSNITGLILTRQGGYSNDNT
VIFRPSGGDWRDIARCQIAGTVVSTQLFLNGSLAE
EEVVIRSEDWRDNAKSICVQLNTSVEINCTGAGHC
NISRAKWNNTLKQIASKLREQYGNKTIIFKPSSGG
DPEFVNHSFNCGGEFFYCNSTQLFNSTWFNST

Mut13 (444, 253, and 268)
                            (SEQ ID NO: 13)
DTITLPCRPAPPPNCTSNITGLILTRQGGYSNDNT
VIFRPSGGDWRDIARCQIAGNVTSTQLFLNGSLAG
NGTVIRSEDWRDNAKSICVQLNTSVEINCTGAGHC
NISRAKWNNTLKQIASKLREQYGNKTIIFKPSSGG
DPEFVNHSFNCGGEFFYCDSTQLFNSTWFNST Mut14 (444, 482, and 268)
                            (SEQ ID NO: 14)
DTITLPCRPAPPPNCTSNITGLILTRQGGYSNDNT
VIFRPSGGDWRDIARCNITGTVVSTQLFLNGSLAG
NGTVIRSEDWRDNAKSICVQLNTSVEINCTGAGHC
NISRAKWNNTLKQIASKLREQYGNKTIIFKPSSGG
DPEFVNHSFNCGGEFFYCDSTQLFNSTWFNST Mut15 (419, 482, and 268)
                            (SEQ ID NO: 15)
DTITLPCNGTGPPPHCSSNITGLILTRQGGYSNDN
TVIFRPSGGDWRDIARCNITGTVVSTQLFLNGSLA
GNGTVIRSEDWRDNAKSICVQLNTSVEINCTGAGH
CNISRAKWNNTLKQIASKLREQYGNKTIIFKPSSG
GDPEFVNHSFNCGGEFFYCDSTQLFNSTWFNST Mut16
(444, 482, 268, 299, and 380)
                            (SEQ ID NO: 16)
DTITLPCRPAPPPNCTSNITGLILTRQGGYSNDNT
VIFRPSGGDWRDIARCNITGTVVSTQLFLNGSLAG
NGTVIRSEDWRDNAKSICVQLNTSVEINCTGNGTC
```

```
Mut17
(444, 482, 268, 299, and 377)
                            (SEQ ID NO: 17)
DTITLPCRPAPPPNCTSNITGLILTRQGGYSNDNT

VIFRPSGGDWRDIARCNITGTVVSTQLFLNGSLAG

NGTVIRSEDWRDNAKSICVQLNTSVEINCTGNGTC

NISRAKWNNTLKQIASKLREQYGNKTIIFKPSSGG

DPEFVNHSFNCTGEFFYCDSTQLFNSTWFNST

Mut18
(413, 444, 482, 253, 268, and 377)
                            (SEQ ID NO: 18)
DNITLPCRPAPPPNCTSNITGLILTRQGGYSNDNT

VIFRPSGGDWRDIARCNITGNVTSTQLFLNGSLAG

NGTVIRSEDWRDNAKSICVQLNTSVEINCTGAGHC

NISRAKWNNTLKQIASKLREQYGNKTIIFKPSSGG

DPEFVNHSFNCTGEFFYCDSTQLFNSTWFNST

Mut19
(413, 444, 267, 299, and 377)
                            (SEQ ID NO: 19)
DNITLPCRPAPPPNCTSNITGLILTRQGGYSNDNT

VIFRPSGGDWRDIARCQIAGTVVSTQLFLNGSLAN

GTVVIRSEDWRDNAKSICVQLNTSVEINCTGNGTC

NISRAKWNNTLKQIASKLREQYGNKTIIFKPSSGG

DPEFVNHSFNCTGEFFYCDSTQLFNSTWFNST

Mut20
(413, 268, and 347)
                            (SEQ ID NO: 20)
DNITLPCRPAPPPHCSSNITGLILTRQGGYSNDNT

VIFRPSGGDWRDIARCQIAGTVVSTQLFLNGSLAG

NGTVIRSEDWRDNAKSICVQLNTSVEINCTGAGHC

NISRAKWNNTLKQIANKTREQYGNKTIIFKPSSGG

DPEFVNHSFNCGGEFFYCDSTQLFNSTWFNST

Mut21
(419, 444, 482, 267, 299, and 380)
                            (SEQ ID NO: 21)
DTITLPCNGTGPPPNCTSNITGLILTRQGGYSNDN

TVIFRPSGGDWRDIARCNITGTVVSTQLFLNGSLA

NGTVVIRSEDWRDNAKSICVQLNTSVEINCTGNGT

CNISRAKWNNTLKQIASKLREQYGNKTIIFKPSSG

GDPEFVNHSFNCGNVTFYCDSTQLFNSTWFNST

Mut22
(413, 444, 482, 253, 271, with
Mutations E267G and E268G)
                            (SEQ ID NO: 22)
DNITLPCRPAPPPNCTSNITGLILTRQGGYSNDNT

VIFRPSGGDWRDIARCNITGNVTSTQLFLNGSLAG

GEVNGTSEDWRDNAKSICVQLNTSVEINCTGAGHC

NISRAKWNNTLKQIASKLREQYGNKTIIFKPSSGG

DPEFVNHSFNCGNVTFYCDSTQLFNSTWFNST

Mut23
(271 with Mutations E267G
and E268G)
                            (SEQ ID NO: 23)
DTITLPCRPAPPPHCSSNITGLILTRQGGYSNDNT

VIFRPSGGDWRDIARCQIAGTVVSTQLFLNGSLAG

GEVNGTSEDWRDNAKSICVQLNTSVEINCTGAGHC

NISRAKWNNTLKQIASKLREQYGNKTIIFKPSSGG

DPEFVNHSFNCGGEFFYCDSTQLFNSTWFNST

Mut24 (268 and 287)
                            (SEQ ID NO: 24)
DTITLPCRPAPPPHCSSNITGLILTRQGGYSNDNT

VIFRPSGGDWRDIARCQIAGTVVSTQLFLNGSLAG

NGTVIRSEDWRDNAKSICVNLTTSVEINCTGAGHC

NISRAKWNNTLKQIASKLREQYGNKTIIFKPSSGG

DPEFVNHSFNCGGEFFYCDSTQLFNSTWFNST

Mut25 (419 and 268)
                            (SEQ ID NO: 25)
DTITLPCNGTGPPPHCSSNITGLILTRQGGYSNDN

TVIFRPSGGDWRDIARCQIAGTVVSTQLFLNGSLA

GNGTVIRSEDWRDNAKSICVQLNTSVEINCTGAGH

CNISRAKWNNTLKQIASKLREQYGNKTIIFKPSSG

GDPEFVNHSFNCGGEFFYCDSTQLFNSTWFNST

Mut26 (268, 299, and 380)
                            (SEQ ID NO: 26)
DTITLPCRPAPPPHCSSNITGLILTRQGGYSNDNT

VIFRPSGGDWRDIARCQIAGTVVSTQLFLNGSLAG

NGTVIRSEDWRDNAKSICVQLNTSVEINCTGNGTC

NISRAKWNNTLKQIASKLREQYGNKTIIFKPSSGG

DPEFVNHSFNCGNVTFYCDSTQLFNSTWFNST

Mut27 (268, 287, 299, and 380)
                            (SEQ ID NO: 27)
DTITLPCRPAPPPHCSSNITGLILTRQGGYSNDNT

VIFRPSGGDWRDIARCQIAGTVVSTQLFLNGSLAG

NGTVIRSEDWRDNAKSICVNLTTSVEINCTGNGTC

NISRAKWNNTLKQIASKLREQYGNKTIIFKPSSGG

DPEFVNHSFNCGNVTFYCDSTQLFNSTWFNST

Mut28 (482, 268, 299, and 380)
                            (SEQ ID NO: 28)
DTITLPCRPAPPPHCSSNITGLILTRQGGYSNDNT

VIFRPSGGDWRDIARCNITGTVVSTQLFLNGSLAG

NGTVIRSEDWRDNAKSICVQLNTSVEINCTGNGTC

NISRAKWNNTLKQIASKLREQYGNKTIIFKPSSGG

DPEFVNHSFNCGNVTFYCDSTQLFNSTWFNST
```

Mut29 (253, 268, 299, and 380)
(SEQ ID NO: 29)
DTITLPCRPAPPPHCSSNITGLILTRQGGYSNDNT

VIFRPSGGDWRDIARCQIAGNVTSTQLFLNGSLAG

NGTVIRSEDWRDNAKSICVQLNTSVEINCTGNGTC

NISRAKWNNTLKQIASKLREQYGNKTIIFKPSSGG

DPEFVNHSFNCGNVTFYCDSTQLFNSTWFNST

Mut30 (413, 268, 299, and 380)
(SEQ ID NO: 30)
DNITLPCRPAPPPHCSSNITGLILTRQGGYSNDNT

VIFRPSGGDWRDIARCQIAGTVVSTQLFLNGSLAG

NGTVIRSEDWRDNAKSICVQLNTSVEINCTGNGTC

NISRAKWNNTLKQIASKLREQYGNKTIIFKPSSGG

DPEFVNHSFNCGNVTFYCDSTQLFNSTWFNST

Mut31 (268, 299, 347, and 380)
(SEQ ID NO: 31)
DTITLPCRPAPPPHCSSNITGLILTRQGGYSNDNT

VIFRPSGGDWRDIARCQIAGTVVSTQLFLNGSLAG

NGTVIRSEDWRDNAKSICVQLNTSVEINCTGNGTC

NISRAKWNNTLKQIANKTREQYGNKTIIFKPSSGG

DPEFVNHSFNCGNVTFYCDSTQLFNSTWFNST

Mut32 (268, 299, 380, and 386)
(SEQ ID NO: 32)
DTITLPCRPAPPPHCSSNITGLILTRQGGYSNDNT

VIFRPSGGDWRDIARCQIAGTVVSTQLFLNGSLAG

NGTVIRSEDWRDNAKSICVQLNTSVEINCTGNGTC

NISRAKWNNTLKQIASKLREQYGNKTIIFKPSSGG

DPEFVNHSFNCGNVTFYCNSTQLFNSTWFNST

Mut33
(419, 482, 268, and 380)
(SEQ ID NO: 33)
DTITLPCNGTGPPPHCSSNITGLILTRQGGYSNDN

TVIFRPSGGDWRDIARCNITGTVVSTQLFLNGSLA

GNGTVIRSEDWRDNAKSICVQLNTSVEINCTGAGH

CNISRAKWNNTLKQIASKLREQYGNKTIIFKPSSG

GDPEFVNHSFNCGNVTFYCDSTQLFNSTWFNST

Mut34
(413, 419, 482, 268, and 380)
(SEQ ID NO: 34)
DNITLPCNGTGPPPHCSSNITGLILTRQGGYSNDN

TVIFRPSGGDWRDIARCNITGTVVSTQLFLNGSLA

GNGTVIRSEDWRDNAKSICVQLNTSVEINCTGAGH

CNISRAKWNNTLKQIASKLREQYGNKTIIFKPSSG

GDPEFVNHSFNCGNVTFYCDSTQLFNSTWFNST

Mut35
(413, 419, 482, 268, and 386)
(SEQ ID NO: 35)
DNITLPCNGTGPPPHCSSNITGLILTRQGGYSNDN

TVIFRPSGGDWRDIARCNITGTVVSTQLFLNGSLA

GNGTVIRSEDWRDNAKSICVQLNTSVEINCTGAGH

CNISRAKWNNTLKQIASKLREQYGNKTIIFKPSSG

GDPEFVNHSFNCGGEFFYCNSTQLFNSTWFNST

Mut36
(419, 482, 268, 299, and 380)
(SEQ ID NO: 36)
DTITLPCNGTGPPPHCSSNITGLILTRQGGYSNDN

TVIFRPSGGDWRDIARCNITGTVVSTQLFLNGSLA

GNGTVIRSEDWRDNAKSICVQLNTSVEINCTGNGT

CNISRAKWNNTLKQIASKLREQYGNKTIIFKPSSG

GDPEFVNHSFNCGNVTFYCDSTQLFNSTWFNST

Mut37
(419, 482, 268, 380, and 386)
(SEQ ID NO: 37)
DTITLPCNGTGPPPHCSSNITGLILTRQGGYSNDN

TVIFRPSGGDWRDIARCNITGTVVSTQLFLNGSLA

GNGTVIRSEDWRDNAKSICVQLNTSVEINCTGAGH

CNISRAKWNNTLKQIASKLREQYGNKTIIFKPSSG

GDPEFVNHSFNCGNVTFYCNSTQLFNSTWFNST

Mut38
(419, 482, 268, 299, and 380)
(SEQ ID NO: 38)
DTITLPCNGTGPPPHCSSNITGLILTRQGGYSNDN

TVIFRPSGGDWRDIARCNITGTVVSTQLFLNGSLA

GNGTVIRSEDWRDNAKSICVQLNTSVEINCTGNGT

CNISRAKWNNTLKQIASKLREQYGNKTIIFKPSSG

GDPEFVNHSFNCGGEFFYCNSTQLFNSTWFNST

Mut39
(419, 482, 268, and 287)
(SEQ ID NO: 39)
DTITLPCNGTGPPPHCSSNITGLILTRQGGYSNDN

TVIFRPSGGDWRDIARCNITGTVVSTQLFLNGSLA

GNGTVIRSEDWRDNAKSICVNLTTSVEINCTGAGH

CNISRAKWNNTLKQIASKLREQYGNKTIIFKPSSG

GDPEFVNHSFNCGGEFFYCDSTQLFNSTWFNST

Mut40
(419, 482, 268, 380, with
Mutations I477L and D478N)
(SEQ ID NO: 40)
DTITLPCNGTGPPPHCSSNITGLILTRQGGYSNDN

TVIFRPSGGDWRNLARCNITGTVVSTQLFLNGSLA

GNGTVIRSEDWRDNAKSICVQLNTSVEINCTGAGH

CNISRAKWNNTLKQIASKLREQYGNKTIIFKPSSG

GDPEFVNHSFNCGNVTFYCDSTQLFNSTWFNST

Mut41
(419, 482, 268, 380, 386, with
Mutations I477L and D478N)
(SEQ ID NO: 41)
DTITLPCNGTGPPPHCSSNITGLILTRQGGYSNDT

VIFRPSGGDWRNLARCNITGTVVSTQLFLNGSLAG

NGTVIRSEDWRDNAKSICVQLNTSVEINCTGAGHC

```
Mut42
(419, 482, 268, and 276)
                                        (SEQ ID NO: 42)
DTITLPCNGTGPPPHCSSNITGLILTRQGGYSNDN

TVIFRPSGGDWRDIARCNITGTVVSTQLFLNGSLA

GNGTVIRSENFTDNAKSICVQLNTSVEINCTGAGH

CNISRAKWNNTLKQIASKLREQYGNKTIIFKPSSG

GDPEFVNHSFNCGGEFFYCDSTQLFNSTWFNST

Mut43
(419, 463, 482, 268, and 276)
                                        (SEQ ID NO: 43)
DTITLPCNGTGPPPHCSSNITGLILTRQGGYSNNG

TVIFRPSGGDWRDIARCNITGTVVSTQLFLNGSLA

GNGTVIRSENFTDNAKSICVQLNTSVEINCTGAGH

CNISRAKWNNTLKQIASKLREQYGNKTIIFKPSSG

GDPEFVNHSFNCGGEFFYCDSTQLFNSTWFNST

Mut44
(444, 482, 268, 276, 299, and 380)
                                        (SEQ ID NO: 44)
DTITLPCRPAPPPNCTSNITGLILTRQGGYSNDNT

VIFRPSGGDWRDIARCNITGTVVSTQLFLNGSLAG

NGTVIRSENFTDNAKSICVQLNTSVEINCTGNGTC

NISRAKWNNTLKQIASKLREQYGNKTIIFKPSSGG

DPEFVNHSFNCGNVTFYCDSTQLFNSTWFNST

Mut45
(419, 482, 268, 276, 380, with
Mutations I477L and D478N)
                                        (SEQ ID NO: 45)
DTITLPCNGTGPPPHCSSNITGLILTRQGGYSNDN

TVIFRPSGGDWRNLARCNITGTVVSTQLFLNGSLA

GNGTVIRSENFTDNAKSICVQLNTSVEINCTGAGH

CNISRAKWNNTLKQIASKLREQYGNKTIIFKPSSG

GDPEFVNHSFNCGNVTFYCDSTQLFNSTWFNST

Mut46
(413, 268, 276, 299, and 380)
                                        (SEQ ID NO: 46)
DNITLPCRPAPPPHCSSNITGLILTRQGGYSNDNT

VIFRPSGGDWRDIARCQIAGTVVSTQLFLNGSLAG

NGTVIRSENFTDNAKSICVQLNTSVEINCTGNGTC

NISRAKWNNTLKQIASKLREQYGNKTIIFKPSSGG

DPEFVNHSFNCGNVTFYCDSTQLFNSTWFNST

Mut47
(482, 268, 276, 299, and 380)
                                        (SEQ ID NO: 47)
DTITLPCRPAPPPHCSSNITGLILTRQGGYSNDNT

VIFRPSGGDWRDIARCNITGTVVSTQLFLNGSLAG

NGTVIRSENFTDNAKSICVQLNTSVEINCTGNGTC

NISRAKWNNTLKQIASKLREQYGNKTIIFKPSSGG

DPEFVNHSFNCGNVTFYCNSTQLFNSTWFNST

Mut48
(419, 482, 268, 276, 380, and 386)
                                        (SEQ ID NO: 48)
DTITLPCNGTGPPPHCSSNITGLILTRQGGYSNDN

TVIFRPSGGDWRDIARCNITGTVVSTQLFLNGSLA

GNGTVIRSENFTDNAKSICVQLNTSVEINCTGAGH

CNISRAKWNNTLKQIASKLREQYGNKTIIFKPSSG

GDPEFVNHSFNCGNVTFYCNSTQLFNSTWFNST

Mut49
(253, 268, and 380)
                                        (SEQ ID NO: 79)
DTITLPCRPAPPPHCSSNITGLILTRQGGYSNDNT

VIFRPSGGDWRDIARCQIAGNVTSTQLFLNGSLAG

NGTVIRSEDWRDNAKSICVQLNTSVEINCTGAGHC

NISRAKWNNTLKQIASKLREQYGNKTIIFKPSSGG

DPEFVNHSFNCGNVTFYCDSTQLFNSTWFNST

Mut50
(253, 271, 380, with
Mutations E267G and E268G)
                                        (SEQ ID NO: 80)
DTITLPCRPAPPPHCSSNITGLILTRQGGYSNDNT

VIFRPSGGDWRDIARCQIAGNVTSTQLFLNGSLAG

GEVNGTSEDWRDNAKSICVQLNTSVEINCTGAGHC

NISRAKWNNTLKQIASKLREQYGNKTIIFKPSSGG

DPEFVNHSFNCGNVTFYCDSTQLFNSTWFNST

Mut51
(419, 253, 267, 271, and 380)
                                        (SEQ ID NO: 81)
DTITLPCNGTGPPPHCSSNITGLILTRQGGYSNDN

TVIFRPSGGDWRDIARCQIAGNVTSTQLFLNGSLA

NGTVNGTSEDWRDNAKSICVQLNTSVEINCTGAGH

CNISRAKWNNTLKQIASKLREQYGNKTIIFKPSSG

GDPEFVNHSFNCGNVTFYCDSTQLFNSTWFNST

Mut52
(444, 268, 299, and 380)
                                        (SEQ ID NO: 82)
DTITLPCRPAPPPNCTSNITGLILTRQGGYSNDNT

VIFRPSGGDWRDIARCQIAGTVVSTQLFLNGSLAG

NGTVIRSEDWRDNAKSICVQLNTSVEINCTGNGTC

NISRAKWNNTLKQIASKLREQYGNKTIIFKPSSGG

DPEFVNHSFNCGNVTFYCDSTQLFNSTWFNST
```

Each of these eOD mutants was linked to the C-terminus of a lumazine synthase subunit by a flexible peptide linker. The sequence of the lumazine synthase subunit is as follows:

```
                                        (SEQ ID NO: 93)
MPMGSLQPLATLYLLGMLVASVLAMQIYEGKLTAE

GLRFGIVASRFNHALVDRLVEGAIDAIVRHGGREE
```

```
DITLVRVPGSWEIPVAAGELARKEDIDAVIAIGVL

IRGATPHFDYIASEVSKGLADLSLELRKPITFGVI

TADTLEQAIERAGTKHGNKGWEAALSAIEMANLFK

SLR
```

Residues 1-24 (MPMGSLQPLATLYLLGMLVASVLA) of SEQ ID NO: 93 are a signal peptide, which is typically cleaved from the subunit during cellular processing. Therefore, purified protein nanoparticles including the eOD linked to the lumazine synthase subunit typically do not include the signal peptide sequence.

Any appropriate signal peptide can be used to express the eOD linked to the lumazine synthase subunit. Another example is set forth as:

```
                                    (SEQ ID NO: 49)
MGWSCIILFLVATATGVHSMQIYEGKLTAEGLRFG

IVASRFNHALVDRLVEGAIDAIVRHGGREEDITLV

RVPGSWEIPVAAGELARKEDIDAVIAIGVLIRGAT

PHFDYIASEVSKGLADLSLELRKPITFGVITADTL

EQAIERAGTKHGNKGWEAALSAIEMANLFKSLR
```

Residues 1-19 (MGWSCIILFLVATATGVHS) of SEQ ID NO: 49 are a signal peptide, which is typically cleaved from the subunit during cellular processing. Therefore, purified protein nanoparticles including the eOD linked to the lumazine synthase subunit typically do not include the SEQ ID NO: 49 signal peptide sequence.

The sequence of the peptide linker used to link the eOD to the lumazine synthase subunit is set forth as GGSGGSGGSGGSGGG (SEQ ID NO: 50). Exemplary sequences of lumazine synthase subunit-linker-eOD (including the signal peptide of residues 1-24 (MPMGSLQPLATLYLLGMLVASVLA) of SEQ ID NO: 93) are set forth below:

```
Mut15_lumazine synthase
                                    (SEQ ID NO: 94)
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDTITLPCNGTGPPPHCS

SNITGLILTRQGGYSNDNTVIFRPSGGDWRDIARC

NITGTVVSTQLFLNGSLAGNGTVIRSEDWRDNAKS

ICVQLNTSVEINCTGAGHCNISRAKWNNTLKQIAS

KLREQYGNKTIIFKPSSGGDPEFVNHSFNCGGEFF

YCDSTQLFNSTWFNST

Mut16_lumazine synthase
                                    (SEQ ID NO: 95)
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDTITLPCRPAPPPNCTS

NITGLILTRQGGYSNDNTVIFRPSGGDWRDIARCN

ITGTVVSTQLFLNGSLAGNGTVIRSEDWRDNAKSI

CVQLNTSVEINCTGNGTCNISRAKWNNTLKQIASK

LREQYGNKTIIFKPSSGGDPEFVNHSFNCGNVTFY

CDSTQLFNSTWFNST

Mut17_lumazine synthase
                                    (SEQ ID NO: 96)
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDTITLPCRPAPPPNCTS

NITGLILTRQGGYSNDNTVIFRPSGGDWRDIARCN

ITGTVVSTQLFLNGSLAGNGTVIRSEDWRDNAKSI

CVQLNTSVEINCTGNGTCNISRAKWNNTLKQIASK

LREQYGNKTIIFKPSSGGDPEFVNHSFNCTGEFFY

CDSTQLFNSTWFNST

Mut18_lumazine synthase
                                    (SEQ ID NO: 97)
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDNITLPCRPAPPPNCTS

NITGLILTRQGGYSNDNTVIFRPSGGDWRDIARCN

ITGNVTSTQLFLNGSLAGNGTVIRSEDWRDNAKSI

CVQLNTSVEINCTGAGHCNISRAKWNNTLKQIASK

LREQYGNKTIIFKPSSGGDPEFVNHSFNCTGEFFY

CDSTQLFNSTWFNST

Mut19_lumazine synthase
                                    (SEQ ID NO: 98)
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDNITLPCRPAPPPNCTS

NITGLILTRQGGYSNDNTVIFRPSGGDWRDIARCQ
```

```
IAGTVVSTQLFLNGSLANGTVVIRSEDWRDNAKSI

CVQLNTSVEINCTGNGTCNISRAKWNNTLKQIASK

LREQYGNKTIIFKPSSGGDPEFVNHSFNCTGEFFY

CDSTQLFNSTWFNST
```

Mut21_lumazine synthase
(SEQ ID NO: 99)
```
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDTITLPCNGTGPPPNCT

SNITGLILTRQGGYSNDNTVIFRPSGGDWRDIARC

NITGTVVSTQLFLNGSLANGTVVIRSEDWRDNAKS

ICVQLNTSVEINCTGNGTCNISRAKWNNTLKQIAS

KLREQYGNKTIIFKPSSGGDPEFVNHSFNCGNVTF

YCDSTQLFNSTWFNST
```

Mut27_lumazine synthase
(SEQ ID NO: 100)
```
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDTITLPCRPAPPPHCSS

NITGLILTRQGGYSNDNTVIFRPSGGDWRDIARCQ

IAGTVVSTQLFLNGSLAGNTVIRSEDWRDNAKSI

CVNLTTSVEINCTGNGTCNISRAKWNNTLKQIASK

LREQYGNKTIIFKPSSGGDPEFVNHSFNCGNVTFY

CDSTQLFNSTWFNST
```

Mut28_lumazine synthase
(SEQ ID NO: 101)
```
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDTITLPCRPAPPPHCSS

NITGLILTRQGGYSNDNTVIFRPSGGDWRDIARCN

ITGTVVSTQLFLNGSLAGNTVIRSEDWRDNAKSI

CVQLNTSVEINCTGNGTCNISRAKWNNTLKQIASK

LREQYGNKTIIFKPSSGGDPEFVNHSFNCGNVTFY

CDSTQLFNSTWFNST
```

Mut29_lumazine synthase
(SEQ ID NO: 102)
```
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDTITLPCRPAPPPHCSS

NITGLILTRQGGYSNDNTVIFRPSGGDWRDIARCQ

IAGNVTSTQLFLNGSLAGNTVIRSEDWRDNAKSI

CVQLNTSVEINCTGNGTCNISRAKWNNTLKQIASK

LREQYGNKTIIFKPSSGGDPEFVNHSFNCGNVTFY

CDSTQLFNSTWFNST
```

Mut33_lumazine synthase
(SEQ ID NO: 103)
```
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDTITLPCNGTGPPPHCS

SNITGLILTRQGGYSNDNTVIFRPSGGDWRDIARC

NITGTVVSTQLFLNGSLAGNTVIRSEDWRDNAKS

ICVQLNTSVEINCTGAGHCNISRAKWNNTLKQIAS

KLREQYGNKTIIFKPSSGGDPEFVNHSFNCGNVTF

YCDSTQLFNSTWFNST
```

Mut34_lumazine synthase
(SEQ ID NO: 104)
```
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDNITLPCNGTGPPPHCS

SNITGLILTRQGGYSNDNTVIFRPSGGDWRDIARC

NITGTVVSTQLFLNGSLAGNTVIRSEDWRDNAKS

ICVQLNTSVEINCTGAGHCNISRAKWNNTLKQIAS

KLREQYGNKTIIFKPSSGGDPEFVNHSFNCGNVTF

YCDSTQLFNSTWFNST
```

Mut35_lumazine synthase
(SEQ ID NO: 105)
```
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI
```

TADTLEQAIERAGTKHGNKGWEAALSAIEMANLFK

SLRGGSGGSGGSGGSGGGDNITLPCNGTGPPPHCS

SNITGLILTRQGGYSNDNTVIFRPSGGDWRDIARC

NITGTVVSTQLFLNGSLAGNGTVIRSEDWRDNAKS

ICVQLNTSVEINCTGAGHCNISRAKWNNTLKQIAS

KLREQYGNKTIIFKPSSGGDPEFVNHSFNCGGEFF

YCNSTQLFNSTWFNST

Mut36_lumazine synthase
(SEQ ID NO: 106)
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDTITLPCNGTGPPPHCS

SNITGLILTRQGGYSNDNTVIFRPSGGDWRDIARC

NITGTVVSTQLFLNGSLAGNGTVIRSEDWRDNAKS

ICVQLNTSVEINCTGNGTCNISRAKWNNTLKQIAS

KLREQYGNKTIIFKPSSGGDPEFVNHSFNCGNVTF

YCDSTQLFNSTWFNST

Mut37_lumazine synthase
(SEQ ID NO: 107)
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDTITLPCNGTGPPPHCS

SNITGLILTRQGGYSNDNTVIFRPSGGDWRDIARC

NITGTVVSTQLFLNGSLAGNGTVIRSEDWRDNAKS

ICVQLNTSVEINCTGAGHCNISRAKWNNTLKQIAS

KLREQYGNKTIIFKPSSGGDPEFVNHSFNCGNVTF

YCNSTQLFNSTWFNST

Mut38_lumazine synthase
(SEQ ID NO: 108)
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDTITLPCNGTGPPPHCS

SNITGLILTRQGGYSNDNTVIFRPSGGDWRDIARC

NITGTVVSTQLFLNGSLAGNGTVIRSEDWRDNAKS

ICVQLNTSVEINCTGNGTCNISRAKWNNTLKQIAS

KLREQYGNKTIIFKPSSGGDPEFVNHSFNCGGEFF

YCNSTQLFNSTWFNST

Mut47_lumazine synthase
(SEQ ID NO: 109)
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDTITLPCRPAPPPHCSS

NITGLILTRQGGYSNDNTVIFRPSGGDWRDIARCN

ITGTVVSTQLFLNGSLAGNGTVIRSENFTDNAKSI

CVQLNTSVEINCTGNGTCNISRAKWNNTLKQIASK

LREQYGNKTIIFKPSSGGDPEFVNHSFNCGNVTFY

CDSTQLFNSTWFNST

Mut49_lumazine synthase
(SEQ ID NO: 110)
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDTITLPCRPAPPPHCSS

NITGLILTRQGGYSNDNTVIFRPSGGDWRDIARCQ

IAGNVTSTQLFLNGSLAGNGTVIRSEDWRDNAKSI

CVQLNTSVEINCTGAGHCNISRAKWNNTLKQIASK

LREQYGNKTIIFKPSSGGDPEFVNHSFNCGNVTFY

CDSTQLFNSTWFNST

Mut50_lumazine synthase
(SEQ ID NO: 111)
MPMGSLQPLATLYLLGMLVASVLAMQIYEGKLTAE

GLRFGIVASRFNHALVDRLVEGAIDAIVRHGGREE

DITLVRVPGSWEIPVAAGELARKEDIDAVIAIGVL

IRGATPHEDYIASEVSKGLADLSLELRKPITFGVI

TADTLEQAIERAGTKHGNKGWEAALSAIEMANLFK

SLRGGSGGSGGSGGSGGGDTITLPCRPAPPPHCSS

NITGLILTRQGGYSNDNTVIFRPSGGDWRDIARCQ

IAGNVTSTQLFLNGSLAGGEVNGTSEDWRDNAKSI

CVQLNTSVEINCTGAGHCNISRAKWNNTLKQIASK

LREQYGNKTIIFKPSSGGDPEFVNHSFNCGNVTFY

CDSTQLFNSTWFNST

Mut51_lumazine synthase
(SEQ ID NO: 112)
MPMGSLQPLATLYLLGMLVASVLAMQIYEGKLTAE
GLRFGIVASRFNHALVDRLVEGAIDAIVRHGGREE
DITLVRVPGSWEIPVAAGELARKEDIDAVIAIGVL
IRGATPHEDYIASEVSKGLADLSLELRKPITFGVI
TADTLEQAIERAGTKHGNKGWEAALSAIEMANLFK
SLRGGSGGSGGSGGSGGGDTITLPCNGTGPPPHCS
SNITGLILTRQGGYSNDNTVIFRPSGGDWRDIARC
QIAGNVTSTQLFLNGSLANGTVNGTSEDWRDNAKS
ICVQLNTSVEINCTGAGHCNISRAKWNNTLKQIAS
KLREQYGNKTIIFKPSSGGDPEFVNHSFNCGNVTF
YCDSTQLFNSTWFNST Mut52_lumazine synthase
(SEQ ID NO: 113)
MPMGSLQPLATLYLLGMLVASVLAMQIYEGKLTAE
GLRFGIVASRFNHALVDRLVEGAIDAIVRHGGREE
DITLVRVPGSWEIPVAAGELARKEDIDAVIAIGVL
IRGATPHEDYIASEVSKGLADLSLELRKPITFGVI
TADTLEQAIERAGTKHGNKGWEAALSAIEMANLFK
SLRGGSGGSGGSGGSGGGDTITLPCRPAPPPNCTS
NITGLILTRQGGYSNDNTVIFRPSGGDWRDIARCQ
IAGTVVSTQLFLNGSLAGNGTVIRSEDWRDNAKSI
CVQLNTSVEINCTGNGTCNISRAKWNNTLKQIASK
LREQYGNKTIIFKPSSGGDPEFVNHSFNCGNVTFY
CDSTQLFNSTWFNST Exemplary sequences of lumazine synthase subunit-linker-eOD (including the signal peptide of residues 1-19 (MGWSCIILFLVATATGVHS) of SEQ ID NO: 49) are set forth below.

Mut15_lumazine synthase
(SEQ ID NO: 51)
MGWSCIILFLVATATGVHSMQIYEGKLTAEGLRFG
IVASRFNHALVDRLVEGAIDAIVRHGGREEDITLV
RVPGSWEIPVAAGELARKEDIDAVIAIGVLIRGAT
PHEDYIASEVSKGLADLSLELRKPITFGVITADTL
EQAIERAGTKHGNKGWEAALSAIEMANLFKSLRGG
SGGSGGSGGSGGGDTITLPCNGTGPPPHCSSNITG
LILTRQGGYSNDNTVIFRPSGGDWRDIARCNITGT
VVSTQLFLNGSLAGNGTVIRSEDWRDNAKSICVQL
NTSVEINCTGAGHCNISRAKWNNTLKQIASKLREQ
YGNKTIIFKPSSGGDPEFVNHSFNCGGEFFYCDST
QLFNSTWFNST Mut16_lumazine synthase
(SEQ ID NO: 52)
MGWSCIILFLVATATGVHSMQIYEGKLTAEGLRFG
IVASRFNHALVDRLVEGAIDAIVRHGGREEDITLV
RVPGSWEIPVAAGELARKEDIDAVIAIGVLIRGAT
PHEDYIASEVSKGLADLSLELRKPITFGVITADTL
EQAIERAGTKHGNKGWEAALSAIEMANLFKSLRGG
SGGSGGSGGSGGGDTITLPCRPAPPPNCTSNITGL
ILTRQGGYSNDNTVIFRPSGGDWRDIARCNITGTV
VSTQLFLNGSLAGNGTVIRSEDWRDNAKSICVQLN
TSVEINCTGNGTCNISRAKWNNTLKQIASKLREQY
GNKTIIFKPSSGGDPEFVNHSFNCGNVTFYCDSTQ
LFNSTWFNST Mut17_lumazine synthase
(SEQ ID NO: 53)
MGWSCIILFLVATATGVHSMQIYEGKLTAEGLRFG
IVASRFNHALVDRLVEGAIDAIVRHGGREEDITLV
RVPGSWEIPVAAGELARKEDIDAVIAIGVLIRGAT
PHEDYIASEVSKGLADLSLELRKPITFGVITADTL
EQAIERAGTKHGNKGWEAALSAIEMANLFKSLRGG
SGGSGGSGGSGGGDTITLPCRPAPPPNCTSNITGL
ILTRQGGYSNDNTVIFRPSGGDWRDIARCNITGTV
VSTQLFLNGSLAGNGTVIRSEDWRDNAKSICVQLN
TSVEINCTGNGTCNISRAKWNNTLKQIASKLREQY
GNKTIIFKPSSGGDPEFVNHSFNCTGEFFYCDSTQ
LFNSTWFNST Mut18_lumazine synthase
(SEQ ID NO: 54)
MGWSCIILFLVATATGVHSMQIYEGKLTAEGLRFG
IVASRFNHALVDRLVEGAIDAIVRHGGREEDITLV
RVPGSWEIPVAAGELARKEDIDAVIAIGVLIRGAT
PHEDYIASEVSKGLADLSLELRKPITFGVITADTL
EQAIERAGTKHGNKGWEAALSAIEMANLFKSLRGG
SGGSGGSGGSGGGDNITLPCRPAPPPNCTSNITGL
ILTRQGGYSNDNTVIFRPSGGDWRDIARCNITGNV
TSTQLFLNGSLAGNGTVIRSEDWRDNAKSICVQLN
TSVEINCTGAGHCNISRAKWNNTLKQIASKLREQY
GNKTIIFKPSSGGDPEFVNHSFNCTGEFFYCDSTQ
LFNSTWFNST Mut19_lumazine synthase
(SEQ ID NO: 55)
MGWSCIILFLVATATGVHSMQIYEGKLTAEGLRFG
IVASRFNHALVDRLVEGAIDAIVRHGGREEDITLV

RVPGSWEIPVAAGELARKEDIDAVIAIGVLIRGAT

PHEDYIASEVSKGLADLSLELRKPITFGVITADTL

EQAIERAGTKHGNKGWEAALSAIEMANLFKSLRGG

SGGSGGSGGSGGGDNITLPCRPAPPPNCTSNITGL

ILTRQGGYSNDNTVIFRPSGGDWRDIARCQIAGTV

VSTQLFLNGSLANGTVVIRSEDWRDNAKSICVQLN

TSVEINCTGNGTCNISRAKWNNTLKQIASKLREQY

GNKTIIFKPSSGGDPEFVNHSFNCTGEFFYCDSTQ

LFNSTWFNST

Mut21_lumazine synthase
(SEQ ID NO: 56)
MGWSCIILFLVATATGVHSMQIYEGKLTAEGLRFG

IVASRFNHALVDRLVEGAIDAIVRHGGREEDITLV

RVPGSWEIPVAAGELARKEDIDAVIAIGVLIRGAT

PHEDYIASEVSKGLADLSLELRKPITFGVITADTL

EQAIERAGTKHGNKGWEAALSAIEMANLFKSLRGG

SGGSGGSGGSGGGDTITLPCNGTGPPPNCTSNITG

LILTRQGGYSNDNTVIFRPSGGDWRDIARCNITGT

VVSTQLFLNGSLANGTVVIRSEDWRDNAKSICVQL

NTSVEINCTGNGTCNISRAKWNNTLKQIASKLREQ

YGNKTIIFKPSSGGDPEFVNHSFNCGNVTFYCDST

QLFNSTWFNST

Mut27_lumazine synthase
(SEQ ID NO: 57)
MGWSCIILFLVATATGVHSMQIYEGKLTAEGLRFG

IVASRFNHALVDRLVEGAIDAIVRHGGREEDITLV

RVPGSWEIPVAAGELARKEDIDAVIAIGVLIRGAT

PHEDYIASEVSKGLADLSLELRKPITFGVITADTL

EQAIERAGTKHGNKGWEAALSAIEMANLFKSLRGG

SGGSGGSGGSGGGDTITLPCRPAPPPHCSSNITGL

ILTRQGGYSNDNTVIFRPSGGDWRDIARCQIAGTV

VSTQLFLNGSLAGNTVIRSEDWRDNAKSICVNLT

TSVEINCTGNGTCNISRAKWNNTLKQIASKLREQY

GNKTIIFKPSSGGDPEFVNHSFNCGNVTFYCDSTQ

LFNSTWFNST

Mut28_lumazine synthase
(SEQ ID NO: 58)
MGWSCIILFLVATATGVHSMQIYEGKLTAEGLRFG

IVASRFNHALVDRLVEGAIDAIVRHGGREEDITLV

RVPGSWEIPVAAGELARKEDIDAVIAIGVLIRGAT

PHEDYIASEVSKGLADLSLELRKPITFGVITADTL

EQAIERAGTKHGNKGWEAALSAIEMANLFKSLRGG

SGGSGGSGGSGGGDTITLPCRPAPPPHCSSNITGL

ILTRQGGYSNDNTVIFRPSGGDWRDIARCNITGTV

VSTQLFLNGSLAGNTVIRSEDWRDNAKSICVQLN

TSVEINCTGNGTCNISRAKWNNTLKQIASKLREQY

GNKTIIFKPSSGGDPEFVNHSFNCGNVTFYCDSTQ

LFNSTWFNST

Mut29_lumazine synthase
(SEQ ID NO: 59)
MGWSCIILFLVATATGVHSMQIYEGKLTAEGLRFG

IVASRFNHALVDRLVEGAIDAIVRHGGREEDITLV

RVPGSWEIPVAAGELARKEDIDAVIAIGVLIRGAT

PHEDYIASEVSKGLADLSLELRKPITFGVITADTL

EQAIERAGTKHGNKGWEAALSAIEMANLFKSLRGG

SGGSGGSGGSGGGDTITLPCRPAPPPHCSSNITGL

ILTRQGGYSNDNTVIFRPSGGDWRDIARCQIAGNV

TSTQLFLNGSLAGNTVIRSEDWRDNAKSICVQLN

TSVEINCTGNGTCNISRAKWNNTLKQIASKLREQY

GNKTIIFKPSSGGDPEFVNHSFNCGNVTFYCDSTQ

LFNSTWFNST

Mut33_lumazine synthase
(SEQ ID NO: 60)
MGWSCIILFLVATATGVHSMQIYEGKLTAEGLRFG

IVASRFNHALVDRLVEGAIDAIVRHGGREEDITLV

RVPGSWEIPVAAGELARKEDIDAVIAIGVLIRGAT

PHEDYIASEVSKGLADLSLELRKPITFGVITADTL

EQAIERAGTKHGNKGWEAALSAIEMANLFKSLRGG

SGGSGGSGGSGGGDTITLPCNGTGPPPHCSSNITG

LILTRQGGYSNDNTVIFRPSGGDWRDIARCNITGT

VVSTQLFLNGSLAGNTVIRSEDWRDNAKSICVQL

NTSVEINCTGAGHCNISRAKWNNTLKQIASKLREQ

YGNKTIIFKPSSGGDPEFVNHSFNCGNVTFYCDST

QLFNSTWFNST

Mut34_lumazine synthase
(SEQ ID NO: 61)
MGWSCIILFLVATATGVHSMQIYEGKLTAEGLRFG

IVASRFNHALVDRLVEGAIDAIVRHGGREEDITLV

RVPGSWEIPVAAGELARKEDIDAVIAIGVLIRGAT

PHEDYIASEVSKGLADLSLELRKPITFGVITADTL

EQAIERAGTKHGNKGWEAALSAIEMANLFKSLRGG

SGGSGGSGGSGGGDNITLPCNGTGPPPHCSSNITG

LILTRQGGYSNDNTVIFRPSGGDWRDIARCNITGT

VVSTQLFLNGSLAGNTVIRSEDWRDNAKSICVQL

NTSVEINCTGAGHCNISRAKWNNTLKQIASKLREQ

YGNKTIIFKPSSGGDPEFVNHSFNCGNVTFYCDST

QLFNSTWFNST

Mut35_lumazine synthase
(SEQ ID NO: 62)
MGWSCIILFLVATATGVHSMQIYEGKLTAEGLRFG
IVASRFNHALVDRLVEGAIDAIVRHGGREEDITLV
RVPGSWEIPVAAGELARKEDIDAVIAIGVLIRGAT
PHEDYIASEVSKGLADLSLELRKPITFGVITADTL
EQAIERAGTKHGNKGWEAALSAIEMANLFKSLRGG
SGGSGGSGGSGGGDNITLPCNGTGPPPHCSSNITG
LILTRQGGYSNDNTVIFRPSGGDWRDIARCNITGT
VVSTQLFLNGSLAGNGTVIRSEDWRDNAKSICVQL
NTSVEINCTGAGHCNISRAKWNNTLKQIASKLREQ
YGNKTIIFKPSSGGDPEFVNHSFNCGGEFFYCNST
QLFNSTWFNST Mut36_lumazine synthase
(SEQ ID NO: 63)
MGWSCIILFLVATATGVHSMQIYEGKLTAEGLRFG
IVASRFNHALVDRLVEGAIDAIVRHGGREEDITLV
RVPGSWEIPVAAGELARKEDIDAVIAIGVLIRGAT
PHEDYIASEVSKGLADLSLELRKPITFGVITADTL
EQAIERAGTKHGNKGWEAALSAIEMANLFKSLRGG
SGGSGGSGGSGGGDTITLPCNGTGPPPHCSSNITG
LILTRQGGYSNDNTVIFRPSGGDWRDIARCNITGT
VVSTQLFLNGSLAGNGTVIRSEDWRDNAKSICVQL
NTSVEINCTGNGTCNISRAKWNNTLKQIASKLREQ
YGNKTIIFKPSSGGDPEFVNHSFNCGNVTFYCDST
QLFNSTWFNST Mut37_lumazine synthase
(SEQ ID NO: 64)
MGWSCIILFLVATATGVHSMQIYEGKLTAEGLRFG
IVASRFNHALVDRLVEGAIDAIVRHGGREEDITLV
RVPGSWEIPVAAGELARKEDIDAVIAIGVLIRGAT
PHEDYIASEVSKGLADLSLELRKPITFGVITADTL
EQAIERAGTKHGNKGWEAALSAIEMANLFKSLRGG
SGGSGGSGGSGGGDTITLPCNGTGPPPHCSSNITG
LILTRQGGYSNDNTVIFRPSGGDWRDIARCNITGT
VVSTQLFLNGSLAGNGTVIRSEDWRDNAKSICVQL
NTSVEINCTGAGHCNISRAKWNNTLKQIASKLREQ
YGNKTIIFKPSSGGDPEFVNHSFNCGNVTFYCNST
QLFNSTWFNST Mut38_lumazine synthase
(SEQ ID NO: 65)
MGWSCIILFLVATATGVHSMQIYEGKLTAEGLRFG
IVASRFNHALVDRLVEGAIDAIVRHGGREEDITLV
RVPGSWEIPVAAGELARKEDIDAVIAIGVLIRGAT
PHEDYIASEVSKGLADLSLELRKPITFGVITADTL
EQAIERAGTKHGNKGWEAALSAIEMANLFKSLRGG
SGGSGGSGGSGGGDTITLPCNGTGPPPHCSSNITG
LILTRQGGYSNDNTVIFRPSGGDWRDIARCNITGT
VVSTQLFLNGSLAGNGTVIRSEDWRDNAKSICVQL
NTSVEINCTGNGTCNISRAKWNNTLKQIASKLREQ
YGNKTIIFKPSSGGDPEFVNHSFNCGGEFFYCNST
QLFNSTWFNST Mut47_lumazine synthase
(SEQ ID NO: 76)
MGWSCIILFLVATATGVHSMQIYEGKLTAEGLRFGI
VASRFNHALVDRLVEGAIDAIVRHGGREEDITLVR
VPGSWEIPVAAGELARKEDIDAVIAIGVLIRGATP
HEDYIASEVSKGLADLSLELRKPITFGVITADTLE
QAIERAGTKHGNKGWEAALSAIEMANLFKSLRGGS
GGSGGSGGSGGGDTITLPCRPAPPPHCSSNITGLI
LTRQGGYSNDNTVIFRPSGGDWRDIARCNITGTVV
STQLFLNGSLAGNGTVIRSENFTDNAKSICVQLNT
SVEINCTGNGTCNISRAKWNNTLKQIASKLREQYG
NKTIIFKPSSGGDPEFVNHSFNCGNVTFYCDSTQL
FNSTWFNST Mut49_lumazine synthase
(SEQ ID NO: 83)
MGWSCIILFLVATATGVHSMQIYEGKLTAEGLRFG
IVASRFNHALVDRLVEGAIDAIVRHGGREEDITLV
RVPGSWEIPVAAGELARKEDIDAVIAIGVLIRGAT
PHEDYIASEVSKGLADLSLELRKPITFGVITADTL
EQAIERAGTKHGNKGWEAALSAIEMANLFKSLRGG
SGGSGGSGGSGGGDTITLPCRPAPPPHCSSNITGL
ILTRQGGYSNDNTVIFRPSGGDWRDIARCQIAGNV
TSTQLFLNGSLAGNGTVIRSEDWRDNAKSICVQLN
TSVEINCTGAGHCNISRAKWNNTLKQIASKLREQY
GNKTIIFKPSSGGDPEFVNHSFNCGNVTFYCDSTQ
LFNSTWFNST Mut50_lumazine synthase
(SEQ ID NO: 84)
MGWSCIILFLVATATGVHSMQIYEGKLTAEGLRFG
IVASRFNHALVDRLVEGAIDAIVRHGGREEDITLV
RVPGSWEIPVAAGELARKEDIDAVIAIGVLIRGAT
PHEDYIASEVSKGLADLSLELRKPITFGVITADTL
EQAIERAGTKHGNKGWEAALSAIEMANLFKSLRGG
SGGSGGSGGSGGGDTITLPCRPAPPPHCSSNITGL
ILTRQGGYSNDNTVIFRPSGGDWRDIARCQIAGNV
TSTQLFLNGSLAGGEV
NGTSEDWRDNAKSICVQLN -continued

TSVEINCTGAGHCNISRAKWNNTLKQIASKLREQY

GNKTIIFKPSSGGDPEFVNHSFNCGNVTFYCDSTQ

LFNSTWFNST

Mut51_lumazine synthase
(SEQ ID NO: 85)
MGWSCIILFLVATATGVHSMQIYEGKLTAEGLRFG

IVASRFNHALVDRLVEGAIDAIVRHGGREEDITLV

RVPGSWEIPVAAGELARKEDIDAVIAIGVLIRGAT

PHEDYIASEVSKGLADLSLELRKPITFGVITADTL

EQAIERAGTKHGNKGWEAALSAIEMANLFKSLRGG

SGGSGGSGGSGGGDTITLPCNGTGPPPHCSSNITG

LILTRQGGYSNDNTVIFRPSGGDWRDIARCQIAGN

VTSTQLFLNGSLANGTVNGTSEDWRDNAKSICVQL

NTSVEINCTGAGHCNISRAKWNNTLKQIASKLREQ

YGNKTIIFKPSSGGDPEFVNHSFNCGNVTFYCDST

QLFNSTWFNST

Mut52_lumazine synthase
(SEQ ID NO: 86)
MGWSCIILFLVATATGVHSMQIYEGKLTAEGLRFG

IVASRFNHALVDRLVEGAIDAIVRHGGREEDITLV

RVPGSWEIPVAAGELARKEDIDAVIAIGVLIRGAT

PHEDYIASEVSKGLADLSLELRKPITFGVITADTL

EQAIERAGTKHGNKGWEAALSAIEMANLFKSLRGG

SGGSGGSGGSGGGDTITLPCRPAPPPNCTSNITGL

ILTRQGGYSNDNTVIFRPSGGDWRDIARCQIAGTV

VSTQLFLNGSLAGNGTVIRSEDWRDNAKSICVQLN

TSVEINCTGNGTCNISRAKWNNTLKQIASKLREQY

GNKTIIFKPSSGGDPEFVNHSFNCGNVTFYCDSTQ

LFNSTWFNST

It is expected that the signal peptide sequence will not affect the sequence of the purified eOD-lumazine synthase subunit because the signal peptide is cleaved from the fusion protein during cellular processing.

Antigenic Assessment of eOD-GT8 60mer Glycan-Masking Mutants

The first 48 mutants were expressed in mammalian Expi293 cells using the same lumazine synthase nanoparticle format as the original eOD-GT8 60mer, and antigenic assessment was carried out directly on the cell supernatants in *Galanthus Nivalis* (GNA)-lectin coated ELISA plates. Two separate panels of antibodies were used: 1) CD4bs-specific antibodies to evaluate the antigenic integrity of the CD4bs, and 2) non-CD4bs-specific antibodies to evaluate the extent of glycan-masking. The former panel included VRC01, its v-gene germline revertant VRC01gl, and the VRC-PG04 v-gene germline revertant VRC-PG04gl (Wu et al., Science, 333: 1593-1602, 2011), whereas the latter panel included a polyclonal rabbit anti-gp120 serum, two non-CD4bs monoclonal antibodies (mAbs) (FIG. 2A, X1A2 and X1C6) isolated from eOD-GT8 60mer-immunized XenoMouse (see Materials and Methods), and two non-CD4bs mAbs (FIG. 2A, mA9 and mE4) isolated from eOD-GT8 60mer-immunized IGHV1-2 knock-in mice (Tian et al., Cell 166: 1471-1484 e1418, 2016). The non-CD4bs-specific antibodies and serum generally recognized eOD-GT8 and eOD-GT8 KO proteins equally well (FIGS. 2A and 7).

Figure 1D:
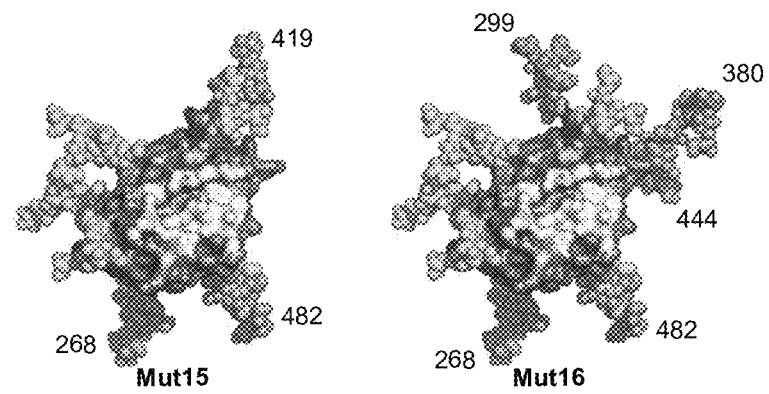
Figure 1D:
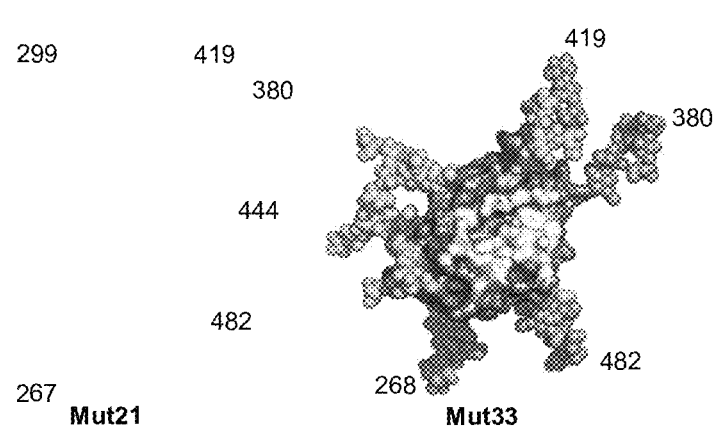
Figure 2A:
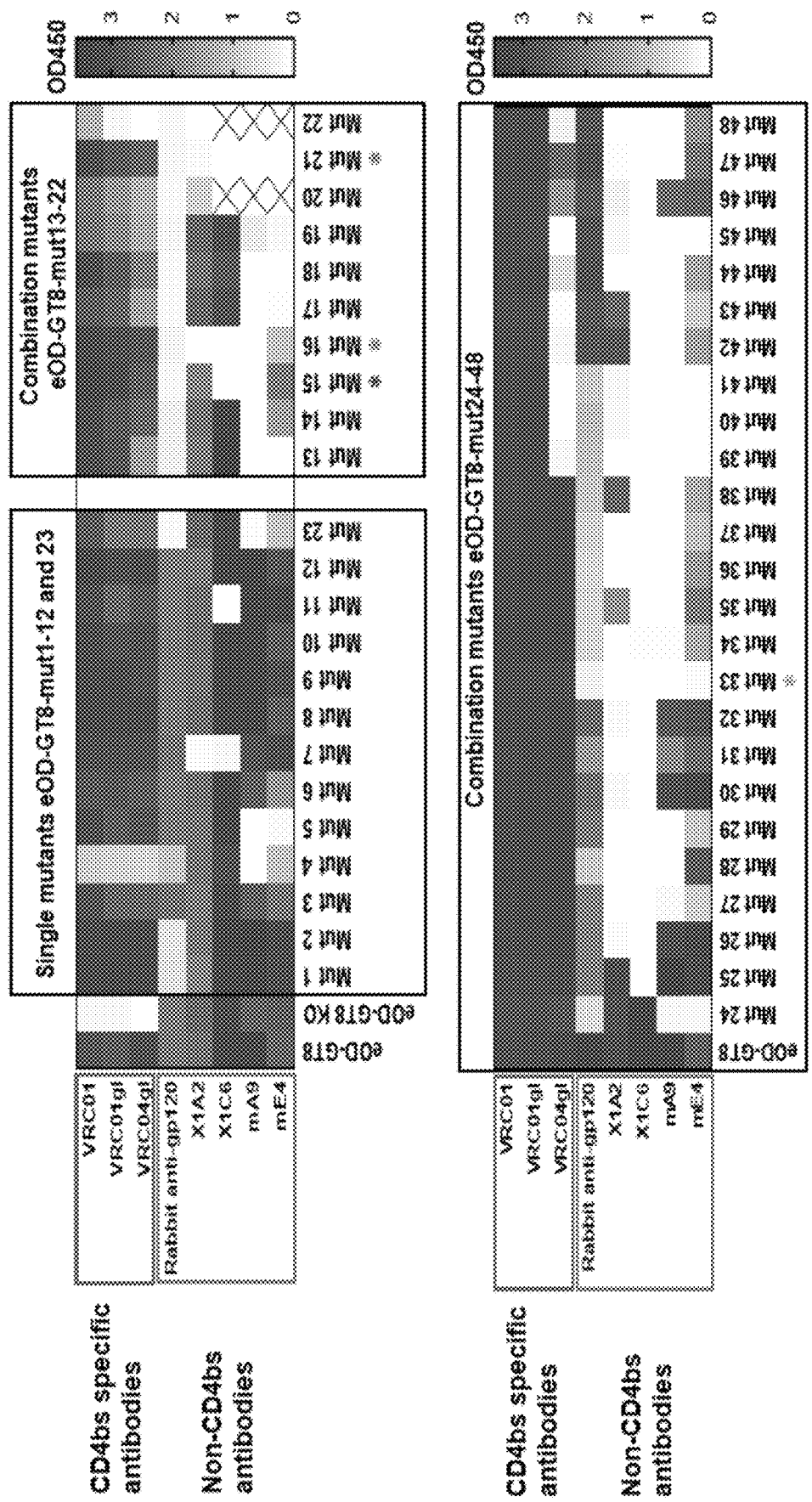
FIGS. 2A-2D. Antigenic characterization of the eOD-GT8 60mer glycan-masking mutants.

All but one (eOD-GT8-mut4 60mer) of the 13 single glycan mutants maintained strong binding to the CD4bs-specific antibodies, but none displayed decreased binding to all the non-CD4bs antibodies (FIG. 2A). Compared to single glycan mutants, four multi-glycan mutants (eOD8-GT8-mut15, -mut16, -mut21, and -mut33 60mer) displayed preferable antigenic profiles (FIG. 2A, marked by stars). Each showed strong recognition by CD4bs-specific mAbs and low binding to all or most non-CD4bs antibodies. Not surprisingly, these four mutants contained glycans which exhibited reduced recognition by non-CD4bs antibodies among the single glycan mutants (eOD8-GT8-mut1, -mut2, -mut4, -mut7 and -mut11 60mer) as well as glycans located on potentially immunogenic protruding loops (from eOD8-GT8-mut7, -mut10, and -mut11 60mer) (FIG. 1D).

Figure 2B:
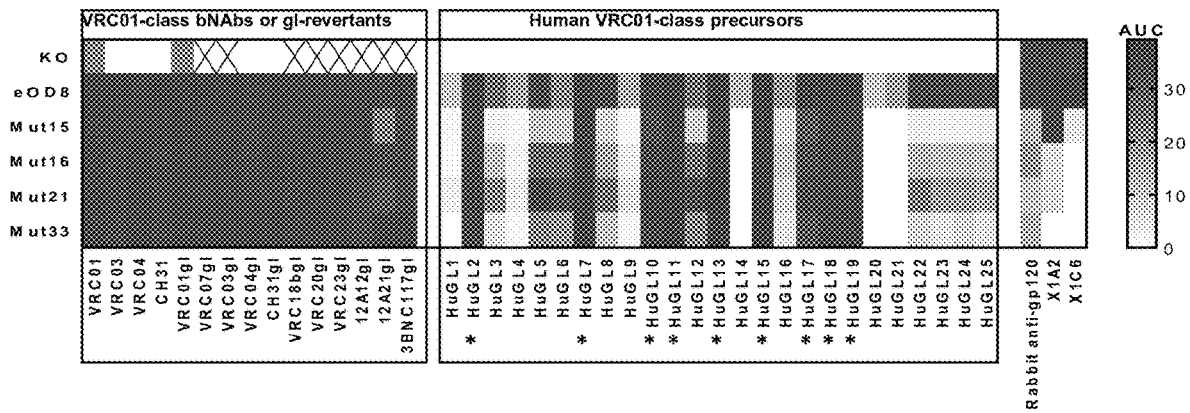
Figure 2C:
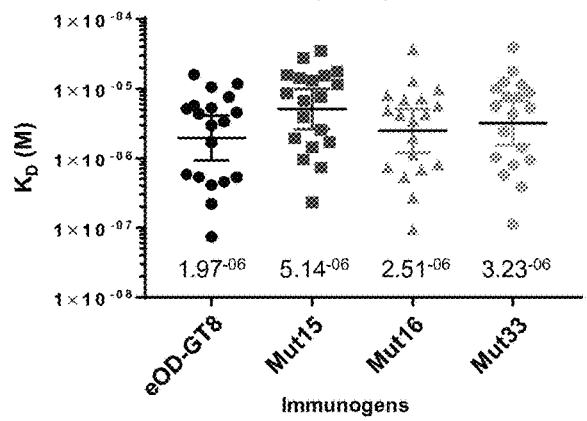

Four of the glycan-masked mutants were purified for further characterization using affinity and size exclusion chromatography (FIG. 8). These were evaluated by ELISA with a panel of 11 VRC01-class germline revertant antibodies and four mature VRC01-class mAbs, and observed to maintain high affinity to all the tested VRC01-class mature mAbs and germline revertants, similar to the parental eOD-GT8 60mer (FIG. 2B, left box). Also investigated was the binding affinities of these glycan-masking mutants to a panel of 25 human VRC01-class precursors (HuGL1-25) isolated from naïve B cells using an eOD-GT8 monomer as a probe (Jardine et al., Science, 351: 1458-1463, 2016). By ELISA, the four glycan mutants were observed to maintain strong binding to the high affinity precursors (FIG. 2B, marked with stars) and to have reduced binding to lower affinity precursors relative to the parental eOD-GT8 60mer. When binding of 19 of these HuGL antibodies was examined by surface plasmon resonance (SPR), the antigen binding fragments (Fabs) of these precursors were observed to have affinities to eOD-GT8 ranging from 0.07 to 16 μM, consistent with the $K_D$ values previously reported (Jardine et al., Science, 351: 1458-1463, 2016). The glycan mutants all showed less than a 4-fold reduction of binding affinity to these precursors relative to eOD-GT8 60mer (FIGS. 2C and 2D). eOD-GT8-mut16 60mer showed the least reduction (1.3-fold) with a geometric mean binding affinity of 2.5 μM to these human VRC01-class precursors compared to 2.0 μM for eOD-GT8 60mer. In summary, out of 48 mutants, eOD-GT8-mut15, -mut16, -mut21 and -mut33 60mer showed the best antigenic profiles for masking non-CD4bs epitopes with minimal reduction in affinity to human VRC01-class antibodies or their precursors.

Electron Microscopy (EM) and Glycan Occupancy Mass Spectrometry Analysis of eOD-GT8 60mer Glycan-Masking Mutants.

Figure 3A:
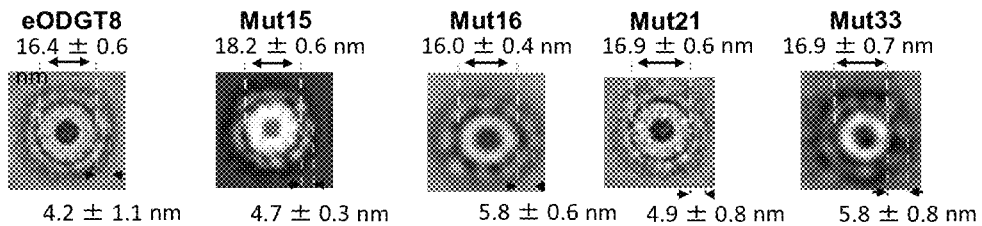
FIGS. 3A-3C. Physical characterization of purified eOD-GT8 60mer and eOD-GT8-mut15, -mut16, -mut21, and -mut33 60mer immunogens.
Figure 3B:
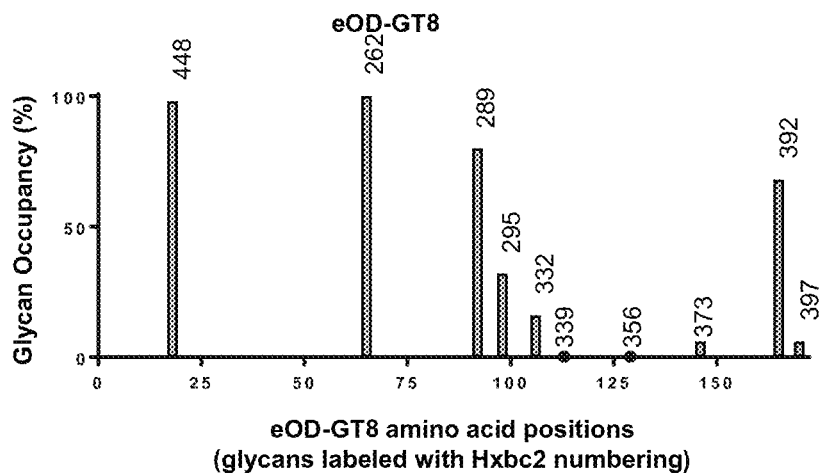
Figure 3B:
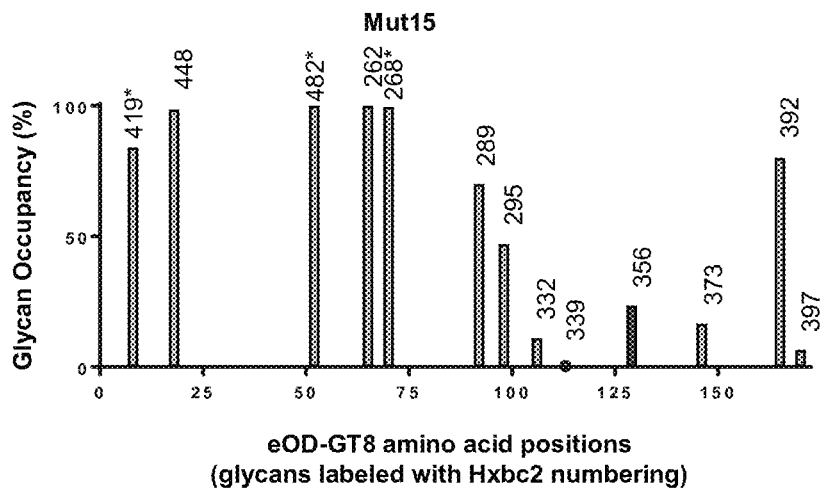
Figure 3C:
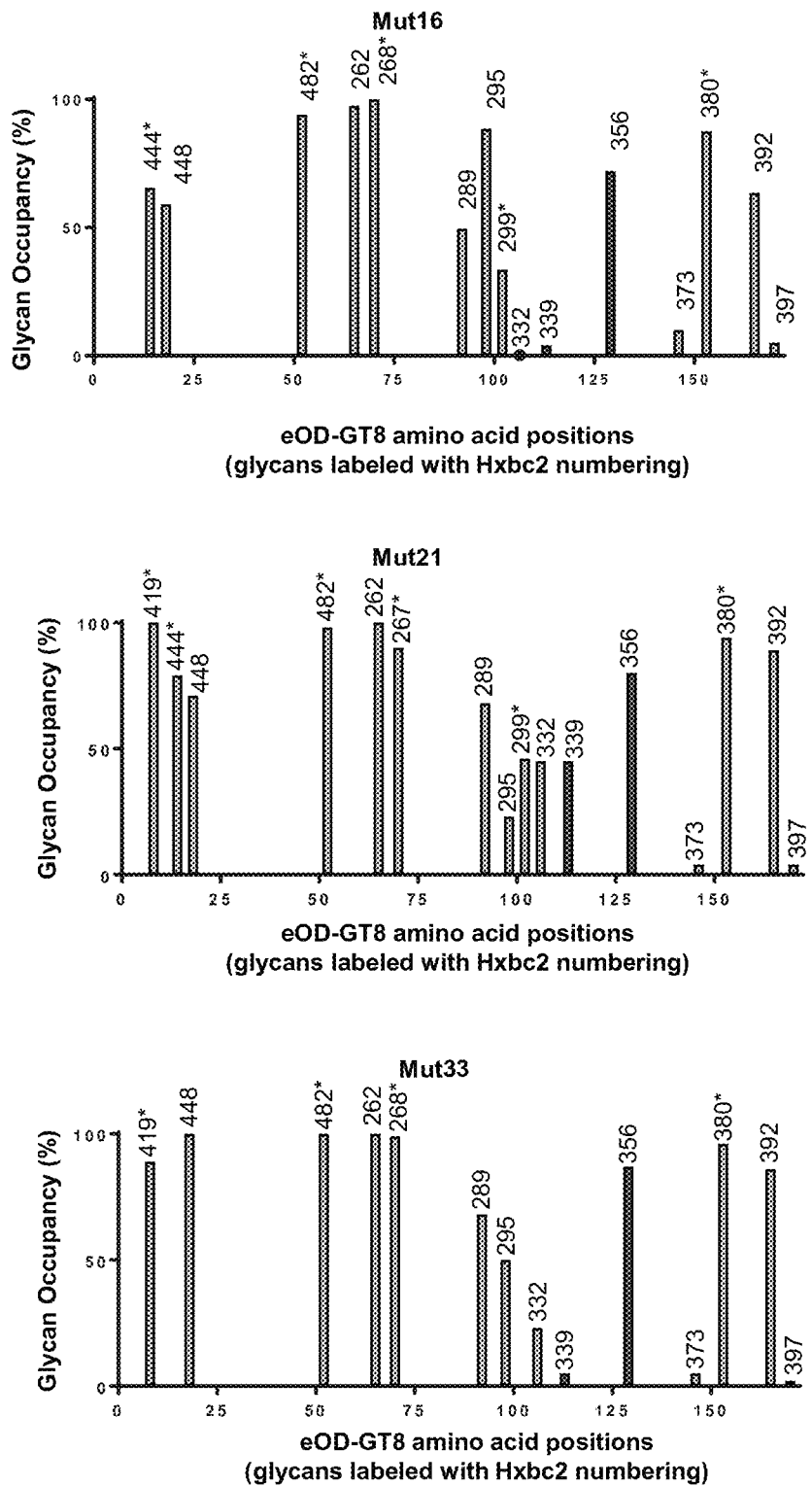

To assess the molecular assembly of the glycan mutant nanoparticles, the four mutants (eOD-GT8-mut15, -mut16, -mut21, and -mut33) were analyzed by negative stain EM. All four mutants formed spherical nanoparticles, similar to the parental eOD-GT8 60mer, with a lumazine synthase inner core of 16-18 nm in diameter and an eOD outer layer of 4.2-5.8 nm in thickness (FIG. 3A). Also examined was the glycan occupancy at each predicted N-linked glycan sequon for the four eOD-GT8 60mer mutants as well as the parental eOD-GT8 60mer by liquid chromatography mass spectrometry (LC-MS). Among the ten predicted native N-linked glycosylation sites in the parental eOD-GT8 60mer, four had greater than 65% glycan occupancy, four had 5-35% occupancy, and two were not glycosylated at all (FIG. 3B, green bars and dots). For eOD-GT8-mut15, 16, 21 and 33 60mer, all added glycosylation sites had occupancies greater than 65% except the added N299 glycan (from single glycan mutant eOD-GT8-mut10 60mer) in eOD-GT8-mut16 and 21 60mer, which showed 34% and 46% occupancies respectively (FIG. 3B, orange bars). Moreover, the addition of extra glycans appeared to enhance the occupancy of native glycans at residues 356 and/or 339 (FIG. 3B, dark green bars). Slower translation during protein synthesis has been observed to increase glycan occupancy (Ujvari et al., *J Biol Chem,* 276: 5924-5931, 2001) and it is thus possible that slower translation associated with the additional glycans may have increased the occupancy of native glycans. In conclusion, eOD-GT8-mut15, -mut16, -mut21 and -mut33 60mer, each of which shared preferred antigenic binding profiles, also formed well assembled particles and were glycosylated at expected engineered locations.

Figure 9A:
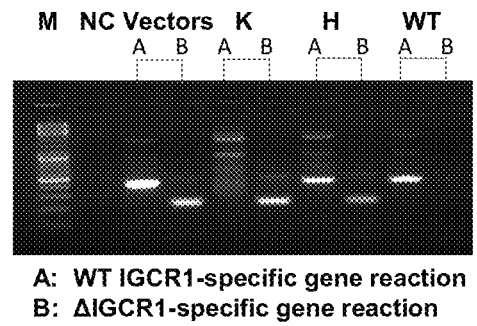
FIGS. 9A-9C. Characterization of IGHV1-2*02 single knock-in mouse.
Figure 9B:
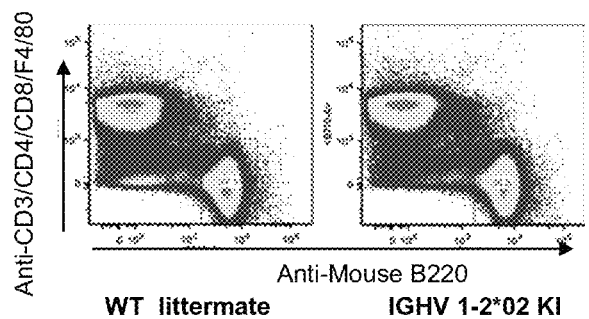
Figure 9C:
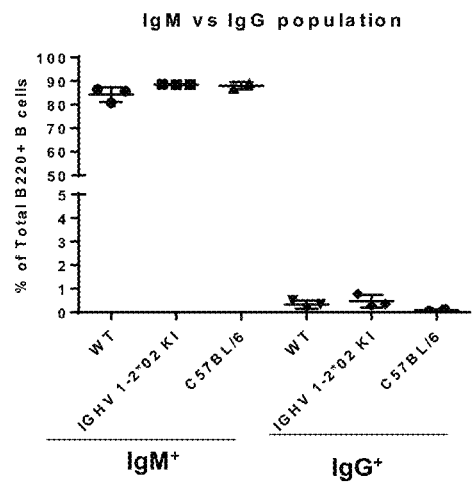

Immunogenicity Analysis of eOD-GT8 60mer Glycan Mutants in IGHV1-2/IGCR1-Knock-In Mice To investigate the extent to which glycan-masking focused the antibody response to the CD4bs and its impact on elicitation of VRC01-class precursors, a previously described homozygous IGHV1-2*02 knock-in mouse model was used (Tian et al., *Cell* 166: 1471-1484 e1418, 2016). In this model, approximately 45% of naive B-cells express a human IGHV1-2*02 gene segment which in a given B cell is recombined with one of the 13 mouse D segments and one of the 4 mouse $J_H$ segments to form diverse CDRH3s, and these IGHV1-2*02-containing heavy chains then pair with any one of the full repertoire of mouse light chains (Chen et al., *Proc Natl Acad Sci USA,* 90: 4528-4532, 1993; Tian et al., *Cell* 166: 1471-1484 e1418, 2016). To confirm the consistency and stability of the genotype of these transgenic mice, the mice were bred and genotyped and the persistence of the knock-in IGHV1-2*02 gene segment confirmed (FIG. 9A). Based on fluorescence-activated cell sorting (FACS) analysis of several cell surface markers, splenic T and B cells, $IgM^+$ and $IgG^+$ B cell populations of IGHV1-2*02 knock-in mice appeared comparable to C57BL/6 and wild-type littermates (FIGS. 9B and 9C).

Figure 4A:
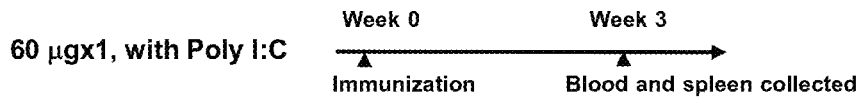
Figure 4B:
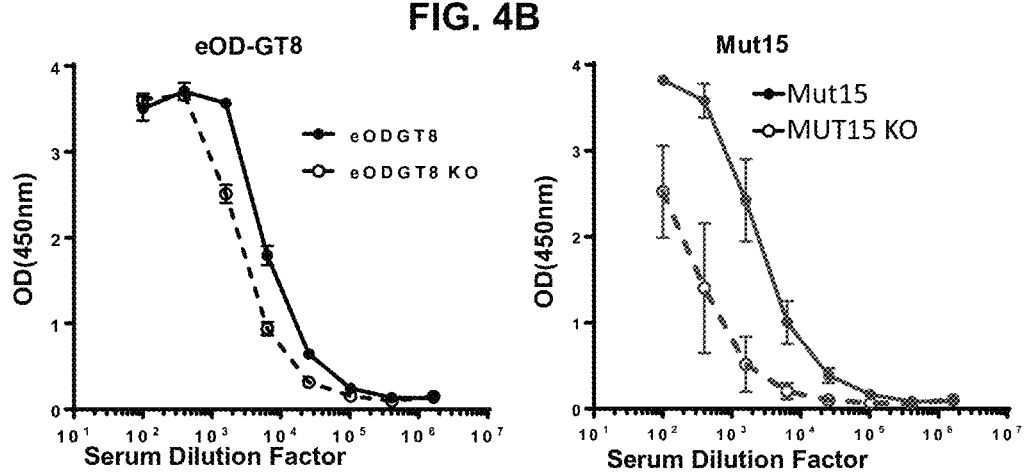
Figure 4B:
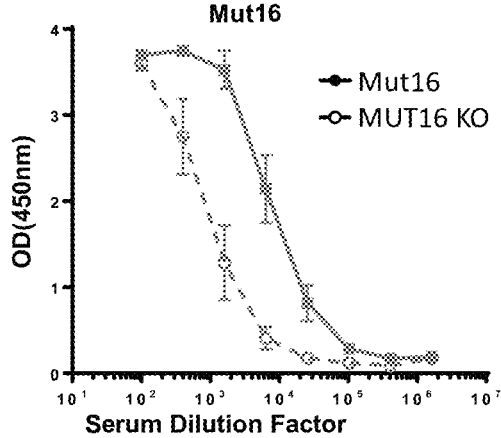
Figure 4B:
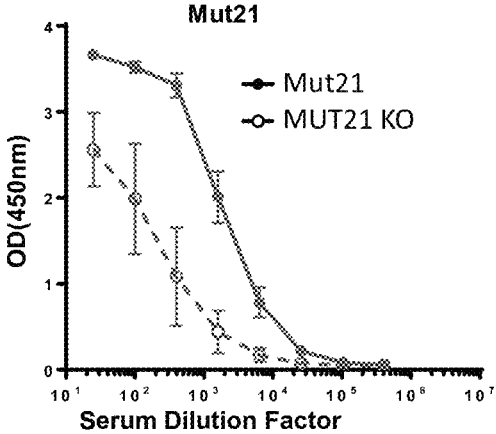
Figure 4B:
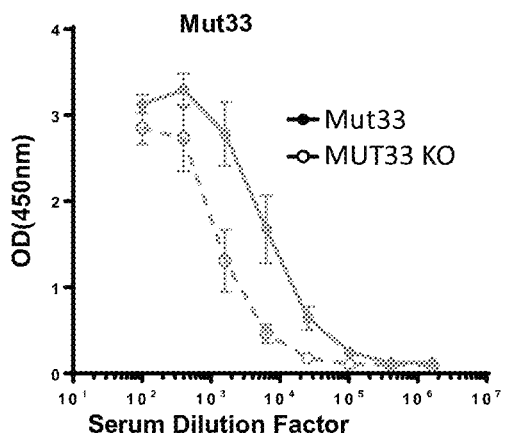
Figures 4C, 4D:
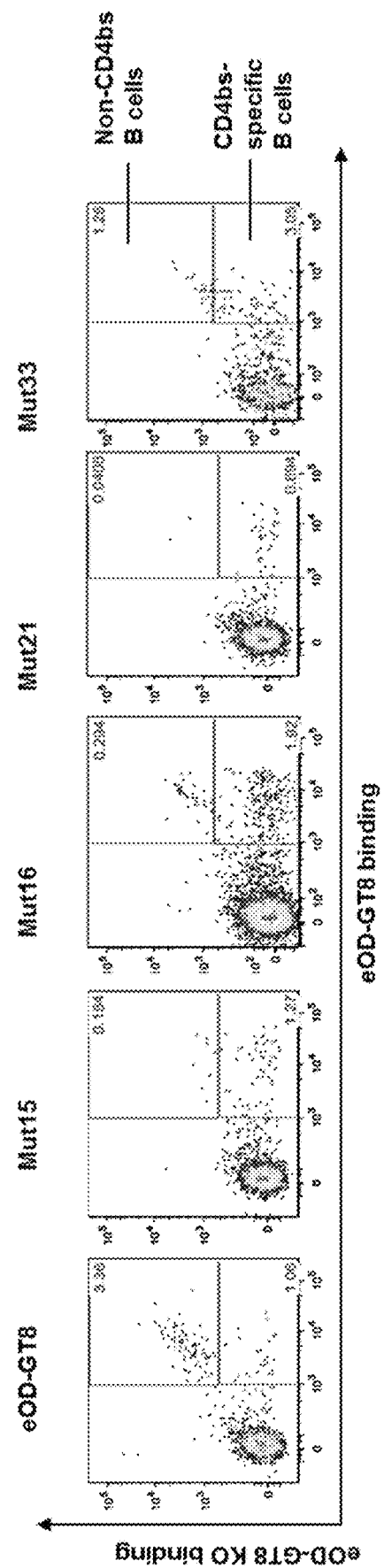

To evaluate the immunogenicity of the four glycan-masked immunogens (eOD-GT8-mut15, -mut16, -mut21, and -mut33 60mer), and the eOD-GT8 60mer control, these mice were immunized once using poly I:C as an adjuvant (FIG. 4A). Two to three weeks after immunization, mice were sacrificed, serum and spleen collected, and the CD4bs-specific immune response in the serum or in the class-switched B cell compartment was analyzed using the eOD-GT8 monomer and its CD4bs-KO mutant as protein probes. As shown previously (Tian et al., *Cell* 166: 1471-1484 e1418, 2016), the sera from eOD-GT8 60mer-immunized mice displayed similar reactivity to eOD-GT8 and the CD4bs mutant eOD-GT8 KO, suggesting that much of the elicited serum response targeted non-CD4bs epitopes on eOD-GT8. By comparison, sera from mice immunized with the eOD-GT8-60mer glycan-masked mutants showed greater reactivity to eOD-GT8 relative to the CD4bs KO mutant (FIG. 4B). Quantification of this difference revealed the percentage of the CD4bs-specific response to increase from 42% in the eOD-GT8 60mer-immunized mice to 93%, 87%, 94% and 74% in the eOD-GT8-mut15, -mut16, -mut21, and -mut33 60mer-immunized mice, respectively (FIG. 4C). Furthermore, the absolute CD4bs-specific serum response, as judged by the serum dilution ($ED_{50}$), from the eOD-GT8-mut15, -mut16, and -mut33 60mer-immunized mice was higher than that from the eOD-GT8 60mer-immunized mice (2956, 7928, 4611 versus 2525, respectively); only eOD-GT8-mut21 60mer-immunized mice showed a decreased CD4bs-specific $ED_{50}$ value (FIG. 4C). These results indicate that the added glycans in eOD-GT8-mut15, -mut16, and -mut33 60mer resulted in a substantially reduced serum response to non-CD4bs epitopes while maintaining accessibility to the CD4bs.

To complement the sera analysis, the frequency of CD4bs-specific B cells among eOD-GT8 specific class-switched B cells ($B220^+IgG^+$) was determined by using fluorophore-labeled eOD-GT8 and eOD-GT8 KO monomers as probes (Jardine et al., *Science,* 349: 156-161, 2015; Sok et al., *Science,* 353, 1557-1560, 2016; Tian et al., *Cell* 166: 1471-1484 e1418, 2016). CD4bs-specific B cells were defined as those binding to eOD-GT8 but not to the CD4bs KO version of eOD-GT8, whereas the non-CD4bs-specific B cells binding to both eOD-GT8 and its CD4bs KO mutant (FIG. 4D). By this measure, the frequency of the CD4bs-specific B cells in the total class-switched B cell population was increased from a mean of 1.1% in the eOD-GT8 60mer-immunized group to 4.2%, 2.7% and 3.3% in the eOD-GT8-mut15, 16 and 33 60mer-immunized groups. Likewise, average non-CD4bs B cell frequency in the total class-switched B cell population was reduced from 2.5% in the eOD-GT8 60mer-immunized group to 0.7%, 1.2% and 1.0% in the eOD-GT8-mut15, 16 and 33 60mer-immunized groups (FIG. 4E). eOD-GT8-mut21 60mer was an exception in that it elicited a reduced frequency of both CD4bs-specific and non-CD4bs class-switched B cells. The frequency of the CD4bs-specific B cells among all elicited eOD-GT8$^+$ B cells increased from a mean of 37% in the eOD-GT8-immunized control group to 87%, 73%, 77% and 83% in eOD-GT8-mut15, 16, 21 and 33 60mer-immunized groups, respectively (FIG. 4F).

Similar increases in frequency of both the CD4bs-specific serum response and the CD4bs-specific class-switched B cell response were consistently observed for eOD-GT8-mut15, -mut16, and -mut21 60mer, relative to eOD-GT8 60mer, when immunizations were performed with different dosages or different adjuvants (FIGS. 5A-5C). Evaluation of two more mutants, eOD-GT8-mut17 and -mut18, in an independent immunization study at a 30 μg dose, also revealed comparable results (FIGS. 5B and 5C). Finally, when we analyzed the results from all immunization experiments together, we observed statistically higher (ANOVA Krustal-Wallis and Mann-Whitney tests) CD4bs-specific serum responses for all tested immunogens except eOD-GT8-mut17 60mer relative to eOD-GT8 60mer (average of 1.9-fold higher, FIG. 6A) and statistically higher frequencies of CD4bs-specific B cells for all six evaluated immunogens relative to eOD-GT8 60mer (average of 2.3-fold higher, FIG. 6B).

Figure 6A:
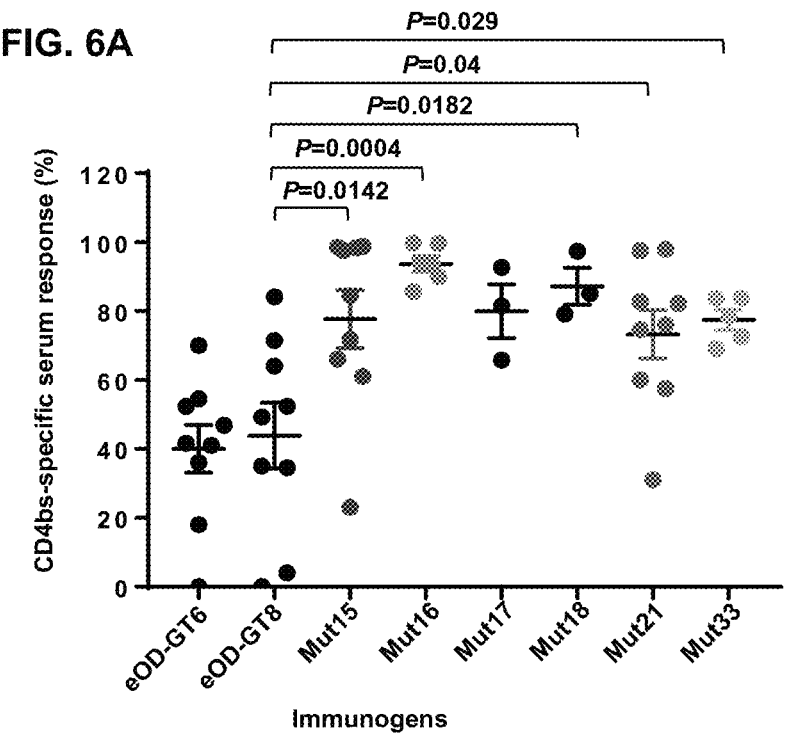
FIGS. 6A-6D. Compilation of three immunization studies to investigate immune focusing by glycan-masked eOD-GT8 mutants.
Figure 6B:
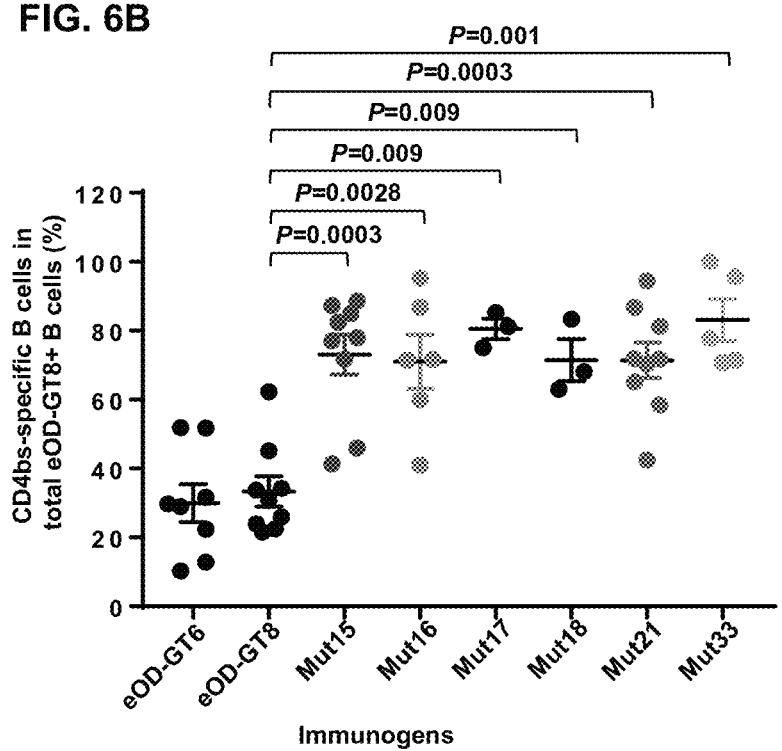

In summary, glycan-masking of the eOD-GT8 60mer immunogen was observed to increase the elicitation of CD4bs-specific serum in both overall titers (FIG. 4C) and as a percentage of antigen-specific response (FIGS. 4C, 5B, and 6A). Moreover, glycan-masking of eOD-GT8 increased the CD4bs-specific B cell frequency among both eOD-GT8-specific B cells (FIGS. 4F, 5C, and 6B) and total class-switched B cells (FIG. 4E).

VRC01-Class Antibodies Elicited by eOD-GT8 60mer and Its Glycan Mutants

Figures 6C, 6D:
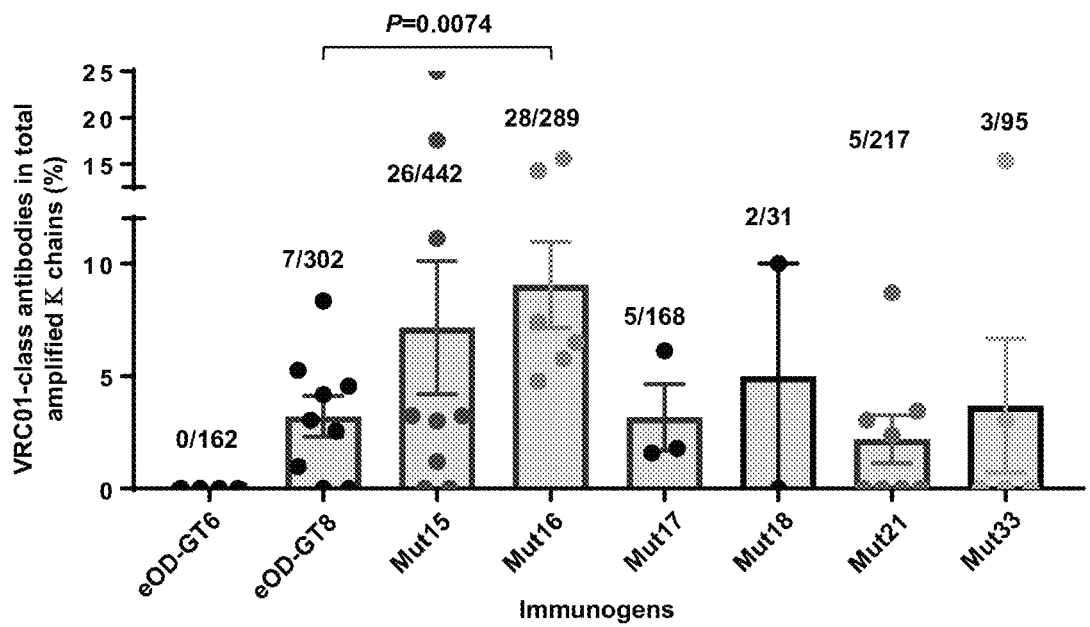
Figure 7A:
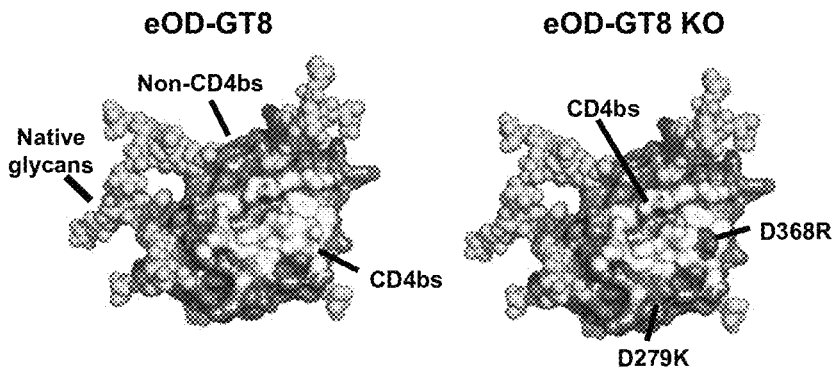
FIGS. 7A-7C. Illustration and evaluation of the eOD-GT8 CD4bs knock out mutant.
Figure 7B:
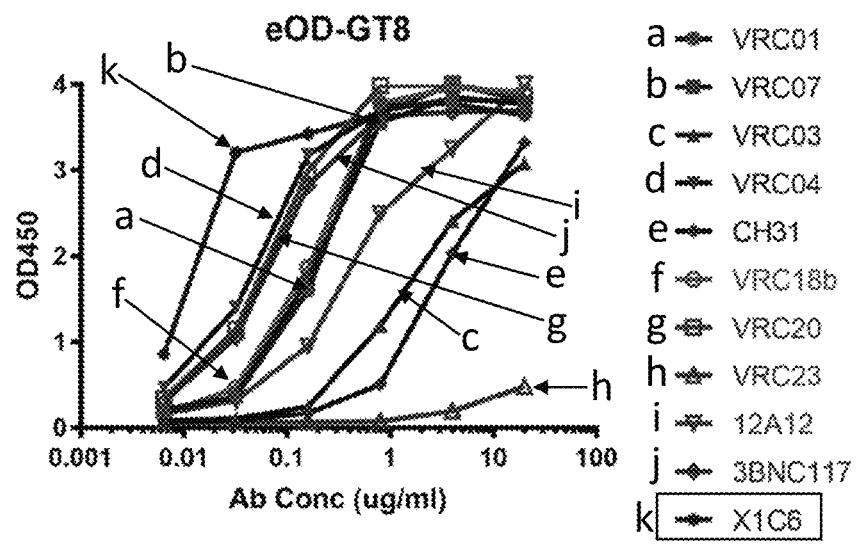
Figure 7B:
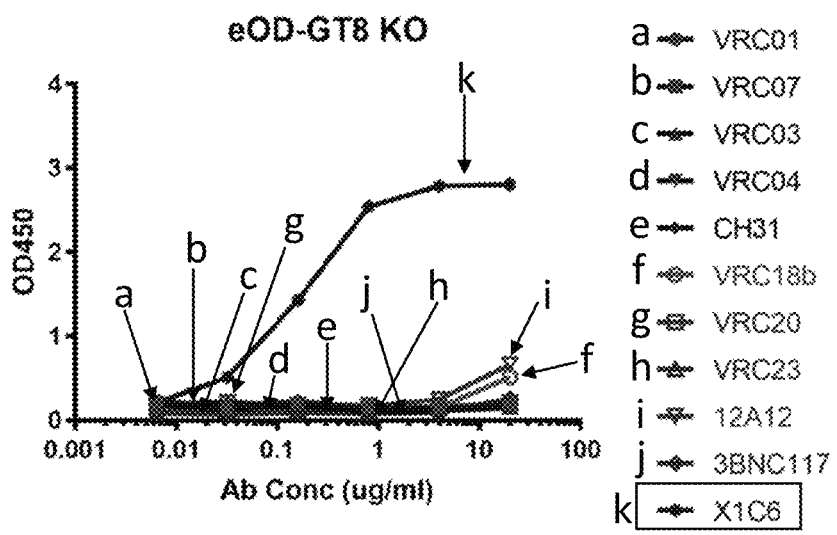
Figure 7C:
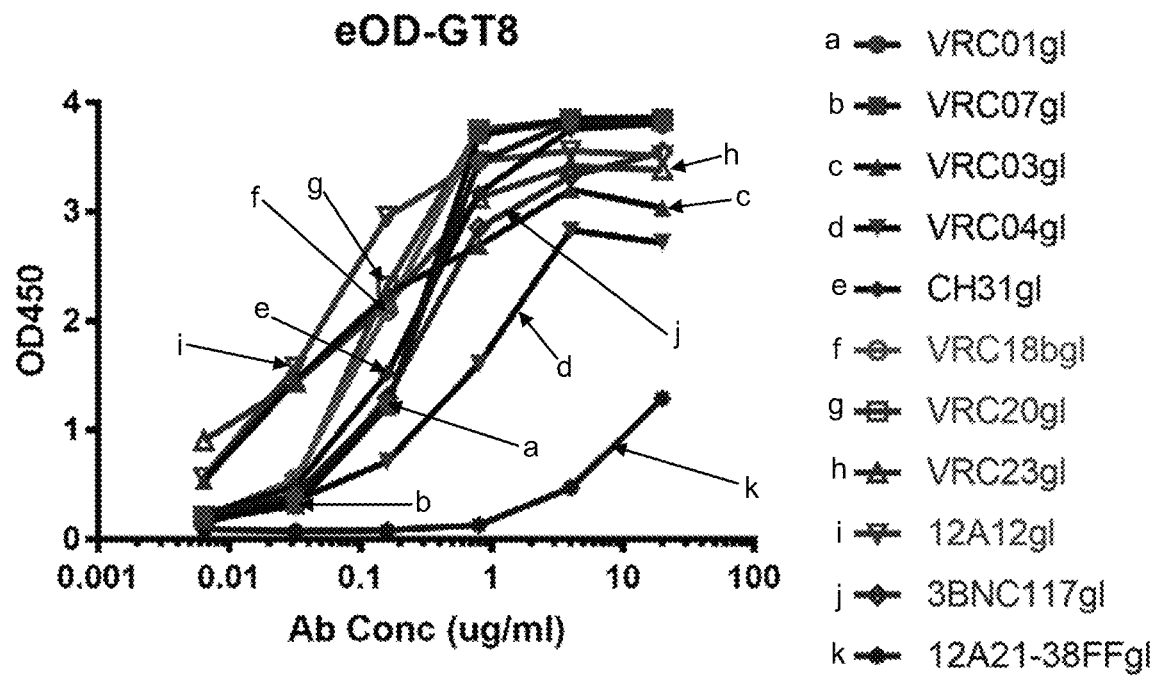
Figure 7C:
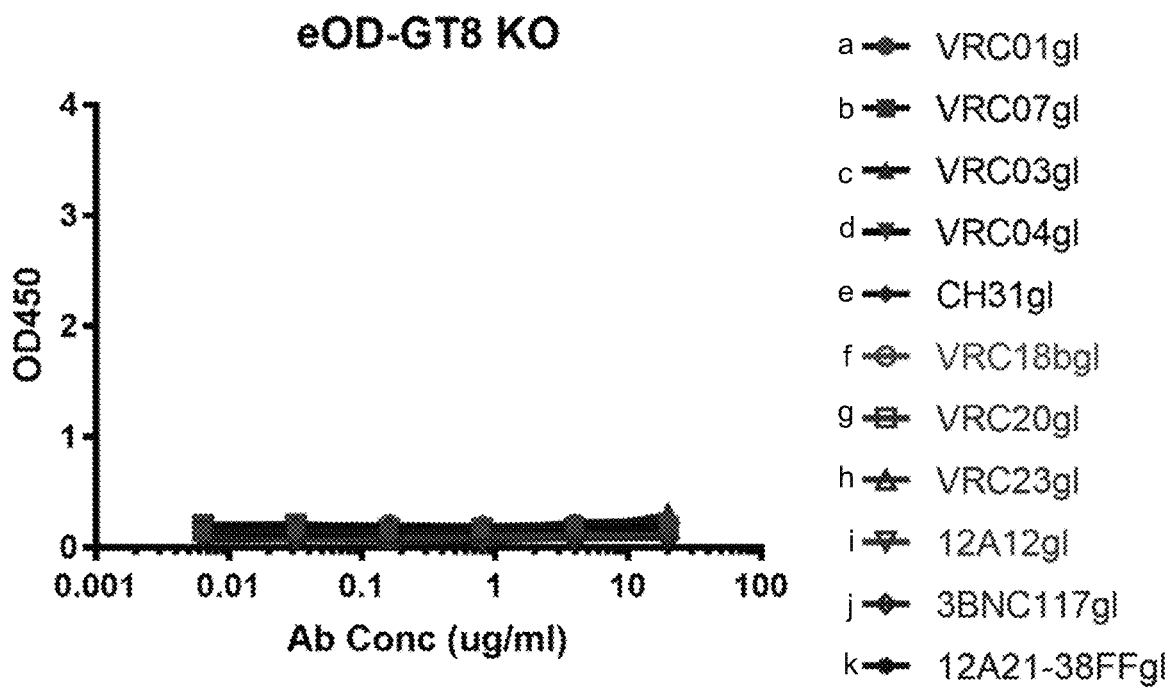

To determine whether glycan-masked eOD-GT8 60mer immunogens elicited VRC01-class precursors in IGHV1-2*02 knock-in mice, single cell RT-PCR was performed on the antigen-sorted CD4bs-specific B cells from these immunized mice as described previously (Tian et al., Cell 166: 1471-1484 e1418, 2016). In most cases, the Igκ light chains of the IgG antibodies expressed by the sorted B cells were first amplified and sequenced to search for a 5-amino acid CDRL3, a signature of VRC01-class antibodies. From those B cells that exhibited this Igκ light chain signature, their corresponding heavy chains were then amplified and sequenced to confirm that the light chains are paired with human IGHV1-2 heavy chains. Importantly, all of the 5-amino acid CDRL3 Igκ light chains for which a paired heavy chain was amplified were found to pair with the human IGHV1-2. Thus, the number of CD4bs-specific B-cells expressing a 5-amino acid CDRL3 Igκ light chain was used as a measure of the number of VRC01-class precursor antibodies (Sok et al., Science, 353, 1557-1560, 2016). Subsequently the frequency of VRC01-class precursors (containing a human IGHV1-2 heavy chain and a mouse light chain with 5-amino acid CDRL3) was calculated by dividing the number of identified VRC01-class precursors with the total number of sequenced Igκ light chains in each respective group (FIGS. 4G and 5D) or in each mouse (FIGS. 6C, 8, and 9). Using this analysis, it was observed for the first study (immunized once with 60 µg eOD-GT8 60mer), an average of 2.3% of the amplified Igκ light chains from CD4bs specific B cells had the VRC01-class antibody signature. In contrast, the mean value of VRC01-class precursors from mice immunized with the same dose of eOD-GT8-mut15, -mut16, or -mut33 60mer was 7.7%, 13.5%, and 3.2%, respectively (FIG. 4G). Remarkably, eOD-GT8-mut16 60mer elicited 5.9-fold more VRC01-class antibodies than eOD-GT8 60mer (13.5% vs 2.3%). Results from the other two 30 µg immunization studies showed enhancement of up to 3-fold for the elicitation of VRC01-class antibody precursors by eOD-GT8-mut15 and -mut16 60mer compared to eOD-GT8 60mer (FIG. 5D). When the sequencing results for each individual mouse from all three studies were combined, a statistically significant increase (ANOVA Krustal-Wallis test, p=0.04 and Mann-Whitney test, p=0.0074) was observed for the elicitation of VRC01-class antibodies by eOD-GT8-mut16 60mer-immunized mice relative to eOD-GT8-immunized mice (FIG. 6C).

The CDRL3s of the isolated VRC01-class antibody precursors elicited by eOD-GT8-mut15, -mut16, -mut17, and -mut21 60mer were found to be enriched for the QQY motif found in the VRC01 antibody. CDRL3 sequences elicited by the eOD-GT8-mut16 60mer also showed some enrichment for Q at position 96 (observed in 11 out of 29 sequences) but the other immunogens did not enrich for the E/Q residue found in mature VRC01-class antibodies (FIG. 6E). Based on the observed Igκ V- and J-gene usage and CDRL3 sequences, five VRC01-class antibody lineages were shared between antibodies elicited by parental eOD-GT8 60mer and glycan-masked eOD-GT8 60mer mutants, suggesting that the same sets of unmutated common ancestors (UCAs) were engaged by these immunogens. The CDRH3s of the cloned VRC01-class precursors varied in sequence and length, ranging from 7-15 amino acids, consistent with the diverse CDRH3s associated with IGHV1-2*02 in this mouse model (Jardine et al., Science, 351: 1458-1463, 2016; Tian et al., Cell 166: 1471-1484 e1418, 2016). Since these mice were immunized only once or twice, heavy chains of the isolated VRC01-class precursors accumulated minimal SHM (<5%).

In summary, these data show that glycan-masking of eOD-GT8 focused the antibody response to the CD4bs and enhanced the elicitation of VRC01-class precursors in the immunized knock-in mice.

Discussion

The existence of naturally occurring broadly neutralizing antibodies to the CD4bs of HIV-1 Env has focused vaccine design efforts toward this region of Env. However, immunogens that reliably elicit such antibodies remain to be developed. The difficulty is due, in part, to the fact that HIV-1 Env is not recognized by germline precursors of CD4bs bNAbs with sufficient affinity to consistently trigger the activation of the corresponding naïve B cells. As a solution to this problem, the eOD-GT8 60mer was designed. This protein is an engineered gp120 outer domain displayed as a nanoparticle immunogen—and has strong affinity to germline revertants of the well characterized VRC01-class bNAb. eOD-GT8 has been shown to selectively engage rare VRC01-class precursors in healthy human PBMCs (Jardine et al., Science, 351: 1458-1463, 2016). Furthermore, eOD-GT8 60mer nanoparticles can elicit VRC01-class precursors in IGHV1-2*02 knock-in mouse models (Dosenovic et al., 2015; Jardine et al., Science, 349: 156-161, 2015; Sok et al., Science, 353, 1557-1560, 2016; Tian et al., Cell 166: 1471-1484 e1418, 2016). The knock-in mouse models used in those studies, however, expressed v-gene-reverted IGHV1-2*02 heavy chains that contained a CDRH3 from mature VRC01 antibodies and thus precluded IGHV1-2 recombination with endogenous mouse $D_H$- and $J_H$-genes. Because of these limitations, immunization in these mouse models may not fully recapitulate the challenges of eliciting VRC01-class antibodies in humans.

The eOD-GT8 60mer has also been shown to elicit VRC01-class precursors in Kymab mice incorporating the entire human Ig loci (Sok et al., Science, 353, 1557-1560, 2016). However, the frequency of IGHV 1-2 heavy chains in Kymab mice is 3 times lower than that in human PBMCs, and light chain 5-amino acid CDRL3s are 50-300 times less abundant than in humans. As a result, Kymab mice have a much lower frequency of VRC01-class precursors than humans by a factor of 150-900 (Sok et al., Science, 353, 1557-1560, 2016). This reduced frequency combined with the small size of the mouse B cell compartment results in only one VRC01-class naïve B cell precursor on average per animal. Thus, elicitation of VRC01-class antibodies in the Kymab mice is likely to be more difficult than in humans. Indeed, eOD-GT8 60mer induced VRC01-class precursor antibodies in only approximately one third of immunized Kymab mice, consistent with less efficient elicitation limited by the extremely low frequency of naïve precursors.

In the mouse model used here, IGHV1-2*02 recombines with the normal complement of mouse $D_H$ and $J_H$ gene segments, thereby allowing the generation of B cells that express a diverse array of CDRH3s in the IGHV1-2*02 heavy chain. Another feature of this mouse model is that IGHV1-2*02 is located at the most proximal end of the mouse $V_H$ cluster relative to D segments. The proximity along with the deletion of the IGCR1 regulatory element in the $V_H$-D intervening region, strongly favors the utilization of IGHV1-2*02 during V(D)J recombination (Tian et al., Cell 166: 1471-1484 e1418, 2016). For this reason, IGHV 1-2*02 heavy chains account for 45% of total heavy chains, a frequency which is approximately 15 times higher than that in human PBMCs (Tian et al., Cell 166: 1471-1484 e1418, 2016). Five-amino acid CDRL3 Igκ chains were detected at a frequency of 0.15% which is 2 times lower than the frequency in human PBMCs (0.27±0.13%) (Tian et al., Cell 166: 1471-1484 e1418, 2016). Overall, it is estimated that the VRC01-class precursors were expressed in this mouse model at a frequency approximately 7-fold higher than in humans. The higher frequency of potential VRC01-class precursors helps to compensate for the small size of the B cell compartment in mice. Thus, in terms of absolute number and diversity of B cells expressing potential VRC01 precursors, the IGHV1-2*02-rearranging mouse model may offer a closer approximation to the human repertoire than conventional knock-in mice, Notably, in this model, eOD-GT6 (Jardine et al., *Science,* 351: 1458-1463, 2016; Jardine et al., *Science,* 349: 156-161, 2015; Sok et al., *Science,* 353, 1557-1560, 2016; Tian et al., *Cell* 166: 1471-1484 e1418, 2016), a VRC01-class germline binder with lower affinity than eOD-GT8, failed to elicit VRC01-class precursors at detectable level, validating the stringency of the model. Although this example described elicitation of VRC01-class antibodies with eOD-GT8 60mer priming as previously reported, many of the elicited antibodies and class-switched B cells targeted non-CD4bs epitopes (Tian et al., *Cell* 166: 1471-1484 e1418, 2016).

To more effectively focus the antibody immune response to the CD4bs, sequence and structural information was used to selectively add N-linked glycans to mask the non-CD4bs regions of eOD-GT8. The immunogenicity of several of the glycan-masking mutants were evaluated in the IGHV1-2-rearranging mouse model. In three independent experiments using different adjuvants and immunization schema, glycan-masking was shown to enhance the specificity of CD4bs response in both sera and the class-switched B cell pool with the best results observed for the eOD-GT8-mut16 60mer. Although eOD-GT8-mut15 and -mut16 both elicited similarly high percentages of CD4bs-specific serum antibodies and B cells, eOD-GT8-mut16 elicited the highest overall titer of CD4bs-specific serum response that was 3-fold higher than the eOD-GT8 60mer. Moreover, single-cell cloning detected the largest increases of VRC01-class precursor B cell receptors (BCRs) from mice immunized with eOD-GT8-mut16 relative to eOD-GT8 when comparing within the same immunization regimen (mean of 13.5% vs. 2.3% for 60 µg with poly I:C and 6.1% vs 2.1% for 30 µg with poly I:C respectively). Thus, this strategy of blocking off-target epitopes was able to reduce the non-CD4bs immune response and facilitated the activation and subsequent elicitation of VRC01-class precursors in this mouse model. Furthermore, among the 25 potential VRC01-class precursors isolated from naïve human B cells, the top nine antibodies (marked by stars in FIG. 2B) recognized all of the glycan mutants with affinities comparable to their interaction with eOD-GT8 60mer. The glycan mutants may therefore preferentially select for high affinity precursors but may have reduced capacity to prime lower affinity precursors. A recent study has shown that antibody precursor affinity towards its cognate immunogen can have a large effect on B cell recruitment, differentiation and antibody maturation (Abbott et al., *Immunity,* 48, 133-146, 2018). Thus, the ability of glycan mutants to further focus the antibody response while maintaining high affinity to target antibody precursors is a meaningful improvement in germline targeting vaccine design.

Figure 2D:
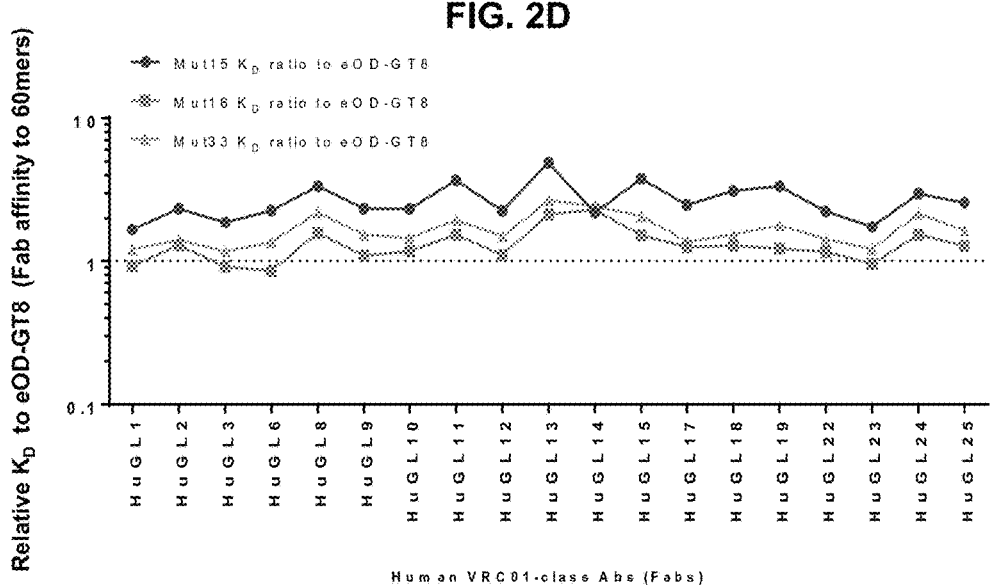

The ELISA analysis in FIG. 2A indicates that, of the 13 individual mutants, eOD-GT8-mut1, -mut2, -mut4, -mut5, -mut7, -mut11, and -mut23 60mer were best at masking the binding of non-CD4bs antibodies. Five of these glycans (from eOD-GT8-mut1, -mut2, -mut4, -mut5, and -mut23) are all clustered together in the same region (cluster 1) on a face opposite the CD4bs (FIG. 10), suggesting that this may be an immunogenic hotspot. The other two glycans, from eOD-GT8-mut7 and -mut11, are both located on nearby protruding loops which may represent another immunogenic hotspot (cluster 2). Only two of these seven glycans, from eOD-GT8-mut1 and -mut2, would be accessible in the context of the envelope trimer. The rest of the glycans mask new surfaces created in the context of an isolated eOD and thus serve to block undesired neoepitopes in this immunogen. Of the four best glycan combination mutants examined (eOD-GT8-mut15, -mut16, -mut21, and -mut33), each had at least two glycans from the first cluster and one or more glycans from the second cluster, suggesting that both glycan clusters may be important for suppressing elicitation of non-CD4bs antibodies. Remarkably, eOD-GT8-mut15 60mer, which had only three added glycans, performed very well in epitope focusing relative to the other three mutants having 4-6 added glycans (FIG. 3). This suggests that the three glycans in eOD-GT8-mut15 suffice to cover the most important off-target epitopes. However, eOD-GT8-mut16 60mer with five added glycans was ultimately the most immunogenic for the elicitation of CD4bs-specific serum and of VRC01-class precursors, which may be in part due to the fact that this mutant retains affinities nearly as high as eOD-GT8 for human naïve VRC01-class precursors (FIG. 2D).

In summary, we used structure-guided glycan-masking, followed by antigenic characterization, to identify variants of the eOD-GT8 60mer immunogen capable of focusing the immune response on the CD4bs and, specifically, to improve the ability of this germline-targeting priming immunogen to elicit VRC01-class responses, an important category of HIV-1 neutralizing antibodies. The enhanced antibody response elicited by these glycan-masked immunogens can be used to facilitate the ability of subsequent booster immunizations to mature these antibody precursors into HIV-1 neutralizing antibodies.

Materials and Methods

Design of eOD-GT8 glycan-masking mutants. Using the crystal structure of eOD-GT8 monomer (Jardine et al., *Science,* 351: 1458-1463, 2016), all surface residues with exposed Cβ atoms greater or equal than 5 Å from the CD4bs were identified. Each position was examined using PyMol (The PyMol Molecular Graphics System, version 1.8.6; Schrödinger, LLC) for the potential structural effects of incorporating an NxT sequon (where X is not a proline). NxT sequons were used instead of NxS since they are known to glycosylate more efficient than NxS sequons. Positions where the introduction of asparagine or the downstream i+2 threonine could potentially decrease protein stability were discarded. The remaining positions were evaluated for sequence-based glycosylation potential using NetNGlyc (cbs.dtu.dk/services/NetNGlyc/). Glycosylation sites with scores less than 0.5 were discarded. Each potential glycan was also modeled onto the eOD-GT8 structure using the program Glycosylate (He and Zhu, *Curr Opin Virol,* 11: 103-112, 2015). The identification of new glycan sites located on protruding loops was performed by examining the monomer eOD-GT8 crystal structure using Pymol. For five of the mutants (eOD-GT8-mut22, 23, 40, 41 and 45), additional set of two residues were also mutated to reduce immunogenicity (E267G and E268G) or to improve overall stability (I477L and D478N). See FIG. 11. All structural figures were created using PyMol.

Generation and characterization of IGHV1-2 single knock-in mouse models. The generation and characterization of the IGHV1-2*02 mouse model used in this study have been described in detail in a previous publication (Tian et al., *Cell* 166: 1471-1484 e1418, 2016). Briefly, human IGHV1-2*02 segment substitutes for the mouse $V_H$81X segment at the IgH locus, and IGCRI was deleted from the same IgH allele. In this setting, IGHV1-2*02 segment is preferentially utilized for V(D)J recombination and accounts for about 45% of heavy chains in the antibody repertoire. These genetic modifications were introduced into EF1 ES cell line, which was derived from an F1 hybrid mouse (129/Sv and C57BL/6). IGHV1-2*02 replacement and IGCRI deletion occurred on the IgH allele from 129/Sv strain. Correctly modified ES clones were injected into Rag2 deficient blastocysts to generate chimeric mice. The chimeric mice were bred with 129/Sv strain mice for germline transmission. Heterozygous IGHV1-2*02 knock-in mice were interbred to produce homozygous knock-in mice, which are used for the experiments in this study. For B cell characterization, splenic B cells were stained with anti-B220, anti-IgM, anti-IgD, anti-IgG antibodies and analyzed with flowcytometry.

Immunizations. 100 μl of immunogen mix, containing 30-60 μg of specified protein immunogen and 60 μg of poly I:C in PBS, was injected to the inner thigh of the two rear legs of each mouse. IGHV1-2 mice were immunized once or twice with 4 weeks interval, and blood and spleens were collected two weeks after the last immunization.

Isolation of non-CD4bs monoclonal antibodies. Transgenic XenoMouse™ that expresses human immunoglobulins (Jakobovits et al., *Nat Biotechnol*, 25: 1134-1143, 2007) were immunized twice with 15 μg of eOD-GT6 60mer (Jardine et al., *Science*, 340: 711-716, 2013) plus 30 μg of poly I:C with one week interval. The mice were sacrificed two weeks after the last injection. Splenocytes were used to sort for B cells stained positively for both eOD-GT6 and eOD-GT6 CD4bs-KO mutant antigen probes. Human IgG heavy and light chains were cloned from these cells as described previously (Wu et al., *Science*, 329: 856-861, 2010) and expressed in pair in Expi293 cells. Two purified XenoMouse IgGs, X1A2 and X1C6, were confirmed to be non-CD4bs specific and eOD-GT8 reactive by ELISA showing equal strong binding to both eOD-GT8 and eOD-GT8 CD4bs KO mutant (FIGS. 2A and 7). Similarly, two non-CD4bs IgGs, mA9 and mE4, were cloned from IGHV1-2*02 single knock-in mice that have been immunized once with 60 μg of eOD-GT8 60mer plus 60 μg of poly I:C (Tian et al., 2016). These two antibodies use human IGHV1-2*02 paired with mouse kappa chains. Both bind eOD-GT8 and eOD-GT8 KO equally well (FIG. 2A).

Protein production. All proteins were produced in transiently transfected Expi293 cells as previously described (Cheng et al., *J Virol*, 90, 2740-2755, 2015; Pancera et al., *Nature*, 514, 455-461, 2014).

Negative-stain electron microscopy. Samples were diluted to ~0.05 mg/ml, adsorbed to freshly glow-discharged carbon-film grids for 15 s, and stained with 0.75% uranyl format. For 2D analysis, images were collected semi-automatically using SerialEM (Mastronarde et al., *J Struct Biol*, 152: 36-51, 2005) on an FEI Tecnai T20 electron microscope equipped with a 2k×2k Eagle CCD camera. Reference-free 2D classification was performed using EMAN2.1 (Tang et al., *J Struct Biol*, 157: 38-46, 2007).

ELISA. ELISA was performed as previously described (Tian et al., *Cell* 166: 1471-1484 e1418, 2016). One exception was for initial screening of eOD-GT8 60mer glycan mutants expressed in Expi293 cell supernatants. For this process, we first coated Costar half area plates with 50 μl/well of 1 μg/ml *Galanthus nivalis* lectin (Sigma) in PBS at 4C overnight, blocked the wells with 1:10 diluted blocking solution (Immune Technology Corp.), and then applied excess amount (base on yield of eOD-GT8 60mer in Expi293) of the cell supernatants containing expressed eOD-GT8 60mer or its glycan mutants to fully load the bound lectin and ensure equal loading of eOD-GT8 60mer or mutant nanoparticles in each well. Later steps of ELISA were the same as described previously (Tian et al., *Cell* 166: 1471-1484 e1418, 2016).

Single B-cell RT-PCR, gene amplification, cloning and mutation analysis of cloned IgH and IgL chains. Reverse transcription and subsequent PCR amplification of heavy and light chain variable genes were performed using SuperScript III (Life Technologies) as previously described (Tiller et al., *J Immunol Methods*, 350: 183-193, 2009; Wu et al., *Science*, 329: 856-861, 2010).

Surface plasmon resonance (SPR). Affinities of antibody-antigen interactions were measured as previously described (Jardine et al., *Science*, 349: 156-161, 2015; Tian et al., *Cell* 166: 1471-1484 e1418, 2016). Briefly, we measured kinetics and affinities of antibody-antigen interactions on a ProteOn XPR36 (Bio-Rad) using GLC Sensor Chip (Bio-Rad) and 1×HBS-EP+ pH 7.4 running buffer (20× stock from Teknova, Cat. No H8022) supplemented with BSA at 1 mg/ml. The Human Antibody Capture Kit instructions were followed (Cat. No BR-1008-39 from GE) to prepare chip surfaces for ligand capture. In a typical experiment, about 6000 RU of capture antibody was amine-coupled in all 6 flow cells of the GLC Chip. Regeneration was accomplished using 3M Magnesium Chloride with 180 seconds contact time and injected four times per each cycle. Raw sensograms were analyzed using ProteOn Manager software (Bio-Rad), including interspot and column double referencing, and either Equilibrium fits or Kinetic fits with Langmuir model, or both, were employed when applicable. Analyte concentrations were measured on a NanoDrop 2000c Spectrophotometer using Absorption signal at 280 nm.

Mass Spectrometry Glycan Analysis. An aliquot of each sample was denatured by incubating with 10 mM of dithiothreitol at 56° C. for an hour and alkylated by 55 mM of iodoacetamide for 45 minutes in dark prior to digestion with proteases optimized based on amino acid sequence of each target protein. Specifically, each aliquot was treated with a combination of proteases including trypsin (Promega), Arg-C (Promega), and Glu-C (Promega). Following digestion, the samples were deglycosylated by Endo-H (Promega) followed by PNGaseF (Glyko®, Prozyme) treatment in the presence of O18-water. The resulting peptides were separated on an Acclaim PepMap RSLC C18 column (75 μm×15 cm) and eluted into the nano-electrospray ion source of an Orbitrap Fusion™ Lumos™ Tribrid™ mass spectrometer (Thermo Fisher Scientific) with a 180-min linear gradient consisting of 0.5-100% solvent B over 150 min at a flow rate of 200 nL/min. The spray voltage was set to 2.2 kV and the temperature of the heated capillary was set to 280° C. Full MS scans were acquired from m/z 300 to 2000 at 60k resolution, and MS2 scans following collision-induced fragmentation were collected in the ion trap for the most intense ions in the Top-Speed mode within a 5-sec cycle using Fusion instrument software (v2.0, Thermo Fisher Scientific). The resulting spectra were analyzed using SEQUEST (Proteome Discoverer 1.4, Thermo Fisher Scientific) with full MS peptide tolerance of 20 ppm and MS2 peptide fragment tolerance of 0.5 Da, and filtered using ProteoIQ (v2.7, Premier Biosoft) at the protein level to generate a 1% false discovery rate for protein assignments. Site occupancy was calculated using spectral counts assigned to the O18-Aspcontaining (PNGaseF-cleaved) and/or HexNAc-modified (EndoH-cleaved) peptides and their unmodified counterparts.

Quantification and statistical analysis. Statistical comparisons using GraphPad Prism 7.01 Software (GraphPad Prism Software, Inc.) were performed only on the combined data sets with n>3. For these comparisons overall nonparametric ANOVA Krustal-Wallis tests were performed and if the p-values were greater than 0.05 they were followed by nonparametric Mann-Whitney tests.

It will be apparent that the precise details of the methods or compositions described may be varied or modified without departing from the spirit of the described embodiments. We claim all such modifications and variations that fall within the scope and spirit of the claims below.

It is claimed:

1. An isolated immunogen, comprising:
    an engineered gp120 outer domain, comprising an amino acid sequence according to SEQ ID NO: 1 further comprising amino acid substitutions, insertions, and/or deletions as follows:
        amino acid substitutions to introduce N-linked glycan sequons beginning at one or more of residues 8, 14, 56, 70, 71, 74, 102, and 153 of SEQ ID NO: 1, wherein a glycine insertion is introduced between residues 10 and 11 if the N-linked glycan sequon beginning at residue 8 is introduced, and an E70G substitution is introduced if the N-linked glycan sequon beginning at residue 71 is introduced, and optionally a GG substitution for the residues at positions corresponding to positions 70 and 71 of SEQ ID NO: 1 if N-linked glycan sequons beginning at residue 70 or 71 are not introduced; and
    wherein:
    the engineered gp120 outer domain comprises N-linked glycan sequons beginning at residues corresponding to residues 18, 65, 92, 98, 106, 113, 129, 146, 165, and 170 of SEQ ID NO: 1;
    the residues of the engineered gp120 outer domain corresponding to residues 25-45, 79-85, and 126-145 of SEQ ID NO: 1 are identical to SEQ ID NO: 1; and
    the remaining residues of the engineered gp120 outer domain comprise an amino acid sequence at least 90% identical to the corresponding residues of SEQ ID NO: 1.

2. The immunogen of claim 1, wherein the remaining residues of the engineered gp120 outer domain comprise an amino acid sequence at least 95% identical, at least 98% identical, at least 99% identical, or identical to the corresponding residues of SEQ ID NO: 1.

3. The immunogen of claim 1, wherein the glycan sequons are NxT sequons.

4. The immunogen of claim 1, wherein the engineered gp120 outer domain comprises or consists essentially of an amino acid sequence set forth as any one of SEQ ID NOs: 19 (Mut19), 27 (Mut27), 29 (Mut29), 81 (Mut51), or 82 (Mut52).

5. The immunogen of claim 1, wherein the engineered gp120 outer domain specifically binds to VRC01 class bnAbs and their inferred germline revertants.

6. The immunogen of claim 1, wherein the engineered gp120 outer domain induces an immune response that targets the VRC01 binding site of gp120.

7. The immunogen of claim 6, wherein the immune response activates memory B cells that bind to the engineered gp120 outer domain, and wherein at least 50% of the memory B cells bind to a VRC01 binding site on the engineered gp120 outer domain.

8. The immunogen of claim 1, wherein the engineered gp120 outer domain is linked to a subunit of a self-assembling protein nanoparticle by a peptide linker, or is directly linked to the subunit of the self-assembling protein nanoparticle.

9. The immunogen of claim 8, wherein the subunit of the self-assembling protein nanoparticle is a lumazine synthase subunit.

10. The immunogen of claim 9, wherein the lumazine synthase comprises, consists essentially of, or consists of:
    an amino acid sequence set forth as SEQ ID NO: 49, or an amino acid sequence at least 90% identical to SEQ ID NO: 49;
    an amino acid sequence set forth as residues 20-173 of SEQ ID NO: 49, or an amino acid sequence at least 90% identical residues 20-173 of SEQ ID NO: 49;
    an amino acid sequence set forth as SEQ ID NO: 67, or an amino acid sequence at least 90% identical to SEQ ID NO: 67;
    an amino acid sequence set forth as SEQ ID NO: 68, or an amino acid sequence at least 90% identical to SEQ ID NO: 68; or
    an amino acid sequence set forth as SEQ ID NO: 69, or an amino acid sequence at least 90% identical to SEQ ID NO: 69.

11. The immunogen of claim 1, wherein the engineered gp120 outer domain is linked to a carrier protein, optionally wherein the engineered gp120 outer domain is linked to the carrier protein by a peptide linker.

12. The immunogen of claim 8, wherein the engineered gp120 outer domain is linked to the subunit of the self-assembling protein nanoparticle or the carrier protein by the peptide linker, and wherein the peptide linker comprises or consists of a glycine-serine peptide linker of no more than 30 amino acids in length.

13. The immunogen of claim 12, wherein the peptide linker comprises or consists of the amino acid sequence set forth as SEQ ID NO: 50 (GGSGGSGGSGGSGGG).

14. The immunogen of claim 1, comprising a multimer of the engineered gp120 outer domain.

15. The immunogen of claim 1, comprising a protein nanoparticle comprising the engineered gp120 outer domain.

16. The immunogen of claim 15, wherein the protein nanoparticle is a lumazine synthase 60mer protein nanoparticle.

17. The immunogen of claim 16, wherein subunits of the lumazine synthase protein nanoparticle comprise or consist of an amino acid sequence set forth as
residues 20-361 of SEQ ID NO: 85 (Mut51); or
residues 20-360 of any one of SEQ ID NOs: 55 (Mut19), 57 (Mut27), 59 (Mut29), or 86 (Mut52).

18. The immunogen of claim 1, linked to a transmembrane domain.

19. The immunogen of claim 1, wherein the glycan sequons other than those beginning at residues corresponding to residues 106, 113, 129, 146, or 170, or a combination thereof, are glycosylated.

20. The immunogen of claim 1, wherein the glycan sequons are glycosylated.

21. A virus-like particle comprising the engineered gp120 outer domain of claim 1.

22. An immunogenic composition comprising the immunogen of claim 1 or a virus-like particle comprising the immunogen, and a pharmaceutically acceptable carrier.

23. A method of generating an immune response to a CD4 binding site on gp120 in a subject, comprising administering an effective amount of the immunogenic composition of claim 22 to the subject.

24. The method of claim 23, wherein administering the effective amount of the immunogen, protein nanoparticle, virus-like particle, nucleic acid molecule, vector, or immunogenic composition to the subject primes the immune response to the CD4 binding site.

25. The method of claim 24, wherein priming the immune response comprises production of IGHV1-2*02 antibodies that bind to the engineered gp120 outer domain of the immunogen.

26. The method of claim 25, wherein the antibodies are germline precursors of VRC01-class antibodies.

27. The method of claim 23, further comprising administering a boost to the subject to generate the immune response, wherein the boost is an HIV-1 Env protein or variant thereof.

28. The method of claim 23, wherein the immune response inhibits or treats HIV-1 infection.

* * * * *